(12) United States Patent
Raitano et al.

(10) Patent No.: US 7,534,417 B2
(45) Date of Patent: May 19, 2009

(54) 103P2D6: TISSUE SPECIFIC PROTEIN HIGHLY EXPRESSED IN VARIOUS CANCERS

(75) Inventors: Arthur B. Raitano, Los Angeles, CA (US); Daniel E. H. Afar, Brisbane, CA (US); Gazelle S. Rastegar, Beverly Hills, CA (US); Steve Chappell Mitchell, Santa Monica, CA (US); Rene S. Hubert, Los Angeles, CA (US); Pia M. Challita-Eid, Encino, CA (US); Mary Faris, Los Angeles, CA (US); Aya Jakobovits, Beverly Hills, CA (US)

(73) Assignee: Agensys, Inc., Santa Monica, CA (US)

( * ) Notice: Subject to any disclaimer, the term of this patent is extended or adjusted under 35 U.S.C. 154(b) by 0 days.

(21) Appl. No.: 09/793,451

(22) Filed: Feb. 26, 2001

(65) Prior Publication Data

US 2003/0157597 A1 Aug. 21, 2003

Related U.S. Application Data

(60) Provisional application No. 60/184,558, filed on Feb. 24, 2000, provisional application No. 60/218,856, filed on Jul. 13, 2000.

(51) Int. Cl.
*A61K 51/10* (2006.01)
*A61K 39/395* (2006.01)
*C07H 21/04* (2006.01)
*C07K 14/00* (2006.01)

(52) U.S. Cl. .............. 424/1.49; 424/178.1; 424/181.1; 424/183.1

(58) Field of Classification Search ....................... None
See application file for complete search history.

(56) References Cited

U.S. PATENT DOCUMENTS 5,980,896 A * 11/1999 Hellstrom et al. .......... 424/183.1
2007/0105122 A1 * 5/2007 Ota et al. .................... 435/6

FOREIGN PATENT DOCUMENTS

| EP | 1074617 A | | 2/2001 |
| WO | WO 97/35614 | * | 10/1997 |
| WO | WO 98 45435 | | 10/1998 |
| WO | WO 00/40229 | * | 7/2000 |
| WO | WO 01 18022 A | | 3/2001 |
| WO | WO02083899 | | 10/2002 |
| WO | WO 03/016470 | * | 2/2003 |
| WO | WO03025148 | | 3/2003 |

OTHER PUBLICATIONS

Waldmann et al, Science, 1991, vol. 252, pp. 1657-1662.*
Chester and Hawkins (TIBTECH, 1995, vol. 13, pp. 294-300.*
MacCallum et al. (Journal of Molecular. Biology, 1996, vol. 262, pp. 732-745).*
Pascalis et al (Journal of Immunology, 2002, vol. 169, pp. 3076-3084.*
Casset et al (Biochemical and Biophysical Research Communications, 2003, vol. 307, pp. 198-205).*
Vajdos et al. (Journal of Molecular biology, 2002, vol. 320, pp. 415-428).*
Holm et al (Molecular Immunology, 2007, vol. 44, pp. 1075-1084).*
Chen et al. (Journal of Molecular Biology, 1999, vol. 293, pp. 865-881).*
Wu et al. (Journal of Molecular Biology, 1999, vol. 294, pp. 151-162).*
Kerr and Thorpe (Immunochemistry LabFax, 1994, pp. ix-xi and 102).*
Database EMBL ID: HS444155; Accession No. H08444, XP 002184240 (abstract).
Database EMBL ID: HS069156; Accession No. H03069, XP 002184241 (abstract).
Database EMBL ID: AI928402; Accession No. AI928402, XP 002184242 (abstract).
Database EMBL; Accession No. AC021941, XP 002184509.
Geluk A. et al. (1994) *Journal of Immunology* 152:5742-5748 (XP 002184475).
Hubert et al., Proc. Natl. Acad. Sci. USA (1999) 96(25):14523-14528.
Klein et al., Nat. Med. (1997) 3:402.
Pinto et al., Clin. Cancer Res. (1996) 2(9):1445-1451.
Reiter et al., Proc. Natl. Acad. Sci. USA (1998) 95:1735.
Su et al., Proc. Natl. Acad. Sci. USA (1996) 93:7252.
Eck et al. in: Goodman & Gilman's The Pharmacological Basis of Therapeutics, Ninth Edition, Goodman and Gilman (eds.), McGraw-Hill, NY (1996) Ch. 5, pp. 77-101.
Power et al., Science (1986) 231:1567-1572.
Orkin et al., Report and Recommendation of the Panel to Assess the NIH Investmen in Research on Gene Therapy, NIH (1995).
Verma et al., Nature (1997) 389:239-242.

* cited by examiner

*Primary Examiner*—Karen A Canella
(74) *Attorney, Agent, or Firm*—Morrison & Foerster LLP

(57) ABSTRACT

A novel gene (designated 103P2D6) and its encoded protein are described. 103P2D6 is not expressed in normal adult tissue, but is highly expressed in prostate tissue xenografts, providing evidence that it is turned on in prostate cancer. 103P2D6 is also expressed in some fetal tissues, and in breast, bladder, lung, bone, colon, pancreatic, testicular, cervical and ovarian cancers. Consequently, 103P2D6 provides a diagnostic and/or therapeutic target for cancers, and the 103P2D6 gene or fragment thereof, or its encoded protein or a fragment thereof can be used to elicit an immune response.

5 Claims, 17 Drawing Sheets

Fig. 1

```
GATCAGCTTTATGGTGTGTGTCTTAAGGCTTCAGAATGAAACTACAAAAAGTTCTGATAAGGCTTATTTA
CAATACCTTGGGAGGTCCTAGTGCTAAGTGCCCTTATAAGAGGAACACTCAGAGGAGGGTTTTGGCAGCT
GAATTCTCGGTAAGACCTGCTTTACTCATCAAAGTTTAGCTAAGGCTTTTTGTCTGCAGCTGCTGTTTGT
TCAGATATTCTCAAAGTAGACTTGTGTCATATTGATGGGTTGTTAGTCCCTTCATTGCCCTATTTGAAAC
TTGACATGAAGTTTCACTGACAAGGAGCTGTGCTGATTGCTGTGGAGATAAGGCTAGGTTCA
```

Fig. 2A

```
   1  CAC CTG TGA CTG TTG ATG TGG AAC TGA TTT ATC GCG TAT TCG TAC TGG CTG AAT CCG GCT
  61  GTC CGC TCT GCG GTG CCC CGC CCC GCC CCA ACC CAG GAT CTT CCC AGC CCC GCT CCG CCC
 121  CAA CCC AGG ATC TTC CCA GCC CTC GTG TGT CCC CGC TCA CTT CAG TTC CCG CCG CGA GCC
 181  TTC TTC TTG GTC TTC TGG CCT GGC GGC GAT CGT CGG CCA GTT TAT CCC TCG GAG TTG CAC
 241  TGG CAG ACA CGC CGC TAC TTT GTA GCG GGT TTC GGG CGG GCC ACG CGT GCG GCG ACA GGA
 301  ACC CAA CCC CGG CCG ACC TTG GGC TCC AGG AAT TCG TTG TCT ACG TCT GCG GAG GTG CGG
 361  CAG CCT CAG TTT TAA GCG CAG GTG ATC AAG TAT ATC TGA AAG TTT TTA GAA GAA AAG ATG
 421  TGT TGT AAC CTC CCT GGA AAA AGA AGA GAC TTT ATG AAG TAC TGC TAA CCA CCT ACA TAG
 481  TCA TCA AAA TAA AAT TCC TGA ATT TGT ACA AGC CAC AGG AAG CTA GAT TGA GAT CAT TAT
 541  ATG ACA ACT GGA AGG CCA AGG CTA TGG GTT ACC TCA AAT TGA GGA ATT CGG CAC CCT ACT
 601  CAC AGG CTC CAT GAG CAG ATG AAG TAG ACA GCT TTA CTC AGT ATC TCA GAC CAA GAA CTT
 661  CAT CTC CAT CTC CAA CTA GCT GAA ACA TCT CCC CTC CTC AAC CTG GAA AAT TCT CTG ACT
 721  TAG AAA TTT AAA CAA AAC CCT CCC CTT TCA TTG AAT CTC CAT TGT CTG GAG TTT GCT TGT
                                                      M   G   S   L   S   N   C   A   L   L   Q   L
 781  TTT AAT CTA GGC TGT TCC TCC ACT ATG GGC TCC CTT TCA AAC TGT GCC CTG CTT CAA CTA
       T   L   T   A   F   L   T   I   L   V   Q   P   Q   H   L   L   A   P   V   F
 841  ACC CTT ACT GCT TTT TTG ACA ATT CTA GTA CAA CCT CAG CAC CTG CTT GCT CCA GTT TTC
       R   T   L   S   I   L   T   N   Q   S   N   C   W   L   C   E   H   L   D   N
 901  CGG ACA CTA TCT ATC TTG ACT AAT CAG TCT AAT TGC TGG TTA TGT GAA CAT CTA GAT AAT
       A   E   Q   P   E   L   V   F   V   P   A   S   A   S   T   W   W   T   Y   S
 961  GCA GAA CAA CCC GAA CTA GTT TTT GTT CCT GCC AGT GCA AGC ACC TGG TGG ACC TAT TCT
       G   Q   W   M   Y   E   R   V   W   Y   P   Q   A   E   V   Q   N   H   S   T
1021  GGA CAA TGG ATG TAT GAA AGG GTG TGG TAT CCA CAA GCA GAA GTA CAG AAT CAC TCT ACT
       S   S   Y   R   K   V   T   W   H   W   E   A   S   M   E   A   Q   G   L   S
1081  TCC TCC TAT CGT AAA GTG ACT TGG CAC TGG GAA GCC TCC ATG GAA GCT CAA GGT CTA TCC
       F   A   Q   V   R   L   L   E   G   N   F   S   L   C   V   E   N   K   N   G
1141  TTT GCT CAA GTA AGG TTA TTG GAG GGA AAT TTT TCT CTT TGC GTA GAA AAT AAA AAT GGC
       S   G   P   F   L   G   N   I   P   K   Q   Y   C   N   Q   I   L   W   F   D
1201  AGT GGA CCC TTC CTA GGT AAT ATA CCT AAA CAA TAC TGT AAT CAA ATA CTA TGG TTT GAT
       S   T   D   G   T   F   M   P   S   I   D   V   T   N   E   S   R   N   D   D
1261  TCT ACA GAT GGC ACC TTC ATG CCC TCT ATA GAT GTT ACA AAT GAA TCC AGG AAC GAT GAT
       D   D   T   S   V   C   L   G   T   R   Q   C   S   R   F   A   G   C   T   N
1321  GAT GAT ACA AGT GTT TGC CTA GGC ACT AGA CAA TGT TCC CGG TTT GCA GGT TGC ACA AAC
       R   T   W   N   S   S   A   V   P   L   I   G   L   P   N   T   Q   D   Y   K
1381  CGG ACC TGG AAC AGC TCA GCT GTT CCC TTG ATT GGT CTG CCC AAT ACC CAA GAC TAC AAA
       W   V   D   R   N   S   G   L   T   W   S   G   N   D   T   C   L   Y   S   C
1441  TGG GTA GAT CGA AAT TCT GGA TTG ACC TGG TCA GGT AAT GAC ACC TGT CTC TAT AGC TGC
       Q   N   Q   T   K   G   L   L   Y   Q   L   F   R   N   L   F   C   S   Y   G
1501  CAA AAC CAA ACC AAA GGC CTT CTG TAC CAG CTA TTT CGC AAC CTA TTT TGC TCT TAT GGC
       L   T   E   A   H   G   K   W   R   C   A   D   A   S   I   T   N   D   K   G
1561  CTG ACA GAG GCA CAT GGG AAA TGG AGA TGT GCA GAT GCC AGC ATA ACT AAT GAC AAA GGT
       H   D   G   H   R   T   P   T   W   W   L   T   G   S   N   L   T   L   S   V
1621  CAT GAT GGA CAC CGG ACC CCC ACC TGG TGG CTC ACA GGT TCC AAT CTG ACC TTG TCT GTG
       N   N   S   G   L   F   F   L   C   G   N   G   V   Y   K   G   F   P   P   K
1681  AAC AAC TCT GGC CTC TTT TTT TTG TGC GGC AAT GGG GTG TAC AAA GGG TTT CCA CCT AAA
       W   S   G   R   C   G   L   G   Y   L   V   P   S   L   T   R   Y   L   T   L
1741  TGG TCT GGG CGA TGT GGA CTT GGG TAT CTT GTA CCT TCC CTC ACC AGA TAC CTC ACC TTA
       N   A   S   Q   I   T   N   L   R   S   F   I   H   K   V   T   P   H   R   C
1801  AAT GCT AGC CAA ATT ACA AAC CTG AGA TCC TTC ATT CAT AAA GTA ACA CCG CAT AGA TGC
       T   Q   G   D   T   D   N   P   P   L   Y   C   N   P   K   D   N   S   T   I
1861  ACC CAA GGA GAC ACA GAC AAT CCA CCT CTG TAT TGC AAC CCC AAG GAC AAT TCA ACA ATA
       R   A   L   F   P   S   L   G   T   Y   D   L   E   K   A   I   L   N   I   S
1921  AGG GCC CTT TTT CCA AGT TTG GGA ACT TAT GAT TTA GAA AAG GCA ATT CTA AAC ATT TCC
       K   A   M   E   Q   E   F   S   A   T   K   Q   T   L   E   A   H   Q   S   K
1981  AAA GCA ATG GAA CAG GAA TTC AGT GCC ACT AAG CAG ACC TTG GAA GCA CAC CAA TCA AAA
       V   S   S   L   A   S   A   R   K   D   H   V   L   D   I   P   T   T   Q
2041  GTT AGC AGT TTA GCC TCT GCA TCC CGA AAG GAT CAT GTC TTG GAT ATA CCG ACC ACC CAA
       R   Q   T   A   C   G   T   V   G   K   Q   C   C   L   Y   I   N   Y   S   E
```

Fig. 2B

```
2101    CGA CAA ACG GCT TGT GGA ACT GTT GGC AAA CAG TGT TGC CTC TAT ATA AAT TAT TCG GAA
         E   I   K   S   N   I   Q   R   L   H   E   A   S   E   N   L   K   N   V   P
2161    GAA ATA AAG TCT AAT ATA CAG CGT CTC CAC GAA GCA TCC GAG AAC CTG AAG AAT GTA CCA
         L   L   D   W   Q   G   I   F   A   K   V   G   D   W   F   R   S   W   G   Y
2221    TTA CTT GAT TGG CAA GGC ATA TTT GCA AAA GTG GGA GAC TGG TTC AGA TCA TGG GGC TAT
         V   L   L   I   V   L   F   C   L   F   I   F   V   L   I   Y   V   R   V   F
2281    GTG CTT TTA ATT GTT CTT TTC TGC TTA TTC ATC TTT GTT TTA ATC TAT GTT CGT GTC TTT
         R   K   S   R   R   S   L   N   S   Q   P   L   N   L   A   L   S   P   Q   Q
2341    CGC AAA TCT CGC AGA TCC CTT AAC TCC CAA CCT CTG AAC CTA GCC TTA TCT CCA CAG CAA
         S   A   Q   L   L   V   S   E   T   S   C   Q   V   S   N   R   A   M   K   G
2401    TCA GCA CAG CTC CTT GTC AGT GAA ACT TCA TGT CAA GTT TCA AAT AGG GCA ATG AAG GGA
         L   T   T   H   Q   Y   D   T   S   L   L
2461    CTA ACA ACC CAT CAA TAT GAC ACA AGT CTA CTT TGA GAA TAT CTG AAC AAA CAG CAG CTG
2521    CAG ACA AAA AGC CTT AGC TAA ACT TTG ATG AGT AAA GCA GGT CTT ACC GAG AAT TCA GCT
2581    GCC AAA ACC CTC CTC TGA GTG TTC CTC TTA TAA GGG CAC TTA GCA CTA GGA CCT CCC AAG
2641    GTA TTG TAA ATA AGC CTT ATC AGA ACT TTT TGT AGT TTC ATT CTG AAG CCT TAA GAC ACA
2701    CAC CAT AAA GCT GAT CTG TAA AAC CTT ACC CCT TGC TGT TCA GAG AGC TAC TCT TTG TAG
2761    TGT TCT TGC ATG CAT ATA TAA TAA ATG TTT TTT CTA TTG ATC TGT TAA TTT GCA AGC CCC
2821    CAA ACA CTG GAA CTA AGT TGG GGG CAG GAT AGT TTC TCC CAA CAG CAC TTT GTA GGC TTC
2881    TGG ATA GAC CAA AGA GTG TGT TTG AAT AGA TAA GGG AAT TTT GTT CCC TTG ATT TTG GTT
2941    GAA GGT AGA AGA ATC CAA TGT ACA CAT ACA CAA AAC TAT GTC CTT AAA TTT GTC TCA AAG
3001    AAT AAA TAT TGG GTA GTC ATC AGA ATT GAC TGA AAA CTT ACT TTA GGG AGA AAG CCA CAA
3061    ATA ATT TAG GCT GGT ATG ATC TGA GCT TTC CTG ATT TCC ATG GGC ATT TAG TGG CTA
3121    ATG GAA TAT TAG TCT GAT ATG CAT TTT AGC CAT CTT ATG AAA TGG GCC GCA GGT GGA AGT
3181    AGG ATG CAG GGA GTG TTG AGG TGG CAT CTA TTA TAT CAA ATG CTT CAC TCT GCC CAG TCC
3241    TCT GTG AGT TCC TTA CAT GCA TCT TTC TAG TTA ATC CTC TCG GTG TTC ATA TTT ACA GAT
3301    TAA TCA ACT CAA AGG GTA GAT AGC TTG CTA AAG ATT ATA CTA TTA CTG AAA AAT AGC AAG
3361    ATG CAG AAC AGC ATA CCT AGT ATG TTA CTC TTT TTT TTT TTT TTT GAG GCA GAG TCT
3421    GGC CCT TTC ACC CAG GCT GGA GTG CAG TGG CTC AAT CTC GGC TCA CTG CAA CCT CTG CCC
3481    CCT TGG GTT CAT GCC ATT CTC CTG CCT CCC AGC CAC TCA GGA GGC TGA GGC AGG AGG ATC
3541    GCT TGA ACC CAG GAA GCG GAG GTT GCG GTG AGC TGA GAT CGC ACC ACT GTA TTC CAG CCT
3601    GGC AAC AGA GTG AGA TTC TGT GGC AAA AAA AAA AAA AAA AAG CAC AGA CTG GGT GTG
3661    GTG GCT CAT GCC TGT AAT TCC AGC ACT TTG CGA GGC TCA GCG ATC CTT TGC CTC GCC
3721    TCC CAA AGT GCA TGA GCC ACC ATG CCT GGC CTG TTT AGT TTT GTT TCA AGT TGA AAT ACC
3781    TTT CTT GTG TTT TCT AAT TAG AAA AGT AAT ATC TAC TCA TTG TAA AAA CTC AAA CAG TGC
3841    AGA AAT GTA GAA AGT AGA AAG TGT AAG TCC CTG GTT GTT CTC GCC TGA GAC AAC CAC
3901    TGC TCA CAG TTT GAT GTA TAT CCT TCC AGA GAC TCT CAA ATT TAA GCA AAT AAT TTT TAT
3961    TAC CAT GTC TTT TTA TTT GAA GAC GTT ACA TTT GCC TCC AAA GTT CAA CAC AAG TTC AAC
4021    TGA CCA TAT CCT TCC ATG ACC TGA ATA GAT GCT ATC CTT TAT CAC GAT GTT CAA TTG CCT
4081    TTG AAA GAG AGT AGT CCA GGT ATA TTC TGA TCA AAA TTT GGC ATT TGA TGA TAC TAC
4141    TCT ACA CAG ATC AGA CTC ATG TGC AGA ATC GTG CCT GAA GAG AGA GGT TTG GTT AAG ACA
4201    GAG ATT TCT GGA AAC ATT CAA ATT GCA AAT GGA AAC TTG AAA CCC ACA ATC TAA TGA GGA
4261    ATG TAC TGG AAA AAT AAT CTG AAG AGT TGA CAA ATT GTG TAC TAG ATT GAA CAC ATG GAA
4321    TGC AAT GCA ATG AGA CTT TCT GCA CTA AAA CTT ATC CTC ATA TGT ACA ACA ATG ATG TGT
4381    GTA TTA TAT AAC AGT GAT GTG TAC ATT TCT GAC ACC CCA TAC ATA ATA TAC ACA GTT TGT
4441    ATA AAT GCA TAC ATT TAA AAA TAT ATA TGT ACA ATA CAG CTA ACA TAA AAC TGT AGT ACG
4501    CCT GAA GGA TAT TAC TAG TGC CTA ATA TTG AGT ATG AGT CAC TGC GTG TTC GCA TCA ACT
4561    TGG AAG TGC AGT AAT TGT TAT AAA ATT AAT CAG TGC AGC CAA CAT TAT TTA TGA ATC ACA
4621    TCT TTG AAA CTG TGC AGT AGC ATA TAC ATA TAT ATT TTT AAA TAA CAT TTT TCA CAG TTT
4681    TCC AGA GTT ACT GTT GAA ATC TGC ATC ACC AAA AAA AAA AAA AAA
```

Fig. 3

```
  1    MGSLSNCALL QLTLTAFLTI LVQP QHLLAP  VFRTLSILTN QSNCWLCEHL
 51    DNAEQPELVF VPASASTWWT YSGQWMYERV WYPQAEVQNH STSSYRKVTW
101    HWEASMEAQG LSFAQVRLLE GNFSLCVENK NGSGPFLGNI PKQYCNQILW
151    FDSTDGTFMP SIDVTNESRN DDDDTSVCLG TRQCSWFAGC TNRTWNSSAV
201    PLIGLPNTQD YKWVDRNSGL TWSGNDTCLY SCQNQTKGLL YQLFRNLFCS
251    YGLTEAHGKW RCADASITND KGHDGHRTPT WWLTGSNLTL SVNNSGLFFL
301    CGNGVYKGFP PKWSGRCGLG YLVPSLTRYL TLNASQITNL RSFIHKVTPH
351    RCTQGDTDNP PLYCNPKDNS TIRALFPSLG TYDLEKAILN ISKAMEQEFS
401    ATKQTLEAHQ SKVSSLASAS RKDHVLDIPT TQRQTACGTV GKQCCLYINY
451    SEEIKSNIQR LHEASENLKN VPLLDWQGIF AKVGDWFRSW GYVLLIVLFC
501    LFIFVLIYVR VFRKSRRSLN SQPLNLALSP QQSAQLLVSE TSCQVSNRAM
551    KGLTTHQYDT SLL*
```

Fig. 4

```
                10        20        30        40
103P2D6    MGSLSNCALLQLTLTAFLTILVQPQHLLAPVFRTLSIL--TNQS---NCWLCE
gp:HSA     SNTSTLMKFYSLLLYSLLFSFPFLCHPLPLPSYLHHTINLTHSLLAASNPSLVNNCWLCI
               10        20        30        40        50        60

50        60        70        80                  90
103P2D6    HLDNAEQPELVFVPASASTWWTYSGQWMYERV------WYPQAEV---QNHSTSSYRKVT
gp:HSA     SLSSSAYTA---VPAVQTDWAT-SPISLHLRTSFNSPHLYPPEELIYFLDRSSKTSPDIS
               70        80        90       100       110       120

100       110       120                    130       140
103P2D6    WHWEASM---EAQGLS--FAQVRLLEGNFS---------LCVENKNGSPFLGNIPKQY
gp:HSA     HQQAAALLRTYLKNLSPYINSTPPIFGPLTTQTTIPVAAPLCISWQRPTGIPLGNLSPSR
              130       140       150       160       170       180

150                  160       170       180
103P2D6    CNQILWFDS-------TDGTFM------PSIDVTNESRNDDDDTSVCLGTR-QC----SW
gp:HSA     CSFTLHLRSPTTNINETIGAFQLHITDKPSIN-TDKLKNIS--SNYCLGRHLPCISLHPW
              190       200       210       220       230       240

190       200       210       220       230       240
103P2D6    FAG-CTNRTW-NSSAVPLIGLP-NTQDYKWVDRNSGLTWSGNDTCLYSCQNQTKGLLYQL
gp:HSA     LSSPCSSDSPPRPSSCLLIPSPENNSERLLVDTRRFLIHHENRT-FPSTQLPHQSPLQPL
                 250       260       270       280       290       300

250       260       270       280       290       300
103P2D6    FRNLFCSYGLTEAHGKWRCADASITNDKGHDGHRTPTWWLTGSNLTLSVNNSGLFFLCGN
gp:HSA     -----TAAALAGSLGVW-VQDTPFS---------TPSHLFT-LHLQFCLAQ-GLFFLCGS
                  310           320              330        340

310       320       330       340       350       360
103P2D6    GVYKGFPPKWSGRCGLGYLVPSLTRYLTLNASQITNLRSFIHKVTPHRCTQGDTDNP--P
gp:HSA     STYMCLPANWTGTCTLVFLTPKIQF-----ANGTEELP--VPLMTP---TQQKRVIPLIP
              350       360       370       380       390

370       380       390       400       410
103P2D6    LYCNPKDNSTIRALFPSLGTYDLEKAILNISKAMEQEFSAT----KQTLEAHQSKVSSLA
gp:HSA     LMVGLGLSASTVAL--GTGIAGISTSVMTF-RSLSNDFSASITDISQTLSVLQAQVDSLA
                    400       410       420       430       440       450

420       430       440       450       460       470
103P2D6    SASRKDHV-LDIPTTQRQTACGTVGKQCCLYINYSEEIKSNIQRLHEASENLKNVPLLDW
gp:HSA     AVVLQNRRGLDLLTAEKGGLCIFLNEECCFYLNQSGLVYDNIKKLKDRAQKLANQASNYA
                460       470       480       490       500       510

480       490       500       510       520       530
103P2D6    QGIFAKVGDWFRSWGYVLLIVLFCLFIFVLIYVRVFRKSRRSLNSQPLNLALSPQQSAQL
gp:HSA     EPPWA-LSNWM-SWVLPIVSPLIPIFLLLLFGPCIFRLVSQFIQNRIQAITNHSIRQMFL
              520       530       540       550       560

540       550       560
103P2D6    LVSETSCQVSNRAMKGLTTHQYDTSLL
gp:HSA     LTSPQYHPLPQDLPSA
              570       580
```

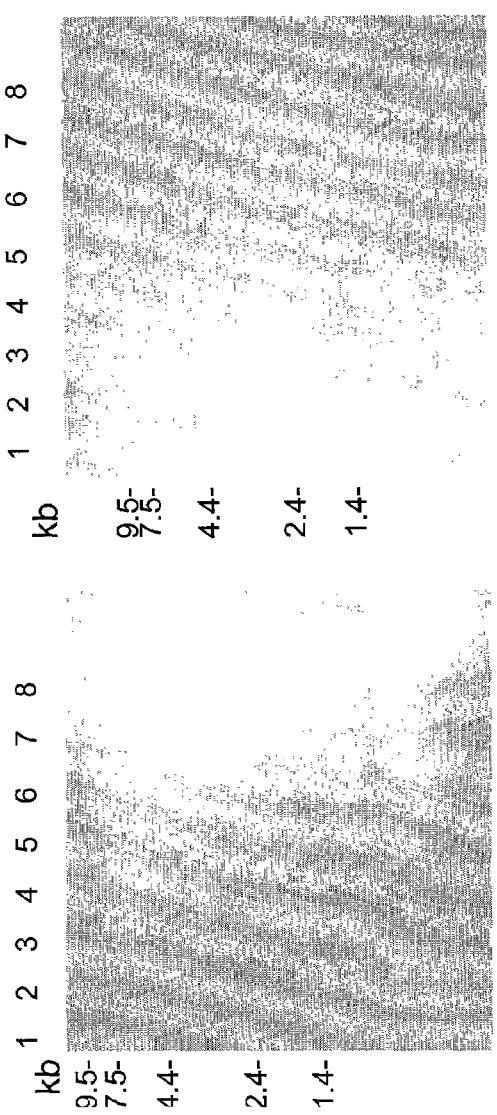

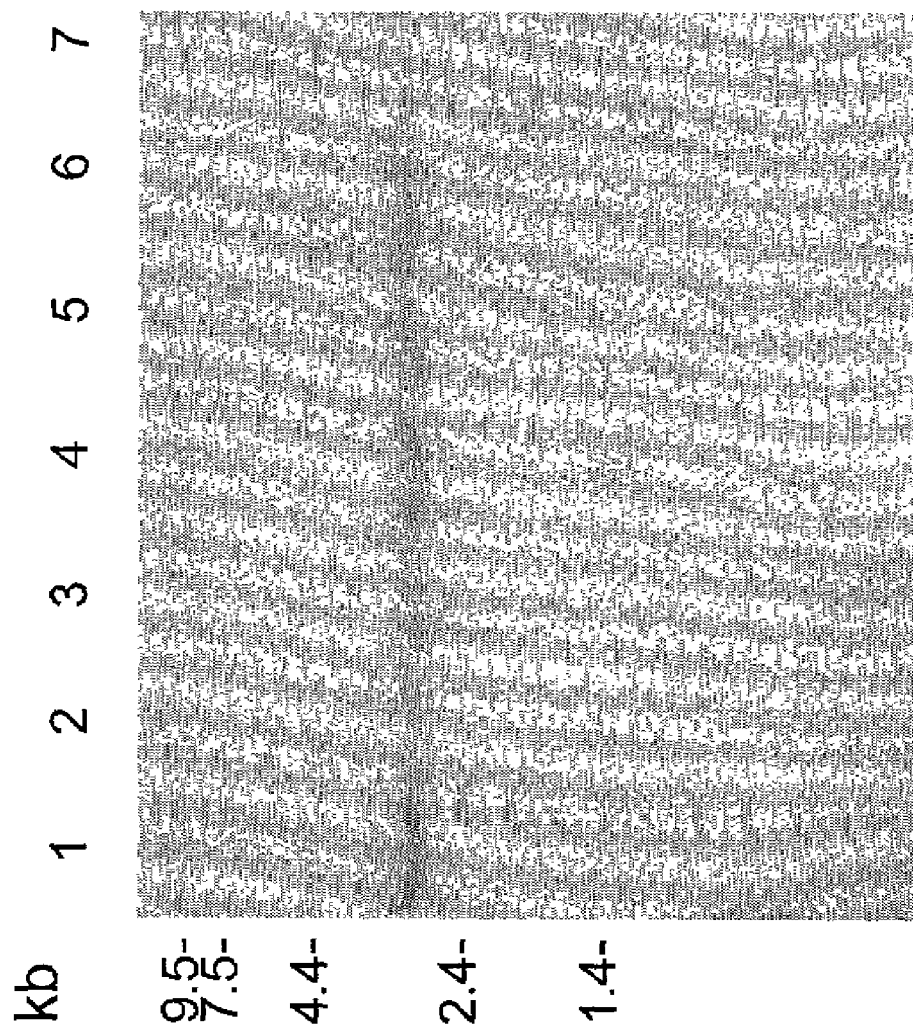

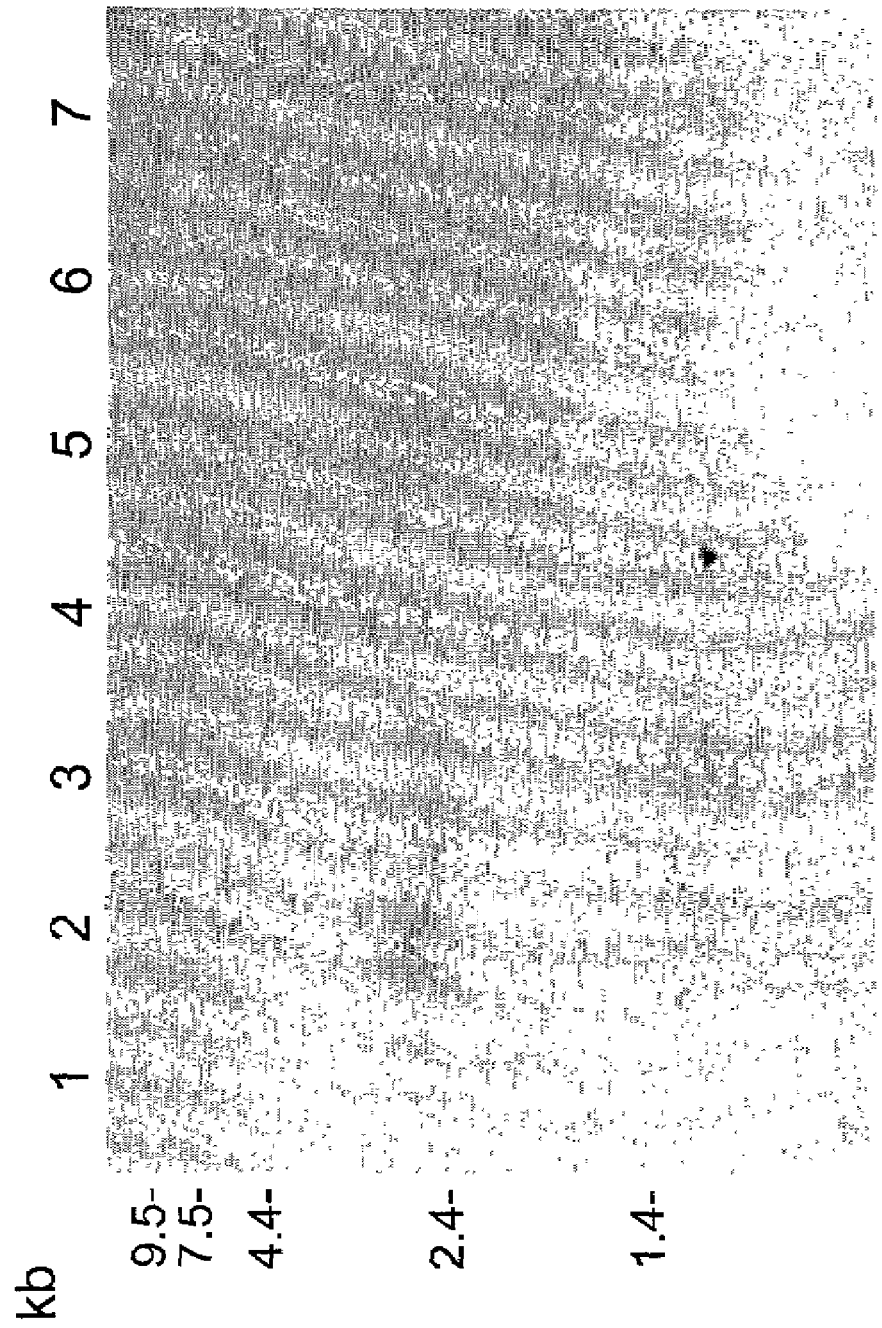

103P2D6: TISSUE SPECIFIC PROTEIN HIGHLY EXPRESSED IN VARIOUS CANCERS

CROSS REFERENCE TO RELATED APPLICATIONS

This application claims the benefit of U.S. provisional application No. 60/184,558, filed Feb. 24, 2000, and U.S. provisional application No. 60/218,856, filed Jul. 13, 2000, the entire contents of each of which are incorporated herein by reference.

FIELD OF THE INVENTION

The invention described herein relates to a novel gene and its encoded protein, termed 103P2D6, and to diagnostic and therapeutic methods and compositions useful in the management of various cancers that express 103P2D6.

BACKGROUND OF THE INVENTION

Cancer is the second leading cause of human death next to coronary disease. Worldwide, millions of people die from cancer every year. In the United States alone, cancer causes the death of well over a half-million people annually, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 40,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med.3:402). More recently identified prostate cancer markers include PCTA-1 (Su et al., 1996, Proc. Natl. Acad. Sci. USA 93: 7252), prostate-specific membrane (PSM) antigen (Pinto et al., Clin Cancer Res 1996 September; 2(9):1445-51), STEAP (Proc Natl Acad Sci USA. 1999 December 7;96(25):14523-8) and prostate stem cell antigen (PSCA) (Reiter et al., 1998, Proc. Natl. Acad. Sci. USA 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

SUMMARY OF THE INVENTION

The present invention relates to a novel gene, designated 103P2D6 that is over-expressed in multiple cancers listed in Table I. Northern blot expression analysis of 103P2D6 gene expression in normal tissues shows a restricted expression pattern in adult tissues. Analysis of 103P2D6 expression in normal prostate and prostate tumor xenografts shows overexpression in LAPC-4 and LAPC-9 prostate tumor xenografts. The nucleotide (FIG. 2) and amino acid (FIG. 2 and FIG. 3) sequences of 103P2D6 are provided. Portions of the 103P2D6 amino acid sequence show some homologies to ESTs in the dbEST database. The tissue-related profile of 103P2D6 in normal adult tissues, combined with the overexpression observed in prostate and other tumors, shows that 103P2D6 is aberrantly over-expressed in at least some cancers, and thus serves as a useful diagnostic and/or therapeutic target for cancers of the tissues listed in Table I.

The invention provides polynucleotides corresponding or complementary to all or part of the 103P2D6 genes, mRNAs, and/or coding sequences, preferably in isolated form, including polynucleotides encoding 103P2D6-related proteins and fragments of 4, 5, 6, 7, 8, 9, 10, 11, 12, 13, 14, 15, 16, 17, 18, 19, 20, 21, 22, 23, 24, 25, or more than 25 amino acids; as well as the peptides/proteins themselves; DNA, RNA, DNA/RNA hybrids, and related molecules, polynucleotides or oligonucleotides complementary or having at least a 90% homology to the 103P2D6 genes or mRNA sequences or parts thereof, and polynucleotides or oligonucleotides that hybridize to the 103P2D6 genes, mRNAs, or to 103P2D6-encoding polynucleotides. Also provided are means for isolating cDNAs and the genes encoding 103P2D6. Recombinant DNA molecules containing 103P2D6 polynucleotides, cells transformed or transduced with such molecules, and host-vector systems for the expression of 103P2D6 gene products are also provided. The invention further provides antibodies that bind to 103P2D6 proteins and polypeptide fragments thereof, including polyclonal and monoclonal antibodies, murine and other mammalian antibodies, chimeric antibodies, humanized and fully human antibodies, and antibodies labeled with a detectable marker.

The invention further provides methods for detecting the presence and status of 103P2D6 polynucleotides and proteins in various biological samples, as well as methods for identifying cells that express 103P2D6. A typical embodiment of this invention provides methods for monitoring 103P2D6 gene products in a tissue or hematology sample having or suspected of having some form of growth dysregulation such as cancer.

The invention further provides various immunogenic or therapeutic compositions and strategies for treating cancers that express 103P2D6 such as prostate cancers, including therapies aimed at inhibiting the transcription, translation, processing or function of 103P2D6 as well as cancer vaccines.

BRIEF DESCRIPTION OF THE FIGURES

FIG. 1. shows the 103P2D6 suppression subtractive hybridization (SSH) DNA sequence (SEQ ID NO: 3).

FIGS. 2A-B. show the nucleotide (SEQ ID NO: 1) and amino acid (SEQ ID NO: 2) sequences of 103P2D6. cDNA and ORF for 103P2D6 clone B, Kozak sequence and start methionine are indicated in bold. See Example 2, infra.

FIG. 3. shows the amino acid sequence (SEQ ID NO: 2) encoded by the open reading frame shown in FIG. 2, and lists the amino acid positions used for proteins/peptides of the invention. The 103P2D6 signal sequence is boxed.

FIG. 4. shows the sequence alignment of 103P2D6 (ORF from clone B; SEQ ID NO: 2) with env protein from human endogenous retroviral HERV-H (FASTA accession: Q9UNM3SEQ ID NO: 4). The 103P2D6 protein sequence has homology to the HERV-H env protein (24.9% identity and 32.8% homology taking account of any gaps).

FIGS. 5A-C. shows the northern blot analysis of 103P2D6 expression in various normal human tissues (using the 103P2D6 SSH fragment as a probe) and LAPC xenografts. Two multiple tissue northern blots (Clontech) and a xenograft northern blot were probed with the 103P2D6 SSH fragment. Size standards in kilobases (kb) are indicated on the side. Each lane contains 2 μg of mRNA for the normal tissues and 10 μg of total RNA for the xenograft tissues. The results show the expression of 103P2D6 in LAPC xenografts, and not in normal prostate and other tissues. Lanes in FIG. 5A represent (1) heart; (2) brain; (3) placenta; (4) lung; (5) liver; (6) skeletal muscle; (7) kidney; (8) pancreas. Lanes in FIG. 5B represent (1) spleen; (2) thymus; (3) prostate; (4) testis; (5) ovary; (6) small intestine; (7) colon; (8) leukocytes. Lanes in FIG. 5C represent (1) prostate; (2) LAPC-4 AD; (3) LAPC-4 AI; (4) LAPC-9 AD; (5) LAPC-9 AI.

FIG. 7. shows the northern blot analysis of 103P2D6 expression in various LAPC-4 AD xenografts, including subcutaneously grown xenografts (sc), intratibially grown xenografts (it), and xenografts grown within human bone explants (LAPC-4 AD$^2$) in SCID mice. Lanes represent (1) LAPC-4 AD sc; (2) LAPC-4 AD sc; (3) LAPC-4 AD sc; (4) LAPC-4 AD it; (5) LAPC-4 AD it; (6) LAPC-4 AD it; (7) LAPC-4 AD$^2$.

FIG. 8. shows a northern blot analysis of 103P2D6 expression in 9 week old fetal tissues, including 6 organs and whole embryo. Lanes represent (1) brain; (2) heart; (3) kidney; (4) liver; (5) lung; (6) muscle; (7) whole embryo.

DETAILED DESCRIPTION OF THE INVENTION

Figure 6A:
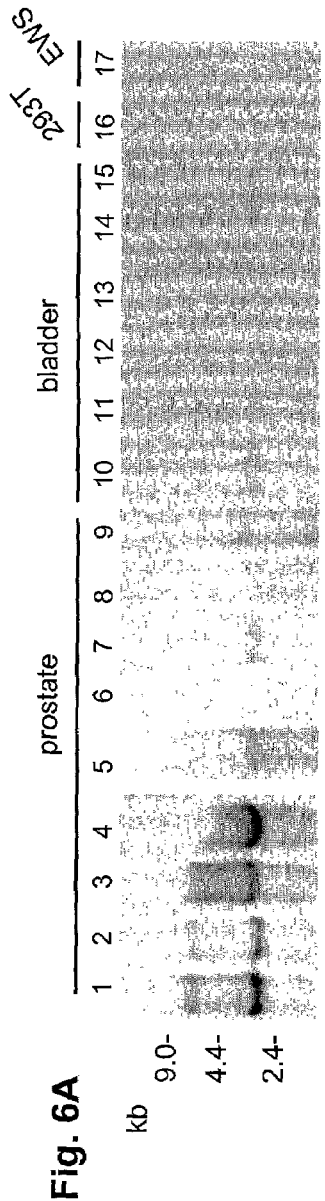
FIGS. 6A-C show the northern blot analysis of 103P2D6 expression in various cancer cell lines. Lanes represent (1) LAPC-4 AD; (2) LAPC-4 AI; (3) LAPC-9 AD; (4) LAPC-9 AI; (5) LNCaP; (6) PC-3; (7) DU145; (8) TsuPr1; (9) LAPC-4 CL; (10) HT1197; (11) SCaBER; (12) UM-UC-3; (13) TCCSUP; (14) J82; (15) 5637; (16) 293T; (17) RD-ES; (18) PANC-1; (19) BxPC-3; (20) HPAC; (21) Capan-1; (22) SK-CO-1; (23) CaCo-2; (24) LoVo; (25) T84; (26) Colo-205; (27) KCL 22; (28) PFSK-1; (29) T98G; (30) SK-ES-1; (31) HOS; (32) U2-OS; (33) RD-ES; (34) CALU-1; (35) A427; (36) NCI-H82; (37) NCI-H146; (38) 769-P; (39) A498; (40) CAKI-1; (41) SW839; (42) BT20; (43) CAMA-1; (44) DU4475; (45) MCF-7; (46) MDA-MB-435s; (47) NTERRA-2; (48) NCCIT; (49) TERA-1; (50) TERA-2; (51) A431; (52) HeLa; (53) OV-1063; (54) PA-1; (55) SW626; (56) CAOV-3.

I.) Definitions:

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence 103P2D6 (either by removing the underlying glycosylation site or by deleting the glycosylation by chemical and/or enzymatic means), and/or adding one or more glycosylation sites that are not present in the native sequence 103P2D6. In addition, the phrase includes qualitative changes in the glycosylation of the native proteins, involving a change in the nature and proportions of the various carbohydrate moieties present.

The term "analog" refers to a molecule that is structurally similar or shares similar or corresponding attributes with another molecule (e.g. a 103P2D6-related protein). For example an analog of the 103P2D6 protein can be specifically bound by an antibody or T cell that specifically binds to 103P2D6.

The term "antibody" is used in the broadest sense. Therefore an "antibody" can be naturally occurring or man-made such as monoclonal antibodies produced by conventional hybridoma technology. Anti-103P2D6 antibodies comprise monoclonal and polyclonal antibodies as well as fragments containing the antigen-binding domain and/or one or more complementarity determining regions of these antibodies.

As used herein, an "antibody fragment" is defined as at least a portion of the variable region of the immunoglobulin molecule that binds to its target, i.e., the antigen-binding region. In one embodiment it specifically covers single anti-103P2D6 antibodies and clones thereof (including agonist, antagonist and neutralizing antibodies) and anti-103P2D6 antibody compositions with polyepitopic specificity.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

The term "cytotoxic agent" as used herein refers to a substance that inhibits or prevents the function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to maytansinoids, ytrium, bismuth ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alphasarcin, gelonin, mitogellin, retstrictocin, phenomycin, enomycin, curicin, crotin, calicheamicin, sapaonaria officinalis inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu. Antibodies may also be conjugated to an anti-cancer pro-drug activating enzyme capable of converting the pro-drug to its active form.

The term "homolog" refers to a molecule which exhibits homology to another molecule, by for example, having sequences of chemical residues that are the same or similar at corresponding positions.

As used herein, the terms "hybridize", "hybridizing", "hybridizes" and the like, used in the context of polynucleotides, are meant to refer to conventional hybridization conditions, preferably such as hybridization in 50% formamide/6×SSC/0.1% SDS/100 µg/ml ssDNA, in which temperatures for hybridization are above 37 degrees C. and temperatures for washing in 0.1×SSC/0.1% SDS are above 55 degrees C.

As used herein, a polynucleotide is said to be "isolated" when it is substantially separated from contaminant polynucleotides that correspond or are complementary to genes other than the 103P2D6 gene or that encode polypeptides other than 103P2D6 gene product or fragments thereof. A skilled artisan can readily employ nucleic acid isolation procedures to obtain an isolated 103P2D6 polynucleotide.

As used herein, a protein is said to be "isolated" when physical, mechanical or chemical methods are employed to remove the 103P2D6 protein from cellular constituents that are normally associated with the protein. A skilled artisan can readily employ standard purification methods to obtain an isolated 103P2D6 protein. Alternatively, an isolated protein can be prepared by chemical means.

The term "manmal" as used herein refers to any organism classified as a mammal, including mice, rats, rabbits, dogs, cats, cows, horses and humans. In one embodiment of the invention, the mammal is a mouse. In another embodiment of the invention, the mammal is a human.

As used herein, the terms "metastatic prostate cancer" and "metastatic disease" mean prostate cancers that have spread to regional lymph nodes or to distant sites, and are meant to include stage D disease under the AUA system and stage TxNxM+under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "monoclonal antibody" as used herein refers to an antibody obtained from a population of substantially homogeneous antibodies, i.e., the antibodies comprising the population are identical except for possible naturally occurring mutations that are present in minor amounts.

As used herein "motif" as in biological motif of an 103P2D6-related protein, refers to any set of amino acids forming part of the primary sequence of a protein, either contiguous or capable of being aligned to certain positions that are generally invariant, that is associated with a particular function (e.g. protein-protein interaction, protein-DNA interaction, etc) or modification (e.g. that is phosphorylated, glycosylated or aridated), or localization (e.g. secretory sequence, nuclear localization sequence, etc.) or a sequence that is correlated with being immunogenic, either humorally or cellularly.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T) (as shown for example in SEQ ID NO: 1) can also be uracil (U); this definition pertains to the differences between the chemical structures of DNA and RNA, in particular the observation that one of the four major bases in RNA is uracil (U) instead of thymidine (T).

As used herein, the term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

As used herein, a "recombinant" DNA or RNA molecule is a DNA or RNA molecule that has been subjected to molecular manipulation in vitro.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 nM sodium chloride, 75 mM sodium citrate at 42° C.; or (3) employ 50% formamide, 5×SSC (0.75 M NaCl, 0.075 M sodium citrate), 50 mM sodium phosphate (PH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and %SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

The term "variant" refers to a molecule that exhibits a variation from a described type or norm, such as a protein that has one or more different amino acid residues in the corresponding position(s) of a specifically described protein (e.g. the 103P2D6 protein shown in FIG. 2 and FIG. 3). An analog is an example of a variant protein.

As used herein, the 103P2D6-related gene and 103P2D6-related protein includes the 103P2D6 genes and proteins specifically described herein, as well as structurally and/or functionally similar variants or analog of the foregoing. 103P2D6 peptide analogs generally share at least about 50%, 60%, 70%, 80%, 90% or more amino acid homology (using BLAST criteria). 103P2D6 nucleotide analogs preferably share 50%, 60%, 70%, 80%, 90% or more nucleic acid homology (using BLAST criteria). In some embodiments, however, lower homology is preferred so as to select preferred residues in view of species-specific codon preferences for optimized protein expression and production and/or immunogenicity-modulated peptide epitopes tailored to a particular target population, e.g. HLA type, as is appreciated by those skilled in the art.

The 103P2D6-related proteins of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different 103P2D6 proteins or fragments thereof, as well as fusion proteins of a 103P2D6 protein and a heterologous polypeptide are also included. Such 103P2D6 proteins are collectively referred to as the 103P2D6-related proteins, the proteins of the invention, or 103P2D6. As used herein, the term "103P2D6-related protein" refers to a polypeptide fragment or an 103P2D6 protein sequence of 4, 5, 6, 7, 8, 9, 10, 11, 12, 13, 14, 15, 16, 17, 18, 19, 20, 21, 22, 23, 24, 25, or more than 25 amino acids.

II.) Properties of 103P2D6.

As disclosed herein, 103P2D6 exhibits specific properties that are analogous to those found in a family of molecules whose polynucleotides, polypeptides, reactive cytotoxic T cells (CTL), reactive helper T cells (HTL) and anti-polypeptide antibodies are used in well known diagnostic assays that examine conditions associated with dysregulated cell growth such as cancer, in particular prostate cancer (see, e.g., both its highly specific pattern of tissue expression as well as its overexpression in prostate cancers as described for example in Example 3). The best-known member of this class is PSA, the archetypal marker that has been used by medical practitioners for years to identify and monitor the presence of prostate cancer (see, e.g., Merrill et al., J. Urol. 163(2): 503-5120 (2000); Polascik et al., J. Urol. August;162(2):293-306 (1999) and Fortier et al., J. Nat. Cancer Inst. 91(19): 1635-1640(1999)). A variety of other diagnostic markers are also used in this context including p53 and K-ras (see, e.g., Tulchinsky et al., Int J Mol Med 1999 July;4(1):99-102 and Minimoto et al., Cancer Detect Prev 2000;24(1):1-12). Therefore, this disclosure of the 103P2D6 polynucleotides and polypeptides (as well as the 103P2D6 polynucleotide probes and anti-103P2D6 antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods that utilize the 103P2D6 polynucleotides, polypeptides, reactive T cells and antibodies are analogous to those methods from well-established diagnostic assays that employ, e.g., PSA polynucleotides, polypeptides, reactive T cells and antibodies. For example, just as PSA polynucleotides are used as probes (for example in Northern analysis, see, e.g., Sharief et al., Biochem. Mol. Biol. Int. 33(3):567-74(1994)) and primers (for example in PCR analysis, see, e.g., Okegawa et al., J. Urol. 163(4): 1189-1190 (2000)) to observe the presence and/or the level of PSA mRNAs in methods of monitoring PSA overexpression or the metastasis of prostate cancers, the 103P2D6 polynucleotides described herein can be utilized in the same way to detect 103P2D6 overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4):560-3 (2000)) or the metastasis of prostate cells (see, e.g., Alanen et al., Pathol. Res. Pract. 192(3):233-7 (1996)), the 103P2D6 polypeptides described herein can be utilized to generate antibodies for use in detecting 103P2D6 overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing 103P2D6 polynucleotides and/or polypeptides can be used to provide evidence of metastasis. For example, when a biological sample from tissue that does not normally contain 103P2D6-expressing cells (lymph node) is found to contain 103P2D6-expressing cells such as the 103P2D6 expression seen in LAPC4 and LAPC9, xenografts isolated from lymph node and bone metastasis, respectively, this finding is indicative of metastasis.

Alternatively 103P2D6 polynucleotides and/or polypeptides can be used to provide evidence of cancer, for example, when cells in a biological sample that do not normally express 103P2D6 or express 103P2D6 at a different level are found to express 103P2D6 or have an increased expression of 103P2D6 (see, e.g., the 103P2D6 expression in kidney, lung and colon cancer cells and in patient samples etc. shown in FIGS. 4-10). In such assays, artisans may further wish to generate supplementary evidence of metastasis by testing the biological sample for the presence of a second tissue restricted marker (in addition to 103P2D6) such as PSA, PSCA etc. (see, e.g., Alanen et al., Pathol. Res. Pract. 192(3): 233-237 (1996)).

Just as PSA polynucleotide fragments and polynucleotide variants are employed by skilled artisans for use in methods of monitoring PSA, 103P2D6 polynucleotide fragments and polynucleotide variants are used in an analogous manner. In particular, typical PSA polynucleotides used in methods of monitoring PSA are probes or primers that consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472-476, 478-480 (1998); Robertson et al., Methods Mol. Biol. 98:121-154 (1998)). An additional illustration of the use of such fragments is provided in Example 3, where a 103P2D6 polynucleotide fragment is used as a probe to show the expression of 103P2D6 RNAs in cancer cells. In addition, variant polynucleotide sequences are typically used as primers and probes for the corresponding mRNAs in PCR and Northern analyses (see, e.g., Sawai et al., Fetal Diagn. Ther. 1996 November-December;11(6):407-13 and Current Protocols In Molecular Biology, Volume 2, Unit 2, Frederick M. Ausubul et al. eds., 1995)). Polynucleotide fragments and variants are useful in this context where they are capable of binding to a target polynucleotide sequence (e.g. the 103P2D6 polynucleotide shown in SEQ ID NO: 1) under conditions of high stringency.

Furthermore, PSA polypeptides which contain an epitope that can be recognized by an antibody or T cell that specifically binds to that epitope are used in methods of monitoring PSA. 103P2D6 polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubul et al. eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. Nos. 5,840,501 and 5,939,533). For example it may be preferable to utilize a polypeptide comprising one of the 103P2D6 biological motifs discussed herein or available in the art. Polypeptide fragments, variants or analogs are typically useful in this context as long as they comprise an epitope capable of generating an antibody or T cell specific for a target polypeptide sequence (e.g. the 103P2D6 polypeptide shown in SEQ ID NO: 2).

As shown herein, the 103P2D6 polynucleotides and polypeptides (as well as the 103P2D6 polynucleotide probes and anti-103P2D6 antibodies or T cells used to identify the presence of these molecules) exhibit specific properties that make them useful in diagnosing cancers of the prostate. Diagnostic assays that measure the presence of 103P2D6 gene products, in order to evaluate the presence or onset of a disease condition described herein, such as prostate cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for PSA alone (see, e.g., Alanen et al., Pathol. Res. Pract. 192(3): 233-237 (1996)), and consequently, materials such as 103P2D6 polynucleotides and polypeptides (as well as the 103P2D6 polynucleotide probes and anti-103P2D6 antibodies used to identify the presence of these molecules) must be employed to confirm metastases of prostatic origin.

Finally, in addition to their use in diagnostic assays, the 103P2D6 polynucleotides disclosed herein have a number of other specific utilities such as their use in the identification of oncogenetic associated chromosomal abnormalities in 2q34, the chromosomal region to which the 103P2D6 gene maps (see Example 7 below). Moreover, in addition to their use in diagnostic assays, the 103P2D6-related proteins and polynucleotides disclosed herein have other utilities such as their use in the forensic analysis of tissues of unknown origin (see, e.g., Takahama K Forensic Sci Int Jun. 28, 1996;80(1-2): 63-9).

Additionally, 103P2D6-related proteins or polynucleotides of the invention can be used to treat a pathologic condition characterized by the over-expression of 103P2D6. For example, the amino acid or nucleic acid sequence of FIG. 2, or fragments thereof, can be used to generate an immune response to the 103P2D6 antigen. Antibodies or other molecules that react with 103P2D6 can be used to modulate the function of this molecule, and thereby provide a therapeutic benefit.

III.) 103P2D6 Polynucleotides

One aspect of the invention provides polynucleotides corresponding or complementary to all or part of an 103P2D6 gene, mRNA, and/or coding sequence, preferably in isolated form, including polynucleotides encoding an 103P2D6-related protein and fragments thereof, DNA, RNA, DNA/RNA hybrid, and related molecules, polynucleotides or oligonucleotides complementary to an 103P2D6 gene or mRNA sequence or a part thereof, and polynucleotides or oligonucleotides that hybridize to an 103P2D6 gene, mRNA, or to an 103P2D6 encoding polynucleotide (collectively, "103P2D6 polynucleotides"). In all instances when referred to in this section, T can also be U in FIG. 2.

Embodiments of a 103P2D6 polynucleotide include: a 103P2D6 polynucleotide having the sequence shown in FIG. 2, the nucleotide sequence of 103P2D6 as shown in FIG. 2, wherein T is U; at least 10 contiguous nucleotides of a polynucleotide having the sequence as shown in FIG. 2; or, at least 10 contiguous nucleotides of a polynucleotide having the sequence as shown in FIG. 2 where T is U. Further 103P2D6 nucleotides comprise, where T can be U:

(a) at least 10 contiguous nucleotides of a polynucleotide having the sequence as shown in FIG. 2, from nucleotide residue number 1 through nucleotide residue number 804; or, (b) at least 10 contiguous nucleotides of a polynucleotide having the sequence as shown in FIG. 2, from nucleotide residue number 977 through nucleotide residue number 1036; or, (c) at least 10 contiguous nucleotides of a polynucleotide having the sequence as shown in FIG. 2, from nucleotide residue number 1414 through nucleotide residue number 1815; or (d) a polynucleotide whose starting base is in the range of 1-804 of FIG. 2 and whose ending base is in the range of 805-2493 of FIG. 2; or (e) a polynucleotide whose starting base is in the range of 977-1036 of FIG. 2 and whose ending base is in the range of 1037-2493 of FIG. 2; or (f) a polynucleotide whose starting base is in the range of 1414-1815 of FIG. 2 and whose ending base is in the range of 1816-2493 of FIG. 2; or (g) a polynucleotide whose starting base is in the range of 805-976 of FIG. 2 and whose ending base is in the range of 977-2493 of FIG. 2; or (h) a polynucleotide whose starting base is in the range of 805-2493 of FIG. 2 and whose ending base is in the range of 2494-4727 of FIG. 2; or (i) a polynucleotide of (d-g) that is at least 10 nucleotide bases in length; or (j) a polynucleotide that selectively hybridizes under stringent conditions to a polynucleotide of (a)-(g);

wherein a range is understood to specifically disclose all whole unit positions thereof. Moreover, a peptide that is encoded by any of the foregoing is also within the scope of the invention.

Also within the scope of the invention is a nucleotide, as well as any peptide encoded thereby, that starts at any of the following positions or ranges, and ends at a higher position or range: 1, 804, a range of 1-804, 805, a range of 805-976; a range of 805-2493; a range of 977-1036, a range of 1037-1413; a range of 1414-1815; a range of 1816-2493; a range of 2494-4727; wherein a range as used in this section is understood to specifically disclose all whole unit positions thereof.

Another embodiment of the invention comprises a polynucleotide that encodes a 103P2D6-related protein whose sequence is encoded by the cDNA contained in the plasmids deposited with American Type Culture Collection as Accession No. PTA-1155 or PTA-1895. Another embodiment comprises a polynucleotide that hybridizes under stringent hybridization conditions, to the human 103P2D6 cDNA shown in SEQ ID NO: 1 or to a polynucleotide fragment thereof.

Typical embodiments of the invention disclosed herein include 103P2D6 polynucleotides that encode specific portions of the 103P2D6 mRNA sequence (and those which are complementary to such sequences) such as those that encode the protein and fragments thereof, for example of 4, 5, 6, 7, 8, 9, 10, 11, 12, 13, 14, 15 or more contiguous amino acids.

For example, representative embodiments of the invention disclosed herein include: polynucleotides and their encoded peptides themselves encoding about amino acid 1 to about amino acid 10 of the 103P2D6 protein shown in FIG. 2 and FIG. 3, polynucleotides encoding about amino acid 10 to about amino acid 20 of the 103P2D6 protein shown in FIG. 2 and FIG. 3, polynucleotides encoding about amino acid 20 to about amino acid 30 of the 103P2D6 protein shown in FIG. 2 and FIG. 3, polynucleotides encoding about amino acid 30 to about amino acid 40 of the 103P2D6 protein shown in FIG. 2 and FIG. 3, polynucleotides encoding about amino acid 40 to about amino acid 50 of the 103P2D6 protein shown in FIG. 2 and FIG. 3, polynucleotides encoding about amino acid 50 to about amino acid 60 of the 103P2D6 protein shown in FIG. 2 and FIG. 3, polynucleotides encoding about amino acid 60 to about amino acid 70 of the 103P2D6 protein shown in FIG. 2 and FIG. 3, polynucleotides encoding about amino acid 70 to about amino acid 80 of the 103P2D6 protein shown in FIG. 2 and FIG. 3, polynucleotides encoding about amino acid 80 to about amino acid 90 of the 103P2D6 protein shown in FIG. 2 and FIG. 3 and polynucleotides encoding about amino acid 90 to about amino acid 100 of the 103P2D6 protein shown in FIG. 2 and FIG. 3, in increments of about 10 amino acids, ending at amino acid 532. Accordingly polynucleotides encoding portions of the amino acid sequence (of about 10 amino acids), of amino acids 100-532 of the 103P2D6 protein are embodiments of the invention. Wherein it is understood that each particular amino acid position discloses that position plus or minus five amino acid residues.

Polynucleotides encoding relatively long portions of the 103P2D6 protein are also within the scope of the invention. Additional illustrative embodiments of the invention disclosed herein include 103P2D6 polynucleotide fragments encoding one or more of the biological motifs contained within the 103P2D6 protein sequence, including one or more of the motif-bearing subsequences of the 103P2D6 protein set forth in Table XIX. In another embodiment, typical polynucleotide fragments of the invention encode one or more of the regions of 103P2D6 that exhibit homology to a known molecule. In another embodiment of the invention, typical polynucleotide fragments can encode one or more of the 103P2D6 N-glycosylation sites, cAMP and cGMP-dependent protein kinase phosphorylation sites, casein kinase II phosphorylation sites or N-myristoylation site and amidation sites.

III.A.) Uses of 103P2D6 Polynucleotides

III.A.1.) Monitoring of Genetic Abnormalities

The polynucleotides of the preceding paragraphs have a number of different specific uses. The human 103P2D6 gene maps to chromosome 4p12-p14 as determined using the GeneBridge4 radiation hybrid panel (see Example 7). For example, because the 103P2D6 gene maps to chromosome 4p12-p14, polynucleotides that encode different regions of the 103P2D6 protein are used to characterize cytogenetic abnormalities on chromosome 4, band p12-p14 that have been identified as being associated with various cancers. In particular, a variety of chromosomal abnormalities in 4p12-p14 including translocations and deletions have been identified as frequent cytogenetic abnormalities in a number of different cancers (see, e.g., Zimonjic, D. B. et al., 1999, Hepatology 29(4):1208-14; Wu, X. et al., 1995, Cancer Res. 55(3):557-61; Arribas, R. et al., 1999, Lab. Invest. 79(2):111-22). Thus, polynucleotides encoding specific regions of the 103P2D6 protein provide new tools that can be used to delineate, with greater precision than previously possible, cytogenetic abnormalities in this region of chromosome 2 that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055-1057 (1994)).

Furthermore, as 103P2D6 was shown to be highly expressed in prostate and other cancers, 103P2D6 polynucleotides are used in methods assessing the status of 103P2D6 gene products in normal versus cancerous tissues. Typically, polynucleotides that encode specific regions of the 103P2D6 protein are used to assess the presence of perturbations (such as deletions, insertions, point mutations, or alterations resulting in a loss of an antigen etc.) in specific regions of the 103P2D6 gene, such as such regions containing one or more motifs. Exemplary assays include both RT-PCR assays as well as single-strand conformation polymorphism (SSCP) analysis (see, e.g., Marrogi et al., J. Cutan. Pathol. 26(8):

369-378 (1999), both of which utilize polynucleotides encoding specific regions of a protein to examine these regions within the protein.

III.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 103P2D6. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the 103P2D6 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 103P2D6. See for example, Jack Cohen, Oligodeoxynucleotides, Antisense Inhibitors of Gene Expression, CRC Press, 1989; and Synthesis 1:1-5 (1988). The 103P2D6 antisense oligonucleotides of the present invention include derivatives such as S-oligonucleotides (phosphorothioate derivatives or 8-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See Iyer, R. P. et al, J. Org. Chem. 55:4693-4698 (1990); and Iyer, R. P. et al., J. Am. Chem. Soc. 112: 1253-1254 (1990). Additional 103P2D6 antisense oligonucleotides of the present invention include morpholino antisense oligonucleotides known in the art (see, e.g., Partridge et al., 1996, Antisense & Nucleic Acid Drug Development 6: 169-175).

The 103P2D6 antisense oligonucleotides of the present invention typically can be RNA or DNA that is complementary to and stably hybridizes with the first 100 5' codons or last 100 3' codons of the 103P2D6 genomic sequence or the corresponding mRNA. Absolute complementarity is not required, although high degrees of complementarity are preferred. Use of an oligonucleotide complementary to this region allows for the selective hybridization to 103P2D6 mRNA and not to mRNA specifying other regulatory subunits of protein kinase. In one embodiment, 103P2D6 antisense oligonucleotides of the present invention are 15 to 30-mer fragments of the antisense DNA molecule that have a sequence that hybridizes to 103P2D6 mRNA. Optionally, 103P2D6 antisense oligonucleotide is a 30-mer oligonucleotide that is complementary to a region in the first 10 5' codons or last 10 3' codons of 103P2D6. Alternatively, the antisense molecules are modified to employ ribozymes in the inhibition of 103P2D6 expression, see, e.g., L. A. Couture & D. T. Stinchcomb; *Trends Genet* 12: 510-515 (1996).

III.A.3.) Primers and Primer Pairs

Further specific embodiments of this nucleotides of the invention include primers and primer pairs, which allow the specific amplification of polynucleotides of the invention or of any specific parts thereof, and probes that selectively or specifically hybridize to nucleic acid molecules of the invention or to any part thereof Probes can be labeled with a detectable marker, such as, for example, a radioisotope, fluorescent compound, bioluminescent compound, a chemiluminescent compound, metal chelator or enzyme. Such probes and primers are used to detect the presence of a 103P2D6 polynucleotide in a sample and as a means for detecting a cell expressing a 103P2D6 protein.

Examples of such probes include polypeptides comprising all or part of the human 103P2D6 cDNA sequences shown in FIG. 2. Examples of primer pairs capable of specifically amplifying 103P2D6 mRNAs are also described in the Examples. As will be understood by the skilled artisan, a great many different primers and probes can be prepared based on the sequences provided herein and used effectively to amplify and/or detect a 103P2D6 mRNA.

The 103P2D6 polynucleotides of the invention are useful for a variety of purposes, including but not limited to their use as probes and primers for the amplification and/or detection of the 103P2D6 gene(s), mRNA(s), or fragments thereof; as reagents for the diagnosis and/or prognosis of prostate cancer and other cancers; as coding sequences capable of directing the expression of 103P2D6 polypeptides; as tools for modulating or inhibiting the expression of the 103P2D6 gene(s) and/or translation of the 103P2D6 transcript(s); and as therapeutic agents.

III.A.4.) Isolation of 103P2D6-Encoding Nucleic Acid Molecules

The 103P2D6 cDNA sequences described herein enable the isolation of other polynucleotides encoding 103P2D6 gene product(s), as well as the isolation of polynucleotides encoding 103P2D6 gene product homologs, alternatively spliced isoforms, allelic variants, and mutant forms of the 103P2D6 gene product as well as polynucleotides that encode analogs of 103P2D6-related proteins. Various molecular cloning methods that can be employed to isolate fall length cDNAs encoding an 103P2D6 gene are well known (See, for example, Sambrook, J. et al., Molecular Cloning: A Laboratory Manual, 2d edition., Cold Spring Harbor Press, New York, 1989; Current Protocols in Molecular Biology. Ausubel et al., Eds., Wiley and Sons, 1995). For example, lambda phage cloning methodologies can be conveniently employed, using commercially available cloning systems (e.g., Lambda ZAP Express, Stratagene). Phage clones containing 103P2D6 gene cDNAs can be identified by probing with a labeled 103P2D6 cDNA or a fragment thereof For example, in one embodiment, the 103P2D6 cDNA (FIG. 2) or a portion thereof can be synthesized and used as a probe to retrieve overlapping and full-length cDNAs corresponding to a 103P2D6 gene. The 103P2D6 gene itself can be isolated by screening genomic DNA libraries, bacterial artificial chromosome libraries (BACs), yeast artificial chromosome libraries (YACs), and the like, with 103P2D6 DNA probes or primers.

III.A.5.) Recombinant Nucleic Acid Molecules and Host-Vector Systems

The invention also provides recombinant DNA or RNA molecules containing an 103P2D6 polynucleotide, fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al, 1989, supra).

The invention further provides a host-vector system comprising a recombinant DNA molecule containing a 103P2D6 polynucleotide, fragment, analog or homologue thereof within a suitable prokaryotic or eukaryotic host cell.

Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 103P2D6 or a fragment, analog or homolog thereof can be used to generate 103P2D6 proteins or fragments thereof using any number of host-vector systems routinely used and widely known in the art.

A wide range of host-vector systems suitable for the expression of 103P2D6 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, 103P2D6 can be expressed in several prostate cancer and non-prostate cell lines, including for example 293, 293T, rat-1, NIH 3T3 and TsuPr1. The host-vector systems of the invention are useful for the production of a 103P2D6 protein or fragment thereof Such host-vector systems can be employed to study the functional properties of 103P2D6 and 103P2D6 mutations or analogs.

Recombinant human 103P2D6 protein or an analog or homolog or fragment thereof can be produced by mammalian cells transfected with a construct encoding a 103P2D6-related nucleotide. For example, 293T cells can be transfected with an expression plasmid encoding 103P2D6 or fragment, analog or homolog thereof, the 103P2D6 or related protein is expressed in the 293T cells, and the recombinant 103P2D6 protein is isolated using standard purification methods (e.g., affinity purification using anti-103P2D6 antibodies). In another embodiment, a 103P2D6 coding sequence is subcloned into the retroviral vector pSRαMSVtkneo and used to infect various mammalian cell lines, such as NIH 3T3, TsuPr1, 293 and rat-1 in order to establish 103P2D6 expressing cell lines. Various other expression systems well known in the art can also be employed. Expression constructs encoding a leader peptide joined in frame to the 103P2D6 coding sequence can be used for the generation of a secreted form of recombinant 103P2D6 protein.

As discussed herein, redundancy in the genetic code permits variation in 103P2D6 gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET such as the world wise wide web address dna.affrc.go.jp/~nakamura/codon.html.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell Biol.*, 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662-2666, (1995) and Kozak NAR 15(20): 8125-8148 (1987)).

IV.) 103P2D6-Related Proteins

Another aspect of the present invention provides 103P2D6-related proteins. Specific embodiments of 103P2D6 proteins comprise a polypeptide having all or part of the amino acid sequence of human 103P2D6 as shown in FIG. 2. Alternatively, embodiments of 103P2D6 proteins comprise variant, homolog or analog polypeptides that have alterations in the amino acid sequence of 103P2D6 shown in FIG. 2.

In general, naturally occurring allelic variants of human 103P2D6 share a high degree of structural identity and homology (e.g., 90% or more homology). Typically, allelic variants of the 103P2D6 protein contain conservative amino acid substitutions within the 103P2D6 sequences described herein or contain a substitution of an amino acid from a corresponding position in a homologue of 103P2D6. One class of 103P2D6 allelic variants are proteins that share a high degree of homology with at least a small region of a particular 103P2D6 amino acid sequence, but further contain a radical departure from the sequence, such as a non-conservative substitution, truncation, insertion or frame shift. In comparisons of protein sequences, the terms, similarity, identity, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III herein; pages 13-15 "Biochemistry" 2$^{nd}$ ED. Lubert Stryer ed (Stanford University); Henikoff et al., PNAS 1992 Vol. 89 10915-10919; Lei et al., J Biol Chem May 19, 1995; 270(20):11882-6).

Embodiments of the invention disclosed herein include a wide variety of art-accepted variants or analogs of 103P2D6 proteins such as polypeptides having amino acid insertions, deletions and substitutions. 103P2D6 variants can be made using methods known in the art such as site-directed mutagenesis, alanine scanning, and PCR mutagenesis. Site-directed mutagenesis (Carter et al., *Nucl. Acids Res.*, 13.4331 (1986); Zoller et al., *Nucl. Acids Res.*, 10:6487 (1987)), cassette mutagenesis (Wells et al., Gene, 34:315 (1985)), restriction selection mutagenesis (Wells et al., *Philos. Trans. R. Soc. London SerA,* 317:415 (1986)) or other known techniques can be performed on the cloned DNA to produce the 103P2D6 variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W. H. Freeman & Co., N.Y.); Chothia, J. Mol. Biol., 150:1 (1976)). If alanine substitution does not yield adequate amounts of variant, an isosteric amino acid can be used.

As defined herein, 103P2D6 variants, analogs or homologs, have the distinguishing attribute of having at least one epitope that is "cross reactive" with a 103P2D6 protein having the amino acid sequence of SEQ ID NO: 2. As used in this sentence, "cross reactive" means that an antibody or T cell that specifically binds to an 103P2D6 variant also specifically binds to the 103P2D6 protein having the amino acid sequence of SEQ ID NO: 2. A polypeptide ceases to be a variant of the protein shown in SEQ ID NO: 2 when it no longer contains any epitope capable of being recognized by an antibody or T cell that specifically binds to the 103P2D6 protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol 2000 165(12): 6949-6955; Hebbes et al., Mol Immunol (1989) 26(9):865-73; Schwartz et al., J Immunol (1985) 135 (4):2598-608.

Another class of 103P2D6-related protein variants share 70%, 75%, 80%, 85% or 90% or more similarity with the amino acid sequence of SEQ ID NO: 2 or a fragment thereof. Another specific class of 103P2D6 protein variants or analogs comprise one or more of the 103P2D6 biological motifs described herein or presently known in the art. Thus, encompassed by the present invention are analogs of 103P2D6 fragments (nucleic or amino acid) that have altered functional (e.g. immunogenic) properties relative to the starting fragment. It is to be appreciated that motifs now or which become part of the art are to be applied to the nucleic or amino acid sequences of FIG. 2.

As discussed herein, embodiments of the claimed invention include polypeptides containing less than the 532 amino acid sequence of the 103P2D6 protein shown in FIG. 2. For example, representative embodiments of the invention comprise peptides/proteins having any 4, 5, 6, 7, 8, 9, 10, 11, 12, 13, 14, 15 or more contiguous amino acids of the 103P2D6 protein shown in FIG. 2 and FIG. 3.

Moreover, representative embodiments of the invention disclosed herein include polypeptides consisting of about amino acid 1 to about amino acid 10 of the 103P2D6 protein shown in FIG. 2 and FIG. 3, polypeptides consisting of about amino acid 10 to about amino acid 20 of the 103P2D6 protein shown in FIG. 2 and FIG. 3, polypeptides consisting of about amino acid 20 to about amino acid 30 of the 103P2D6 protein shown in FIG. 2 and FIG. 3, polypeptides consisting of about amino acid 30 to about amino acid 40 of the 103P2D6 protein shown in FIG. 2 and FIG. 3, polypeptides consisting of about amino acid 40 to about amino acid 50 of the 103P2D6 protein shown in FIG. 2 and FIG. 3, polypeptides consisting of about amino acid 50 to about amino acid 60 of the 103P2D6 protein shown in FIG. 2 and FIG. 3, polypeptides consisting of about amino acid 60 to about amino acid 70 of the 103P2D6 protein shown in FIG. 2 and FIG. 3, polypeptides consisting of about amino acid 70 to about amino acid 80 of the 103P2D6 protein shown in FIG. 2 and FIG. 3, polypeptides consisting of about amino acid 80 to about amino acid 90 of the 103P2D6 protein shown in FIG. 2 and FIG. 3 and polypeptides consisting of about amino acid 90 to about amino acid 100 of the 103P2D6 protein shown in FIG. 2 and FIG. 3, etc. throughout the entirety of the 103P2D6 sequence. Further, this definition defines polypeptides consisting of 10 amino acid stretches of the amino acid sequence of amino acids 100-532 of the 103P2D6 protein. Moreover, polypeptides consisting of about amino acid 1 (or 20 or 30 or 40 etc.) to about amino acid 20, (or 130, or 140 or 150 etc.) of the 103P2D6 protein shown in FIG. 2 and FIG. 3 are embodiments of the invention. It is to be appreciated that the starting and stopping positions in this paragraph refer to the specified position as well as that position plus or minus 5 residues.

103P2D6-related proteins are generated using standard peptide synthesis technology or using chemical cleavage methods well known in the art. Alternatively, recombinant methods can be used to generate nucleic acid molecules that encode a 103P2D6related protein. In one embodiment, nucleic acid molecules provide a means to generate defined fragments of the 103P2D6 protein (or variants, homologs or analogs thereof).

IV.A.) Motif-Bearing Protein Embodiments

Additional illustrative embodiments of the invention disclosed herein include 103P2D6 polypeptides comprising the amino acid residues of one or more of the biological motifs contained within the 103P2D6 polypeptide sequence set forth in FIG. 2 or FIG. 3. Various motifs are known in the art, and a protein can be evaluated for the presence of such motifs by a number of publicly available sites (see, e.g.: http://pfam.wustl.edu/; http://searchlauncher.bcm.tmc.edu/seq-search/struc-predict.html http://psort.ims.u-tokyo.ac.jp/; http://www.cbs.dtu.dk/; http://www.ebi.ac.uk/interpro/scan.html; http://www.expasy.ch/tools/scripsit1.html; Epimatrix™ and Epimer™, Brown University, http://www.brown.edu/Research/TB-HIV_Lab/epiatrix/epimatrix.html; and BIMAS, http://bimas.dert.nih.gov/.).

Motif bearing subsequences of the 103P2D6 protein are set forth and identified in Table XIX.

Table XX sets forth several frequently occurring motifs based on pfam searches (http://pfam.wustl.edu/). The columns of Table XX list (1) motif name abbreviation, (2) percent identity found amongst the different member of the motif family, (3) motif name or description and (4) most common function; location information is included if the motif is relevant for location.

Polypeptides comprising one or more of the 103P2D6 motifs discussed above are useful in elucidating the specific characteristics of a malignant phenotype in view of the observation that the 103P2D6 motifs discussed above are associated with growth dysregulation and because 103P2D6 is overexpressed in certain cancers (See, e.g., Table I). Casein kinase II, cAMP and cCMP-dependent protein kinase, and Protein Kinase C, for example, are enzymes known to be associated with the development of the malignant phenotype (see e.g. Chen et al., Lab Invest., 78(2): 165-174 (1998); Gaiddon et al., Endocrinology 136(10): 4331-4338 (1995); Hall et al., Nucleic Acids Research 24(6): 1119-1126 (1996); Peterziel et al., Oncogene 18(46): 6322-6329 (1999) and O'Brian, Oncol. Rep. 5(2): 305-309 (1998)). Moreover, both glycosylation and myristoylation are protein modifications also associated with cancer and cancer progression (see e.g. Dennis et al., Biochem. Biophys. Acta 1473(1):21-34 (1999); Raju et al., Exp. Cell Res. 235(1): 145-154 (1997)). Amidation is another protein modification also associated with cancer and cancer progression (see e.g. Treston et al., J. Natl. Cancer Inst. Monogr. (13): 169-175 (1992)).

In another embodiment, proteins of the invention comprise one or more of the immunoreactive epitopes identified in accordance with art-accepted methods, such as the peptides set forth in Tables V-XVIII. CTL epitopes can be determined using specific algorithms to identify peptides within an 103P2D6 protein that are capable of optimally binding to specified HLA alleles (e.g., Table IV (A) and Table IV (B); Epimatrix™ and Epimer™, Brown University, which are found at the world wide web address brown.edu/Research/TB-HIV_Lab/epimatrix/epimatrix.html; and BIMAS, bimas.dcrt.nih.gov/. Moreover, processes for identifying peptides that have sufficient binding affinity for HLA molecules and which are correlatedwith being immunogenic epitopes, are well known in the art, and are carried on without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I motifs or Table IV (A) and the HTL motif of Table IV (B)). The epitope is analoged by substituting out an amino acid at one of the specified positions, and replacing it with another amino acid specified for that position.

A variety of references reflect the art regarding the identification and generation of epitopes in a protein of interest as well as analogs thereof. See, for example, WO 9733602 to Chestnut et al.; Sette, Immunogenetics 1999 50(3-4): 201-212; Sette et al., J. Immunol. 2001 166(2): 1389-1397; Sidney et al., Hum. Immunol. 1997 58(1): 12-20; Kondo et al., Immunogenetics 1997 45(4): 249-258; Sidney et al., J. Immunol. 1996 157(8): 3480-90; and Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)); Kast et al., 1994 152(8): 3904-12; Borras-Cuesta et al., Hum. Immunol. 2000 61(3): 266-278; Alexander et al., J. Immunol. 2000 164(3); 164(3): 1625-1633; Alexander et al., PMID: 7895164, UI: 95202582; O'Sullivan et al., J. Immunol. 1991 147(8): 2663-2669; Alexander et al., Immunity 1994 1(9): 751-761 and Alexander et al., Immunol. Res. 1998 18(2): 79-92.

Related embodiments of the inventions include polypeptides comprising combinations of the different motifs set forth in Table XIX, and/or, one or more of the predicted CTL epitopes of Table V through Table XVIII, and/or, one or more of the T cell binding motifs known in the art. Preferred embodiments contain no insertions, deletions or substitutions either within the motifs or the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically the number of N-terminal and/or C-terminal amino acid residues on either side of a motif is between about 1 to about 100 amino acid residues, preferably 5 to about 50 amino acid residues.

103P2D6-related proteins are embodied in many forms, preferably in isolated form. A purified 103P2D6 protein molecule will be substantially free of other proteins or molecules that impair the binding of 103P2D6 to antibody, T cell or other ligand. The nature and degree of isolation and purification will depend on the intended use. Embodiments of a 103P2D6-related proteins include purified 103P2D6-related proteins and functional, soluble 103P2D6-related proteins. In one embodiment, a functional, soluble 103P2D6 protein or fragment thereof retains the ability to be bound by antibody, T cell or other ligand.

The invention also provides 103P2D6 proteins comprising biologically active fragments of the 103P2D6 amino acid sequence shown in FIG. 2. Such proteins exhibit properties of the 103P2D6 protein, such as the ability to elicit the generation of antibodies that specifically bind an epitope associated with the 103P2D6 protein; to be bound by such antibodies; to elicit the activation of HTL or CTL; and/or, to be recognized by HTL or CTL.

103P2D6-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments that contain such structures are particularly useful in generating subunit-specific anti-103P2D6 antibodies, or T cells or in identifying cellular factors that bind to 103P2D6.

CTL epitopes can be determined using specific algorithms to identify peptides within an 103P2D6 protein that are capable of optimally binding to specified HLA alleles (e.g., Table IV (A) and Table IV (B); Epimatrix™ and Epimer™, Brown University (http://www.brown.edu/Research/TB-HIV_Lab/epimatrix/epimatrix.html); and BIMAS, http://bimas.dcrt.nih.gov/). Illustrating this, peptide epitopes from 103P2D6 that are presented in the context of human MHC class I molecules HLA-A1, A2, A3, A11, A24, B7 and B35 were predicted (Tables V-XVIII). Specifically, the complete amino acid sequence of the 103P2D6 protein was entered into the HLA Peptide Motif Search algorithm found in the Bioinformatics and Molecular Analysis Section (BIMAS) web site listed above. The HLA peptide motif search algorithm was developed by Dr. Ken Parker based on binding of specific peptide sequences in the groove of HLA Class I molecules and specifically HLA-A2 (see, e.g., Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for class I HLA-A2, the epitopes preferably contain a leucine (L) or methionine (M) at position 2 and a valine (V) or leucine (L) at the C-terminus (see, e.g., Parker et al., J. Immunol. 149:3580-7 (1992)). Selected results of 103P2D6 predicted binding peptides are shown in Tables V-XVIII herein. In Tables V-XVIII, the top 50 ranking candidates, 9-mers and 10-mers, for each family member are shown along with their location, the amino acid sequence of each specific peptide, and an estimated binding score. The binding score corresponds to the estimated half-time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73-8 (1997) and Peshwa et al., Prostate 36:129-38 (1998)). Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class I motifs available in the art or which become part of the art such as set forth in Table IV (A) and Table IV (B) are to be "applied" to the 103P2D6 protein. As used in this context "applied" means that the 103P2D6 protein is evaluated, e.g., visually or by computer-based patterns finding methods, as appreciated by those of skill in the relevant art. Every subsequence of the 103P2D6 of 8, 9, 10, or 11 amino acid residues that bears an HLA Class I motif, or a subsequence of 9 or more amino acid residues that bear an HLA Class II motif are within the scope of the invention.

IV.B.) Expression of 103P2D6-Related Proteins

In an embodiment described in the examples that follow, 103P2D6 can be conveniently expressed in cells (such as 293T cells) transfected with a commercially available expression vector such as a CMV-driven expression vector encoding 103P2D6 with a C-terminal 6×His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 103P2D6 protein in transfected cells. The secreted HIS-tagged 103P2D6 in the culture media can be purified, e.g., using a nickel column using standard techniques.

IV.C.) Modifications of 103P2D6-Related Proteins

Modifications of 103P2D6-related proteins such as covalent modifications are included within the scope of this invention. One type of covalent modification includes reacting targeted amino acid residues of a 103P2D6 polypeptide with an organic derivatizing agent that is capable of reacting with selected side chains or the N- or C-terminal residues of the 103P2D6. Another type of covalent modification of the 103P2D6 polypeptide included within the scope of this invention comprises altering the native glycosylation pattern of a protein of the invention. Another type of covalent modification of 103P2D6 comprises linking the 103P2D6 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The 103P2D6-related proteins of the present invention can also be modified to form a chimeric molecule comprising 103P2D6 fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of the 103P2D6 sequence (amino or nucleic acid) such that a molecule is created that is not, through its length, directly homologous to the amino or nucleic acid sequences respectively of FIG. 2. Such a chimeric molecule can comprise multiples of the same subsequence of 103P2D6. A chimeric molecule can comprise a fusion of a 103P2D6-related protein with a polyhistidine epitope tag, which provides an epitope to which immobilized nickel can selectively bind. The epitope tag is generally placed at the amino- or carboxyl-terminus of the 103P2D6. In an alternative embodiment, the chimeric molecule can comprise a fusion of a 103P2D6-related protein with an immunoglobulin or a particular region of an immunoglobulin. For a bivalent form of the chimeric molecule (also referred to as an "immnunoadhesin"), such a fusion could be to the Fc region of an IgG molecule. The Ig fusions preferably include the substitution of a soluble (transmembrane domain deleted or inactivated) form of a 103P2D6 polypeptide in place of at least one variable region within an Ig molecule. In a preferred embodiment, the immunoglobulin fusion includes the hinge, CH2 and CH3, or the hinge, CH1, CH2 and CH3 regions of an IgGI molecule. For the production of immunoglobulin fusions see, e.g., U.S. Pat. No. 5,428,130 issued Jun. 27, 1995.

IV.D.) Uses of 103P2D6-Related Proteins

The proteins of the invention have a number of different specific uses. As 103P2D6 is highly expressed in prostate and other cancers, 103P2D6-related proteins are used in methods that assess the status of 103P2D6 gene products in normal versus cancerous tissues, thereby elucidating the malignant phenotype. Typically, polypeptides from specific regions of the 103P2D6 protein are used to assess the presence of perturbations (such as deletions, insertions, point mutations etc.) in those regions (such as regions containing one or more motifs). Exemplary assays utilize antibodies or T cells targeting 103P2D6-related proteins comprising the amino acid residues of one or more of the biological motifs contained within the 103P2D6 polypeptide sequence in order to evaluate the characteristics of this region in normal versus cancerous tissues or to elicit an immune response to the epitope. Alternatively, 103P2D6-related proteins that contain the amino acid residues of one or more of the biological motifs in the 103P2D6 protein are used to screen for factors that interact with that region of 103P2D6.

103P2D6 protein fragments/subsequences are particularly useful in generating and characterizing domain-specific antibodies (e.g., antibodies recognizing an extracellular or intracellular epitope of an 103P2D6 protein), for identifying agents or cellular factors that bind to 103P2D6 or a particular structural domain thereof, and in various therapeutic and diagnostic contexts, including but not limited to diagnostic assays, cancer vaccines and methods of preparing such vaccines.

Proteins encoded by the 103P2D6 genes, or by analogs, homologs or fragments thereof, have a variety of uses, including but not limited to generating antibodies and in methods for identifying ligands and other agents and cellular constituents that bind to an 103P2D6 gene product. Antibodies raised against an 103P2D6 protein or fragment thereof are useful in diagnostic and prognostic assays, and imaging methodologies in the management of human cancers characterized by expression of 103P2D6 protein, such as those listed in Table I. Such antibodies can be expressed intracellularly and used in methods of treating patients with such cancers. 103P2D6-related nucleic acids or proteins are also used in generating HTL or CTL responses.

Various immunological assays useful for the detection of 103P2D6 proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 103P2D6-expressing cells (e.g., in radioscintigraphic imaging methods). 103P2D6 proteins are also particularly useful in generating cancer vaccines, as further described herein.

V.) 103P2D6 Antibodies

Another aspect of the invention provides antibodies that bind to 103P2D6-related proteins. Preferred antibodies specifically bind to a 103P2D6-related protein and do not bind (or bind weakly) to peptides or proteins that are not 103P2D6-related proteins. For example, antibodies bind 103P2D6 can bind 103P2D6-related proteins such as the homologs or analogs thereof.

103P2D6 antibodies of the invention are particularly useful in prostate cancer diagnostic and prognostic assays, and imaging methodologies. Similarly, such antibodies are useful in the treatment, diagnosis, and/or prognosis of other cancers, to the extent 103P2D6 is also expressed or overexpressed in these other cancers. Moreover, intracellularly expressed antibodies (e.g., single chain antibodies) are therapeutically useful in treating cancers in which the expression of 103P2D6 is involved, such as advanced or metastatic prostate cancers.

The invention also provides various immunological assays useful for the detection and quantification of 103P2D6 and mutant 103P2D6-related proteins. Such assays can comprise one or more 103P2D6 antibodies capable of recognizing and binding a 103P2D6-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting prostate cancer and other cancers expressing 103P2D6 are also provided by the invention, including but not limited to radioscintigraphic imaging methods using labeled 103P2D6 antibodies. Such assays are clinically useful in the detection, monitoring, and prognosis of 103P2D6 expressing cancers such as prostate cancer.

103P2D6 antibodies are also used in methods for purifying a 103P2D6-related protein and for isolating 103P2D6 homologues and related molecules. For example, a method of purifying a 103P2D6-related protein comprises incubating an 103P2D6 antibody, which has been coupled to a solid matrix, with a lysate or other solution containing a 103P2D6-related protein under conditions that permit the 103P2D6 antibody to bind to the 103P2D6-related protein; washing the solid matrix to eliminate impurities; and eluting the 103P2D6-related protein from the coupled antibody. Other uses of the 103P2D6 antibodies of the invention include generating anti-idiotypic antibodies that mimic the 103P2D6 protein.

Various methods for the preparation of antibodies are well known in the art. For example, antibodies can be prepared by immunizing a suitable mammalian host using a 103P2D6-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of 103P2D6 can also be used, such as a 103P2D6 GST-fusion protein. In a particular embodiment, a GST fusion protein comprising all or most of the amino acid sequence of FIG. 2 or FIG. 3 is produced, then used as an immunogen to generate appropriate antibodies. In another embodiment, a 103P2D6-related protein is synthesized and used as an immunogen.

In addition, naked DNA immunization techniques known in the art are used (with or without purified 103P2D6-related protein or 103P2D6 expressing cells) to generate an immune response to the encoded immunogen (for review, see Donnelly et al., 1997, Ann. Rev. Immunol. 15: 617-648).

The amino acid sequence of 103P2D6 as shown in FIG. 2 or FIG. 3 can be analyzed to select specific regions of the 103P2D6 protein for generating antibodies. For example, hydrophobicity and hydrophilicity analyses of the 103P2D6 amino acid sequence are used to identify hydrophilic regions in the 103P2D6 structure. Regions of the 103P2D6 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Thus, each region identified by any of these programs or methods is within the scope of the present invention. Methods for the generation of 103P2D6 antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodumide reagents are used; in other instances linking reagents such as those supplied by Pierce Chemical Co., Rockford, Ill., are effective. Administration of a 103P2D6 immunogen is often conducted by injection over a suitable time period and with use of a suitable adjuvant, as is understood in the art. During the immunization schedule, titers of antibodies can be taken to determine adequacy of antibody formation.

103P2D6 monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a 103P2D6-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of the 103P2D6 protein can also be produced in the context of chimeric or complementarity determining region (CDR) grafted antibodies of multiple species origin. Humanized or human 103P2D6 antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmnan et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

Methods for producing fully human monoclonal antibodies include phage display and transgenic methods (for review, see Vaughan et al., 1998, Nature Biotechnology 16: 535-539). Fully human 103P2D6 monoclonal antibodies can be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man, Clark, M. (Ed.), Nottingham Academic, pp 45-64 (1993); Burton and Barbas, Human Antibodies from combinatorial libraries. Id., pp 65-82). Fully human 103P2D6 monoclonal antibodies can also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614; U.S. Pat. No. 6,162,963 issued Dec. 19, 2000; U.S. Pat. No. 6,150,584 issued Nov. 12, 2000; and, U.S. Pat. No. 6,114,598 issued Sep. 5, 2000). This method avoids the in vitro manipulation required with phage display technology and efficiently produces high affinity authentic human antibodies.

Reactivity of 103P2D6 antibodies with an 103P2D6-related protein can be established by a number of well known means, including Western blot, immunoprecipitation, ELISA, and FACS analyses using, as appropriate, 103P2D6-related proteins, 103P2D6-expressing cells or extracts thereof. A 103P2D6 antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 103P2D6 epitopes are generated using methods generally known in the art. Homodimeric antibodies can also be generated by cross-linking techniques known in the art (e.g., Wolff et al., Cancer Res. 53: 2560-2565).

VI.) 103P2D6 Transgenic Animals

Nucleic acids that encode a 103P2D6-related protein can also be used to generate either transgenic animals or "knock out" animals which, in turn, are useful in the development and screening of therapeutically useful reagents. In accordance with established techniques, cDNA encoding 103P2D6 can be used to clone genomic DNA that encodes 103P2D6. The cloned genomic sequences can then be used to generate transgenic animals containing cells that express DNA that encode 103P2D6. Methods for generating transgenic animals, particularly animals such as mice or rats, have become conventional in the art and are described, for example, in U.S. Pat. No. 4,736,866 issued Apr. 12, 1988, and U.S. Pat. No. 4,870,009 issued Sep. 26, 1989. Typically, particular cells would be targeted for 103P2D6 transgene incorporation with tissue-specific enhancers.

Transgenic animals that include a copy of a transgene encoding 103P2D6 can be used to examine the effect of increased expression of DNA that encodes 103P2D6. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 103P2D6 can be used to construct a 103P2D6 "knock out" animal that has a defective or altered gene encoding 103P2D6 as a result of homologous recombination between the endogenous gene encoding 103P2D6 and altered genomic DNA encoding 103P2D6 introduced into an embryonic cell of the animal. For example, cDNA that encodes 103P2D6 can be used to clone genomic DNA encoding 103P2D6 in accordance with established techniques. A portion of the genomic DNA encoding 103P2D6 can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, Cell, 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., Cell, 69:915 (1992)). The selected cells are then injected into a blastocyst of an animal (e.g., a mouse or rat) to form aggregation chimeras (see, e.g., Bradley, in Teratocarcinomas and Embryonic Stem Cells. A Practical Approach, E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of the 103P2D6 polypeptide.

VIII.) Methods for the Detection of 103P2D6

Another aspect of the present invention relates to methods for detecting 103P2D6 polynucleotides and 103P2D6-related proteins, as well as methods for identifying a cell that expresses 103P2D6. The expression profile of 103P2D6 makes it a diagnostic marker for metastasized disease. Accordingly, the status of 103P2D6 gene products provides information useful for predicting a variety of factors including susceptibility to advanced stage disease, rate of progression, and/or tumor aggressiveness. As discussed in detail herein, the status of 103P2D6 gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of 103P2D6 polynucleotides in a biological sample, such as serum, bone, prostate, and other tissues, urine, semen, cell preparations, and the like. Detectable 103P2D6 polynucleotides include, for example, a 103P2D6 gene or fragment thereof, 103P2D6 mRNA, alternative splice variant 103P2D6 mRNAs, and recombinant DNA or RNA molecules that contain a 103P2D6 polynucleotide. A number of methods for amplifying and/or detecting the presence of 103P2D6 polynucleotides are well known in the art and can be employed in the practice of this aspect of the invention.

In one embodiment, a method for detecting an 103P2D6 mRNA in a biological sample comprises producing cDNA from the sample by reverse transcription using at least one primer; amplifying the cDNA so produced using an 103P2D6 polynucleotides as sense and antisense primers to amplify 103P2D6 cDNAs therein; and detecting the presence of the amplified 103P2D6 cDNA. Optionally, the sequence of the amplified 103P2D6 cDNA can be determined.

In another embodiment, a method of detecting a 103P2D6 gene in a biological sample comprises first isolating genomic DNA from the sample; amplifying the isolated genomic DNA using 103P2D6 polynucleotides as sense and antisense primers; and detecting the presence of the amplified 103P2D6 gene. Any number of appropriate sense and antisense probe combinations can be designed from the nucleotide sequences provided for the 103P2D6 (FIG. 2) and used for this purpose.

The invention also provides assays for detecting the presence of an 103P2D6 protein in a tissue or other biological sample such as serum, semen, bone, prostate, urine, cell preparations, and the like. Methods for detecting a 103P2D6-related protein are also well known and include, for example, immunoprecipitation, immunohistochemical analysis, Western blot analysis, molecular binding assays, ELISA, ELIFA and the like. For example, a method of detecting the presence of a 103P2D6-related protein in a biological sample comprises first contacting the sample with a 103P2D6 antibody, a 103P2D6-reactive fragment thereof, or a recombinant protein containing an antigen binding region of a 103P2D6 antibody; and then detecting the binding of 103P2D6-related protein in the sample.

Methods for identifying a cell that expresses 103P2D6 are also within the scope of the invention. In one embodiment, an assay for identifying a cell that expresses a 103P2D6 gene comprises detecting the presence of 103P2D6 mRNA in the cell. Methods for the detection of particular mRNAs in cells are well known and include, for example, hybridization assays using complementary DNA probes (such as in situ hybridization using labeled 103P2D6 riboprobes, Northern blot and related techniques) and various nucleic acid amplification assays (such as RT-PCR using complementary primers specific for 103P2D6, and other amplification type detection methods, such as, for example, branched DNA, SISBA, TMA and the like). Alternatively, an assay for identifying a cell that expresses a 103P2D6 gene comprises detecting the presence of 103P2D6-related protein in the cell or secreted by the cell. Various methods for the detection of proteins are well known in the art and are employed for the detection of 103P2D6-related proteins and cells that express 103P2D6-related proteins.

103P2D6 expression analysis is also useful as a tool for identifying and evaluating agents that modulate 103P2D6 gene expression. For example, 103P2D6 expression is significantly upregulated in prostate cancer, and is expressed in cancers of the tissues listed in Table I. Identification of a molecule or biological agent that inhibits 103P2D6 expression or over-expression in cancer cells is of therapeutic value. For example, such an agent can be identified by using a screen that quantifies 103P2D6 expression by RT-PCR, nucleic acid hybridization or antibody binding.

VIII.) Methods for Monitoring the Status of 103P2D6-Related Genes and Their Products Oncogenesis is known to be a multistep process where cellular growth becomes progressively dysregulated and cells progress from a normal physiological state to precancerous and then cancerous states (see, e.g., Alers et al., Lab Invest. 77(5): 437-438 (1997) and Isaacs et al., Cancer Surv. 23: 19-32 (1995)). In this context, examining a biological sample for evidence of dysregulated cell growth (such as aberrant 103P2D6 expression in cancers) allows for early detection of such aberrant physiology, before a pathologic state such as cancer has progressed to a stage that therapeutic options are more limited and or the prognosis is worse. In such examinations, the status of 103P2D6 in a biological sample of interest can be compared, for example, to the status of 103P2D6 in a corresponding normal sample (e.g. a sample from that individual or alternatively another individual that is not effected by a pathology). An alteration in the status of 103P2D6 in the biological sample (as compared to the normal sample) provides evidence of dysregulated cellular growth. In addition to using a biological sample that is not effected by a pathology as a normal sample, one can also use a predetermined normative value such as a predetermined normal level of mRNA expression (see, e.g., Grever et al., J. Comp. Neurol. 1996 Dec. 9;376(2):306-14 and U.S. Pat. No. 5,837,501) to compare 103P2D6 status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 103P2D6 expressing cells) as well as the, level, and biological activity of expressed gene products (such as 103P2D6 mRNA polynucleotides and polypeptides). Typically, an alteration in the status of 103P2D6 comprises a change in the location of 103P2D6 and/or 103P2D6 expressing cells and/or an increase in 103P2D6 mRNA and/or protein expression.

103P2D6 status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of the 103P2D6 gene and gene products are found, for example in Ausubul et al. eds., 1995, Current Protocols In Molecular Biology, Units 2 (Northern Blotting), 4 (Southern Blotting), 15 (Immunoblotting) and 18 (PCR Analysis). Thus, the status of 103P2D6 in a biological sample is evaluated by various methods utilized by skilled artisans including, but not limited to genomic Southern analysis (to examine, for example perturbations in the 103P2D6 gene), Northern analysis and/or PCR analysis of 103P2D6 mRNA (to examine, for example alterations in the polynucleotide sequences or expression levels of 103P2D6 m-RNAs), and, Western and/or immunohistochemical analysis (to examine, for example alterations in polypeptide sequences, alterations in polypeptide localization within a sample, alterations in expression levels of 103P2D6 proteins and/or associations of 103P2D6 proteins with polypeptide binding partners). Detectable 103P2D6 polynucleotides include, for example, a 103P2D6 gene or fragment thereof, 103P2D6 mRNA, alternative splice variants, 103P2D6 mRNAs, and recombinant DNA or RNA molecules containing a 103P2D6 polynucleotide.

The expression profile of 103P2D6 makes it a diagnostic marker for local and/or metastasized disease, and provides information on the growth or oncogenic potential of a biological sample. In particular, the status of 103P2D6 provides information useful for predicting susceptibility to particular disease stages, progression, and/or tumor aggressiveness. The invention provides methods and assays for determining 103P2D6 status and diagnosing cancers that express 103P2D6, such as cancers of the tissues listed in Table I. For example, because 103P2D6 mRNA is so highly expressed in prostate and other cancers relative to normal prostate tissue, assays that evaluate the levels of 103P2D6 mRNA transcripts or proteins in a biological sample can be used to diagnose a disease associated with 103P2D6 dysregulation, and can provide prognostic information useful in defining appropriate therapeutic options.

The expression status of 103P2D6 provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 103P2D6 in biological samples such as those from individuals suffering from, or suspected of suffering from a pathology characterized by dysregulated cellular growth, such as cancer.

As described above, the status of 103P2D6 in a biological sample can be examined by a number of well-known procedures in the art. For example, the status of 103P2D6 in a biological sample taken from a specific location in the body can be examined by evaluating the sample for the presence or absence of 103P2D6 expressing cells (e.g. those that express 103P2D6 mRNAs or proteins). This examination can provide evidence of dysregulated cellular growth, for example, when 103P2D6-expressing cells are found in a biological sample that does not normally contain such cells (such as a lymph node), because such alterations in the status of 103P2D6 in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315-317 (2000);Su et al., Sermn. Surg. Oncol. 18(1): 17-28 (2000) and Freeman et al., J Urol 1995 August;154(2 Pt 1):474-8).

In one aspect, the invention provides methods for monitoring 103P2D6 gene products by determining the status of 103P2D6 gene products expressed by cells from an individual suspected of having a disease associated with dysregulated cell growth (such as hyperplasia or cancer) and then comparing the status so determined to the status of 103P2D6 gene products in a corresponding normal sample. The presence of aberrant 103P2D6 gene products in the test sample relative to the normal sample provides an indication of the presence of dysregulated cell growth within the cells of the individual.

In another aspect, the invention provides assays useful in determining the presence of cancer in an individual, comprising detecting a significant increase in 103P2D6 mRNA or protein expression in a test cell or tissue sample relative to expression levels in the corresponding normal cell or tissue. The presence of 103P2D6 mRNA can, for example, be evaluated in tissue samples including but not limited to those listed in Table I. The presence of significant 103P2D6 expression in any of these tissues is useful to indicate the emergence, presence and/or severity of a cancer, since the corresponding normal tissues do not express 103P2D6 mRNA or express it at lower levels.

In a related embodiment, 103P2D6 status is determined at the protein level rather than at the nucleic acid level. For example, such a method comprises determining the level of 103P2D6 protein expressed by cells in a test tissue sample and comparing the level so determined to the level of 103P2D6 expressed in a corresponding normal sample. In one embodiment, the presence of 103P2D6 protein is evaluated, for example, using immunohistochemical methods. 103P2D6 antibodies or binding partners capable of detecting 103P2D6 protein expression are used in a variety of assay formats well known in the art for this purpose.

In a further embodiment, one can evaluate the status 103P2D6 nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369-378). For example, a mutation in the sequence of 103P2D6 may be indicative of the presence or promotion of a tumor. Such assays therefore have diagnostic and predictive value where a mutation in 103P2D6 indicates a potential loss of function or increase in tumor growth.

A wide variety of assays for observing perturbations in nucleotide and amino acid sequences are well known in the art. For example, the size and structure of nucleic acid or amino acid sequences of 103P2D6 gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. No. 5,382,510 issued Sep. 7, 1999, and U.S. Pat. No. 5,952, 170 issued Jan. 17, 1995).

Additionally, one can examine the methylation status of the 103P2D6 gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of cases of high-grade prostatic intraepithelial neoplasia (PIN) (Brooks et al, Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76(6): 903-908 (1998)). A variety of assays for examining methylation status of a gene are well known in the art. For example, one can utilize, in Southern hybridization approaches, methylation-sensitive restriction enzymes which cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubul et al. eds., 1995.

Gene amplification is an additional method for assessing the status of 103P2D6. Gene amplification is measured in a sample directly, for example, by conventional Southern blotting or Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect 103P2D6 expression. The presence of RT-PCR amplifiable 103P2D6 mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373-384; Ghossein et al., 1995, J. Clin. Oncol. 13:1195-2000; Heston et al., 1995, Clin. Chem. 41:1687-1688).

A further aspect of the invention is an assessment of the susceptibility that an individual has for developing cancer. In one embodiment, a method for predicting susceptibility to cancer comprises detecting 103P2D6 mRNA or 103P2D6 protein in a tissue sample, its presence indicating susceptibility to cancer, wherein the degree of 103P2D6 mRNA expression correlates to the degree of susceptibility. In a specific embodiment, the presence of 103P2D6 in prostate or other tissue is examined, with the presence of 103P2D6 in the sample providing an indication of prostate cancer susceptibility (or the emergence or existence of a prostate tumor). Similarly, one can evaluate the integrity 103P2D6 nucleotide and amino acid sequences in a biological sample, in order to identify perturbations in the structure of these molecules such as insertions, deletions, substitutions and the like. The presence of one or more perturbations in 103P2D6 gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of 103P2D6 mRNA or 103P2D6 protein expressed by tumor cells, comparing the level so determined to the level of 103P2D6 mRNA or 103P2D6 protein expressed in a corresponding normal tissue taken from the same individual or a normal tissue reference sample, wherein the degree of 103P2D6 mRNA or 103P2D6 protein expression in the tumor sample relative to the normal sample indicates the degree of aggressiveness. In a specific embodiment, aggressiveness of a tumor is evaluated by determining the extent to which 103P2D6 is expressed in the tumor cells, with higher expression levels indicating more aggressive tumors. Another embodiment is the evaluation of the integrity of 103P2D6 nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 103P2D6 mRNA or 103P2D6 protein expressed by cells in a sample of the tumor, comparing the level so determined to the level of 103P2D6 mRNA or 103P2D6 protein expressed in an equivalent tissue sample taken from the same individual at a different time, wherein the degree of 103P2D6 mRNA or 103P2D6 protein expression in the tumor sample over time provides information on the progression of the cancer. In a specific embodiment, the progression of a cancer is evaluated by determining 103P2D6 expression in the tumor cells over time, where increased expression over time indicates a progression of the cancer. Also, one can evaluate the integrity 103P2D6 nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of 103P2D6 gene and 103P2D6 gene products (or perturbations in 103P2D6 gene and 103P2D6 gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking et al., 1984, Anal. Quant. Cytol. 6(2):74-88; Eptsein, 1995, Hum. Pathol. 26(2):223-9; Thorson et al., 1998, Mod. Pathol. 11(6):543-51; Baisden et al., 1999, Am. J. Surg. Pathol. 23(8):918-24). Methods for observing a coincidence between the expression of 103P2D6 gene and 103P2D6 gene products (or perturbations in 103P2D6 gene and 103P2D6 gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of 103P2D6 gene and 103P2D6 gene products (or perturbations in 103P2D6 gene and 103P2D6 gene products) and another factor associated with malignancy entails detecting the overexpression of 103P2D6 mRNA or protein in a tissue sample, detecting the overexpression of PSA mRNA or protein in a tissue sample (or PSCA or PSM expression), and observing a coincidence of 103P2D6 mRNA or protein and PSA mRNA or protein overexpression (or PSCA or PSM expression). In a specific embodiment, the expression of 103P2D6 and PSA mRNA in prostate tissue is examined, where the coincidence of 103P2D6 and PSA mRNA overexpression in the sample indicates the existence of prostate cancer, prostate cancer susceptibility or the emergence or status of a prostate tumor.

Methods for detecting and quantifying the expression of 103P2D6 mRNA or protein are described herein, and standard nucleic acid and protein detection and quantification technologies are well known in the art. Standard methods for the detection and quantification of 103P2D6 mRNA include in situ hybridization using labeled 103P2D6 riboprobes, Northern blot and related techniques using 103P2D6 polynucleotide probes, RT-PCR analysis using primers specific for 103P2D6, and other amplification type detection methods, such as, for example, branched DNA, SISBA, TMA and the like. In a specific embodiment, semi-quantitative RT-PCR is used to detect and quantify 103P2D6 mRNA expression. Any number of primers capable of amplifying 103P2D6 can be used for this purpose, including but not limited to the various primer sets specifically described herein. In a specific embodiment, polyclonal or monoclonal antibodies specifically reactive with the wild-type 103P2D6 protein can be used in an immunohistochemical assay of biopsied tissue.

IX.) Identifying Molecules that Interact with 103P2D6

The 103P2D6 protein and nucleic acid sequences disclosed herein allow a skilled artisan to identify proteins, small molecules and other agents that interact with 103P2D6, as well as pathways activated by 103P2D6 via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. No. 5,955,280 issued Sep. 21, 1999, U.S. Pat. No. 5,925,523 issued Jul. 20, 1999, U.S. Pat. No. 5,846,722 issued Dec. 8, 1998 and U.S. Pat. No. 6,004,746 issued Dec. 21, 1999.

Alternatively one can screen peptide libraries to identify molecules that interact with 103P2D6 protein sequences. In such methods, peptides that bind to a molecule such as 103P2D6 are identified by screening libraries that encode a random or controlled collection of amino acids. Peptides encoded by the libraries are expressed as fusion proteins of bacteriophage coat proteins, the bacteriophage particles are then screened against the protein of interest.

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 103P2D6 protein sequences are disclosed for example in U.S. Pat. No. 5,723,286 issued Mar. 3, 1998 and U.S. Pat. No. 5,733,731 issued Mar. 31, 1998.

Alternatively, cell lines that express 103P2D6 are used to identify protein-protein interactions mediated by 103P2D6. Such interactions can be examined using immunoprecipitation techniques (see, e.g., Hamilton B J, et al. Biochem. Biophys. Res. Commun. 1999, 261:646-51). 103P2D6 protein can be immunoprecipitated from 103P2D6-expressing cell lines using anti-103P2D6 antibodies. Alternatively, antibodies against His-tag can be used in a cell line engineered to express 103P2D6 (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with 103P2D6 can be identified through related embodiments of such screening assays. For example, small molecules can be identified that interfere with protein function, including molecules that interfere with 103P2D6's ability to mediate phosphorylation and de-phosphorylation, second messenger signaling or tumorigenesis. Similarly, ligands that regulate 103P2D6 function can be identified based on their ability to bind 103P2D6 and activate a reporter construct. Typical methods are discussed for example in U.S. Pat. No. 5,928,868 issued Jul. 27, 1999, and include methods for forming hybrid ligands in which at least one ligand is a small molecule. In an illustrative embodiment, cells engineered to express a fusion protein of 103P2D6 and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying both activators and inhibitors of 103P2D6.

An embodiment of this invention comprises a method of screening for a molecule that interacts with an 103P2D6 amino acid sequence shown in FIG. 2 and FIG. 3, comprising the steps of contacting a population of molecules with the 103P2D6 amino acid sequence, allowing the population of molecules and the 103P2D6 amino acid sequence to interact under conditions that facilitate an interaction, determining the presence of a molecule that interacts with the 103P2D6 amino acid sequence, and then separating molecules that do not interact with the 103P2D6 amino acid sequence from molecules that do. In a specific embodiment, the method further comprises purifying a molecule that interacts with the 103P2D6 amino acid sequence. The identified molecule can be used to modulate a function performed by 103P2D6. In a preferred embodiment, the 103P2D6 amino acid sequence is contacted with a library of peptides.

X.) Therapeutic Methods and Compositions

The identification of 103P2D6 as a protein that is normally expressed in a restricted set of tissues, but which is also expressed in prostate and other cancers, opens a number of therapeutic approaches to the treatment of such cancers. As discussed herein, it is possible that 103P2D6 functions as a transcription factor involved in activating tumor-promoting genes or repressing genes that block tumorigenesis.

Accordingly, therapeutic approaches that inhibit the activity of the 103P2D6 protein are useful for patients suffering a cancer that expresses 103P2D6. These therapeutic approaches generally fall into two classes. One class comprises various methods for inhibiting the binding or association of the 103P2D6 protein with its binding partner or with others proteins. Another class comprises a variety of methods for inhibiting the transcription of the 103P2D6 gene or translation of 103P2D6 mRNA.

X.A.) 103P2D6 as a Target for Antibody-Based Therapy

103P2D6 is an attractive target for antibody-based therapeutic strategies. A number of antibody strategies are known in the art for targeting both extracellular and intracellular molecules (see, e.g., complement and ADCC mediated killing as well as the use of intrabodies). Because 103P2D6 is expressed by cancer cells of various lineages and not by corresponding normal cells, systemic administration of 103P2D6-immunoreactive compositions are prepared that exhibit excellent sensitivity without toxic, non-specific and/or non-target effects caused by binding of the immunoreactive composition to non-target organs and tissues. Antibodies specifically reactive with domains of 103P2D6 are useful to treat 103P2D6-expressing cancers systemically, either as conjugates with a toxin or therapeutic agent, or as naked antibodies capable of inhibiting cell proliferation or function.

103P2D6 antibodies can be introduced into a patient such that the antibody binds to 103P2D6 and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 103P2D6, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of the 103P2D6 sequence shown in FIG. 2. In addition, skilled artisans understand that it is routine to conjugate antibodies to cytotoxic agents. When cytotoxic and/or therapeutic agents are delivered directly to cells, such as by conjugating them to antibodies specific for a molecule expressed by that cell (e.g. 103P2D6), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-103P2D6 antibody) that binds to a marker (e.g. 103P2D6) expressed, accessible to binding or localized on the cell surfaces. A typical embodiment is a method of delivering a cytotoxic and/or therapeutic agent to a cell expressing 103P2D6, comprising conjugating the cytotoxic agent to an antibody that immunospecifically binds to a 103P2D6 epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-103P2D6 antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin, such as the conjugation of $^{131}$I to anti-CD20 antibodies (e.g., Rituxan™, IDEC Pharmaceuticals Corp.), while others involve co-administration of antibodies and other therapeutic agents, such as Herceptin™ (trastuzumab) with paclitaxel (Genentech, Inc.). To treat prostate cancer, for example, 103P2D6 antibodies can be administered in conjunction with radiation, chemotherapy or hormone ablation.

Although 103P2D6 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 103P2D6 expression, preferably using immunohistochemical assessments of tumor tissue, quantitative 103P2D6 imaging, or other techniques that reliably indicate the presence and degree of 103P2D6 expression. Immunohistochemical analysis of tumor biopsies or surgical specimens is preferred for this purpose. Methods for immunohistochemical analysis of tumor tissues are well known in the art.

Anti-103P2D6 monoclonal antibodies that treat prostate and other cancers include those that initiate a potent immune response against the tumor or those that are directly cytotoxic. In this regard, anti-103P2D6 monoclonal antibodies (mAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-103P2D6 mAbs that exert a direct biological effect on tumor growth are useful to treat cancers that express 103P2D6. Mechanisms by which directly cytotoxic mAbs act include: inhibition of cell growth, modulation of cellular differentiation, modulation of tumor angiogenesis factor profiles, and the induction of apoptosis. The mechanism(s) by which a particular anti-103P2D6 mAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric mAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target 103P2D6 antigen with high affinity but exhibit low or no antigenicity in the patient.

Therapeutic methods of the invention contemplate the administration of single anti-103P2D6 mAbs as well as combinations, or cocktails, of different mabs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, anti-103P2D6 mAbs can be administered concomitantly with other therapeutic modalities, including but not limited to various chemotherapeutic agents, androgen-blockers, immune modulators (e.g., IL-2, GM-CSF), surgery or radiation. The anti-103P2D6 mAbs are administered in their "naked" or unconjugated form, or can have a therapeutic agent(s) conjugated to them.

Anti-103P2D6 antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti-103P2D6 antibody preparation, via an acceptable route of administration such as intravenous injection (IV), typically at a dose in the range of about 0.1 to about 10 mg/kg body weight. In general, doses in the range of 10-500 mg mAb per week are effective and well tolerated.

Based on clinical experience with the Herceptin mAb in the treatment of metastatic breast cancer, an initial loading dose of approximately 4 mg/kg patient body weight IV, followed by weekly doses of about 2 mg/kg IV of the anti-103P2D6 mAb preparation represents an acceptable dosing regimen. Preferably, the initial loading dose is administered as a 90 minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or mAbs used, the degree of 103P2D6 expression in the patient, the extent of circulating shed 103P2D6 antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 103P2D6 in a given sample (e.g. the levels of circulating 103P2D6 antigen and/or 103P2D6 expressing cells) in order to assist in the determination of the most effective dosing regimen, etc. Such evaluations are also used for monitoring purposes throughout therapy, and are useful to gauge therapeutic success in combination with the evaluation of other parameters (such as serum PSA levels in prostate cancer therapy).

X.B.) Anti-Cancer Vaccines

The invention further provides cancer vaccines comprising a 103P2D6-related protein or 103P2D6-related nucleic acid. In view of the expression of 103P2D6, cancer vaccines prevent and/or treat 103P2D6-expressing cancers without creating non-specific effects on non-target tissues. The use of a tumor antigen in a vaccine that generates humoral and/or cell-mediated immune responses as anti-cancer therapy is well known in the art and has been employed in prostate cancer using human PSMA and rodent PAP immunogens (Hodge et al., 1995, Int. J. Cancer 63:231-237; Fong et al., 1997, J. Immunol. 159:3113-3117).

Genetic immunization methods can be employed to generate prophylactic or therapeutic humoral and cellular immune responses directed against cancer cells expressing 103P2D6. Constructs comprising DNA encoding a 103P2D6-related protein/immunogen and appropriate regulatory sequences can be injected directly into muscle or skin of an individual, such that the cells of the muscle or skin take-up the construct and express the encoded 103P2D6 protein/immunogen. Alternatively, a vaccine comprises a 103P2D6-related protein. Expression of the 103P2D6-related protein immunogen results in the generation of prophylactic or therapeutic humoral and cellular immunity against cells that bear 103P2D6 protein. Various prophylactic and therapeutic genetic immunization techniques known in the art can be used (for review, see information and references published at Internet address www.genweb.com).

Such methods can be readily practiced by employing a 103P2D6-related protein, or an 103P2D6-encoding nucleic acid molecule and recombinant vectors capable of expressing and presenting the 103P2D6 immunogen (which typically comprises a number of antibody or T cell epitopes). Skilled artisans understand that a wide variety of vaccine systems for delivery of immunoreactive epitopes are known in the art (see, e.g., Heryln et al., Ann Med February 1999;31(1):66-78; Maruyama et al., Cancer Immunol Immunother June 2000; 49(3):123-32) Briefly, such methods of generating an immune response (e.g. humoral and/or cell-mediated) in a mammal, comprise the steps of: exposing the manmmal's immune system to an immunoreactive epitope (e.g. an epitope present in the 103P2D6 protein shown in SEQ ID NO: 2 or analog or homolog thereof) so that the mammal generates an immune response that is specific for that epitope (e.g. generates antibodies that specifically recognize that epitope). In a preferred method, the 103P2D6 immunogen contains a biological motif.

CTL epitopes can be determined using specific algorithms to identify peptides within 103P2D6 protein that are capable of optimally binding to specified HLA alleles (e.g., Table IV (A) and Table IV (B); Epimatrix™, Brown University which are found at the world wide web address (brown.edu/edu/Research/TB-HIV_Lab/epimatrix/epimatrix.html); and, BIMAS, (bimas.dert.nih.gov/). In a preferred embodiment, the 103P2D6 immunogen contains one or more amino acid sequences identified using one of the pertinent analytical techniques well known in the art, such as the sequences shown in Tables V-XVIII or a peptide of 8, 9, 10 or 11 amino acids specified by an HLA Class I motif (e.g., Table IV (A)) and/or a peptide of at least 9 amino acids that comprises an HLA Class II motif (e.g., Table IV (B)). As is appreciated in the art, the HLA Class I binding grove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, but can be longer than 25 amino acids.

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. the 103P2D6 protein) so that an immune response is generated. A typical embodiment consists of a method for generating an immune response to 103P2D6 in a host, by contacting the host with a sufficient amount of at least one 103P2D6 B cell or cytotoxic T-cell epitope or analog thereof; and at least one periodic interval thereafter re-contacting the host with the 103P2D6 B cell or cytotoxic T-cell epitope or analog thereof. A specific embodiment consists of a method of generating an immune response against a 103P2D6-related protein or a man-made multiepitopic peptide comprising: administering 103P2D6 immunogen (e.g. the 103P2D6 protein or a peptide fragment thereof, an 103P2D6 fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., J. Immunol. 2000 164(3); 164(3): 1625-1633; Alexander et al., Immunity 1994 1(9): 751-761 and Alexander et al., Immunol. Res. 1998 18(2): 79-92). An alternative method comprises generating an immune response in an individual against a 103P2D6 immunogen by: administering in vivo to muscle or skin of the individual's body a DNA molecule that comprises a DNA sequence that encodes an 103P2D6 immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). The DNA can be dissociated from an infectious agent. Optionally a genetic vaccine facilitator such as anionic lipids; saponins; lectins; estrogenic compounds; hydroxylated lower alkyls; dimethyl sulfoxide; and urea is also administered.

Thus, viral gene delivery systems are used to deliver a 103P2D6-related nucleic acid molecule. Various viral gene delivery systems that can be used in the practice of the invention include, but are not limited to, vaccinia, fowlpox, canarypox, adenovirus, influenza, poliovirus, adeno-associated virus, lentivirus, and sindbus virus (Restifo, 1996, Curr. Opin.

Immunol. 8:658-663). Non-viral delivery systems can also be employed by introducing naked DNA encoding a 103P2D6-related protein into the patient (e.g., intramuscularly or intradermally) to induce an anti-tumor response. In one embodiment, the full-length human 103P2D6 cDNA is employed. In another embodiment, 103P2D6 nucleic acid molecules encoding specific cytotoxic T lymphocyte (CTL) and/or antibody epitopes are employed.

Various ex vivo strategies can also be employed to generate an immune response. One approach involves the use of antigen presenting cells (APCs) such as dendritic cells to present 103P2D6 antigen to a patient's immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65-69; Murphy et al., 1996, Prostate 29:371-380). Thus, dendritic cells can be used to present 103P2D6 peptides to T cells in the context of MHC class I or II molecules. In one embodiment, autologous dendritic cells are pulsed with 103P2D6 peptides capable of binding to MHC class I and/or class II molecules. In another embodiment, dendritic cells are pulsed with the complete 103P2D6 protein. Yet another embodiment involves engineering the overexpression of the 103P2D6 gene in dendritic cells using various implementing vectors known in the art, such as adenovirus (Arthur et al., 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2865-2869), or tumor-derived RNA transfection (Ashley et al., 1997, J. Exp. Med. 186:1177-1182). Cells that express 103P2D6 can also be engineered to express immune modulators, such as GM-CSF, and used as immunizing agents.

Anti-idiotypic anti-103P2D6 antibodies can also be used in anti-cancer therapy as a vaccine for inducing an immune response to cells expressing a 103P2D6-related protein. In particular, the generation of anti-idiotypic antibodies is well known in the art; this methodology can readily be adapted to generate anti-idiotypic anti-103P2D6 antibodies that mimic an epitope on a 103P2D6-related protein (see, for example, Wagner et al., 1997, Hybridoma 16: 33-40; Foon et al., 1995, J. Clin. Invest. 96:334-342; Herlyn et al., 1996, Cancer Immunol. Immunother. 43:65-76). Such an anti-idiotypic antibody can be used in cancer vaccine strategies.

XI.) Inhibition of 103P2D6 Protein Function

The invention includes various methods and compositions for inhibiting the binding of 103P2D6 to its binding partner or its association with other protein(s) as well as methods for inhibiting 103P2D6 function.

XI.A.) Inhibition of 103P2D6 with Intracellular Antibodies

In one approach, a recombinant vector that encodes single chain antibodies that specifically bind to 103P2D6 are introduced into 103P2D6 expressing cells via gene transfer technologies. Accordingly, the encoded single chain anti-103P2D6 antibody is expressed intracellularly, binds to 103P2D6 protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to precisely target the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 103P2D6 in the nucleus, thereby preventing its activity within the nucleus. Nuclear targeting signals are engineered into such 103P2D6 intrabodies in order to achieve the desired targeting. Such 103P2D6 intrabodies are designed to bind specifically to a particular 103P2D6 domain. In another embodiment, cytosolic intrabodies that specifically bind to the 103P2D6 protein are used to prevent 103P2D6 from gaining access to the nucleus, thereby preventing it from exerting any biological activity within the nucleus (e.g., preventing 103P2D6 from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued Jul. 6, 1999).

XI.B.) Inhibition of 103P2D6 with Recombinant Proteins

In another approach, recombinant molecules bind to 103P2D6 and thereby inhibit 103P2D6 function. For example, these recombinant molecules prevent or inhibit 103P2D6 from accessing/binding to its binding partner(s) or associating with other protein(s). Such recombinant molecules can, for example, contain the reactive part(s) of a 103P2D6 specific antibody molecule. In a particular embodiment the 103P2D6 binding domain of a 103P2D6 binding partner is engineered into a dimeric fusion protein, whereby the fusion protein comprises two 103P2D6 ligand binding domains linked to the Fc portion of a human IgG, such as human IgG1. Such IgG portion can contain, for example, the $C_H2$ and $C_H3$ domains and the hinge region, but not the $C_H1$ domain. Such dimeric fusion proteins are administered in soluble form to patients suffering from a cancer associated with the expression of 103P2D6, whereby the dimeric fusion protein specifically binds to 103P2D6 and blocks 103P2D6 interaction with a binding partner. Such dimeric fusion proteins are further combined into multimeric proteins using known antibody linking technologies.

XI.C.) Inhibition of 103P2D6 Transcription or Translation

The present invention also comprises various methods and compositions for inhibiting the transcription of the 103P2D6 gene. Similarly, the invention also provides methods and compositions for inhibiting the translation of 103P2D6 mRNA into protein.

In one approach, a method of inhibiting the transcription of the 103P2D6 gene comprises contacting the 103P2D6 gene with a 103P2D6 antisense polynucleotide. In another approach, a method of inhibiting 103P2D6 mRNA translation comprises contacting the 103P2D6 mRNA with an antisense polynucleotide. In another approach, a 103P2D6 specific ribozyme is used to cleave the 103P2D6 message, thereby inhibiting translation. Such antisense and ribozyme based methods can also be directed to the regulatory regions of the 103P2D6 gene, such as the 103P2D6 promoter and/or enhancer elements. Similarly, proteins capable of inhibiting a 103P2D6 gene transcription factor are used to inhibit 103P2D6 mRNA transcription. The various polynucleotides and compositions useful in the aforementioned methods have been described above. The use of antisense and ribozyme molecules to inhibit transcription and translation is well known in the art.

Other factors that inhibit the transcription of 103P2D6 by interfering with 103P2D6 transcriptional activation are also useful to treat cancers expressing 103P2D6. Similarly, factors that interfere with 103P2D6 processing are useful to treat cancers that express 103P2D6. Cancer treatment methods utilizing such factors are also within the scope of the invention.

XI.D.) General Considerations for Therapeutic Strategies

Gene transfer and gene therapy technologies can be used to deliver therapeutic polynucleotide molecules to tumor cells synthesizing 103P2D6 (i.e., antisense, ribozyme, polynucleotides encoding intrabodies and other 103P2D6 inhibitory molecules). A number of gene therapy approaches are known in the art. Recombinant vectors encoding 103P2D6 antisense polynucleotides, ribozymes, factors capable of interfering with 103P2D6 transcription, and so fort, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of 103P2D6 to a binding partner, etc.

In vivo, the effect of a 103P2D6 therapeutic composition can be evaluated in a suitable animal model. For example, xenogenic prostate cancer models can be used, wherein human prostate cancer explants or passaged xenograft tissues are introduced into immune compromised animals, such as nude or SCID mice (Klein et al., 1997, Nature Medicine 3: 402-408). For example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like. In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing nice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XII.) Kits

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. Such probe can be an antibody or polynucleotide specific for a 103P2D6-related protein or a 103P2D6 gene or message, respectively. Where the method utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label. The kit can include all or part of the amino acid sequence of FIG. 2 or analogs thereof, or a nucleic acid molecule that encodes such amino acid sequences.

The kit of the invention will typically comprise the container described above and one or more other containers comprising materials desirable from a commercial and user standpoint, including buffers, diluents, filters, needles, syringes, and package inserts with instructions for use.

A label can be present on the container to indicate that the composition is used for a specific therapy or non-therapeutic application, and can also indicate directions for either in vivo or in vitro use, such as those described above. Directions and or other information can also be included on an insert which is included with the kit.

p103P2D6-B (clone B) has been deposited under the requirements of the Budapest Treaty on May 19, 2000 with the American Type Culture Collection (ATCC), 10801 University Blvd., Manassas, Va. 20110-2209 USA, and has been identified as ATCC Accession No. PTA-1895. p 103P2D6-2 (clone 2) has been deposited under the requirements of the Budapest Treaty on Jan. 6, 2000 with the American Type Culture Collection (ATCC), 10801 University Blvd., Manassas, Va. 20110-2209 USA, and has been identified as ATCC Accession No. PTA-1155.

EXAMPLES

Various aspects of the invention are further described and illustrated by way of the several examples that follow, none of which are intended to limit the scope of the invention.

Example 1

SSH-Generated Isolation of a cDNA Fragment of the 103P2D6 Gene

Characterization of 103P2D6 by Suppression Subtractive Hybridization (SSH)

As discussed in detail below, experiments with the LAPC-4 AD xenograft in male SCID mice have resulted in the identification of genes that are involved in the progression of androgen dependent (AD) prostate cancer to androgen independent (AI) cancer. Briefly, mice that harbored LAPC-4 AD xenografts were castrated when the tumors reached a size of 1 cm in diameter. The tumors regressed in size and temporarily stopped producing the androgen dependent protein PSA. Seven to fourteen days post-castration, PSA levels were detectable again in the blood of the mice. Eventually such tumors develop an AI phenotype and start growing again in the castrated males. Tumors were harvested at different time points after castration to identify genes that are turned on or off during the transition to androgen independence.

Suppression subtractive hybridization (SSH) (Diatchenko et al., 1996, PNAS 93:6025) was then used to identify novel genes, such as those that are overexpressed in prostate cancer, by comparing cDNAs from various androgen dependent and androgen independent LAPC xenografts. This strategy resulted in the identification of novel genes exhibiting prostate cancer specific expression. One of these genes, designated 103P2D6, was identified from a subtraction where cDNA derived from an LAPC-4 AD tumor grown in an intact male was subtracted from cDNA derived from an LAPC-4 AD tumor, 21 days post-castration. The SSH DNA sequence of about 342 bp (FIG. 1) is novel and exhibits no homology to sequences in the public databases.

103P2D6, encodes a transmembrane protein that exhibits tumor-specific expression. Expression analysis of 103P2D6 indicates that it is exclusively expressed in cancer of the prostate and other cancer tissues. 103P2D6 is expressed in fetal heart, kidney and lung, but not in normal adult tissues. The expression of 103P2D6 in cancer provides evidence that this protein has a functional role in tumor progression and/or initiation. It is possible that 103P2D6 functions as a receptor involved in activating or modulating proliferation signals involved in tumorigenesis and regulation of cell growth.

As is further described herein, the 103P2D6 gene and protein have been characterized using a number of analytical approaches. For example, analyses of nucleotide coding and amino acid sequences were conducted in order to identify potentially related molecules, as well as recognizable structural domains, topological features, and other elements within the 103P2D6 mRNA and protein structures. Northern blot analyses of 103P2D6 mRNA expression were conducted in order to establish the range of normal and cancerous tissues expressing 103P2D6 message.

Materials and Methods

LAPC Xenoyrafts and Human Tissues:

LAPC xenografts were obtained from Dr. Charles Sawyers (UCLA) and generated as described (Klein et al, 1997, Nature Med. 3: 402-408; Craft et al., 1999, Cancer Res. 59: 5030-5036). Androgen dependent and independent LAPC-4 xenografts (LAPC-4 AD and AI, respectively) and LAPC-9 xenografts (LAPC-9 AD and AI, respectively) were grown in intact male SCID mice or in castrated males, respectively, and were passaged as small tissue chunks in recipient males. LAPC-4 AI xenografts were derived from LAPC-4 AD tumors and LAPC-9 AI xenografts were derived from LAPC-9 AD tumors. To generate the AI xenografts, male mice bearing LAPC AD tumors were castrated and maintained for 2-3 months. After the LAPC tumors re-grew, the tumors were harvested and passaged in castrated males or in female SCID mice.

Cell Lines:

Human cell lines (e.g., HeLa) were obtained from the ATCC and were maintained in DMEM with 5% fetal calf serum.

RNA Isolation:

Tumor tissue and cell lines were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.
DPNCDN (cDNA Synthesis Primer):
5'TTTTGATCAAGCTT$_{30}$3' (SEQ ID NO: 7)

```
Adaptor 1:

5'CTAATACGACTCACTATAGGGCTCGAGCGGCCGCCCGGGCAG3'    (SEQ ID NO: 8)
                              3'CGGCCCGTCCTAG5'    (SEQ ID NO: 9)
```

```
-continued

Adaptor 2:

5'GTAATACGACTCACTATAGGGCAGCGTGGTCGCGGCCGAG3'      (SEQ ID NO: 10)
                              3'CGGCTCCTAG5'     (SEQ ID NO: 11)

PCR primer 1:

5'CTAATACGACTCACTATAGGGC3'                        (SEQ ID NO: 12)

Nested primer (NP) 1:

5'TCGAGCGGCCGCCCGGGCAGGA3'                        (SEQ ID NO: 13)

Nested primer (NP)2:

5'AGCGTGGTCGCGGCCGAGGA3'                          (SEQ ID NO: 14)
```

Suppression Subtractive Hybridization:

Suppression subtractive hybridization (SSH) was used to identify cDNAs corresponding to genes that may be differentially expressed in prostate cancer. The SSH reaction utilized cDNA from two LAPC-4 AD xenografts. Specifically, the 103P2D6 SSH sequence was identified from a subtraction where cDNA derived from an LAPC-4 AD tumor grown in an intact male was subtracted from cDNA derived from an LAPC-4 AD tumor, 21 days post-castration. The LAPC-4 AD xenograft tumor, 21 days post-castration, was used as the source of the "tester" cDNA, while the cDNA from the LAPC-4 AD tumor grown in an intact male was used as the source of the "driver" cDNA.

Double stranded cDNAs corresponding to tester and driver cDNAs were synthesized from 2 μg of poly(A)+ RNA isolated from the relevant xenograft tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs. at 37° C. Digested cDNA was extracted with phenol/chloroform (1:1) and ethanol precipitated.

Driver cDNA was generated by combining in a 1:1 ratio Dpn II digested cDNA from the relevant xenograft source (see above) with a mix of digested cDNAs derived from human benign prostatic hyperplasia (BPH), the human cell lines HeLa, 293, A431, Colo205, and mouse liver.

Tester cDNA was generated by diluting 1 μl of Dpn II digested cDNA from the relevant xenograft source (see above) (400 ng) in 5 μl of water. The diluted cDNA (2 μl, 160 ng) was then ligated to 2 II of Adaptor 1 and Adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 III (600 ng) of driver cDNA to each of two tubes containing 1.5 μl (20 ng) Adaptor 1- and Adaptor 2-ligated tester cDNA. In a final volume of 4 μl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10×reaction buffer (CLONTECH) and 0.5 μl 50×Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10-12 cycles of 94° C. for 10 sec, 68° C. for 30 sec, and 72° C. for 1.5 minutes. The PCR products were analyzed using 2% agarose gel electrophoresis.

The PCR products were inserted into pCR2.1 using the T/A vector cloning kit (Invitrogen). Transformed *E. coli* were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dbest, and NCI-CGAP databases.

Results

Two SSH experiments described in the Materials and Methods, supra, led to the isolation of numerous candidate gene fragment clones (SSH clones). All candidate clones were sequenced and subjected to homology analysis against all sequences in the major public gene and EST databases in order to provide information on the identity of the corresponding gene and to help guide the decision to analyze a particular gene for differential expression. In general, gene fragments that had no homology to any known sequence in any of the searched databases, and thus considered to represent novel genes, as well as gene fragments showing homology to previously sequenced expressed sequence tags (ESTs), were subjected to differential expression analysis by RT-PCR and/or northern analysis.

One of the SHH clones comprising about 342 bp, showed no homology to any known gene Or to any sequences in the public databases, and was designated 103P2D6. Northern expression analysis of first strand cDNAs from 16 normal tissues showed a highly prostate tumor-specific expression pattern in adult tissues (FIG. 5A-C).

Example 2

Full Length Cloning of 103P2D6 and Homology Comparison to Known Sequences

A partial 103P2D6 cDNA clone (clone 2) of 1687 base pairs (bp) was cloned from an LAPC-4 AD cDNA library (Lambda ZAP Express, Stratagene). A full-length 103P2D6 cDNA clone (FIG. 2) (clone B) of 4728 base pairs (b.p.) was cloned from a human fetal brain library (Pangene Inc.). The cDNA encodes a putative open reading frame (ORF) of 563 amino acids. Its calculated molecular weight (MW) is 63.4 kDa and its pI is 8.15. At the protein level, 103P2D6 shows 24.9% identity and 32.8% homology, taking account of any gaps, to an Envelope protein (Q9UNM3) isolated from a human endogenous retroviral protein HERV-H (Virology 1999, 258:441). The 103P2D6 nucleic acid sequence overlaps with some ESTs derived from kidney, fetus, brain and placenta.

The full-length 103P2D6 cDNA (clone B) was deposited on May 19, 2000, with the American Type Culture Collection (ATCC; Manassas, Va.) as plasmid p103P2D6-B, and has been assigned Accession No. PTA-1895. The partial 103P2D6 cDNA (clone 2) was deposited on Jan. 6, 2000, with the American Type Culture Collection (ATCC; Manassas, Va.) as plasmid p103P2D6-2, and has been assigned Accession No. PTA-1155.

Example 3

103P2D6 Gene & Protein Expression Analysis

Northern Expression Analysis:

103P2D6 mRNA expression in normal human tissues was analyzed by northern blotting of multiple tissue blots (Clontech; Palo Alto, Calif.), comprising a total of 16 different normal human tissues, using labeled 103P2D6 SSH fragment (Example 1) as a probe. RNA samples were quantitatively normalized with a β-actin probe. Northern blot analysis using an 103P2D6 SSH fragment probe performed on 16 normal tissues failed to show expression in any normal tissues, including brain, ovary, heart, lung, liver, kidney, pancreas, small intestine, placenta, leukocytes, testis, prostate, colon, skeletal muscle, thymus and spleen (FIG. 5).

Figure 6B:
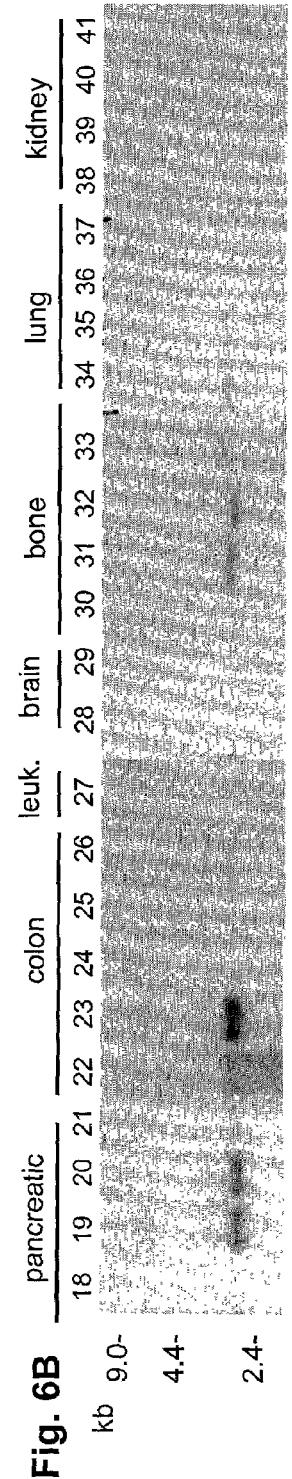
Figure 6C:
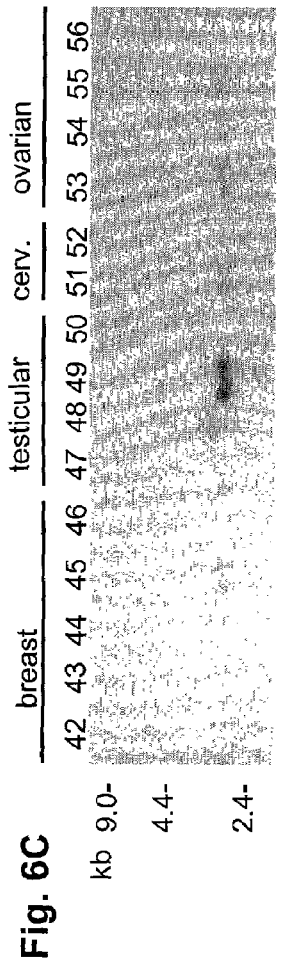

To analyze 103P2D6 expression in cancer tissues, northern blotting was performed on RNA derived from the LAPC xenografts, and several prostate and non-prostate cancer cell lines. The results show high expression levels of a 3 kb transcript in LAPC-4 AD, LAPC-4 Al, LAPC-9 AD, and LAPC-9 AI (FIG. 5, FIG. 6). More detailed analysis of the LAPC-4 xenografts shows that 103P2D6 is expressed at equal levels whether the xenografts are grown subcutaneously (LAPC-4 sc) or within the tibia of mice (LAPC-4 AD it) (FIG. 7). Expression was also detected in a xenograft that was grown within human bone explants in SCID mice (the LAPC-4 AD$^2$). This indicates that bone growth of these prostate cancer tissues does not diminish their expression.

Expression of 103P2D6 was detected in several cancer cell lines derived from prostate (LNCaP, DU145, LAPC-4 CL), bladder (HT1197, 5637), pancreas (BxPC-3, HPAC, CAPAN-1), colon (SK-CO-1, CACO-2), bone (HOS, U2-OS, RD-ES), lung (CALU-1), breast (MCF-7), testis (NCCIT, TERA-1), cervix (A431), and ovary (OV-1063, PA-1, SW626) (FIG. 6). These results suggest that the 103P2D6 is generally up-regulated in cancer cells and cancer tissues, especially in prostate, kidney and bladder cancer, and serves as a suitable target for cancer therapy.

Northern blot analysis of 103P2D6 showed expression only in cancer tissues and cell lines, but not in normal adult tissues. Furthermore, the 103P2D6 gene was cloned from a fetal brain library, suggesting that it is a fetal gene that is activated during tumorigenesis. To investigate this hypothesis, 9 week old fetal RNA derived from 6 organs and from the whole embryo were analyzed by Northern blotting using a 103P2D6 SSH probe. The results (FIG. 8) show that 103P2D6 is expressed in fetal heart, kidney and lung at the 9 week stage. This indicates that 103P2D6 is indeed a fetal gene that is turned on in cancer and serves a role in cancer biology.

Figure 13:
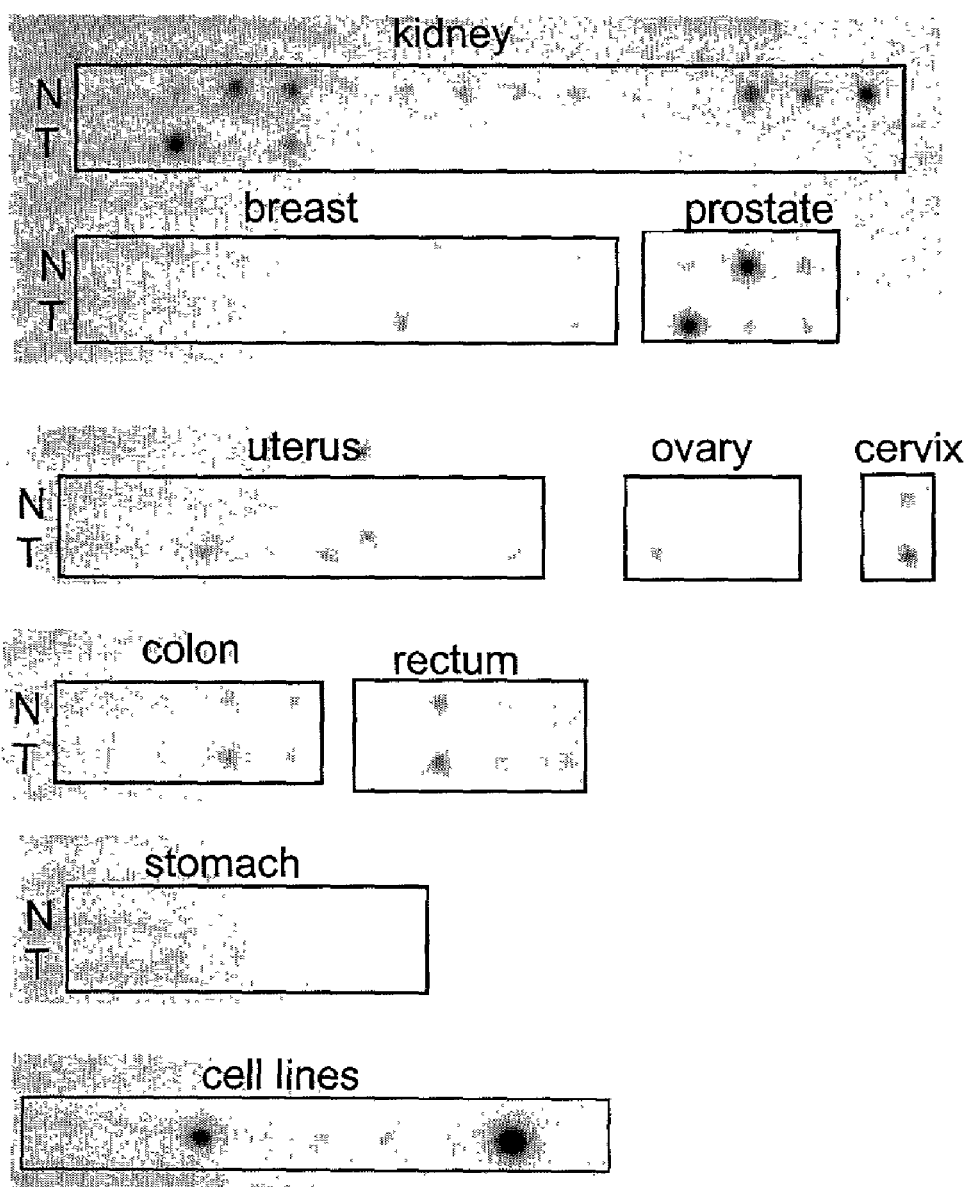
FIG. 13 shows the expression of 103P2D6 as assayed in a panel of human cancers (T) and their respective matched normal tissues (N) on RNA dot blots. 103P2D6 expression was seen in cancers of the kidney, breast, prostate, uterus, ovary, cervix, colon, stomach and rectum. 103P2D6 was also found to be highly expressed in the two human cancer cell lines, the CML line K562 and the colorectal carcinoma SW480. The expression detected in normal adjacent tissues (isolated from diseased tissues) but not in normal tissues, isolated from healthy donors, indicates that these tissues are not fully normal and that 103P2D6 may be expressed in early stage tumors and that it has utility as a diagnostic marker. Cancer cell lines are, from left to right, HeLa (cervical carcinoma); Daudi (Burkiff's lymphoma); K562 (CML); HL-60 (PML); G361 (melanoma); A549 (lung carcinoma); MOLT-4 (lymphoblastic leuk.); SW480 (colorectal carcinoma); Raji (Burkitt's lymphoma).

Expression of 103P2D6 was assayed in a panel of human cancers (T) and their respective matched normal tissues (N) on RNA dot blots (FIG. 13). 103P2D6 expression was seen in cancers of the kidney, breast, prostate, uterus, ovary, cervix, colon, stomach and rectum. 103P2D6 was also found to be highly expressed in the two human cancer cell lines, the CML line K562 and the colorectal carcinoma SW480. The expression detected in normal adjacent tissues (isolated from diseased tissues) but not in normal tissues, isolated from healthy donors, indicates that these tissues are not fully normal and that 103P2D6 may be expressed in early stage tumors and that it has utility as a diagnostic marker.

Figure 14:
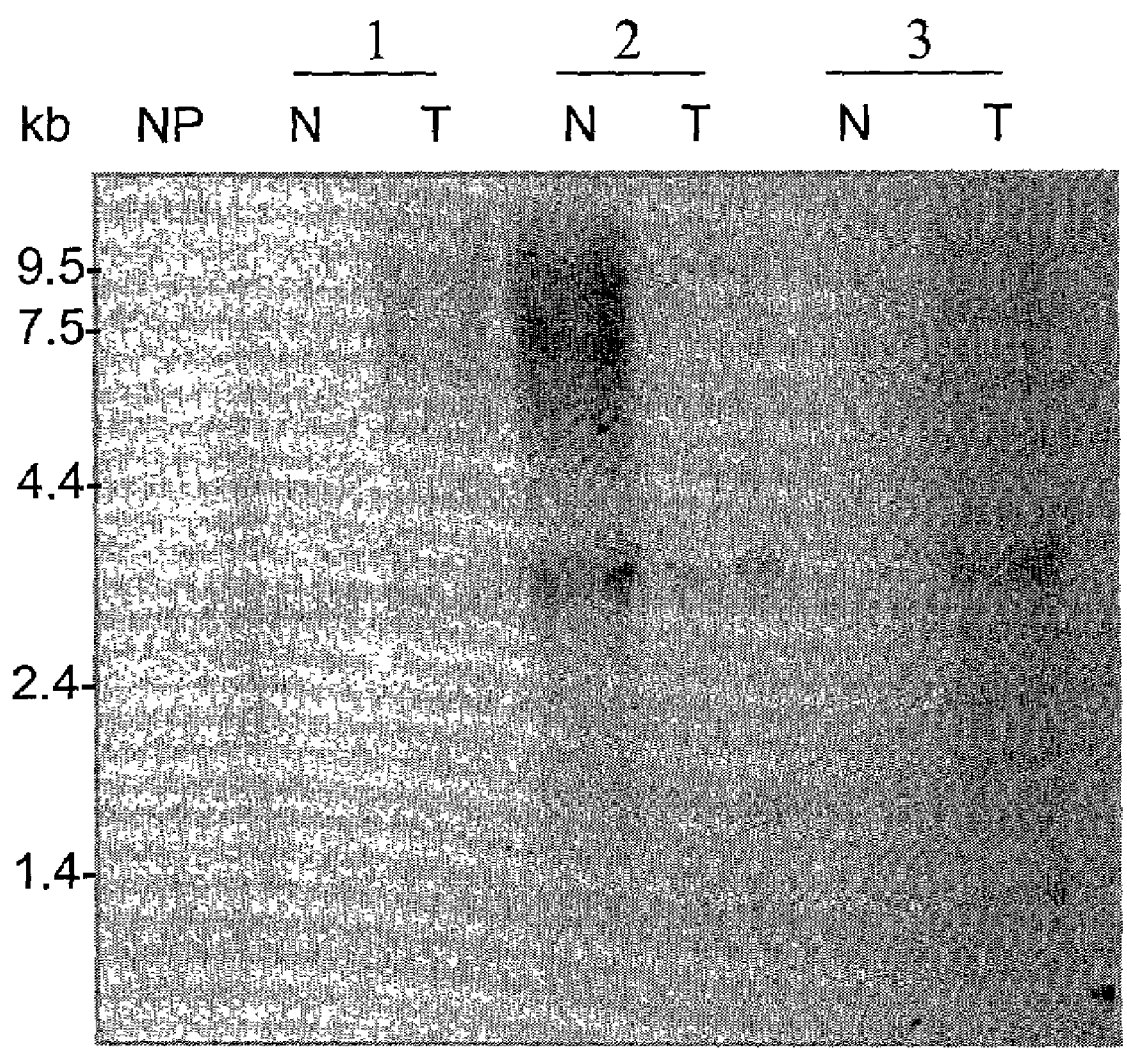
FIG. 14 shows data where RNA was isolated from prostate tumors (T) and their adjacent normal tissues (N) obtained from the following prostate cancer patients (Pt); patient 1, Gleason score 4+5; patient 2, Gleason score 3+4; and, patient 3, Gleason score 4+3. NP=normal prostate. Northern analysis was performed using 10 µg of total RNA for each sample. Expression of 103P2D6 was seen in all three tumor samples tested and their respective normal tissues.

FIG. 14 shows Northern data where RNA was isolated from prostate tumors (T) and their adjacent normal tissues (N) obtained from the following prostate cancer patients (Pt); patient 1, Gleason score 4+5; patient 2, Gleason score 3+4; and, patient 3, Gleason score 4+3. Northern analysis was performed using 10 μg of total RNA for each sample. Expression of 103P2D6 was seen in all three tumor samples tested and their respective normal tissues.

Figure 15:
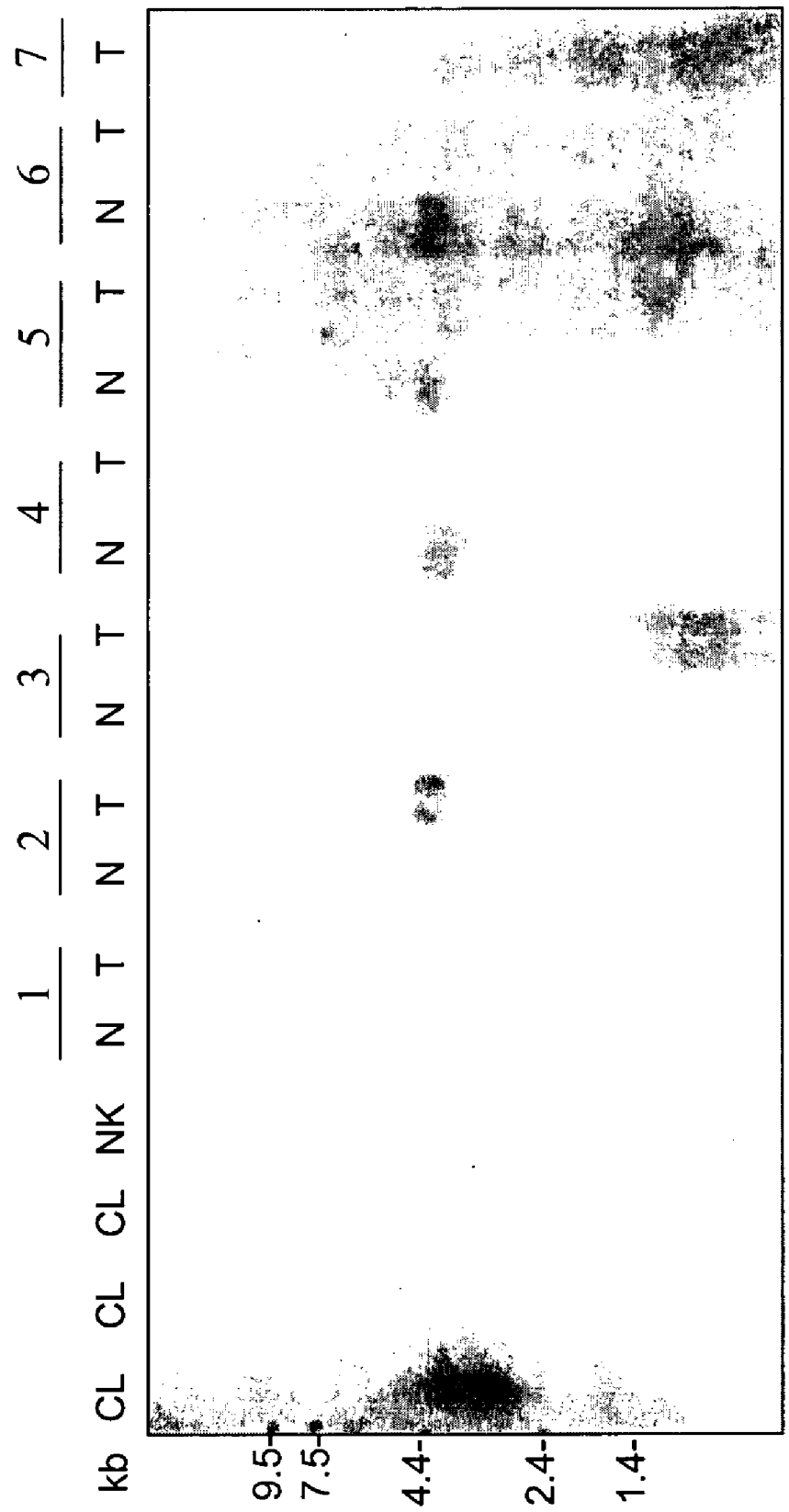
FIG. 15 provides data for Northern experiments where RNA was isolated from kidney tumors (T) and their adjacent normal tissues (N) obtained from the following kidney cancer patients: Patient 1-Papillary Type, Stage I, Grade 2/4; Patient 2—Invasive papillary carcinoma, Grade 2/4; Patient 3—Clear cell type Grade 1/3, focally 2/3; Patient 4—Clear cell type, stage III, Grade 2/4; Patient 5—Clear cell type, stage III, Grade 3/4; Patient 6—Clear cell type, stage III, Grade 3/4; Patient 7—Clear cell type, Grade III. CL=Cell lines (from left to right): 769-P, A498, SW839; NK=Normal kidney; N=Normal adjacent tissue; T=Tumor. The Northern analysis was performed using long of total RNA for each sample. Elevated expression of 103P2D6 was observed in kidney tumors and normal adjacent tissues isolated from kidney cancer patients as compared to normal kidney.

Data from a Northern analysis where RNA was isolated from kidney tumors (T) and their adjacent normal tissues (N) obtained from kidney cancer patients is shown in FIG. 15. The patient specifications are as follows: Patient 1—Papillary Type, Stage I, Grade 2/4; Patient 2—Invasive papillary carcinoma, Grade 2/4; Patient 3—Clear cell type Grade 1/3, focally 2/3; Patient 4—Clear cell type, stage III, Grade 2/4; Patient 5—Clear cell type, stage III, Grade 3/4; Patient 6—Clear cell type, stage III, Grade 3/4; Patient 7—Clear cell type, Grade III. In FIG. 15, CL=Cell lines (from left to right): 769-P, A498, SW839; NK=Normal kidney; N=Normal adjacent tissue; T=Tumor. The Northern analysis was performed using 10 μg of total RNA for each sample. Elevated expression of 103P2D6 was observed in kidney tumors and normal adjacent tissues isolated from kidney cancer patients as compared to normal kidney.

Figure 16:
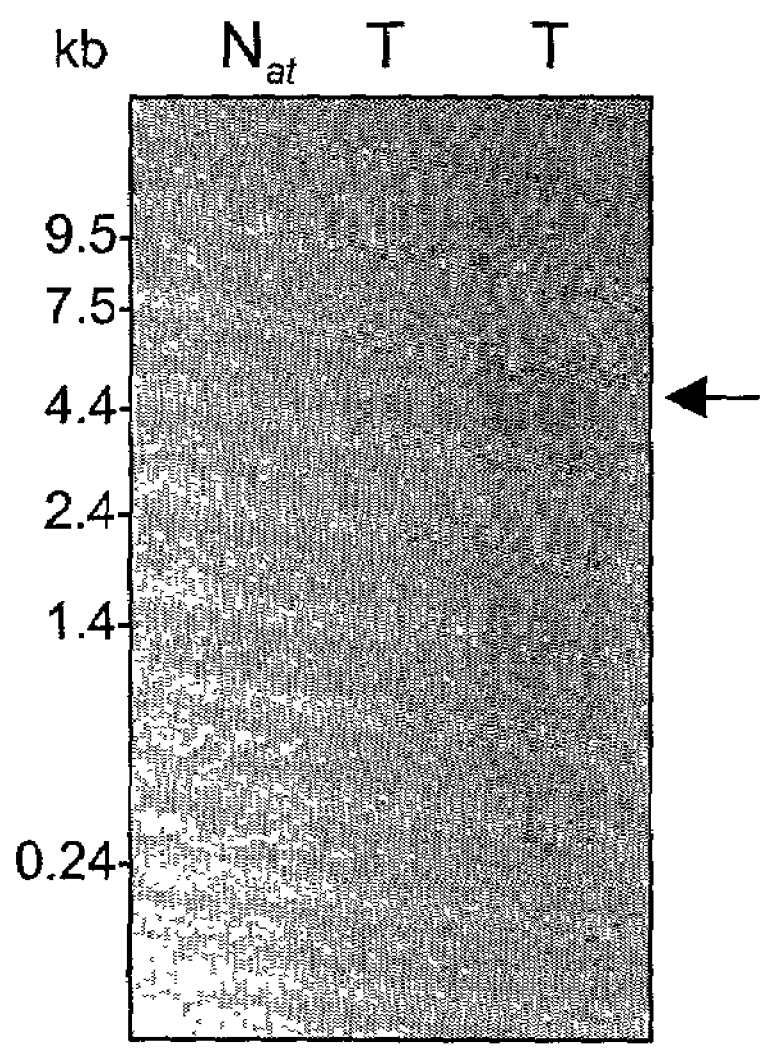
FIG. 16 shows the results of Northern analysis where RNA was isolated from bladder cancers and adjacent normal tissue obtained from bladder cancer patients. The Northern analysis was performed using 10 µg of total RNA for each sample. Expression of 103P2D6 was seen in bladder tumor but not in normal adjacent tissue. $N_{at}$=Normal adjacent tissue; T=Tumor.

FIG. 16 shows the results of Northern analysis where RNA was isolated from bladder cancers and adjacent normal tissue obtained from the bladder cancer patients. The Northern analysis was performed using 10 μg of total RNA for each sample. Expression of 103P2D6 was seen in bladder tumor but not in normal adjacent tissue.

RT-PCR Expression Analysis:

First strand cDNAs can be generated from 1 μg of mRNA with oligo (dT)12-18 priming using the Gibco-BRL Superscript Preamplification system. The manufacturer's protocol was used, which included an incubation for 50 min at 42° C.

with reverse transcriptase, followed by RNAse H treatment at 37° C. for 20 min. After completing the reaction, the volume can be increased to 200 µl with water prior to normalization. First strand cDNAs from 16 different normal human tissues can be obtained from Clontech.

Normalization of the first strand cDNAs from multiple tissues was performed by using the primers 5'-ATATCGC-CGCGCTCGTCGTCGACAA-3' (SEQ ID NO: 749) and 5'-AGCCACACGCAGCTCATTGTAGAAGG-3' (SEQ ID NO: 750) to amplify β-actin. First strand cDNA (5 µl) were amplified in a total volume of 50 µl containing 0.4 µM primers, 0.2 µM each dNTPs, 1XPCR buffer (Clontech, 10 mM Tris-HCL, 1.5 mM MgCl$_2$, 50 mM KCl, pH 8.3) and 1×Klentaq DNA polymerase (Clontech). Five µl of the PCR reaction can be removed at 18, 20, and 22 cycles and used for agarose gel electrophoresis. PCR was performed using an MJ Research thermal cycler under the following conditions: Initial denaturation can be at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 b.p. β-actin bands from multiple tissues were compared by visual inspection. Dilution factors for the first strand cDNAs were calculated to result in equal β-actin band intensities in all tissues after 22 cycles of PCR. Three rounds of normalization can be required to achieve equal band intensities in all tissues after 22 cycles of PCR.

To determine expression levels of the 103P2D6 gene, 5 µl of normalized first strand cDNA were analyzed by PCR using 25, 30, and 35 cycles of amplification. Semi quantitative expression analysis can be achieved by comparing the PCR products at cycle numbers that give light band intensities.

Figure 9:
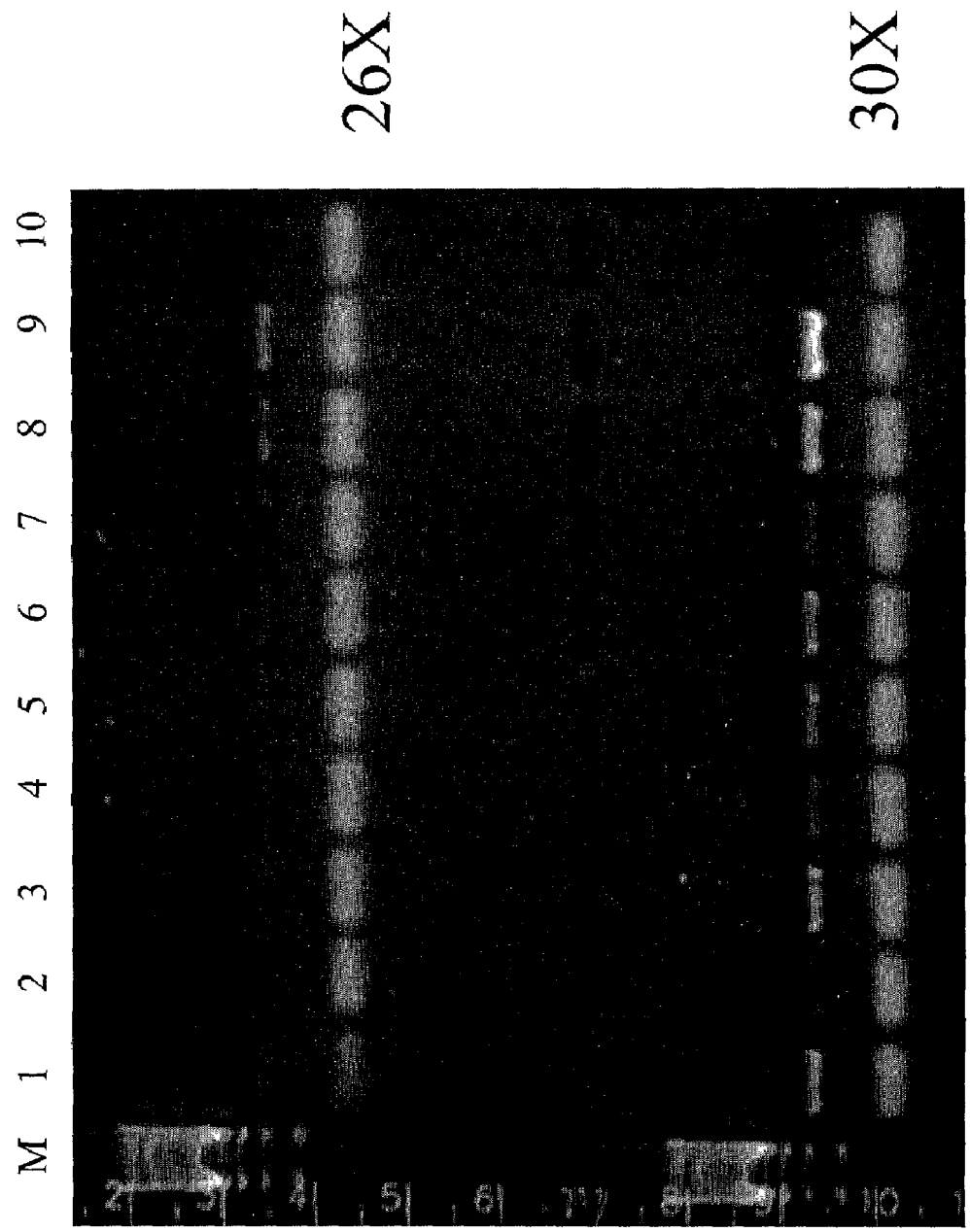
FIG. 9 shows a RT-PCR Expression analysis of 103P2D6. cDNAs generated using pools of tissues from multiple normal and cancer tissues were normalized using beta-actin primers and used to study the expression of 103P2D6. Aliquots of the RT-PCR mix after 26 (upper portion of this figure) and 30 cycles (lower portion of this figure) were run on the agarose gel to allow semi-quantitative evaluation of the levels of expression between samples. The first strand cDNAs in the various lanes of this figure are as follows: Lane 1 (VP-1) contains liver, lung, and kidney first strand cDNA from normal tissues; lane 2 (VP-2) stomach, spleen, and pancreas from normal tissues; lane 3 (xenograft tissue pool) LAPC4AD, LAPC4AI, LAPC9AD, and LAPC9AI; lane 4 is normal prostate tissue pool; lane 5 is prostate cancer tissue pool; lane 6 is bladder cancer tissue pool; lane 7 is kidney cancer tissue pool; lane 8 is colon cancer tissue pool; lane 9 is from a lung cancer patient; and lane 10 is water blank.
Figure 10:
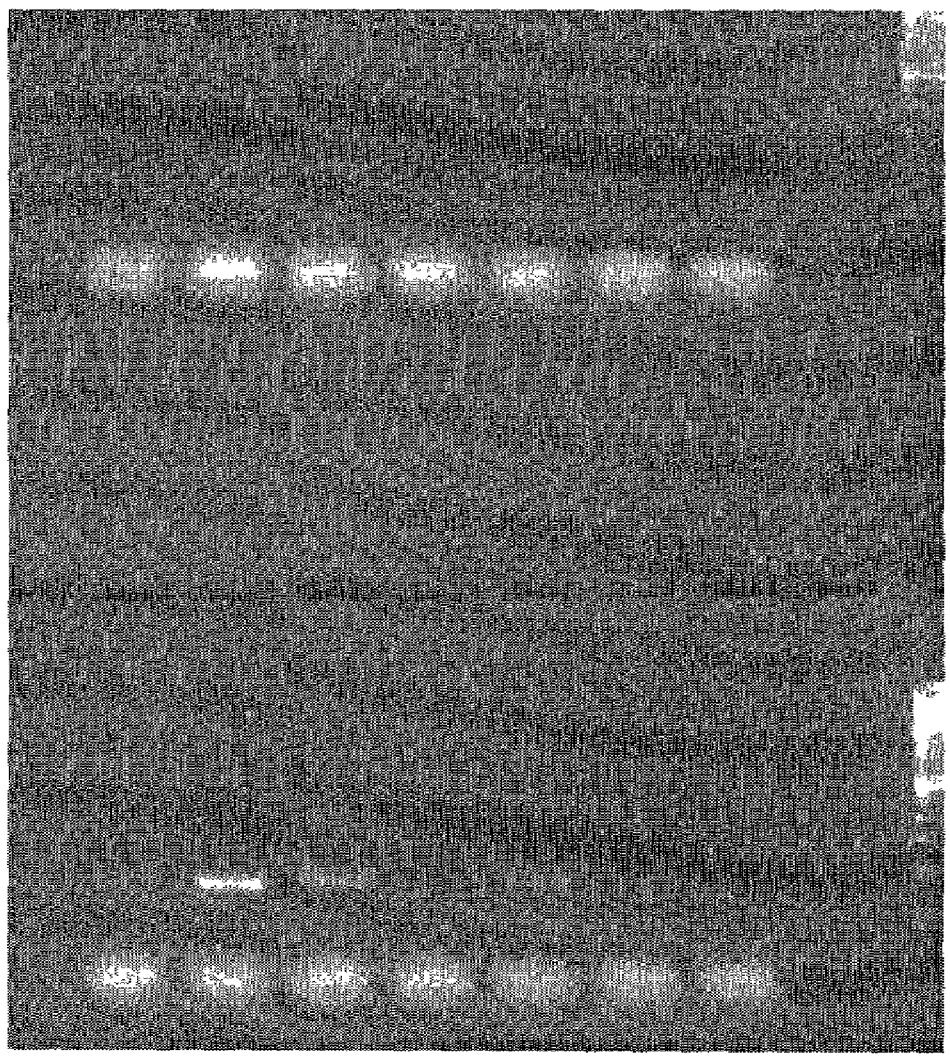
FIG. 10. shows the results of RT-PCR analysis of 103P2D6 expression in patient-derived cancers. Lane 1 contains a sample from normal prostate; lane 2 from normal kidney; lane 3 from a prostate tumor pool; lane 4 from a kidney tumor pool; lane 5 from a bladder tumor pool; lane 6 from HeLa cells; and for lane 7 water was used.

In a typical RT-PCR expression analysis shown in FIG. 9, RT-PCR expression analysis was performed on first strand cDNAs generated using pools of tissues from multiple samples. The cDNAs were subsequently normalized using beta-actin PCR. The highest expression was observed in colon cancer pool, xenograft pool, and a lung cancer patient. Lower levels of expression were also observed normal prostate, prostate cancer, bladder cancer, and kidney cancer tissue pools.

In an additional analysis, RT-PCR was used to analyze expression of 103P2D6 in normal tissues and in patient-derived cancers. First strand cDNAs were generated from 1 µg of mRNA with oligo (dT)12-18 priming using the Gibco-BRL Superscript Preamplification system. The manufacturers protocol was used and included an incubation for 50 min at 42° C. with reverse transcriptase followed by RNAse H treatment at 37° C. for 20 min. After completing the reaction, the volume was increased to 200 µl with water prior to normalization. First strand cDNAs were prepared from normal prostate, normal kidney and HeLa cancer cells, as well as a prostate tumor pool, a kidney tumor pool and a bladder tumor pool. The tumor pools were prepared from patient-derived tumor tissue. Normalization was performed by PCR using primers to actin and GAPDH. Semi-quantitative PCR was performed using primers to 103P2D6. The 103P2D6 primers used for RT-PCR were: CTTGGGAGGTCCTAGT-GCTAAGTG (SEQ. ID NO: 751) and CAATGAAGGGAC-TAACAACCCATC (SEQ. ID NO:752). The results are shown in FIG. 9, and confirm that 103P2D6 is expressed in cancerous tissues, particularly in prostate and bladder cancer tissues derived from patients.

Figure 11A:
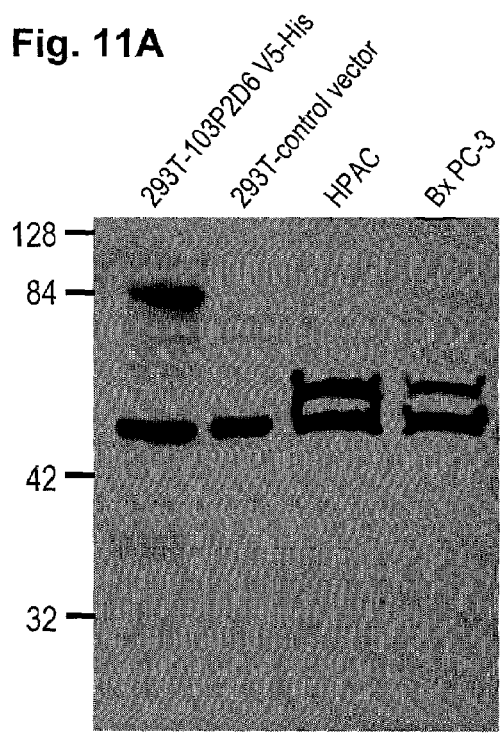
FIGS. 11A-C. shows expression of 103P2D6 in pancreatic, colon, and prostate cancer cell lines. In panels A and B, cell lysates (~25 μg) from the indicated cell lines were separated by SDS-PAGE and subjected to Western blot analysis using an anti-103P2D6 pAb. Indicated with an arrow is a strong anti-103P2D6 pAb immunoreactive band of approximately 60 kD present in the pancreatic cancer cell lines HPAC and Bx PC-3, the colon cancer cell line CaCo-2, and a less intense band in LAPC9 prostate cancer cells indicative of endogenous 103P2D6 protein expression. Also indicated with an arrow is the 85 kD immunoreactive band present in 293T cells transfected with V5-His tagged 103P2D6 cDNA. In panel C, Bx PC-3 pancreatic cancer cells were stained with anti-103P2D6 pAb (10 μg/ml) or control rabbit IgG Ab and subjected to flow cytometric analysis following incubation with anti-rabbit IgG-FITC conjugated secondary Ab. Bx PC-3 cells stained with the anti-103P2D6 pAb exhibited a fluorescence shift compared to the cells stained with control rabbit IgG, indicating cell surface expression of 103P2D6.
Figure 11B:
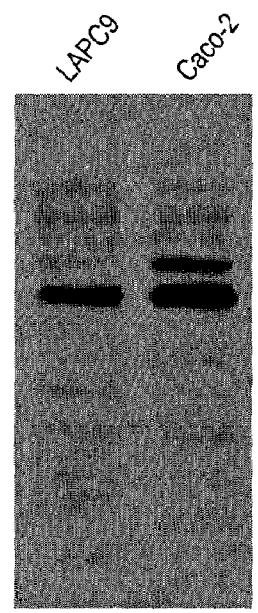

Protein Expression Analysis:

Expression of 103P2D6 protein was analyzed in pancreatic, colon, and prostate cancer cell lines using both western blot and flow cytometric analysis. As shown in FIGS. 11A-B, cell lysates (~25 µg) from the indicated cell lines were separated by SDS-PAGE and subjected to Western blot analysis using an anti-103P2D6 pAb (see Example 4, below). Indicated with an arrow is a strong anti-103P2D6 pAb immunoreactive band of approximately 60 kD present in the pancreatic cancer cell lines HPAC and Bx PC-3, the colon cancer cell line CaCo-2, and a less intense band in LAPC9 prostate cancer cells, indicative of endogenous 103P2D6 protein expression. Also indicated with an arrow is the 85 kD immunoreactive band present in 293T cells transfected with V5-His tagged 103P2D6 cDNA.

Figure 11C:
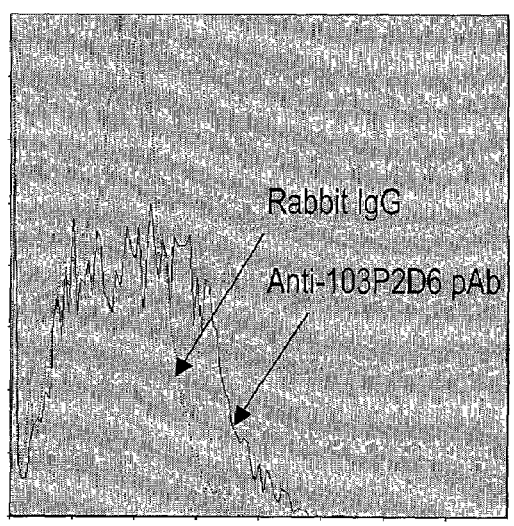

Bx PC-3 pancreatic cancer cells were stained with anti-103P2D6 pAb (10 µg/ml) or control rabbit IgG Ab and subjected to flow cytometric analysis following incubation with anti-rabbit IgG-FITC conjugated secondary Ab. Bx PC-3 cells stained with the anti-103P2D6 pAb exhibited a fluorescence shift compared to the cells stained with control rabbit IgG, indicating cell surface expression of 103P2D6. The results are shown in FIG. 11C.

Example 4

Generation of 103P2D6 Polyclonal Antibodies

Generation of Polyclonal Antibodies (pAbs)

To generate polyclonal antibodies (pAb) to 103P2D6, a peptide was synthesized corresponding to amino acids 163-176 (DVTNESRNDDDDTS; SEQ ID NO: 5) of the 103P2D6 protein sequence. The peptide was coupled to Keyhole limpet hemacyanin (KLH) and used to immunize a rabbit as follows. The rabbit was initially immunized with 200 µg of peptide-KLH mixed in complete Freund's adjuvant. The rabbit was then injected every two to three weeks with 200 µg of peptide-KLH in incomplete Freund's adjuvant. Bleeds were taken approximately 7-10 days following each immunization. The titer of the serum was at least 1:64,000 as determined by ELISA to the peptide.

Figure 12A:
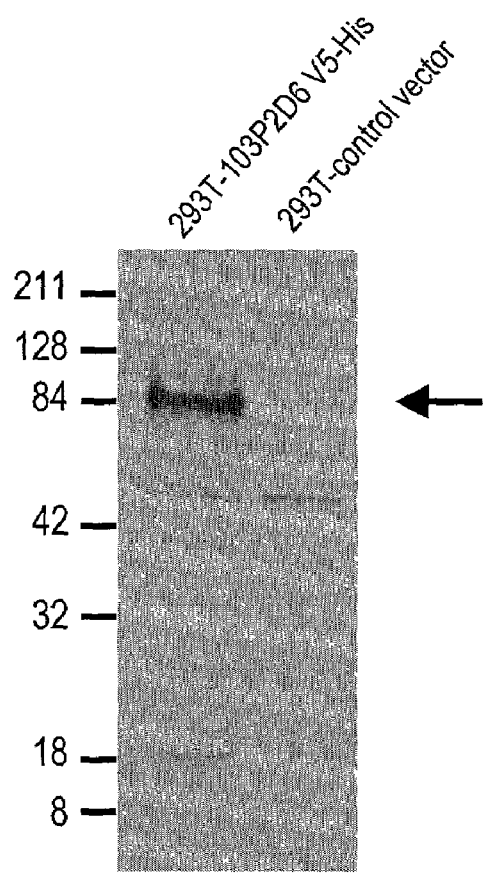
FIGS. 12A-B shows expression of 103P2D6 protein in 293T cells. For the data in panel A, 293T cells were transiently transfected with either pCDNA 3.1 V5-His 103P2D6 plasmid or with empty control vector and harvested 2 days later. Cells were lysed in SDS-PAGE sample buffer and lysates were separated by SDS-PAGE gel and transferred to nitrocellulose. Western blotting was carried out with an anti-103P2D6 rabbit pAb (2 μg/ml) raised against a peptide encoding amino acids 163-176 in the 103P2D6 extracellular domain. Anti-103P2D6 immunoreactive bands were detected by incubation with anti-rabbit-HRP conjugated secondary Ab and developed using enhanced chemiluminescence and exposure to autoradiographic film. Indicated by arrow is a specific anti-103P2D6 immunoreactive band of approximately 85 kD in 103P2D6-transfected cells but not in control cells. For the data in panel B, 103P2D6 transfected and vector transfected cells were stained with 10 μg/ml of anti-103P2D6 pAb and subjected to flow cytometry following incubation with anti-rabbit-FITC conjugated secondary Ab. Shown is a fluorescent shift in 103P2D6-transfected cells compared to the vector transfected cells, indicating cell surface expression of 103P2D6 protein.
Figure 12B:
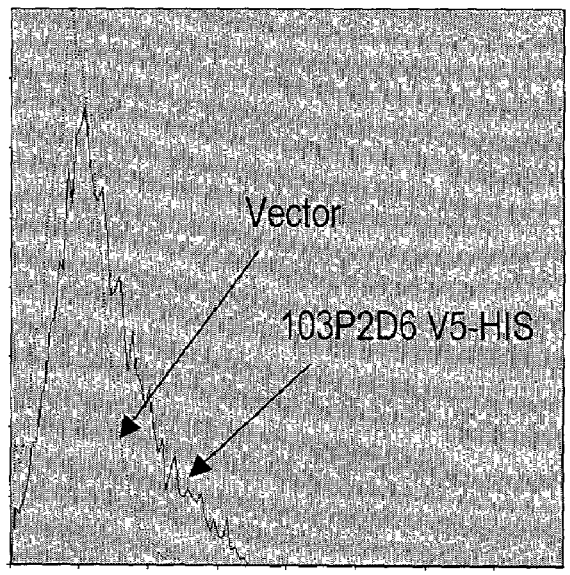

Affinity purified 103P2D6 polyclonal antibodies were prepared by passage of crude serum from the immunized rabbit over an affinity matrix comprised of 103P2D6 peptide covalently coupled to Affigel 10 (BioRad). After extensive washing of the matrix with PBS, antibodies specific to 103P2D6 peptide were eluted with low pH glycine buffer (0.1M, pH 2.5). Western blotting using the affinity purified pAb revealed the appearance of an anti-103P2D6 immunoreactive band of approximately 85 kD in 293T cells transiently transfected with the 103P2D6 cDNA in the pcDNA 3.1 V5-His vector, but not with the control empty vector (FIG. 12A). This pAb also detected cell surface expression of 103P2D6 protein in transfected 293T cells as determined by flow cytometry (FIG. 12B).

PAbs are also prepared by immunization of mice, rabbits, goats, and sheep with recombinant bacterial fusion proteins encoding full length or various regions of the 103P2D6 sequence. The recombinant bacterial proteins include glutathione-S-transferase (GST), maltose binding protein (MBP), and HIS tagged fusion proteins of 103P2D6 that are purified from induced bacteria using the appropriate affinity matrix. Mammalian expressed secreted Tag5 or FC-fusion proteins encoding the extracellular domain are also used as immunogens for pAb production.

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. For example, 103P2D6, recombinant bacterial fusion proteins or peptides encoding various regions of the 103P2D6 sequence are used to immunize New Zealand White rabbits. Typically a peptide can be designed from a coding region of 103P2D6. The peptide can be conjugated to keyhole limpet hemocyanin (KLH) and used to immunize a rabbit. Alternatively the immunizing agent may include all or portions of the 103P2D6 protein, analogs or fusion proteins thereof. For example, the 103P2D6 amino acid sequence can be fused to any one of a variety of fusion protein partners that are well known in the art, such as maltose binding protein, LacZ, thioredoxin or an immunoglobulin constant region (see e.g. *Current Protocols In Molecular Biology*, Volume 2, Unit 16, Frederick M. Ausubul et al. eds., 1995; Linsley, P.S., Brady, W., Umes, M., Grosmaire, L., Damle, N., and Ledbetter, L.(1991) *J. Exp. Med.* 174, 561-566). Other recombinant bacterial proteins include glutathione-S-transferase (GST), and HIS tagged fusion proteins of 103P2D6 that are purified from induced bacteria using the appropriate affinity matrix.

It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate).

In a typical protocol, rabbits are initially immunized subcutaneously with about 200 µg of fusion protein or peptide conjugated to KLH mixed in complete Freund's adjuvant. Rabbits are then injected subcutaneously every two weeks with 200 µg of immunogen in incomplete Freund's adjuvant. Test bleeds are taken approximately 7-10 days following each immunization and used to monitor the titer of the antiserum by ELISA.

To test serum, such as rabbit serum, for reactivity with 103P2D6 proteins, the full-length 103P2D6 cDNA can be cloned into an expression vector such as one that provides a 6His tag at the carboxyl-terminus (pcDNA 3.1 myc-his, Invitrogen). After transfection of the constructs into 293T cells, cell lysates can be probed with anti-His antibody (Santa Cruz Biotechnologies, Santa Cruz, Calif.) and the anti-103P2D6 serum using Western blotting. Alternatively specificity of the antiserum is tested by Western blot and immunoprecipitation analyses using lysates of cells that express 103P2D6. Serum from rabbits immunized with GST or MBP fusion proteins is first semi-purified by removal of anti-GST or anti-MBP antibodies by passage over GST and MBP protein columns respectively. Sera from His-tagged protein and peptide immunized rabbits as well as depleted GST and MBP protein sera are purified by passage over an affinity column composed of the respective immunogen covalently coupled to Affigel matrix (BioRad).

Example 5

Production of Recombinant 103P2D6 in Bacterial and Mammalian Systems

Bacterial Constructs pGEX Constructs

To express 103P2D6 in bacterial cells, portions of 103P2D6 were fused to the glutathione S-transferase (GST) gene by cloning into pGEX-6P-1 (Amersham Pharmacia Biotech, NJ). The constructs were made in order to generate recombinant 103P2D6 protein sequences with GST fused at the N-terminus and a six histidine epitope at the C-terminus. The six histidine epitope tag is generated by adding the histidine codons to the cloning primer at the 3' end of the open reading frame (ORF). A PreScission™ recognition site permits cleavage of the GST tag from 103P2D6-related protein. The ampicillin resistance gene and pBR322 origin permits selection and maintenance of the plasmid in *E. coli*. For example, cDNA encoding the following fragments of 103P2D6 protein were cloned into pGEX-6P-1: amino acids 24 to 487; amino acids 39 to 176; amino acids 170 to 360; and amino acids 1 to 536, or any 8, 9, 10, 11, 12, 13, 14 or 15 contiguous amino acids from 103P2D6 or an analog thereof.

pMAL Constructs

To express 103P2D6in bacterial cells, all or part of the 103P2D6nucleic acid sequence are fused to the maltose-binding protein (MBP) gene by cloning into pMAL-c2X and pMAL-p2X (New England Biolabs, MA). The constructs are made to generate recombinant 103P2D6protein sequences with MBP-fused at the N-terminus and a six histidine epitope at the C-terminus. The six histidine epitope tag is generated by adding the histidine codons to the 3' cloning primer. A Factor Xa recognition site permits cleavage of the GST tag from 103P2D6. The pMAL-c2X and pMAL-p2X vectors are optimized to express the recombinant protein in the cytoplasm or periplasm respectively. Periplasm expression enhances folding of proteins with disulfide bonds. For example, cDNA encoding the following fragments of 103P2D6 protein are cloned into pGEX-6P-1: amino acids 24 to 487; amino acids 39 to 176; amino acids 170 to 360; and amino acids 1 to 536, or any 8, 9, 10, 11, 12, 13, 14 or 15 contiguous amino acids from 103P2D6 or an analog thereof.

pCRII

To generate 103P2D6 sense and anti-sense riboprobes for RNA in situ investigations, a pCRII construct was generated using cDNA sequence encoding amino acids 44-181. The pCRII vector has Sp6 and T7 promoters flanking the insert to drive the production of 108P5H8 RNA riboprobes which will be used in RNA in situ hybridization experiments.

Mammalian Constructs

To express recombinant 103P2D6, the full or partial length 103P2D6cDNA can be cloned into any one of a variety of expression vectors known in the art. The constructs can be transfected into any one of a wide variety of mammalian cells such as 293T cells. Transfected 293T cell lysates can be probed with the anti-103P2D6polyclonal serum, described in Example 4 above, in a Western blot.

The 103P2D6genes can also be subcloned into the retroviral expression vector pSRαMSVtkneo and used to establish 103P2D6-expressing cell lines as follows: The 103P2D6 coding sequence (from translation initiation ATG and Kozak translation start consensus sequence to the termination codons) is amplified by PCR using ds cDNA template from 103P2D6 cDNA. The PCR product is subcloned into pSRαMSVtkneo vector and transformed into DH5α competent cells. Colonies are picked to screen for clones with unique internal restriction sites on the cDNA. The positive clone is confirmed by sequencing of the cDNA insert. The retroviral vectors can thereafter be used for infection and generation of various cell lines using, for example, NIH 3T3, TsuPr1, 293 or rat-1 cells.

Additional illustrative mammalian and bacterial systems are discussed below.

pcDNA4/HisMax-TOPO Constructs To express 103P2D6 in mammalian cells, the 103P2D6 ORF is cloned into pcDNA4/HisMax-TOPO Version A (cat# K864-20, Invitrogen, Carlsbad, Calif.). Protein expression is driven from the cytomegalovirus (CMV) promoter and the SP163 translational enhancer. The recombinant protein has Xpress™ and six histidine epitopes fused to the N-terminus to aid in detection and purification of the recombinant protein. The pcDNA4/HisMax-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in *E. coli*.

pcDNA3.1/MycHis Constructs

To express 103P2D6 in mammalian cells, the ORF with consensus Kozak translation initiation site is cloned into pcDNA3.11MycHis_Version A (Invitrogen, Carlsbad, Calif.). Protein expression is driven from the cytomegalovirus (CMV) promoter. The recombinant protein has the myc epitope and six histidines fused to the C-terminus to aid in detection and purification of the recombinant protein. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in *E. coli*.

pcDNA 3.1/V5His-TOPO Constructs

To express 103P2D6 in mammalian cells, the cDNA encoding the 103P2D6 ORF and Kozak consensus translation initiation sequence was cloned into pcDNA4NV5His-TOPO (cat# K4800-01, Invitrogen, Carlsbad, Calif.). Protein expression is driven from the cytomegalovirus (CMV) promoter. The recombinant protein has $V_5$™ and six histidine epitopes fused at the C-terminus to aid in detection and purification of the recombinant protein. The pcDNA4/V5His-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in *E. coli*.

Protein Expression

The mammalian expression vector pcDNA 3.1 VS-His encoding the 103P2D6 cDNA was used to transfect 293T human embryonic kidney cells to assess 103P2D6 protein expression. Western analysis of cell lysates using an anti-103P2D6 pAb reveals an immoreactive band of approximately 85 kD seen in 293T cells transiently transfected with the 103P2D6 cDNA but not in cells transfected with the control empty vector (FIG. 12A). Flow cytometric analysis of the same cells stained with the anti-103P2D6 pAb reveals a fluorescent shift of the 103P2D6 transfected cells compared to control cells indicating cell surface expression of the 103P2D6 protein (FIG. 12B). Western analysis of 103P2D6 mRNA positive HPAC and Bx PC-3 pancreatic cancer cells, CaCo-2 colon cancer cells, and LAPC9 prostate cancer cells, reveals expression of a 60 kD anti-103P2D6 immunoreactive band indicating significant endogenous expression of the 103P2D6 protein (Example 3, above; FIGS. 11A-B). The increased molecular weight of 103P2D6 in transfected 293T cells (85 kD) may be due to the presence of the VS-His amino acid tag present in the cDNA or post-translational processing or modification of 103P2D6 when overexpressed in 293T cells. 103P2D6 protein is expressed on the cell surface of Bx PC-3 cells as indicated by flow cytometric analysis (Example 3, above; FIG. 11C)

pcDNA3.1CT-GFP-TOPO Construct

To express 103P2D6 in mammalian cells and to allow detection of the recombinant protein using fluorescence, the ORF with consensus Kozak translation initiation site is cloned into pcDNA3.1CT-GFP-TOPO (Invitrogen, CA). Protein expression is driven from the cytomegalovirus (CMV) promoter. The recombinant protein has the Green Fluorescent Protein (GFP) fused to the C-terminus facilitating non-invasive, in vivo detection and cell biology studies. The pcDNA3.1/MycHis vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in *E. coli*. An additional construct with a N-terminal GFP fusion is made in pcDNA3.1NT-GFP-TOPO spanning the entire length of the 103P2D6protein.

pAPtag Constructs

The cDNA encoding 103P2D6 amino acids 24-487 is cloned into pAPtag-5 (GenHunter Corp. Nashville, TN). This construct generates an alkaline phosphatase fusion at the C-terminus of the 103P2D6protein while fusing the IgGK signal sequence to N-terminus. The resulting recombinant 103P2D6 protein is optimized for secretion into the media of transfected mammalian cells and can be used to identify proteins such as ligands or receptors that interact with the 103P2D6protein. Protein expression is driven from the CMV promoter and the recombinant protein also contains myc and six histidines fused to the C-terminus of alkaline phosphatase to aid in detection and purification of the recombinant protein. The Zeosin resistance gene allows for selection of mammalian cells expressing the protein and the ampicillin resistance gene permits selection of the plasmid in *E. coli*.

ptag5 Constructs

The cDNA encoding for 103P2D6 amino acids 24-487, 24-174, 24-233, and 234-487, was cloned into pTag-5. This vector is similar to pAPtag but without the alkaline phosphatase fusion. This construct generates an immunoglobulin G1 Fc fusion at the C-terminus of the 103P2D6protein while fusing the IgGK signal sequence to the N-terminus. The resulting recombinant 103P2D6 protein is optimized for secretion into the media of transfected mammalian cells, and can be used to identify proteins such as ligands or receptors that interact with the 103P2D6protein. Protein expression is driven from the CMV promoter and the recombinant protein also contains myc and six histidines fused to the C-terminus to aid in detection and purification of the recombinant protein. The Zeocin resistance gene allows for selection of mammalian cells expressing the protein, and the ampicillin resistance gene permits selection of the plasmid in *E. coli*.

psecFc Constructs

The cDNA encoding for 103P2D6 amino acids 24-487, 24-233, and 234-487, was cloned into psecFc. The psecFc vector was assembled by cloning immunoglobulin G1 Fc (hinge, CH2, CH3 regions) into pSecTag2 (Invitrogen, California). This construct generates an immunoglobulin G1 Fc fusion at the C-terminus of the 103P2D6protein, while fusing the IgGK signal sequence to N-terminus. The resulting recombinant 103P2D6 protein is optimized for secretion into the media of transfected mammalian cells, and can be used to identify proteins such as ligands or receptors that interact with the 103P2D6 protein. Protein expression is driven from the CMV promoter. The Zeocin resistance gene allows for selection of mammalian cells that express the protein, and the ampicillin resistance gene permits selection of the plasmid in E. coli.

pSRαConstructs

To generate mammalian cell lines that express 103P2D6 constitutively, the ORF was cloned into pSRα constructs. Amphotropic and ecotropic retroviruses are generated by transfection of pSRα constructs into the 293T-10A1 packaging line or co-transfection of pSRα and a helper plasmid (φ~) in the 293 cells, respectively. The retrovirus can be used to infect a variety of mammalian cell lines, resulting in the integration of the cloned gene, 103P2D6, into the host celllines. Protein expression is driven from a long terminal repeat (LTR). The Neomycin resistance gene allows for selection of mammalian cells that express the protein, and the ampicillin resistance gene and ColE1 origin permit selection and maintenance of the plasmid in E. coli.

An additional pSRα construct was made that fused the FLAG tag to the C-terminus to allow detection using anti-FLAG antibodies. The FLAG sequence 5' gat tac aag gat gac gac gat aag 3' (SEQ ID NO: 6) was added to cloning primer at the 3' end of the ORF.

Additional pSRα constructs are made to produce both N-terminal and C-terminal GFP and myc/6 HIS fusion proteins of the full-length 103P2D6protein.

Example 6

Production of Recombinant 103P2D6in a Baculovirus System

To generate a recombinant 103P2D6 protein in a baculovirus expression system, cDNA sequence encoding the 103P2D6 protein is cloned into the baculovirus transfer vector pBlueBac 4.5 (Invitrogen), which provides a His-tag at the N-terminus Specifically, pBlueBac—103P2D6 is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 103P2D6protein is then generated by infection of HighFive insect cells (Invitrogen) with the purified baculovirus. Recombinant 103P2D6 protein can be detected using anti-103P2D6 antibody. 103P2D6 protein can be purified and used in various cell-based assays or as immunogen to generate polyclonal and monoclonal antibodies specific for 103P2D6.

Example 7

Chromosomal Mapping of the 103P2D6 Gene

The chromosomal localization of 103P2D6 was determined using the GeneBridge4 Human/Hamster radiation hybrid (RH) panel (Walter et al., 1994, Nat. Genetics 7:22) (Research Genetics, Huntsville Ala.).

The following PCR primers were used to localize 103P2D6:

103P2D6.1 cftgggaggtcctagtgctaagtg

103P2D6.2 caatgaagggactaacaacccatc

The resulting mapping vector for the 93 radiation hybrid panel DNAs was: 0100011101011010011011111100112001001000010011100111110010001011011001001101101101 10101000011. This vector and the mapping program are at the world wide web address genome.wi.mit.edu/cgi-bincontig/rhmapper.pl placed 103P2D6 on chromosome 4p12-p14 (D4S3197-D4S1577).

Example 8

Identification of Potential Signal Transduction Pathways

Based on its surface localization, 103P2D6 can regulate key signaling pathways. Several pathways known to play a role in cancer biology can be regulated by 103P2D6, including phospholipid pathways such as P13K, AKT, etc, as well as mitogenic/survival cascades such as ERK, p38, etc (Cell Growth Differ. 2000,11:279; J. Biol. Chem. 1999, 274:801; Oncogene. 2000, 19:3003.). The role that 103P2D6 plays in the regulation of these pathways can be investigated using, Western blotting techniques and reporter assays. Cells lacking 103P2D6 and cells expressing 103P2D6 are either left untreated or stimulated with serum, cytokines, androgen or antibodies. Cell lysates are analyzed using anti-phosphosspecific antibodies (Cell Signaling, Santa Cruz Biotechnology) in order to detect phosphorylation and regulation of ERK, p38, AKT, P13K, PLC and other signaling molecules. When 103P2D6 plays a role in the regulation of signaling pathways, 103P2D6 is used as a target for diagnostic, preventative and therapeutic purposes.

To determine whether 103P2D6 directly or indirectly activates known signal transduction pathways in cells, luciferase (luc) based transcriptional reporter assays are carried out in cells that express 103P2D6. These transcriptional reporters contain consensus binding sites for known transcription factors that lie downstream of well-characterized signal transduction pathways. Some of the reporters and examples of these associated transcription factors, signal transduction pathways, and activation stimuli are listed below.

1. NFkB-luc, NFkB/Rel; Ilk-kinase/SAPK: growth/apoptosis/stress
2. SRE-luc, SRF/TCF/ELK1; MAPK/SAPK: growth/differentiation
3. AP-1-luc, FOS/JUN; MAPK/SAPK/PKC: growth/apoptosis/stress
4. ARE-luc, androgen receptor; steroids/MAPK: growth/differentiation/apoptosis
5. p53-luc, p53; SAPK: growth/differentiation/apoptosis
6. CRE-luc, CREB/ATF2: PKA/p38; growth/apoptosis/stress When 103P2D6 plays a role in the regulation of growth, apoptosis, stress, or differentiation, 103P2D6 is used as a target for diagnostic, preventative and therapeutic purposes.

103P2D6-mediated effects are assayed in cells showing 103P2D6 mRNA expression. For example, Luciferase reporter plasmids can be introduced by lipid-mediated transfection (TFX-50, Promega). Luciferase activity, an indicator of relative transcriptional activity, is measured by incubation of cell extracts with luciferin substrate and luminescence of the reaction is monitored in a luminometer. This assay allows one to determine the effect of signaling pathways activation. When 103P2D6 plays a role in activation signaling pathways, 103P2D6 is used as a target for diagnostic, preventative and therapeutic purposes.

Example 9

Generation of 103P2D6 Monoclonal Antibodies (mAbs)

To generate mAbs to 103P2D6, mice are immunized intraperitoneally with 10-50 µg of protein immunogen mixed in complete Freund's adjuvant. Protein immunogens include peptides, recombinant 103P2D6 proteins, and, mammalian expressed human IgG FC fusion proteins. Mice are then subsequently immunized every 2-4 weeks with 10-50 µg of antigen mixed in Freund's incomplete adjuvant. Alternatively, Ribi adjuvant is used for initial immunizations. In addition, a DNA-based immunization protocol is used in which a mammalian expression vector used to immunize mice by direct injection of the plasmid DNA. For example, a pcDNA 3.1 encoding 103P2D6 cDNA alone or as an IgG FC fusion is used. This protocol is used alone or in combination with protein immunogens. Test bleeds are taken 7-10 days following immunization to monitor titer and specificity of the immune response. Once appropriate reactivity and specificity is obtained as determined by ELISA, Western blotting, and immunoprecipitation analyses, fusion and hybridoma generation is then carried with established procedures well known in the art (Harlow and Lane, 1988).

In an illustrative method for generating 103P2D6 monoclonal antibodies, a glutathione-S-transferase (GST) fusion protein encompassing a 103P2D6 protein is synthesized and used as immunogen. Balb C mice are initially immunized intraperitoneally with 200 µg of the GST-103P2D6 fusion protein mixed in complete Freund's adjuvant. Mice are subsequently immunized every two weeks with 75 µg of GST-103P2D6 protein mixed in Freund's incomplete adjuvant for a total of three immunizations. Reactivity of serum from immunized mice to full-length 103P2D6 protein is monitored by ELISA using a partially purified preparation of HIS-tagged 103P2D6 protein expressed from 293T cells (Example 5). Mice showing the strongest reactivity are rested for three weeks and given a final injection of fusion protein in PBS and then sacrificed four days later. The spleens of the sacrificed mice are then harvested and fused to SPO/2 myeloma cells using standard procedures (Harlow and Lane, 1988). Supernatants from growth wells following HAT selection are screened by ELISA and Western blot to identify 103P2D6 specific antibody-producing clones.

The binding affinity of a 103P2D6 monoclonal antibody is determined using standard technologies. Affinity measurements quantify the strength of antibody to epitope binding and can be used to help define which 103P2D6 monoclonal antibodies are preferred for diagnostic or therapeutic use. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 10

Involvement of 103P2D6 in Cancer Growth and Progression

The finding that 103P2D6 is differentially expressed in cancer cells suggests that 103P2D6 participates in the process of tumor formation and/or progression. This is supported by the presence of other envelope-like proteins in prostate, colon and endothelial tumor lines but not normal cells (Pathobiology. 1997, 65:123; Cancer Lett. 1998, 124:213). For example, HERV-K, another envelope protein, is expressed in teratocarcinoma and tumor cell lines (3 Gen Virol. 1996; 77: 2983), and HERV-R is expressed in gonadoblastomas (Virchows Arch. 1999; 434:11).

103P2D6 contributes to the growth of prostate and other cancer cells (See Table I) by several mechanisms. The 103P2D6 protein can function as a cell surface receptor or as a transporter and contribute to tumor growth by regulating tumor cell proliferation or responding to tumor cells, endothelial cells or stroma. Alternatively, 103P2D6 contributes to tumor growth by mediating cellular adhesion, transformation or downstream gene expression. The functions of 103P2D6 can be evaluated, e.g., by using engineered cell lines that express 103P2D6. For example, primary cells such as PrEC, cancer cell lines and NIH 3T3 cells engineered to stably express 103P2D6 are evaluated for cell growth potential. When 103P2D6 participates in neoplastic cell growth, 103P2D6 is used as a target for diagnostic, preventative and therapeutic purposes.

Moreover, the role 103P2D6 plays in transformation is evaluated. Primary cells, such as PrEC, and NIH3T3 cells engineered to express 103P2D6 are compared to 103P2D6-negative cells, to evaluate their ability to form colonies in soft agar (Song Z. et al. Cancer Res. 2000; 60:6730), where colony formation indicates the presence of transformed cells. When 103P2D6 mediates transformation, 103P2D6 is used as a target for diagnostic, preventative and therapeutic purposes.

The expression of 103P2D6 in the various cancers listed in Table I indicates that this gene has a functional role in tumor progression. 103P2D6 function can be assessed in mammalian cells using in vitro approaches. Mammalian cells infected with the retroviral vector pSRαtkneo or pSRα-103P2D6 are compared (Muller et al., 1991, MCB 11:1785) using a variety of assays, including cell proliferation in tissue culture and in vitro invasion using a membrane invasion culture system (Welch et al., Int. J. Cancer 43: 449-457). Cell lines expressing 103P2D6 are assayed for invasive and migratory properties by measuring passage of cells through a matrigel coated Transwell™ system (Becton Dickinson) (Cancer Res. 1999; 59:6010). Passage of cells through the membrane to the opposite side is monitored using a fluorescent assay (Becton Dickinson Technical Bulletin #428). For example, cells lacking 103P2D6 and cells expressing 103P2D6 are loaded with the fluorescent dye, calcein, and plated in the top well of the Transwell insert. Invasion is determined by fluorescence of cells in the lower chamber relative to the fluorescence of the entire cell population. When 103P2D6 is involved with cell invasion, 103P2D6 is used as a target for diagnostic, preventative and therapeutic purposes.

Envelope proteins have been shown to exhibit chemotactic abilities (Lin C L, Sewell A K, Gao fGF, Whelan K T, Phillips R E, Austyn J M. J Exp Med. 2000, 192:587). In view of its similarity to envelope proteins, and to determine whether 103P2D6-expressing cells have such chemoattractant properties, indicator cells are monitored for passage through the Transwell system toward a gradient of 103P2D6-conditioned media compared to control media. This assay can also be used to qualify and quantify specific neutralization of 103P2D6 effects. For example, the neutralization can be effected by candidate cancer therapeutic compositions. When 103P2D6 mediates tissue invasion, such as by chemotaction, 103P2D6 is used as a target for diagnostic, preventative and therapeutic purposes.

The function of 103P2D6 can be evaluated using anti-sense RNA technology coupled to the various functional assays described herein, e.g. growth, invasion and migration. Antisense RNA oligonucleotides can be introduced into 103P2D6 expressing cells, thereby preventing the expression of 103P2D6. Control and anti-sense containing cells can be analyzed for proliferation, invasion, migration, apoptotic and transcriptional potential. The local as well as systemic effect of the loss of 103P2D6 expression can be evaluated.

Example 11

Protein Association and Cell Adhesion

Envelope proteins have been shown to mediate cell adhesion and syncytium formation (J. Immunol. 1996, 156:1307; AIDS. 1991, 5:1425). Based on its similarity with envelope proteins, 103P2D6 can mediate protein-protein association resulting in multimeric complexes. The association of proteins into large complexes is critical in several biological processes, including signal transduction, cell communication, ubiquitination, transcriptional regulation, etc.

Alternatively, 103P2D6 can participate in regulating cell adhesion and communication. To determine the degree to which expression of 103P2D6 regulates cell adhesion, cells lacking 103P2D6 are compared to cells expressing 103P2D6, using techniques known in the art (see, e.g., Haier et al, Br. J. Cancer. 1999, 80:1867; Lehr and Pienta, J. Natl. Cancer Inst. 1998, 90:118). Briefly, in one embodiment, cells labeled with a fluorescent indicator, such as calcein, are incubated on tissue culture wells coated with media alone or with matrix proteins. Adherent cells are detected by fluorimetric analysis. Confirmation of the role 103P2D6 plays in adhesion can be obtained using anti-103P2D6 antibodies. Since cell adhesion plays a critical role in tumor growth, progression, and, colonization, the inhibition of 103P2D6-mediated interactions serves as a diagnostic, preventative and therapeutic modality.

Example 12

In vivo Assay for 103P2D6 Tumor Growth Promotion

The effect of the 103P2D6 protein on tumor cell growth can be evaluated in vivo by gene overexpression in tumor-bearing mice. For example, SCID mice can be injected SQ on each flank with $1\times10^6$ of either PC3, TSUPR1, or DU145 cells containing tkneo empty vector or 103P2D6. At least two strategies may be used: (1) Constitutive 103P2D6 expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems. (2) Regulated expression under control of an inducible vector system, such as ecdysone, tet, etc., can be used provided such promoters are compatible with the host cell systems. Tumor volume is then monitored at the appearance of palpable tumors and is followed over time to determine if 103P2D6-expressing cells grow at a faster rate and whether tumors produced by 103P2D6-expressing cells demonstrate characteristics of altered aggressiveness (e.g. enhanced metastasis, vascularization, reduced responsiveness to chemotherapeutic drugs). Additionally, mice can be implanted with $1\times10^5$ of the same cells orthotopically to determine if 103P2D6 has an effect on local growth in the prostate or on the ability of the cells to metastasize, specifically to lungs, lymph nodes, and bone marrow. Also see saffron et al, "Anti-PSCA mAbs inhibit tumor growth and metastasis formation and prolong the survival of mice bearing human prostate cancer xenografts" PNAS (in press, 2001).

The assay is also useful to determine the 103P2D6 inhibitory effect of candidate therapeutic compositions, such as for example, 103P2D6 intrabodies, 103P2D6 antisense molecules and ribozymes.

Example 13

Western Analysis of 103P2D6 Expression in Subcellular Fractions

The cellular location of 103P2D6 can be assessed using subcellular fractionation techniques widely used in cellular biology (Storrie B, et al. Methods Enzymol. 1990; 182:203-25). Prostate or other cell lines can be separated into nuclear, cytosolic and membrane fractions. The expression of 103P2D6 in the different fractions can be tested using Western blotting techniques.

Alternatively, to determine the subcellular localization of 103P2D6, 293T cells can be transfected with an expression vector encoding HIS-tagged 103P2D6 (PCDNA 3.1 MYC/HIS, Invitrogen). The transfected cells can be harvested and subjected to a differential subcellular fractionation protocol as previously described (Pemberton, P. A. et al, 1997, J of Histochemistry and Cytochemistry, 45:1697-1706.) This protocol separates the cell into fractions enriched for nuclei, heavy membranes (lysosomes, peroxisomes, and mitochondria), light membranes (plasma membrane and endoplasmic reticulum), and soluble proteins.

Example 14

Localization of 103P2D6

Based on its structure, 103P2D6 is understood to be associated with the cell surface. Surface staining experiments confirm that 103P2D6 cDNA is expressed at the cell surface (see, e.g., FIGS. 11-12). When located at the cell membrane, the potential functions of 103P2D6 include (1) a surface receptor that transmits signals to the cell nucleus, or (2) a transporter that moves ions and proteins from in and out of the cell, or (3) a mediator of cell adhesion and cell-cell interaction. The cellular location of 103P2D6 can be assessed using subcellular fractionation techniques widely used in cellular biology (see, e.g., Storrie B, et al. Methods Enzymol. 1990; 182:203-25). Prostate, colon, bladder, kidney or pancreas tumor cell lines are separated into nuclear, cytosolic, heavy membranes (lysosomes, peroxisomes, and mitochondria) and light membranes (plasma membrane and endoplasmic reticulum) fractions. The expression of 103P2D6 is followed in each fraction by Western blotting. When 103P2D6 participates in cell adhesion or cell-cell communication, 103P2D6 is used as a target for diagnostic, preventative and therapeutic purposes.

Example 15

Protein-Protein Interactions Mediated by 103P2D6

The determination of the specific proteins with which 103P2D6 associates, including cytoskeleton and integrins, can be made, e.g., using co-precipitation and Western blotting techniques (see, e.g., Hamilton B J, et al. Biochem Biophys. Res. Commun. 1999, 261:646). Immunoprecipitates from cells expressing 103P2D6 and cells lacking 103P2D6 are compared for specific protein-protein associations. 103P2D6 also associates with effector molecules, such as C2-domain containing proteins. Studies comparing 103P2D6 positive and 103P2D6 negative cells as well as studies comparing unstimulated/resting cells and cells treated with epithelial cell activators, such as cytokines, androgen and antibodies reveal unique interactions. In addition, protein-protein interactions can be studied using two yeast hybrid methodology (see, e.g., Curr Opin Chem Biol. 1999, 3:64). A vector carrying a library of proteins fused to the activation domain of a transcription factor is introduced into yeast expressing a 103P2D6-DNA-binding domain fusion protein and a reporter construct. Protein-protein interaction is detected by calorimetric reporter activity. Specific association with effector molecules and transcription factors directs one of skill to the mode of action of 103P2D6, and thus identifies therapeutic, preventative and/or diagnostic targets for cancer.

Example 16

Regulation of Transcription by 103P2D6

The 103P2D6 protein contains a leucine zipper at its amino-terminus. Leucine zippers play a role in protein dimerization and determine sequence-specific DNA binding (Luscher B, Larsson L G. Oncogene. 1999; 18:2955), and are therefore transcriptional regulators. Analogously, 103P2D6 can regulate tumor progression by regulating gene expression. The role that 103P2D6 plays in regulating gene expression can be evaluated, e.g., by studying gene expression in cells expressing or lacking 103P2D6. For example, RNA from parental and 103P2D6-expressing NIH3T3 and PC3 cells is extracted and hybridized to commercially available gene arrays (Clontech). Resting cells as well as cells treated with serum, cytokines, androgen or antibodies are compared. Differentially expressed genes are identified and mapped to biological pathways. When 103P2D6 regulates transcription, 103P2D6 is used as a target for diagnostic, preventative and therapeutic purposes.

Example 17

103P2D6 Monoclonal Antibody Mediated Inhibition of Prostate Tumors in vivo

The significant expression of 103P2D6, in cancer tissues, together with its restrictive expression in normal tissues makes 103P2D6 a target for antibody therapy. Similarly, 103P2D6 is a target for T cell-based immunotherapy. Thus, the therapeutic efficacy of anti-103P2D6 mAbs in human prostate cancer xenograft mouse models is evaluated by using the androgen-dependent LAPC-9 xenograft (Craft, N., et al., Cancer Res, 1999. 59(19): p. 5030-6) and the androgen independent recombinant cell line PC3-103P2D6 (see, e.g., Kaighn, M. E., et al., Invest Urol, 1979. 17(1): p. 16-23).

Antibody efficacy on tumor growth and metastasis formation is studied, e.g., in a mouse orthotopic prostate cancer xenograft model. These studies demonstrate that anti-103P2D6 MAbs inhibit formation of both the androgen-dependent LAPC-9 and androgen-independent PC3-103P2D6 tumor xenografts. Anti-103P2D6 mAbs also retard the growth of established orthotopic tumors significantly and prolonged survival of tumor-bearing mice. These results indicate the utility of anti-103P2D6 mAbs in the treatment of local and advanced stages of prostate cancer.

Administration of the anti-103P2D6 mAbs led to retardation of established orthotopic tumor growth and inhibition of metastasis to distant sites, resulting in a significant prolongation in the survival of tumor-bearing mice. These studies indicate that 103P2D6 as an attractive target for immunotherapy and demonstrate the therapeutic potential of anti-103P2D6 mAbs for the treatment of local and metastatic prostate cancer. This example demonstrates that unconjugated 103P2D6 monoclonal antibodies are effective to inhibit the growth of human prostate tumor xenografts grown in SCID mice; accordingly a combination of such efficacious monoclonal antibodies is also effective.

Tumor Inhibition using Multiple Unconjugated 103P2D6 mAbs

Materials and Methods

103P2D6 Monoclonal Antibodies:

Monoclonal antibodies are raised against 103P2D6 as described in Example 9.

Antibodies are characterized by ELISA, Western blot, FACS, and immunoprecipitation for their capacity to bind 103P2D6. Epitope mapping data for the anti-103P2D6 mAbs, as determined by ELISA and Western analysis, recognize epitopes on the 103P2D6 protein. Immunohistochemical analysis of prostate cancer tissues and cells with these antibodies is performed.

Antibody Formulation:

The monoclonal antibodies are purified from hybridoma tissue culture supernatants by Protein-G Sepharose chromatography, dialyzed against PBS, filter sterilized, and stored at −20° C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of LAPC-9 prostate tumor xenografts.

Prostate Cancer Xenografts and Cell Lines.

The LAPC-9 xenograft, which expresses a wild-type androgen receptor and produces prostate-specific antigen (PSA), is passaged in 6- to 8-week-old male ICR-severe combined imiunodeficient (SCID) mice (Taconic Farms) by s.c. trocar implant (Craft, N., et al., supra). Single-cell suspensions of LAPC-9 tumor cells are prepared as described in Craft, et al. The prostate carcinoma cell line PC3 (American Type Culture Collection) is maintained in DMEM supplemented with L-glutamine and 10% (vol/vol) FBS.

A PC3-103P2D6 cell population is generated by retroviral gene transfer as described in Hubert, R. S., et al., Proc Natl Acad Sci USA, 1999. 96(25): p. 14523-8. Anti-103P2D6 staining is detected by using an FITC-conjugated goat antimouse antibody (Southern Biotechnology Associates) followed by analysis on a Coulter Epics-XL flow cytometer.

Xenograft Mouse Models.

Subcutaneous (s.c.) tumors are generated by injection of 1×10⁶ LAPC-9, PC3, or PC3-103P2D6 cells mixed at a 1:1 dilution with Matrigel (Collaborative Research) in the right flank of male SCID mice. To test antibody efficacy on tumor formation, i.p. antibody injections are started on the same day as tumor-cell injections. As a control, mice are injected with either purified mouse IgG (ICN) or PBS; or a purified monoclonal antibody that recognizes an irrelevant antigen not expressed in human cells. In preliminary studies, no difference is found between mouse IgG or PBS on tumor growth. Tumor sizes are determined by vernier caliper measurements, and the tumor volume is calculated as length×width×height. Mice with s.c. tumors greater than 1.5 cm in diameter are sacrificed. PSA levels are determined by using a PSA ELISA kit (Anogen, Mississauga, Ontario). Circulating levels of anti-103P2D6 mAbs are determined by a capture ELISA kit (Bethyl Laboratories, Montgomery, Tex.).

Orthotopic injections are performed under anesthesia by using ketamine/xylazine. An incision is made through the abdominal muscles to expose the bladder and seminal vesicles, which then are delivered through the incision to expose the dorsal prostate. LAPC-9 cells (5×10⁵) mixed with Matrigel are injected into each dorsal lobe in a 10-μl volume. To monitor tumor growth, mice are bled on a weekly basis for determination of PSA levels. Based on the PSA levels, the mice are segregated into groups for the appropriate treatments. To test the effect of anti-103P2D6 mAbs on established orthotopic tumors, i.p. antibody injections are started when PSA levels reach 2-80 ng/ml.

Anti-103P2D6 mAbs Inhibit Formation of 103P2D6-Expressing Prostate-Cancer Tumors We next test the effect of anti-103P2D6 mAbs on tumor formation by using the LAPC-9 orthotopic model. As compared with the s.c. tumor model, the orthotopic model, which requires injection of tumor cells directly in the mouse prostate, results in a local tumor growth, development of metastasis in distal sites, deterioration of mouse health, and subsequent death (Saffran, D., et al., PNAS 10:1073-1078 or at the world wide web address pnas.oflvcgi/doi/10.1073/pnas.051624698; Fu, X., et al., Int J Cancer, 1992. 52(6): p. 987-90; Kubota, T., J Cell Biochem, 1994. 56(1): p. 4-8). The features make the orthotopic model more representative of human disease progression and allowed us to follow the therapeutic effect of mAbs on clinically relevant end points.

Accordingly, LAPC-9 tumor cells are injected into the mouse prostate, and 2 days later, the mice are segregated into two groups and treated with either 200μg of 1G8 mAb or PBS three times per week for two weeks. Mice are monitored weekly for circulating PSA levels as an indicator of tumor growth.

A major advantage of the orthotopic prostate-cancer model is the ability to study the development of metastases. Formation of metastasis in mice bearing established orthotopic tumors is studies by IHC analysis on lung sections using an antibody against a prostate-specific cell-surface protein STEAP expressed at high levels in LAPC-9 xenografts (Hubert, R. S., et al., Proc Natl Acad Sci USA, 1999. 96(25): p. 14523-8).

Mice bearing established orthotopic LAPC-9 tumors are administered 11 injections of either anti-103P2D6 mAb or PBS over a 4-week period. Mice in both groups are allowed to establish a high tumor burden (PSA levels greater than 300 ng/ml), to ensure a high frequency of metastasis formation in mouse lungs. Mice then are killed and their prostate and lungs are analyzed for the presence of LAPC-9 cells by anti-STEAP IHC analysis.

These studies demonstrate a broad anti-tumor efficacy of anti-103P2D6 antibodies on initiation and progression of prostate cancer in xenograft mouse models. Anti-103P2D6 antibodies inhibit tumor formation of both androgen-dependent and androgen-independent tumors as well as retarding the growth of already established tumors and prolong the survival of treated mice. Moreover, anti-103P2D6 mAbs demonstrate a dramatic inhibitory effect on the spread of local prostate tumor to distal sites, even in the presence of a large tumor burden. Thus, anti-103P2D6 mAbs are efficacious on major clinically relevant end points/PSA levels (tumor growth), prolongation of survival, and health.

Throughout this application, various publications are referenced (within parentheses for example). The disclosures of these publications are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE I

| Cancer Tissues That Express 103P2D6 |
| --- |
| prostate |
| colon |
| stomach |
| lung |
| pancreas |
| breast |
| bladder |
| bone |
| kidney |
| testis |
| cervix |
| ovary |
| uterus |

TABLE II

| AMINO ACID ABBREVIATIONS | | |
| --- | --- | --- |
| SINGLE LETTER | THREE LETTER | FULL NAME |
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |

TABLE II-continued

AMINO ACID ABBREVIATIONS

| SINGLE LETTER | THREE LETTER | FULL NAME |
|---|---|---|
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

AMINO ACID SUBSTITUTION MATRIX
Adapted from the GCG Software 9.0 BLOSUM62 amino acid substitution matrix (block substitution matrix). The higher the value, the more likely a substitution is found in related, natural proteins.

| A | C | D | E | F | G | H | I | K | L | M | N | P | Q | R | S | T | V | W | Y | |
|---|---|---|---|---|---|---|---|---|---|---|---|---|---|---|---|---|---|---|---|---|
| 4 | 0 | -2 | -1 | -2 | 0 | -2 | -1 | -1 | -1 | -1 | -2 | -1 | -1 | -1 | 1 | 0 | 0 | -3 | -2 | A |
|  | 9 | -3 | -4 | -2 | -3 | -3 | -1 | -3 | -1 | -1 | -3 | -3 | -3 | -3 | -1 | -1 | -1 | -2 | -2 | C |
|  |  | 6 | 2 | -3 | -1 | -1 | -3 | -1 | -4 | -3 | 1 | -1 | 0 | -2 | 0 | -1 | -3 | -4 | -3 | D |
|  |  |  | 5 | -3 | -2 | 0 | -3 | 1 | -3 | -2 | 0 | -1 | 2 | 0 | 0 | -1 | -2 | -3 | -2 | E |
|  |  |  |  | 6 | -3 | -1 | 0 | -3 | 0 | 0 | -3 | -4 | -3 | -3 | -2 | -2 | -1 | 1 | 3 | F |
|  |  |  |  |  | 6 | -2 | -4 | -2 | -4 | -3 | 0 | -2 | -2 | -2 | 0 | -2 | -3 | -2 | -3 | G |
|  |  |  |  |  |  | 8 | -3 | -1 | -3 | -2 | 1 | -2 | 0 | 0 | -1 | -2 | -3 | -2 | 2 | H |
|  |  |  |  |  |  |  | 4 | -3 | 2 | 1 | -3 | -3 | -3 | -3 | -2 | -1 | 3 | -3 | -1 | I |
|  |  |  |  |  |  |  |  | 5 | -2 | -1 | 0 | -1 | 1 | 2 | 0 | -1 | -2 | -3 | -2 | K |
|  |  |  |  |  |  |  |  |  | 4 | 2 | -3 | -3 | -2 | -2 | -2 | -1 | 1 | -2 | -1 | L |
|  |  |  |  |  |  |  |  |  |  | 5 | -2 | -2 | 0 | -1 | -1 | -1 | 1 | -1 | -1 | M |
|  |  |  |  |  |  |  |  |  |  |  | 6 | -2 | 0 | 0 | 1 | 0 | -3 | -4 | -2 | N |
|  |  |  |  |  |  |  |  |  |  |  |  | 7 | -1 | -2 | -1 | -1 | -2 | -4 | -3 | P |
|  |  |  |  |  |  |  |  |  |  |  |  |  | 5 | 1 | 0 | -1 | -2 | -2 | -1 | Q |
|  |  |  |  |  |  |  |  |  |  |  |  |  |  | 5 | -1 | -1 | -3 | -3 | -2 | R |
|  |  |  |  |  |  |  |  |  |  |  |  |  |  |  | 4 | 1 | -2 | -3 | -2 | S |
|  |  |  |  |  |  |  |  |  |  |  |  |  |  |  |  | 5 | 0 | -2 | -2 | T |
|  |  |  |  |  |  |  |  |  |  |  |  |  |  |  |  |  | 4 | -3 | -1 | V |
|  |  |  |  |  |  |  |  |  |  |  |  |  |  |  |  |  |  | 11 | 2 | W |
|  |  |  |  |  |  |  |  |  |  |  |  |  |  |  |  |  |  |  | 7 | Y |

TABLE IV A

HLA CLASS I SUPERMOTIFS

| SUPERMOTIF | POSITION 2 | C-TERMINUS |
|---|---|---|
| A2 | L, I, V, M, A, T, Q | L, . I, V, M, A, T |
| A3 | A, V, I, L, M, S, T | R, K |
| B7 | P | A, L, I, M, V, F, W, Y |
| B44 | D, E | F, W, Y, L, I, M, V, A |
| A1 | T, S, L, I, V, M | F, W, Y |
| A24 | F, W, Y, L, V, I, M, T | F, I, Y, W, L, M |
| B27 | R, H, K | A, L, I, V, M, Y, F, W |
| B58 | A, S, T | F, W, Y, L, I, V |
| B62 | L, V, M, P, I, Q | F, W, Y, M, I, V |

TABLE IV B

HLA CLASS II SUPERMOTIF

| 1 | 6 | 9 |
|---|---|---|
| W, F, Y, V, .I, L | A, V, I, L, P, C, S, T | A, V, I, L, C, S, T, M, Y |

TABLE V

Scoring Results 103P2D6 HLA peptides A1 9MERS
(SEQ ID NOs: 15-64, respectively)

| Rank | Start Position | Subsequence Residue Listing | Score (Estimate of Half Time of Disassociation of a Molecule Containing This Subsequence) |
|---|---|---|---|
| 1 | 52 | NAEQPELVF | 45.000 |
| 2 | 253 | LTEAHGKWR | 22.500 |
| 3 | 105 | SMEAQGLSF | 22.500 |
| 4 | 356 | DTDNPPLYC | 6.250 |
| 5 | 153 | STDGTFMPS | 6.250 |

TABLE V-continued

Scoring Results 103P2D6 HLA peptides A1 9MERS
(SEQ ID NOs: 15-64, respectively)

| Rank | Start Position | Subsequence Residue Listing | Score (Estimate of Half Time of Disassociation of a Molecule Containing This Subsequence) |
|---|---|---|---|
| 6 | 161 | SIDVTNESR | 5.000 |
| 7 | 321 | YLVPSLTRY | 5.000 |
| 8 | 374 | ALFPSLGTY | 5.000 |
| 9 | 425 | VLDIPTTQR | 5.000 |
| 10 | 473 | LLDWQGIFA | 2.500 |
| 11 | 500 | CLFIFVLIY | 2.500 |
| 12 | 208 | TQDYKWVDR | 1.500 |
| 13 | 538 | VSETSCQVS | 1.350 |
| 14 | 450 | YSEEIKSNI | 1.350 |
| 15 | 203 | IGLPNTQDY | 1.250 |
| 16 | 69 | WTYSGQWMY | 1.250 |
| 17 | 506 | LIYVRVFRK | 1.000 |
| 18 | 434 | QTACGTVGK | 1.000 |
| 19 | 378 | SLGTYDLEK | 1.000 |
| 20 | 405 | TLEAHQSKV | 0.900 |
| 21 | 461 | LHEASENLK | 0.900 |
| 22 | 118 | LLEGNFSLC | 0.900 |

TABLE V-continued

Scoring Results 103P2D6 HLA peptides A1 9MERS
(SEQ ID NOs: 15-64, respectively)

| Rank | Start Position | Subsequence Residue Listing | Score (Estimate of Half Time of Disassociation of a Molecule Containing This Subsequence) |
|---|---|---|---|
| 23 | 126 | CVENKNGSG | 0.900 |
| 24 | 84 | QAEVQNHST | 0.900 |
| 25 | 520 | NSQPLNLAL | 0.750 |
| 26 | 63 | ASASTWWTY | 0.750 |
| 27 | 222 | WSGNDTCLY | 0.750 |
| 28 | 233 | QNQTKGLLY | 0.625 |
| 29 | 21 | LVQPQHLLA | 0.500 |
| 30 | 404 | QTLEAHQSK | 0.500 |
| 31 | 136 | FLGNIPKQY | 0.500 |
| 32 | 496 | IVLFCLFIF | 0.500 |
| 33 | 291 | SVNNSGLFF | 0.500 |
| 34 | 383 | DLEKAILNI | 0.450 |
| 35 | 394 | AMEQEFSAT | 0.450 |
| 36 | 55 | QPELVFVPA | 0.450 |
| 37 | 299 | FLCGNGVYK | 0.400 |
| 38 | 313 | WSGRCGLGY | 0.375 |
| 39 | 442 | KQCCLYINY | 0.375 |
| 40 | 414 | SSLASASRK | 0.300 |
| 41 | 413 | VSSLASASR | 0.300 |
| 42 | 71 | YSGQWMYER | 0.300 |
| 43 | 134 | GPFLGNIPK | 0.250 |
| 44 | 354 | QGDTDNPPL | 0.250 |
| 45 | 174 | DTSVCLGTR | 0.250 |
| 46 | 224 | GNDTCLYSC | 0.250 |
| 47 | 540 | ETSCQVSNR | 0.250 |
| 48 | 150 | WFDSTDGTF | 0.250 |
| 49 | 502 | FIFVLIYVR | 0.200 |
| 50 | 505 | VLIYVRVFR | 0.200 |

TABLE VI

Scoring Results 103P2D6 HLA peptides A1 10- MERS
(SEQ ID NOs: 65-114, respectively)

| Rank | Start Position | Subsequence Residue Listing | Score (Estimate of Half Time of Disassociation of a Molecule Containing This Subsequence) |
|---|---|---|---|
| 1 | 473 | LLDWQGIFAK | 50.000 |
| 2 | 394 | AMEQEFSATK | 18.000 |
| 3 | 354 | QGDTDNPPLY | 12.500 |
| 4 | 262 | CADASITNDK | 10.000 |
| 5 | 483 | VGDWFRSWGY | 6.250 |
| 6 | 118 | LLEGNFSLCV | 4.500 |
| 7 | 464 | ASENLKNVPL | 2.700 |
| 8 | 538 | VSETSCQVSN | 2.700 |
| 9 | 153 | STDGTFMPSI | 2.500 |
| 10 | 356 | DTDNPPLYCN | 2.500 |
| 11 | 337 | ITNLRSFIHK | 2.500 |
| 12 | 499 | FCLFIFVLIY | 2.500 |
| 13 | 451 | SEEIKSNIQR | 2.250 |
| 14 | 253 | LTEAHGKWRC | 2.250 |
| 15 | 46 | LCEHLDNAEQ | 1.800 |
| 16 | 52 | NAEQPELVFV | 1.800 |
| 17 | 450 | YSEEIKSNIQ | 1.350 |
| 18 | 438 | GTVGKQCCLY | 1.250 |
| 19 | 505 | VLIYVRVFRK | 1.000 |
| 20 | 49 | HLDNAEQPEL | 1.000 |
| 21 | 84 | QAEVQNHSTS | 0.900 |
| 22 | 405 | TLEAHQSKVS | 0.900 |
| 23 | 104 | ASMEAQGLSF | 0.750 |
| 24 | 290 | LSVNNSGLFF | 0.750 |
| 25 | 203 | IGLPNTQDYK | 0.500 |
| 26 | 161 | SIDVTNESRN | 0.500 |
| 27 | 202 | LIGLPNTQDY | 0.500 |

TABLE VI-continued

Scoring Results 103P2D6 HLA peptides A1 10- MERS
(SEQ ID NOs: 65-114, respectively)

| Rank | Start Position | Subsequence Residue Listing | Score (Estimate of Half Time of Disassociation of a Molecule Containing This Subsequence) |
|---|---|---|---|
| 28 | 425 | VLDIPTTQRQ | 0.500 |
| 29 | 358 | DNPPLYCNPK | 0.500 |
| 30 | 373 | RALFPSLGTY | 0.500 |
| 31 | 207 | NTQDYKWVDR | 0.500 |
| 32 | 495 | LIVLFCLFIF | 0.500 |
| 33 | 86 | EVQNHSTSSY | 0.500 |
| 34 | 198 | SAVPLIGLPN | 0.500 |
| 35 | 55 | QPELVFVPAS | 0.450 |
| 36 | 105 | SMEAQGLSFA | 0.450 |
| 37 | 542 | SCQVSNRAMK | 0.400 |
| 38 | 232 | CQNQTKGLLY | 0.375 |
| 39 | 413 | VSSLASASRK | 0.300 |
| 40 | 520 | NSQPLNLALS | 0.300 |
| 41 | 213 | WVDRNSGLTW | 0.250 |
| 42 | 307 | KGFPPKWSGR | 0.250 |
| 43 | 133 | SGPFLGNIPK | 0.250 |
| 44 | 461 | LHEASENLKN | 0.225 |
| 45 | 412 | KVSSLASASR | 0.200 |
| 46 | 504 | FVLIYVRVFR | 0.200 |
| 47 | 460 | RLHEASENLK | 0.200 |
| 48 | 228 | CLYSCQNQTK | 0.200 |
| 49 | 527 | ALSPQQSAQL | 0.200 |
| 50 | 377 | PSLGTYDLEK | 0.150 |

TABLE VII

Scoring Results 103P2D6 HLA peptides A2 9MERS
(SEQ ID NOs: 115-164, respectively)

| Rank | Start Position | Subsequence Residue Listing | Score (Estimate of Half Time of Disassociation of a Molecule Containing This Subsequence) |
|---|---|---|---|
| 1 | 497 | VLFCLFIFV | 4571.688 |
| 2 | 117 | RLLEGNFSL | 1879.592 |
| 3 | 493 | VLLIVLFCL | 1792.489 |
| 4 | 45 | WLCEHLDNA | 105.596 |
| 5 | 282 | WLTGSNLTL | 98.267 |
| 6 | 492 | YVLLIVLFC | 93.592 |
| 7 | 13 | TLTAFLTIL | 76.550 |
| 8 | 10 | LQLTLTAFL | 74.930 |
| 9 | 75 | WMYERVWYP | 61.634 |
| 10 | 495 | LIVLFCLFI | 50.968 |
| 11 | 79 | RVWYPQAEV | 50.512 |
| 12 | 318 | GLGYLVPSL | 49.134 |
| 13 | 329 | YLTLNASQI | 47.991 |
| 14 | 241 | YQLFRNLFC | 47.151 |
| 15 | 339 | NLRSFIHKV | 46.199 |
| 16 | 239 | LLYQLFRNL | 44.160 |
| 17 | 11 | QLTLTAFLT | 43.222 |
| 18 | 460 | RLHEASENL | 42.917 |
| 19 | 537 | LVSETSCQV | 42.418 |
| 20 | 20 | ILVQPQHLL | 36.316 |
| 21 | 228 | CLYSCQNQT | 23.846 |
| 22 | 110 | GLSFAQVRL | 21.362 |
| 23 | 518 | SLNSQPLNL | 21.362 |
| 24 | 289 | TLSVNNSGL | 21.362 |
| 25 | 393 | KAMEQEFSA | 21.249 |
| 26 | 473 | LLDWQGIFA | 18.580 |
| 27 | 535 | QLLVSETSC | 18.382 |
| 28 | 8 | ALLQLTLTA | 18.382 |
| 29 | 292 | VNNSGLFFL | 17.393 |
| 30 | 53 | AEQPELVFV | 17.108 |
| 31 | 27 | LLAPVFRTL | 13.800 |
| 32 | 108 | AQGLSFAQV | 13.398 |

TABLE VII-continued

Scoring Results 103P2D6 HLA peptides A2 9MERS
(SEQ ID NOs: 115-164, respectively)

| Rank | Start Position | Subsequence Residue Listing | Score (Estimate of Half Time of Disassociation of a Molecule Containing This Subsequence) |
|---|---|---|---|
| 33 | 26 | HLLAPVFRT | 12.506 |
| 34 | 19 | TILVQPQHL | 10.868 |
| 35 | 119 | LEGNFSLCV | 8.737 |
| 36 | 336 | QITNLRSFI | 7.890 |
| 37 | 219 | GLTWSGNDT | 7.452 |
| 38 | 552 | GLTTHQYDT | 7.452 |
| 39 | 246 | NLFCSYGLT | 5.377 |
| 40 | 405 | TLEAHQSKV | 4.451 |
| 41 | 242 | QLFRNLFCS | 3.678 |
| 42 | 238 | GLLYQLFRN | 3.678 |
| 43 | 156 | GTFMPSIDV | 3.574 |
| 44 | 322 | LVPSLTRYL | 3.495 |
| 45 | 38 | LTNQSNCWL | 2.774 |
| 46 | 36 | SILTNQSNC | 2.527 |
| 47 | 387 | AILNISKAM | 2.527 |
| 48 | 499 | FCLFIFVLI | 2.202 |
| 49 | 106 | MEAQGLSFA | 2.077 |
| 50 | 490 | WGYVLLIVL | 1.936 |

TABLE VIII

Scoring Results 103P2D6 HLA peptides A2 10-MERS
(SEQ ID NOs: 165-214, respectively)

| Rank | Start Position | Subsequence Residue Listing | Score (Estimate of Half Time of Disassociation of a Molecule Containing This Subsequence) |
|---|---|---|---|
| 1 | 500 | CLFIFVLIYV | 3255.381 |
| 2 | 497 | VLFCLFIFVL | 2792.698 |
| 3 | 492 | YVLLIVLFCL | 424.398 |
| 4 | 496 | IVLFCLFIFV | 400.023 |
| 5 | 494 | LLIVLFCLFI | 370.677 |
| 6 | 296 | GLFFLCGNGV | 257.342 |
| 7 | 502 | FIFVLIYVRV | 244.154 |
| 8 | 37 | ILTNQSNCWL | 199.738 |
| 9 | 9 | LLQLTLTAFL | 199.738 |
| 10 | 117 | RLLEGNFSLC | 143.193 |
| 11 | 291 | SVNNSGLFFL | 137.144 |
| 12 | 136 | FLGNIPKQYC | 125.690 |
| 13 | 536 | LLVSETSCQV | 118.238 |
| 14 | 321 | YLVPSLTRYL | 108.094 |
| 15 | 13 | TLTAFLTILV | 69.552 |
| 16 | 148 | ILWFDSTDGT | 51.522 |
| 17 | 331 | TLNASQITNL | 49.134 |
| 18 | 3 | SLSNCALLQL | 49.134 |
| 19 | 238 | GLLYQLFRNL | 30.036 |
| 20 | 118 | LLEGNFSLCV | 28.756 |
| 21 | 22 | VQPQHLLAPV | 27.573 |
| 22 | 10 | LQLTLTAFLT | 27.564 |
| 23 | 527 | ALSPQQSAQL | 21.362 |
| 24 | 11 | QLTLTAFLTI | 19.822 |
| 25 | 445 | CLYTNYSEEI | 16.359 |
| 26 | 338 | TNLRSFIHKV | 14.682 |
| 27 | 404 | QTLEAHQSKV | 14.654 |
| 28 | 329 | YLTLNASQIT | 14.054 |
| 29 | 518 | SLNSQPLNLA | 11.426 |
| 30 | 19 | TILVQPQHLL | 10.868 |
| 31 | 393 | KAMEQEFSAT | 10.441 |
| 32 | 110 | GLSFAQVRLL | 9.827 |
| 33 | 472 | PLLDWQGIFA | 9.119 |
| 34 | 353 | TQGDTDNPPL | 8.880 |
| 35 | 20 | ILVQPQHLLA | 8.446 |
| 36 | 318 | GLGYLVPSLT | 7.452 |
| 37 | 12 | LTLTAFLTIL | 6.687 |

TABLE VIII-continued

Scoring Results 103P2D6 HLA peptides A2 10-MERS
(SEQ ID NOs: 165-214, respectively)

| Rank | Start Position | Subsequence Residue Listing | Score (Estimate of Half Time of Disassociation of a Molecule Containing This Subsequence) |
|---|---|---|---|
| 38 | 205 | LPNTQDYKWV | 6.368 |
| 39 | 335 | SQITNLRSFI | 5.818 |
| 40 | 378 | SLGTYDLEKA | 5.599 |
| 41 | 439 | TVGKQCCLYI | 5.021 |
| 42 | 234 | NQTKGLLYQL | 4.982 |
| 43 | 325 | SLTRYLTLNA | 4.968 |
| 44 | 525 | NLALSPQQSA | 4.968 |
| 45 | 544 | QVSNRAMKGL | 4.299 |
| 46 | 220 | LTWSGNDTCL | 4.186 |
| 47 | 58 | LVFVPASAST | 4.101 |
| 48 | 488 | RSWGYVLLIV | 3.554 |
| 49 | 61 | VPASASTWWT | 3.411 |
| 50 | 343 | FIHKVTPHRC | 3.142 |

TABLE IX

Scoring Results 103P2D6 HLA PEPTIDES A3 9-MERS
(SEQ ID NOs: 215-264, respectively)

| Rank | Start Position | Subsequence Residue Listing | Score (Estimate of Half Time of Disassociation of a Molecule Containing This Subsequence) |
|---|---|---|---|
| 1 | 500 | CLFIFVLIY | 360.000 |
| 2 | 378 | SLGTYDLEK | 120.000 |
| 3 | 304 | GVYKGFPPK | 90.000 |
| 4 | 506 | LIYVRVFRK | 90.000 |
| 5 | 204 | GLPNTQDYK | 60.000 |
| 6 | 299 | FLCGNGVYK | 30.000 |
| 7 | 321 | YLVPSLTRY | 13.500 |
| 8 | 374 | ALFPSLGTY | 13.500 |
| 9 | 505 | VLIYVRVFR | 9.000 |
| 10 | 494 | LLIVLFCLF | 9.000 |
| 11 | 502 | FIFVLIYVR | 9.000 |
| 12 | 493 | VLLIVLFCL | 6.075 |
| 13 | 425 | VLDIPTTQR | 6.000 |
| 14 | 134 | GPFLGNIPK | 6.000 |
| 15 | 497 | VLFCLFIFV | 6.000 |
| 16 | 318 | GLGYLVPSL | 5.400 |
| 17 | 117 | RLLEGNFSL | 4.050 |
| 18 | 178 | CLGTRQCSR | 4.000 |
| 19 | 105 | SMEAQGLSF | 4.000 |
| 20 | 136 | FLGNIPKQY | 3.000 |
| 21 | 69 | WTYSGQWMY | 3.000 |
| 22 | 9 | LLQLTLTAF | 3.000 |
| 23 | 13 | TLTAFLTIL | 2.700 |
| 24 | 404 | QTLEAHQSK | 2.250 |
| 25 | 26 | HLLAPVFRT | 2.025 |
| 26 | 447 | YINYSEEIK | 2.000 |
| 27 | 110 | GLSFAQVRL | 1.800 |
| 28 | 282 | WLTGSNLTL | 1.800 |
| 29 | 20 | ILVQPQHLL | 1.350 |
| 30 | 75 | WMYERVWYP | 1.350 |
| 31 | 496 | IVLFCLFIF | 1.350 |
| 32 | 518 | SLNSQPLNL | 1.200 |
| 33 | 434 | QTACGTVGK | 1.000 |
| 34 | 552 | GLTTHQYDT | 0.900 |
| 35 | 118 | LLEGNFSLC | 0.900 |
| 36 | 339 | NLRSFIHKV | 0.900 |
| 37 | 239 | LLYQLFRNL | 0.900 |
| 38 | 460 | RLHEASENL | 0.900 |
| 39 | 543 | CQVSNRAMK | 0.900 |
| 40 | 242 | QLFRNLFCS | 0.900 |
| 41 | 442 | KQCCLYINY | 0.720 |
| 42 | 289 | TLSVNNSGL | 0.600 |

TABLE IX-continued

Scoring Results 103P2D6 HLA PEPTIDES A3 9-MERS
(SEQ ID NOs: 215-264, respectively)

| Rank | Start Position | Subsequence Residue Listing | Score (Estimate of Half Time of Disassociation of a Molecule Containing This Subsequence) |
|---|---|---|---|
| 43 | 359 | NPPLYCNPK | 0.600 |
| 44 | 343 | FIHKVTPHR | 0.600 |
| 45 | 329 | YLTLNASQI | 0.600 |
| 46 | 508 | YVRVFRKSR | 0.600 |
| 47 | 8 | ALLQLTLTA | 0.600 |
| 48 | 495 | LIVLFCLFI | 0.540 |
| 49 | 383 | DLEKAILNI | 0.540 |
| 50 | 228 | CLYSCQNQT | 0.500 |

TABLE X

Scoring Results 103P2D6 HLA peptides A3 10-MERS
(SEQ ID NOs: 265-314, respectively)

| Rank | Start Position | Subsequence Residue Listing | Score (Estimate of Half Time of Disassociation of a Molecule Containing This Subsequence) |
|---|---|---|---|
| 1 | 505 | VLIYVRVFRK | 270.000 |
| 2 | 228 | CLYSCQNQTK | 100.000 |
| 3 | 473 | LLDWQGIFAK | 90.000 |
| 4 | 394 | AMEQEFSATK | 60.000 |
| 5 | 242 | QLFRNLFCSY | 60.000 |
| 6 | 497 | VLFCLFIFVL | 40.500 |
| 7 | 460 | RLHEASENLK | 30.000 |
| 8 | 239 | LLYQLFRNLF | 30.000 |
| 9 | 252 | GLTEAHGKWR | 9.000 |
| 10 | 493 | VLLIVLFCL | 9.000 |
| 11 | 445 | CLYINYSEEI | 9.000 |
| 12 | 337 | ITNLRSFIHK | 6.000 |
| 13 | 549 | AMKGLTTHQY | 6.000 |
| 14 | 494 | LLIVLFCLFI | 5.400 |
| 15 | 500 | CLFIFVLIYV | 4.500 |
| 16 | 8 | ALLQLTLTAF | 4.500 |
| 17 | 478 | GIFAKVGDWF | 4.500 |
| 18 | 11 | QLTLTAFLTI | 3.600 |
| 19 | 296 | GLFFLCGNGV | 3.000 |
| 20 | 142 | KQYCNQILWF | 2.700 |
| 21 | 178 | CLGTRQCSRF | 2.000 |
| 22 | 121 | GNFSLCVENK | 1.800 |
| 23 | 73 | GQWMYERVWY | 1.800 |
| 24 | 118 | LLEGNFSLCV | 1.800 |
| 25 | 3 | SLSNCALLQL | 1.800 |
| 26 | 403 | KQTLEAHQSK | 1.800 |
| 27 | 204 | GLPNTQDYKW | 1.800 |
| 28 | 495 | LIVLFCLFIF | 1.350 |
| 29 | 117 | RLLEGNFSLC | 1.350 |
| 30 | 438 | GTVGKQCCLY | 1.350 |
| 31 | 412 | KVSSLASASR | 1.200 |
| 32 | 499 | FCLFIFVLIY | 1.080 |
| 33 | 331 | TLNASQITNL | 0.900 |
| 34 | 304 | GVYKGFPPKW | 0.900 |
| 35 | 527 | ALSPQQSAQL | 0.900 |
| 36 | 504 | FVLIYVRVFR | 0.900 |
| 37 | 467 | NLKNVPLLDW | 0.900 |
| 38 | 424 | HVLDIPTTQR | 0.900 |
| 39 | 238 | GLLYQLFRNL | 0.810 |
| 40 | 75 | WMYERVWYPQ | 0.675 |
| 41 | 492 | YVLLIVLFCL | 0.608 |
| 42 | 49 | HLDNAEQPEL | 0.600 |
| 43 | 219 | GLTWSGNDTC | 0.600 |
| 44 | 246 | NLFCSYGLTE | 0.600 |
| 45 | 20 | ILVQPQHLLA | 0.600 |
| 46 | 9 | LLQLTLTAFL | 0.600 |

TABLE X-continued

Scoring Results 103P2D6 HLA peptides A3 10-MERS
(SEQ ID NOs: 265-314, respectively)

| Rank | Start Position | Subsequence Residue Listing | Score (Estimate of Half Time of Disassociation of a Molecule Containing This Subsequence) |
|---|---|---|---|
| 47 | 289 | TLSVNNSGLF | 0.600 |
| 48 | 37 | ILTNQSNCWL | 0.600 |
| 49 | 433 | RQTACGTVGK | 0.600 |
| 50 | 110 | GLSFAQVRLL | 0.540 |

TABLE XI

Scoring Results 103P2D6 HLA peptides A11 9 MERS
(SEQ ID NOs: 315-364, respectively)

| Rank | Start Position | Subsequence Residue Listing | Score (Estimate of half Time of Disassociation of a Molecule Containing This Subsequence) |
|---|---|---|---|
| 1 | 304 | GVYKGFPPK | 12.000 |
| 2 | 134 | GPFLGNIPK | 2.400 |
| 3 | 506 | LIYVRVFRK | 2.400 |
| 4 | 404 | QTLEAHQSK | 1.500 |
| 5 | 204 | GLPNTQDYK | 1.200 |
| 6 | 434 | QTACGTVGK | 1.000 |
| 7 | 543 | CQVSNRAMK | 0.900 |
| 8 | 378 | SLGTYDLEK | 0.800 |
| 9 | 320 | GYLVPSLTR | 0.720 |
| 10 | 229 | LYSCQNQTK | 0.400 |
| 11 | 447 | YINYSEEIK | 0.400 |
| 12 | 299 | FLCGNGVYK | 0.400 |
| 13 | 502 | FIFVLIYVR | 0.320 |
| 14 | 122 | NFSLCVENK | 0.200 |
| 15 | 508 | YVRVFRKSR | 0.200 |
| 16 | 359 | NPPLYCNPK | 0.200 |
| 17 | 338 | TNLRSFIHK | 0.120 |
| 18 | 474 | LDWQGIFAK | 0.120 |
| 19 | 156 | GTFMPSIDV | 0.120 |
| 20 | 505 | VLIYVRVFR | 0.120 |
| 21 | 208 | TQDYKWVDR | 0.120 |
| 22 | 308 | GFPPKWSGR | 0.120 |
| 23 | 79 | RVWYPQAEV | 0.120 |
| 24 | 253 | LTEAHGKWR | 0.100 |
| 25 | 496 | IVLFCLFIF | 0.090 |
| 26 | 178 | CLGTRQCSR | 0.080 |
| 27 | 425 | VLDIPTTQR | 0.080 |
| 28 | 343 | FIHKVTPHR | 0.080 |
| 29 | 161 | SIDVTNESR | 0.080 |
| 30 | 480 | FAKVGDWFR | 0.080 |
| 31 | 142 | KQYCNQILW | 0.072 |
| 32 | 540 | ETSCQVSNR | 0.060 |
| 33 | 395 | MEQEFSATK | 0.060 |
| 34 | 174 | DTSVCLGTR | 0.060 |
| 35 | 117 | RLLEGNFSL | 0.054 |
| 36 | 438 | GTVGKQCCL | 0.045 |
| 37 | 365 | NPKDNSTIR | 0.040 |
| 38 | 21 | LVQPQHLLA | 0.040 |
| 39 | 69 | WTYSGQWMY | 0.040 |
| 40 | 291 | SVNNSGLFF | 0.040 |
| 41 | 89 | NHSTSSYRK | 0.040 |
| 42 | 333 | NASQITNLR | 0.040 |
| 43 | 237 | KGLLYQLFR | 0.036 |
| 44 | 393 | KAMEQEFSA | 0.036 |
| 45 | 442 | KQCCLYINY | 0.036 |
| 46 | 251 | YGLTEAHGK | 0.030 |
| 47 | 414 | SSLASASRK | 0.030 |
| 48 | 12 | LTLTAFLTI | 0.030 |
| 49 | 337 | ITNLRSFIH | 0.030 |
| 50 | 380 | GTYDLEKAI | 0.030 |

TABLE XII

Scoring Results 103P2D6 HLA peptides A11 10-MERS
(SEQ ID NOs: 365-414, respectively)

| Rank | Start Position | Subsequence Residue Listing | Score (Estimate of half Time of Disassociation of a Molecule Containing This Subsequence) |
|---|---|---|---|
| 1 | 337 | ITNLRSFIHK | 2.000 |
| 2 | 505 | VLIYVRVFRK | 1.800 |
| 3 | 433 | RQTACGTVGK | 1.800 |
| 4 | 403 | KQTLEAHQSK | 1.800 |
| 5 | 473 | LLDWQGIFAK | 1.200 |
| 6 | 412 | KVSSLASASR | 1.200 |
| 7 | 460 | RLHEASENLK | 1.200 |
| 8 | 228 | CLYSCQNQTK | 0.800 |
| 9 | 504 | FVLIYVRVFR | 0.600 |
| 10 | 446 | LYINYSEEIK | 0.600 |
| 11 | 424 | HVLDIPTTQR | 0.600 |
| 12 | 508 | YVRVFRKSRR | 0.400 |
| 13 | 250 | SYGLTEAHGK | 0.400 |
| 14 | 394 | AMEQEFSATK | 0.400 |
| 15 | 298 | FFLCGNGVYK | 0.300 |
| 16 | 121 | GNFSLCVENK | 0.240 |
| 17 | 542 | SCQVSNRAMK | 0.200 |
| 18 | 262 | CADASITNDK | 0.200 |
| 19 | 207 | NTQDYKWVDR | 0.200 |
| 20 | 70 | TYSGQWMYER | 0.160 |
| 21 | 87 | VQNHSTSSYR | 0.120 |
| 22 | 304 | GVYKGFPPKW | 0.120 |
| 23 | 108 | AQGLSFAQVR | 0.120 |
| 24 | 384 | LEKAILNISK | 0.120 |
| 25 | 252 | GLTEAHGKWR | 0.120 |
| 26 | 501 | LFIFVLIYVR | 0.120 |
| 27 | 492 | YVLLIVLFCL | 0.090 |
| 28 | 479 | IFAKVGDWFR | 0.080 |
| 29 | 88 | QNHSTSSYRK | 0.080 |
| 30 | 142 | KQYCNQILWF | 0.072 |
| 31 | 193 | RTWNSSAVPL | 0.060 |
| 32 | 291 | SVNNSGLFFL | 0.060 |
| 33 | 97 | KVTWHWEASM | 0.060 |
| 34 | 380 | GTYDLEKAIL | 0.060 |
| 35 | 177 | VCLGTRQCSR | 0.060 |
| 36 | 496 | IVLFCLFIFV | 0.060 |
| 37 | 507 | IYVRVFRKSR | 0.060 |
| 38 | 342 | SFIHKVTPHR | 0.060 |
| 39 | 438 | GTVGKQCCLY | 0.045 |
| 40 | 439 | TVGKQCCLYI | 0.040 |
| 41 | 213 | WVDRNSGLTW | 0.040 |
| 42 | 133 | SGPFLGNIPK | 0.040 |
| 43 | 73 | GQWMYERVWY | 0.036 |
| 44 | 303 | NGVYKGFPPK | 0.030 |
| 45 | 203 | IGLPNTQDYK | 0.030 |
| 46 | 307 | KGFPPKWSGR | 0.024 |
| 47 | 478 | GIFAKVGDWF | 0.024 |
| 48 | 451 | SEEIKSNIQR | 0.024 |
| 49 | 204 | GLPNTQDYKW | 0.024 |
| 50 | 296 | GLFFLCGNGV | 0.024 |

TABLE XIII

Scoring Results 103P2D6 HLA peptides A24 9-MERS
(SEQ ID NOs: 415-464, respectively)

| Rank | Start Position | Subsequence Residue Listing | Score (Estimate of half Time of Disassociation of a Molecule Containing This Subsequence) |
|---|---|---|---|
| 1 | 381 | TYDLEKAIL | 200.000 |
| 2 | 491 | GYVLLIVLF | 180.000 |
| 3 | 240 | LYQLFRNLF | 180.000 |
| 4 | 143 | QYCNQILWF | 100.000 |
| 5 | 446 | LYINYSEEI | 82.500 |
| 6 | 398 | EFSATKQTL | 24.000 |
| 7 | 486 | WFRSWGYVL | 20.000 |
| 8 | 498 | LFCLFIFVL | 20.000 |
| 9 | 511 | VFRKSRRSL | 20.000 |
| 10 | 212 | KWVDRNSGL | 14.400 |
| 11 | 117 | RLLEGNFSL | 14.400 |
| 12 | 479 | IFAKVGDWF | 14.000 |
| 13 | 507 | IYVRVFRKS | 13.860 |
| 14 | 245 | RNLFCSYGL | 12.000 |
| 15 | 150 | WFDSTDGTF | 10.000 |
| 16 | 460 | RLHEASENL | 9.600 |
| 17 | 520 | NSQPLNLAL | 8.640 |
| 18 | 493 | VLLIVLFCL | 8.400 |
| 19 | 27 | LLAPVFRTL | 8.064 |
| 20 | 81 | WYPQAEVQN | 7.500 |
| 21 | 529 | SPQQSAQLL | 7.200 |
| 22 | 10 | LQLTLTAFL | 7.200 |
| 23 | 322 | LVPSLTRYL | 7.200 |
| 24 | 19 | TILVQPQHL | 7.200 |
| 25 | 94 | SYRKVTWHW | 7.000 |
| 26 | 210 | DYKWVDRNS | 7.000 |
| 27 | 38 | LTNQSNCWL | 6.000 |
| 28 | 449 | NYSEEIKSN | 6.000 |
| 29 | 20 | ILVQPQHLL | 6.000 |
| 30 | 545 | VSNRAMKGL | 6.000 |
| 31 | 4 | LSNCALLQL | 6.000 |
| 32 | 292 | VNNSGLFFL | 6.000 |
| 33 | 231 | SCQNQTKGL | 6.000 |
| 34 | 528 | LSPQQSAQL | 6.000 |
| 35 | 2 | GSLSNCALL | 6.000 |
| 36 | 518 | SLNSQPLNL | 6.000 |
| 37 | 438 | GTVGKQCCL | 6.000 |
| 38 | 232 | CQNQTKGLL | 6.000 |
| 39 | 466 | ENLKNVPLL | 6.000 |
| 40 | 194 | TWNSSAVPL | 6.000 |
| 41 | 371 | TIRALFPSL | 5.760 |
| 42 | 239 | LLYQLFRNL | 5.760 |
| 43 | 305 | VYKGFPPKW | 5.500 |
| 44 | 362 | LYCNPKDNS | 5.000 |
| 45 | 6 | NCALLQLTL | 4.800 |
| 46 | 235 | QTKGLLYQL | 4.800 |
| 47 | 42 | SNCWLCEHL | 4.800 |
| 48 | 103 | EASMEAQGL | 4.800 |
| 49 | 490 | WGYVLLIVL | 4.800 |
| 50 | 318 | GLGYLVPSL | 4.800 |

TABLE XIV

Scoring Results 103P2D6 HLA peptides A24 10-MERS
(SEQ ID NOs: 465-514, respectively)

| Rank | Start Position | Subsequence Residue Listing | Score (Estimate of half Time of Disassociation of a Molecule Containing This Subsequence) |
|---|---|---|---|
| 1 | 328 | RYLTLNASQI | 150.000 |
| 2 | 449 | NYSEEIKSNI | 84.000 |
| 3 | 375 | LFPSLGTYDL | 30.000 |
| 4 | 486 | WFRSWGYVLL | 20.000 |
| 5 | 503 | IFVLIYVRVF | 15.000 |
| 6 | 517 | RSLNSQPLNL | 12.000 |
| 7 | 491 | GYVLLIVLFC | 10.500 |
| 8 | 26 | HLLAPVFRTL | 10.080 |
| 9 | 370 | STIRALFPSL | 8.640 |
| 10 | 238 | GLLYQLFRNL | 8.640 |
| 11 | 321 | YLVPSLTRYL | 8.640 |
| 12 | 498 | LFCLFIFVLI | 8.400 |
| 13 | 492 | YVLLIVLFCL | 8.400 |
| 14 | 510 | RVFRKSRRSL | 8.000 |

TABLE XIV-continued

Scoring Results 103P2D6 HLA peptides A24 10-MERS
(SEQ ID NOs: 465-514, respectively)

| Rank | Start Position | Subsequence Residue Listing | Score (Estimate of half Time of Disassociation of a Molecule Containing This Subsequence) |
|---|---|---|---|
| 15 | 193 | RTWNSSAVPL | 8.000 |
| 16 | 240 | LYQLFRNLFC | 7.500 |
| 17 | 320 | GYLVPSLTRY | 7.500 |
| 18 | 76 | MYERVWYPQA | 7.500 |
| 19 | 41 | QSNCWLCEHL | 7.200 |
| 20 | 18 | LTILVQPQHL | 7.200 |
| 21 | 528 | LSPQQSAQLL | 7.200 |
| 22 | 9 | LLQLTLTAFL | 7.200 |
| 23 | 317 | CGLGYLVPSL | 7.200 |
| 24 | 109 | QGLSFAQVRL | 6.000 |
| 25 | 29 | APVFRTLSIL | 6.000 |
| 26 | 331 | TLNASQITNL | 6.000 |
| 27 | 464 | ASENLKNVPL | 6.000 |
| 28 | 288 | LTLSVNNSGL | 6.000 |
| 29 | 231 | SCQNQTKGLL | 6.000 |
| 30 | 281 | WWLTGSNLTL | 6.000 |
| 31 | 362 | LYGNPKDNST | 6.000 |
| 32 | 291 | SVNNSGLFFL | 6.000 |
| 33 | 12 | LTLTAFLTIL | 6.000 |
| 34 | 19 | TILVQPQHLL | 6.000 |
| 35 | 381 | TYDLEKAILN | 5.000 |
| 36 | 305 | VYKGFPPKWS | 5.000 |
| 37 | 489 | SWGYVLLIVL | 4.800 |
| 38 | 234 | NQTKGLLYQL | 4.800 |
| 39 | 380 | GTYDIEKAIL | 4.800 |
| 40 | 519 | LNSQpLNLAL | 4.800 |
| 41 | 140 | IPKQyCNQIL | 4.800 |
| 42 | 5 | SNCAlLQLTL | 4.800 |
| 43 | 353 | TQGDtDNPPL | 4.800 |
| 44 | 527 | ALSPqQSAQL | 4.800 |
| 45 | 49 | HLDNaEQPEL | 4.400 |
| 46 | 493 | VLLIvLFCLF | 4.320 |
| 47 | 544 | QVSNrAMKGL | 4.000 |
| 48 | 323 | VPSLtRYLTL | 4.000 |
| 49 | 1 | MGSLsNCALL | 4.000 |
| 50 | 485 | DWFRsWGYVL | 4.000 |

TABLE XV

Scoring Results 103P2D6 HLA peptides B7 9-MERS
(SEQ ID NOs: 465-514, respectively)

| Rank | Start Position | Subsequence Residue Listing | Score (Estimate of half Time of Disassociation of a Molecule Containing This Subsequence) |
|---|---|---|---|
| 1 | 376 | FPSLFTYDL | 80.000 |
| 2 | 529 | SPQQSAQLL | 80.000 |
| 3 | 371 | TIRALFPSL | 40.000 |
| 4 | 314 | SGRCGLGYL | 40.00 |
| 5 | 29 | APVFRTLSI | 24.000 |
| 6 | 322 | LVPSLTRYL | 20.000 |
| 7 | 103 | EASMEAQGL | 12.000 |
| 8 | 418 | SASRKDHVL | 12.000 |
| 9 | 471 | VPLLDWQGI | 8.000 |
| 10 | 140 | IPKQYCNQI | 8.000 |
| 11 | 20 | ILVQPQHLL | 6.000 |
| 12 | 197 | SSAVPLIGL | 6.000 |
| 13 | 275 | GHRTPTWWL | 6.000 |
| 14 | 511 | VFRKSRRSL | 6.000 |
| 15 | 235 | QTKGLLYQL | 4.000 |
| 16 | 453 | EIKSNIQRL | 4.000 |
| 17 | 110 | GLSFAQVRL | 4.000 |
| 18 | 493 | VLLIVLFCL | 4.000 |
| 19 | 486 | WFRSWGYVL | 4.000 |
| 20 | 282 | WLTGSNLTL | 4.000 |
| 21 | 4 | LSNCALLQL | 4.000 |

TABLE XV-continued

Scoring Results 103P2D6 HLA peptides B7 9-MERS
(SEQ ID NOs: 465-514, respectively)

| Rank | Start Position | Subsequence Residue Listing | Score (Estimate of half Time of Disassociation of a Molecule Containing This Subsequence) |
|---|---|---|---|
| 22 | 545 | VSNRAMKGL | 4.000 |
| 23 | 520 | NSQPLNLAL | 4.000 |
| 24 | 42 | SNCWLCEHL | 4.000 |
| 25 | 231 | SCQNQTKGL | 4.000 |
| 26 | 239 | LLYQLFRNL | 4.000 |
| 27 | 528 | LSPQQSAQL | 4.000 |
| 28 | 13 | TLTAFLTIL | 4.000 |
| 29 | 10 | LQLTLTAFL | 4.000 |
| 30 | 490 | WGYVLLIVL | 4.000 |
| 31 | 27 | LLAPVFRTL | 4.000 |
| 32 | 111 | LSFAQVRLL | 4.000 |
| 33 | 466 | ENLKNVPLL | 4.000 |
| 34 | 518 | SLNSQPLNL | 4.000 |
| 35 | 2 | GSLSNCALL | 4.000 |
| 36 | 19 | TILVQPQHL | 4.000 |
| 37 | 6 | NCALLQLTL | 4.000 |
| 38 | 318 | GLGYLVPSL | 4.000 |
| 39 | 332 | LNASQITNL | 4.000 |
| 40 | 460 | RLHEASENL | 4.000 |
| 41 | 1 | MGSLSNCAL | 4.000 |
| 42 | 289 | TLSVNNSGL | 4.000 |
| 43 | 23 | QPQHLLAPV | 4.000 |
| 44 | 438 | GTVGKQCCL | 4.000 |
| 45 | 232 | CQNQTKGLL | 4.000 |
| 46 | 245 | RNLFCSYGL | 4.000 |
| 47 | 38 | LTNQSNCWL | 4.000 |
| 48 | 117 | RLLEGNFSL | 4.000 |
| 49 | 292 | VNNSGLFFL | 4.000 |
| 50 | 554 | TTHQYDTSL | 4.000 |

TABLE XVI

Scoring Results 103P2D6 HLA peptides B7 10-MERS
(SEQ ID NOs: 565-614, respectively)

| Rank | Start Position | Subsequence Residue Listing | Score (Estimate of half Time of Disassociation of a Molecule Containing This Subsequence) |
|---|---|---|---|
| 1 | 29 | APVFRTLSIL | 240.000 |
| 2 | 140 | IPKQYCNQIL | 80.000 |
| 3 | 323 | VPSLTRYLTL | 80.000 |
| 4 | 510 | RVFRKSRRSL | 30.000 |
| 5 | 492 | YVLLIVLFCL | 20.000 |
| 6 | 291 | SVNNSGLFFL | 20.000 |
| 7 | 544 | QVSNRAMKGL | 20.000 |
| 8 | 310 | PPKWSGRCGL | 12.000 |
| 9 | 417 | ASASRKDHVL | 12.000 |
| 10 | 527 | ALSPQQSAQL | 12.000 |
| 11 | 407 | EAHQSKVSSL | 12.000 |
| 12 | 419 | ASRKDHVLDI | 12.000 |
| 13 | 196 | NSSAVPLIGL | 6.000 |
| 14 | 274 | DGHRTPTWWL | 6.000 |
| 15 | 19 | TILVQPQHLL | 6.000 |
| 16 | 97 | KVTWHWEASM | 5.000 |
| 17 | 109 | QGLSFAQVRL | 4.000 |
| 18 | 220 | LTWSGNDTCL | 4.000 |
| 19 | 528 | LSPQQSAQLL | 4.000 |
| 20 | 331 | TLNASQITNL | 4.000 |
| 21 | 370 | STIRALFPSL | 4.000 |
| 22 | 437 | CGTVGKQCCL | 4.000 |
| 23 | 110 | GLSFAQVRLL | 4.000 |
| 24 | 231 | SCQNQTKGLL | 4.000 |
| 25 | 353 | TQGDTDNPPL | 4.000 |
| 26 | 193 | RTWNSSAVPL | 4.000 |
| 27 | 517 | RSLNSQPLNL | 4.000 |
| 28 | 41 | QSNCWLCEHL | 4.000 |

TABLE XVI-continued

Scoring Results 103P2D6 HLA peptides B7 10-MERS
(SEQ ID NOs: 565-614, respectively)

| Rank | Start Position | Subsequence Residue Listing | Score (Estimate of half Time of Disassociation of a Molecule Containing This Subsequence) |
|---|---|---|---|
| 29 | 519 | LNSQPLNLAL | 4.000 |
| 30 | 238 | GLLYQLFRNL | 4.000 |
| 31 | 26 | HLLAPVFRTL | 4.000 |
| 32 | 234 | NQTKGLLYQL | 4.000 |
| 33 | 205 | LPNTQDYKWV | 4.000 |
| 34 | 128 | ENKNGSGPFL | 4.000 |
| 35 | 486 | WFRSWGYVLL | 4.000 |
| 36 | 12 | LTLTAFLTIL | 4.000 |
| 37 | 529 | SPQQSAQLLV | 4.000 |
| 38 | 553 | LTTHQYDTSL | 4.000 |
| 39 | 317 | CGLGYLVPSL | 4.000 |
| 40 | 288 | LTLSVNNSGL | 4.000 |
| 41 | 380 | GTYDLEKAIL | 4.000 |
| 42 | 18 | LTILVQPQHL | 4.000 |
| 43 | 554 | TTHQYDTSLL | 4.000 |
| 44 | 37 | ILTNQSNCWL | 4.000 |
| 45 | 515 | SRRSLNSQPL | 4.000 |
| 46 | 9 | LLQLTLTAFL | 4.000 |
| 47 | 321 | YLVPSLTRYL | 4.000 |
| 48 | 497 | VLFCLFIFVL | 4.000 |
| 49 | 5 | SNCALLQLTL | 4.000 |
| 50 | 3 | SLSNCALLQL | 4.000 |

TABLE XVII

Scoring Results 103P2D6 HLA peptides B35 9-MERS
(SEQ ID NOs: 615-664, respectively)

| Rank | Start Position | Subsequence Residue Listing | Score (Estimate of half Time of Disassociation of a Molecule Containing This Subsequence) |
|---|---|---|---|
| 1 | 140 | IPKQYCNQI | 24.000 |
| 2 | 376 | FPSLGTYDL | 20.000 |
| 3 | 529 | SPQQSAQLL | 20.000 |
| 4 | 222 | WSGNDTCLY | 15.000 |
| 5 | 391 | ISKAMEQEF | 15.000 |
| 6 | 471 | VPLLDWQGI | 12.000 |
| 7 | 63 | ASASTWWTY | 10.000 |
| 8 | 313 | WSGRCGLGY | 10.000 |
| 9 | 61 | VPASASTWW | 10.000 |
| 10 | 205 | LPNTQDYKW | 10.000 |
| 11 | 29 | APVFRTLSI | 8.000 |
| 12 | 528 | LSPQQSAQL | 5.000 |
| 13 | 520 | NSQPLNLAL | 5.000 |
| 14 | 545 | VSNRAMKGL | 5.000 |
| 15 | 197 | SSAVPLIGL | 5.000 |
| 16 | 111 | LSFAQVRLL | 5.000 |
| 17 | 2 | GSLSNCALL | 5.000 |
| 18 | 290 | LSVNNSGLF | 5.000 |
| 19 | 4 | LSNCALLQL | 5.000 |
| 20 | 103 | EASMEAQGL | 4.500 |
| 21 | 23 | QPQHLLAPV | 4.000 |
| 22 | 117 | RLLEGNFSL | 4.000 |
| 23 | 460 | RLHEASENL | 4.000 |
| 24 | 442 | KQCCLYINY | 4.000 |
| 25 | 488 | RSWGYVLLI | 4.000 |
| 26 | 314 | SGRCGLGYL | 3.000 |
| 27 | 235 | QTKGLLYQL | 3.000 |
| 28 | 453 | EIKSNIQRL | 3.000 |
| 29 | 418 | SASRKDHVL | 3.000 |
| 30 | 128 | ENKNGSGPF | 3.000 |
| 31 | 371 | TIRALFPSL | 3.000 |
| 32 | 115 | QVRLLEGNF | 3.000 |
| 33 | 92 | TSSYRKVTW | 2.500 |

TABLE XVII-continued

Scoring Results 103P2D6 HLA peptides B35 9-MERS
(SEQ ID NOs: 615-664, respectively)

| Rank | Start Position | Subsequence Residue Listing | Score (Estimate of half Time of Disassociation of a Molecule Containing This Subsequence) |
|---|---|---|---|
| 34 | 167 | ESRNDDDT | 2.250 |
| 35 | 69 | WTYSGQWMY | 2.000 |
| 36 | 482 | KVGDWFRSW | 2.000 |
| 37 | 200 | VPLIGLPNT | 2.000 |
| 38 | 309 | FPPKWSGRC | 2.000 |
| 39 | 323 | VPSLTRYLT | 2.000 |
| 40 | 203 | IGLPNTQDY | 2.000 |
| 41 | 136 | FLGNIPKQY | 2.000 |
| 42 | 500 | CLFIFVLIY | 2.000 |
| 43 | 387 | AILNISKAM | 2.000 |
| 44 | 245 | RNLFCSYGL | 2.000 |
| 45 | 439 | TVGKQCCLY | 2.000 |
| 46 | 321 | YLVPSLTRY | 2.000 |
| 47 | 428 | IPTTQRQTA | 2.000 |
| 48 | 132 | GSGPFLGNI | 2.000 |
| 49 | 98 | VTWHWEASM | 2.000 |
| 50 | 278 | TPTWWLTGS | 2.000 |

TABLE XVIII

Scoring Results 103P2D6 HLA peptides A35 10-MERS
(SEQ ID NOs: 665-714, respectively)

| Rank | Start Position | Subsequence Residue Listing | Score (Estimate of half Time of Disassociation of a Molecule Containing This Subsequence) |
|---|---|---|---|
| 1 | 140 | IPKQYCNQIL | 60.000 |
| 2 | 323 | VPSLTRYLTL | 20.000 |
| 3 | 23 | QPQHLLAPVF | 20.000 |
| 4 | 471 | VPLLDWQGIF | 20.000 |
| 5 | 29 | APVFRTLSIL | 20.000 |
| 6 | 365 | NPKDNSTIRA | 12.000 |
| 7 | 386 | KAILNISKAM | 12.000 |
| 8 | 373 | RALFPSLGTY | 12.000 |
| 9 | 517 | RSLNSQPLNL | 10.000 |
| 10 | 104 | ASMEAQGLSF | 10.000 |
| 11 | 541 | TSCQVSNRAM | 10.000 |
| 12 | 549 | AMKGLTTHQY | 6.000 |
| 13 | 310 | PPKWSGRCGL | 6.000 |
| 14 | 205 | LPNTQDYKWV | 6.000 |
| 15 | 419 | ASRKDHVLDI | 6.000 |
| 16 | 528 | LSPQQSAQLL | 5.000 |
| 17 | 230 | YSCQNQTKGL | 5.000 |
| 18 | 334 | ASQITNLRSF | 5.000 |
| 19 | 313 | WSGRCGLGYL | 5.000 |
| 20 | 41 | QSNCWLCEHL | 5.000 |
| 21 | 417 | ASASRKDHVL | 5.000 |
| 22 | 196 | NSSAVPLIGL | 5.000 |
| 23 | 290 | LSVNNSGLFF | 5.000 |
| 24 | 529 | SPQQSAQLLV | 4.000 |
| 25 | 97 | KVTWHWEASM | 4.000 |
| 26 | 353 | TQGDTDNPPL | 3.000 |
| 27 | 235 | QTKGLLYQLF | 3.000 |
| 28 | 128 | ENKNGSGPFL | 3.000 |
| 29 | 380 | GTYDLEKAIL | 3.000 |
| 30 | 407 | EAHQSKVSSL | 3.000 |
| 31 | 73 | GQWMYERVWY | 3.000 |
| 32 | 93 | SSYRKVTWHW | 2.500 |
| 33 | 391 | ISKAMEQEFS | 2.250 |
| 34 | 167 | ESRNDDDTS | 2.250 |
| 35 | 438 | GTVGKQCCLY | 2.000 |
| 36 | 82 | YPQAEVQNHS | 2.000 |
| 37 | 232 | CQNQTKGLLY | 2.000 |
| 38 | 242 | QLFRNLFCSY | 2.000 |
| 39 | 61 | VPASASTWWT | 2.000 |

TABLE XVIII-continued

Scoring Results 103P2D6 HLA peptides A35 10-MERS
(SEQ ID NOs: 665-714, respectively)

| Rank | Start Position | Subsequence Residue Listing | Score (Estimate of half Time of Disassociation of a Molecule Containing This Subsequence) |
|---|---|---|---|
| 40 | 510 | RVFRKSRRSL | 2.000 |
| 41 | 51 | DNAEQPELVF | 2.000 |
| 42 | 159 | MPSIDVTNES | 2.000 |
| 43 | 343 | TPHRCTQGDT | 2.000 |
| 44 | 488 | RSWGYVLLIV | 2.000 |
| 45 | 278 | TPTWWLTGSN | 2.000 |
| 46 | 142 | KQYCNQILWF | 2.000 |
| 47 | 193 | RTWNSSAVPL | 2.000 |
| 48 | 86 | EVQNHSTSSY | 2.000 |
| 49 | 202 | LIGLPNTQDY | 2.000 |
| 50 | 499 | FCLFIFVLIY | 2.000 |

TABLE XIX

Motif-bearing Subsequences of the 103P2D6 Protein
Post-translational modification Sites 15 N-glycosylation sites (SEQ ID NOS: 715-729, respectively)

| 1 | 40-43 NQSN |
| --- | --- |
| 2 | 89-92 NHST |
| 3 | 122-125 NFSL |
| 4 | 131-134 NGSG |
| 5 | 166-169 NESR |
| 6 | 192-195 NRTW |
| 7 | 196-199 NSSA |
| 8 | 225-228 NDTC |
| 9 | 234-237 NQTK |
| 10 | 287-290 NLTL |
| 11 | 293-296 NNSG |
| 12 | 333-336 NASQ |
| 13 | 369-372 NSTI |
| 14 | 390-393 NISK |
| 15 | 449-452 NYSE |

One cAMP- and cGMP-dependent protein kinase phosphorylation site
(SEQ ID NO: 730)

| 1 | 96-99 RKVT |
| --- | --- |

Eight protein kinase C phosphorylation sites

| 1 | 94-96 SYR |
| --- | --- |
| 2 | 191-193 TNR |
| 3 | 314-316 SGR |
| 4 | 371-373 TIR |
| 5 | 420-422 SRK |
| 6 | 431-433 TQR |
| 7 | 515-517 SRR |
| 8 | 546-548 SNR |

Signicance of Post translational modications
Four casein kinase II phosphorylation site
(SEQ ID NOS: 731-734, respectively)

| 1 | 168-171 SRND |
| --- | --- |
| 2 | 223-226 SGND |
| 3 | 353-356 TQGD |
| 4 | 420-423 SRKD |

Nine N-myristoylation sites (SEQ ID NOS: 735-743, respectively)

| 1 | 2-7 GSLSNC |
| --- | --- |
| 2 | 110-115 GLSFAQ |
| 3 | 180-185 GTRQCS |
| 4 | 204-209 GLPNTQ |
| 5 | 219-224 GLTWSG |
| 6 | 224-229 GNDTCL |
| 7 | 252-257 GLTEAH |
| 8 | 285-290 GSNLTL |
| 9 | 304-309 GVYKGF |

Glycosylation, or attachment of carbohydrate chains to asparagines, serine or threonine moieties, plays an important role in protein folding, stability and protection from degradation (Biochem J. 2000, 348:1). In addition, glycosylation allows sorting of proteins from the endoplasmic reticulum along the secretory pathway, thereby contributing to protein localization (FEBS Lett. 2000, 476:32). Also, glycosylation often contributes to cell adhesion and immune recognition (J. Mol. Biol. 1999, 293:351).

Phosphorylation, whether by PKC, cAMP and c-GMP dependent kinases, or casein kinases, exhorts a profound effect on proteins. Phosphorylation mediates protein-protein interactions as well as signaling pathway activation. Phosphorylation also controls protein localization, translocation and enzymatic activity, and regulates transcriptional activation (Mol Immunol. 2000, 37: 1; Cell Mol Life Sci. 2000, 57:1172-83). By means of post-translational modification of protein, phosphorylation regulates cellular functions, including proliferation, migration and gene expression (Cell Prolif. 2000, 33:341; Mol Biol Cell. 2001, 12:351).

Myristoylation serves to anchor numerous proteins to the cytoplasmic face of the plasma membrane. This process serves to facilitate protein recruitment, complex assembly and signaling through proteins (Current Opinion Cell Biol. 1994, 6:219; J. Biol. Chem. 1996, 271:1573).

Motifs found in 103P2D6

14-35 Leucine zipper pattern LTAFLTILVQPQHLLAPV-FRTL 484-516 Large-conductance mechanosensitive channel, GDWFRSWGYVLLIVLFCLFIFVLIYVRVFRKSRR 487-507 Sodium/chloride neurotransmitter symporter signature FRSWGYVLLIVLFCLFIFVLI Topology and Transmembrane Domains Using three different prediction programs, 103P2D6 is proposed to be a membrane associated protein, primarily expressed at the cell surface (64%). There is a possibility that 103P2D6 is associated with the endoplasmic reticulum (21%).

Several possibilities for transmembrane domains and topologies:

PSORT (http://psort.nibb.ac.jp) indicates the presence of 1 TM domain at aa 493-509 (VLLIVLFCLFIFVLIYV), and 1 signal sequence at aa 1-24 (MGSLSN-CALLQLTLTAFLTILVQP), with a cleavage site between aa 24 and aa 25.

TMpred (www.ch.3 mbnet.org) indicates that 103P2D6 may have four transmembrane domains, which are listed below:

TM1 aa 4-22-o-i

TM2 aa 58-77-i-o

TM3 aa 283-300-o-i

TM4 aa 493-509-i-o

Although this scenario is less likely to occur, in view of the similarity with envelope protein which has a single transmembrane domain, it is possible that 103P2D6 exhibits a multiple TM configuration In all cases, the N-terminus extends outside the cell, while the C-terminus is intracellular.

TABLE XX

Frequently Occurring Motifs

| Name | avg. % identity | Description | Potential Function |
| --- | --- | --- | --- |
| zf-C2H2 | 34% | Zinc finger, C2H2 type | Nucleic acid-binding protein functions as tanscription factor, nuclear location probable |
| cytochrome b N | 68% | Cytochrome b(N-terminal)/b6/petB | membrane bound oxidase, generate superoxide |
| ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein-protein interactions |
| pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30-40 amino-acid long found in the extracellular domain of membrane-bound proteins or in secreted proteins |
| rvt | 49% | Reverse transcriptase (RNA-dependent DNA polymerase) | |
| ank | 25% | Ank repeat | Cytoplasmic protein, associates integral membrane proteins to the cytoskeleton |
| oxidored q1 | 32% | NADH-Ubiquinone/plastoquinone (complex I), various chains | membrane associated. Involved in proton translocation across the membrane |
| efhand | 24% | EF hand | calcium-binding domain, consists of a 12 residue loop flanked on both side by a 12 residue alpha-helical domain |
| rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |
| fn3 | 20% | Fibronectin type III domain | Located in the extracellular ligand-binding region of receptors and is about 200 amino acid residues long with two pairs of cysteines involved in disulfide bonds |
| 7tm 1 | 19% | 7 transmembrane receptor (rhodopsin family) | seven hydrophobic transmembrane regions, with the N-terminus located extracellularly while the C-terminus is cytoplasmic. Signal through G proteins |

The invention claimed is:

1. An antibody or fragment thereof labeled with a cytotoxic or a therapeutic agent, wherein the antibody or fragment thereof specifically binds to a protein consisting of the amino acid sequence of SEQ ID NO: 2.

2. The antibody or fragment thereof of claim 1, wherein the cytotoxic agent is selected from the group consisting of maytansinoids, yttrium, bismuth, ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, phenomycin, enomycin, curicin, crotin, calichearnicin, Saponaria officinalis inhibitor, and glucocorticoid.

3. The antibody or fragment thereof of claim 1, wherein the cytotoxic or therapeutic agent is a radioisotope selected from the group consisting of $^{212}$Bi, $^{131}$I, $^{131}$In, $^{90}$Y, and $^{186}$Re.

4. The antibody or fragment thereof of claim 1, which is a human antibody.

5. The antibody of claim 1, which comprises murine antigen binding region residues and human antibody residues.

* * * * *

```
                        SEQUENCE LISTING

<160> NUMBER OF SEQ ID NOS: 752

<210> SEQ ID NO 1
<211> LENGTH: 4728
<212> TYPE: DNA
<213> ORGANISM: homo sapiens
<220> FEATURE:
<221> NAME/KEY: CDS
<222> LOCATION: (805)...(2496)

<400> SEQUENCE: 1
cacctgtgac tgttgatgtg gaactgattt atcgcgtatt cgtactggct gaatccggct      60
gtccgctctg cggtgccccg ccccgcccca acccaggatc ttcccagccc cgctccgccc     120
```

```
caacccagga tcttcccagc cctcgtgtgt ccccgctcac ttcagttccc gccgcgagcc      180
ttcttcttgg tcttctggcc tggcggcgat cgtcggccag tttatccctc ggagttgcac      240
tggcagacac gccgctactt tgtagcgggt tcgggcggg ccacgcgtgc ggcgacagga       300
acccaacccc ggccgacctt gggctccagg aattcgttgt ctacgtctgc ggaggtgcgg      360
cagcctcagt tttaagcgca ggtgatcaag tatatctgaa agttttttaga agaaaagatg     420 tgttgtaacc tccctggaaa agaagagac cttatgaagt actgctaacc acctacatag       480
tcatcaaaat aaaattcctg aatttgtaca agccacagga agctagattg agatcattat      540
atgacaactg gaaggccaag gctatgggtt acctcaaatt gaggaatttc ggcacctact      600
cacaggctcc atgagcagat gaagtagaca gctttactca gtatctcaga ccaagaactt      660
catctccatc tccaactagc tgaaacatct tccctcctca acctggaaaa ttctctgact      720
tagaaattta acaaaaccc tccccttta ttgaatctcc attgtctgga gtttgcttgt        780
tttaatctag gctgttcctc cact atg ggc tcc ctt tca aac tgt gcc ctg        831
                              Met Gly Ser Leu Ser Asn Cys Ala Leu
                                1               5 ctt caa cta acc ctt act gct ttt ttg aca att cta gta caa cct cag        879
Leu Gln Leu Thr Leu Thr Ala Phe Leu Thr Ile Leu Val Gln Pro Gln
 10              15                  20                  25 cac ctg ctt gct cca gtt ttc cgg aca cta tct atc ttg act aat cag        927
His Leu Leu Ala Pro Val Phe Arg Thr Leu Ser Ile Leu Thr Asn Gln
             30                  35                  40 tct aat tgc tgg tta tgt gaa cat cta gat aat gca gaa caa ccc gaa        975
Ser Asn Cys Trp Leu Cys Glu His Leu Asp Asn Ala Glu Gln Pro Glu
         45                  50                  55 cta gtt ttt gtt cct gcc agt gca agc acc tgg tgg acc tat tct gga       1023
Leu Val Phe Val Pro Ala Ser Ala Ser Thr Trp Trp Thr Tyr Ser Gly
     60                  65                  70 caa tgg atg tat gaa agg gtg tgg tat cca caa gca gaa gta cag aat       1071
Gln Trp Met Tyr Glu Arg Val Trp Tyr Pro Gln Ala Glu Val Gln Asn
 75                  80                  85 cac tct act tcc tcc tat cgt aaa gtg act tgg cac tgg gaa gcc tcc       1119
His Ser Thr Ser Ser Tyr Arg Lys Val Thr Trp His Trp Glu Ala Ser
 90                  95                 100                 105 atg gaa gct caa ggt cta tcc ttt gct caa gta agg tta ttg gag gga       1167
Met Glu Ala Gln Gly Leu Ser Phe Ala Gln Val Arg Leu Leu Glu Gly
            110                 115                 120 aat ttt tct ctt tgc gta gaa aat aaa aat ggc agt gga ccc ttc cta       1215
Asn Phe Ser Leu Cys Val Glu Asn Lys Asn Gly Ser Gly Pro Phe Leu
        125                 130                 135 ggt aat ata cct aaa caa tac tgt aat caa ata cta tgg ttt gat tct       1263
Gly Asn Ile Pro Lys Gln Tyr Cys Asn Gln Ile Leu Trp Phe Asp Ser
    140                 145                 150 aca gat ggc acc ttc atg ccc tct ata gat gtt aca aat gaa tcc agg       1311
Thr Asp Gly Thr Phe Met Pro Ser Ile Asp Val Thr Asn Glu Ser Arg
155                 160                 165 aac gat gat gat gat aca agt gtt tgc cta ggc act aga caa tgt tcc       1359
Asn Asp Asp Asp Asp Thr Ser Val Cys Leu Gly Thr Arg Gln Cys Ser
170                 175                 180                 185 cgg ttt gca ggt tgc aca aac cgg acc tgg aac agc tca gct gtt ccc       1407
Arg Phe Ala Gly Cys Thr Asn Arg Thr Trp Asn Ser Ser Ala Val Pro
                190                 195                 200 ttg att ggt ctg ccc aat acc caa gac tac aaa tgg gta gat cga aat       1455
Leu Ile Gly Leu Pro Asn Thr Gln Asp Tyr Lys Trp Val Asp Arg Asn
            205                 210                 215
```

```
tct gga ttg acc tgg tca ggt aat gac acc tgt ctc tat agc tgc caa    1503
Ser Gly Leu Thr Trp Ser Gly Asn Asp Thr Cys Leu Tyr Ser Cys Gln
        220                 225                 230 aac caa acc aaa ggc ctt ctg tac cag cta ttt cgc aac cta ttt tgc    1551
Asn Gln Thr Lys Gly Leu Leu Tyr Gln Leu Phe Arg Asn Leu Phe Cys
    235                 240                 245 tct tat ggc ctg aca gag gca cat ggg aaa tgg aga tgt gca gat gcc    1599
Ser Tyr Gly Leu Thr Glu Ala His Gly Lys Trp Arg Cys Ala Asp Ala
250                 255                 260                 265 agc ata act aat gac aaa ggt cat gat gga cac cgg acc ccc acc tgg    1647
Ser Ile Thr Asn Asp Lys Gly His Asp Gly His Arg Thr Pro Thr Trp
                270                 275                 280 tgg ctc aca ggt tcc aat ctg acc ttg tct gtg aac aac tct ggc ctc    1695
Trp Leu Thr Gly Ser Asn Leu Thr Leu Ser Val Asn Asn Ser Gly Leu
            285                 290                 295 ttt ttt ttg tgc ggc aat ggg gtg tac aaa ggg ttt cca cct aaa tgg    1743
Phe Phe Leu Cys Gly Asn Gly Val Tyr Lys Gly Phe Pro Pro Lys Trp
        300                 305                 310 tct ggg cga tgt gga ctt ggg tat ctt gta cct tcc ctc acc aga tac    1791
Ser Gly Arg Cys Gly Leu Gly Tyr Leu Val Pro Ser Leu Thr Arg Tyr
    315                 320                 325 ctc acc tta aat gct agc caa att aca aac ctg aga tcc ttc att cat    1839
Leu Thr Leu Asn Ala Ser Gln Ile Thr Asn Leu Arg Ser Phe Ile His
330                 335                 340                 345 aaa gta aca ccg cat aga tgc acc caa gga gac aca gac aat cca cct    1887
Lys Val Thr Pro His Arg Cys Thr Gln Gly Asp Thr Asp Asn Pro Pro
                350                 355                 360 ctg tat tgc aac ccc aag gac aat tca aca ata agg gcc ctt ttt cca    1935
Leu Tyr Cys Asn Pro Lys Asp Asn Ser Thr Ile Arg Ala Leu Phe Pro
            365                 370                 375 agt ttg gga act tat gat tta gaa aag gca att cta aac att tcc aaa    1983
Ser Leu Gly Thr Tyr Asp Leu Glu Lys Ala Ile Leu Asn Ile Ser Lys
        380                 385                 390 gca atg gaa cag gaa ttc agt gcc act aag cag acc ttg gaa gca cac    2031
Ala Met Glu Gln Glu Phe Ser Ala Thr Lys Gln Thr Leu Glu Ala His
    395                 400                 405 caa tca aaa gtt agc agt tta gcc tct gca tcc gaa aag gat cat gtc    2079
Gln Ser Lys Val Ser Ser Leu Ala Ser Ala Ser Arg Lys Asp His Val
410                 415                 420                 425 ttg gat ata ccg acc acc caa cga caa acg gct tgt gga act gtt ggc    2127
Leu Asp Ile Pro Thr Thr Gln Arg Gln Thr Ala Cys Gly Thr Val Gly
                430                 435                 440 aaa cag tgt tgc ctc tat ata aat tat tcg gaa gaa ata aag tct aat    2175
Lys Gln Cys Cys Leu Tyr Ile Asn Tyr Ser Glu Glu Ile Lys Ser Asn
            445                 450                 455 ata cag cgt ctc cac gaa gca tcc gag aac ctg aag aat gta cca tta    2223
Ile Gln Arg Leu His Glu Ala Ser Glu Asn Leu Lys Asn Val Pro Leu
        460                 465                 470 ctt gat tgg caa ggc ata ttt gca aaa gtg gga gac tgg ttc aga tca    2271
Leu Asp Trp Gln Gly Ile Phe Ala Lys Val Gly Asp Trp Phe Arg Ser
    475                 480                 485 tgg ggc tat gtg ctt tta att gtt ctc ttc tgc tta ttc atc ttt gtt    2319
Trp Gly Tyr Val Leu Leu Ile Val Leu Phe Cys Leu Phe Ile Phe Val
490                 495                 500                 505 tta atc tat gtt cgt gtc ttt cgc aaa tct cgc aga tcc ctt aac tcc    2367
Leu Ile Tyr Val Arg Val Phe Arg Lys Ser Arg Arg Ser Leu Asn Ser
                510                 515                 520 caa cct ctg aac cta gcc tta tct cca cag caa tca gca cag ctc ctt    2415
Gln Pro Leu Asn Leu Ala Leu Ser Pro Gln Gln Ser Ala Gln Leu Leu
            525                 530                 535
```

```
gtc agt gaa act tca tgt caa gtt tca aat agg gca atg aag gga cta    2463
Val Ser Glu Thr Ser Cys Gln Val Ser Asn Arg Ala Met Lys Gly Leu
    540                 545                 550 aca acc cat caa tat gac aca agt cta ctt tga gaatatctga acaaacagca   2516
Thr Thr His Gln Tyr Asp Thr Ser Leu Leu *
    555                 560 gctgcagaca aaaagcctta gctaaacttt gatgagtaaa gcaggtctta ccgagaattc   2576
agctgccaaa accctcctct gagtgttcct cttataaggg cacttagcac taggacctcc   2636
caaggtattg taaataagcc ttatcagaac tttttgtagt ttcattctga agccttaaga   2696
cacacaccat aaagctgatc tgtaaaacct tacccccttgc tgttcagaga gctactcttt   2756
gtagtgttct tgcatgcata taataaat gttttttcta ttgatctgtt aatttgcaag    2816
cccccaaaca ctggaactaa gttggggggca ggatagtttc tcccaacagc actttgtagg  2876
cttctggata gaccaaagag tgtgtttgaa tagataaggg aattttgttc ccttgatttt   2936
ggttgaaggt agaagaatcc aatgtacaca tacacaaaac tatgtcctta aatttgtctc   2996
aaagaataaa tattgggtag tcatcagaat tgactgaaaa cttactttag ggagaaagcc   3056
acaaataatt taggctggta tgatctgagc tttcctgatt tcccatgggc attttagtgg   3116
tctaatggaa tattagtctg atatgcattt tagccatctt atgaaatggg ccgcaggtgg   3176
aagtaggatg cagggagtgt tgaggtggca tctattatat caaatgcttc actctgccca   3236
gtcctctgtg agttccttac atgcatcttt ctagttaatc ctctcggtgt tcatatttac   3296
agattaatca actcaaaggg tagatagctt gctaaagatt atactattac tgaaaaatag   3356
caagatgcag aacagcatac ctagtatgtt actcttttt ttttttttt tgaggcaga    3416 gtctggcccct tcacccagg ctggagtgca gtggctcaat ctcggctcac tgcaacctct   3476 gccccccttgg gttcatgcca ttctcctgcc tccagccac tcaggaggct gaggcaggag   3536
gatcgcttga acccaggaag cggaggttgc ggtgagctga atcgcacca ctgtattcca    3596 gcctggcaac agagtgagat tctgtggcaa aaaaaaaaa aaaaaaagc acagactggg    3656 tgtggtggct catgcctgta attccagcac tttgcgaggc tcaagcgatc ctttggcctc   3716
ggcctcccaa agtgcatgag ccaccatgcc tggcctgttt agttttgttt caagttgaaa   3776
tacctttctt gtgttttcta attagaaaag taatatctac tcattgtaaa aactcaaaca   3836
gtgcagaaat gtagaaagta gaaagtgtaa gtccctggtt gtcccttctg cctgagacaa   3896
ccactgctca cagtttgatg tatatccttc cagagactct caaatttaag caaataattt   3956
ttattaccat gtcttttat ttgaagacgt tacattgcc tccaaagttc aacacaagtt    4016
caactgacca tatccttcca tgacctgaat agatgctatc ctttatcacg atgttcaatt   4076
gcctttgaaa gagagtagtc caggtatatt cctgatcaaa atttggcatt tttgatgata   4136
ctactctaca cagatcagac tcatgtgcag aatcgtgcct gaagagagag gtttggttaa   4196
gacagagatt tctggaaaca ttcaaattgc aaatggaaac ttgaaaccca caatctaatg   4256
aggaatgtac tggaaaaata atctgaagag ttgacaaatt gtgtactaga ttaacacat   4316 ggaatgcaat gcaatgagac tttctgcact aaaacttatc ctcatatgta caacaatgat   4376
gtgtgtatta tataacagtg atgtgtacat ttctgacacc ccatacataa tatacacagt   4436
ttgtataaat gcatacattt aaaaatatat atgtacaata cagctaacat aaaactgtag   4496
tacgcctgaa ggatattact agtgcctaat attgagtatg agtcactgcg tgttcgcatc   4556
aacttggaag tgcagtaatt gttataaaat taatcagtgc agccaacatt atttatgaat   4616
```

-continued

```
cacatctttg aaactgtgca gtagcatata catatatatt tttaaataac atttttcaca    4676
gttttccaga gttactgttg aaatctgcat caccaaaaaa aaaaaaaaaa aa            4728
```

<210> SEQ ID NO 2
<211> LENGTH: 563
<212> TYPE: PRT
<213> ORGANISM: homo sapiens

<400> SEQUENCE: 2

```
Met Gly Ser Leu Ser Asn Cys Ala Leu Leu Gln Leu Thr Leu Thr Ala
 1               5                  10                  15

Phe Leu Thr Ile Leu Val Gln Pro Gln His Leu Leu Ala Pro Val Phe
                20                  25                  30

Arg Thr Leu Ser Ile Leu Thr Asn Gln Ser Asn Cys Trp Leu Cys Glu
            35                  40                  45

His Leu Asp Asn Ala Glu Gln Pro Glu Leu Val Phe Val Pro Ala Ser
        50                  55                  60

Ala Ser Thr Trp Trp Thr Tyr Ser Gly Gln Trp Met Tyr Glu Arg Val
 65                  70                  75                  80

Trp Tyr Pro Gln Ala Glu Val Gln Asn His Ser Thr Ser Ser Tyr Arg
                85                  90                  95

Lys Val Thr Trp His Trp Glu Ala Ser Met Glu Ala Gln Gly Leu Ser
            100                 105                 110

Phe Ala Gln Val Arg Leu Leu Glu Gly Asn Phe Ser Leu Cys Val Glu
        115                 120                 125

Asn Lys Asn Gly Ser Gly Pro Phe Leu Gly Asn Ile Pro Lys Gln Tyr
    130                 135                 140

Cys Asn Gln Ile Leu Trp Phe Asp Ser Thr Asp Gly Thr Phe Met Pro
145                 150                 155                 160

Ser Ile Asp Val Thr Asn Glu Ser Arg Asn Asp Asp Asp Thr Ser
                165                 170                 175

Val Cys Leu Gly Thr Arg Gln Cys Ser Arg Phe Ala Gly Cys Thr Asn
            180                 185                 190

Arg Thr Trp Asn Ser Ser Ala Val Pro Leu Ile Gly Leu Pro Asn Thr
        195                 200                 205

Gln Asp Tyr Lys Trp Val Asp Arg Asn Ser Gly Leu Thr Trp Ser Gly
    210                 215                 220

Asn Asp Thr Cys Leu Tyr Ser Cys Gln Asn Gly Thr Lys Gly Leu Leu
225                 230                 235                 240

Tyr Gln Leu Phe Arg Asn Leu Phe Cys Ser Tyr Gly Leu Thr Glu Ala
                245                 250                 255

His Gly Lys Trp Arg Cys Ala Asp Ala Ser Ile Thr Asn Asp Lys Gly
            260                 265                 270

His Asp Gly His Arg Thr Pro Thr Trp Trp Leu Thr Gly Ser Asn Leu
        275                 280                 285

Thr Leu Ser Val Asn Asn Ser Gly Leu Phe Phe Leu Cys Gly Asn Gly
    290                 295                 300

Val Tyr Lys Gly Phe Pro Pro Lys Trp Ser Gly Arg Cys Gly Leu Gly
305                 310                 315                 320

Tyr Leu Val Pro Ser Leu Thr Arg Tyr Leu Thr Leu Asn Ala Ser Gln
                325                 330                 335

Ile Thr Asn Leu Arg Ser Phe Ile His Lys Val Thr Pro His Arg Cys
            340                 345                 350

Thr Gln Gly Asp Thr Asp Asn Pro Pro Leu Tyr Cys Asn Pro Lys Asp
```

-continued

```
              355                 360                 365
Asn Ser Thr Ile Arg Ala Leu Phe Pro Ser Leu Gly Thr Tyr Asp Leu
    370                 375                 380

Glu Lys Ala Ile Leu Asn Ile Ser Lys Ala Met Glu Gln Glu Phe Ser
385                 390                 395                 400

Ala Thr Lys Gln Thr Leu Glu Ala His Gln Ser Lys Val Ser Ser Leu
                405                 410                 415

Ala Ser Ala Ser Arg Lys Asp His Val Leu Asp Ile Pro Thr Thr Gln
                420                 425                 430

Arg Gln Thr Ala Cys Gly Thr Val Gly Lys Gln Cys Cys Leu Tyr Ile
                435                 440                 445

Asn Tyr Ser Glu Glu Ile Lys Ser Asn Ile Gln Arg Leu His Glu Ala
    450                 455                 460

Ser Glu Asn Leu Lys Asn Val Pro Leu Leu Asp Trp Gln Gly Ile Phe
465                 470                 475                 480

Ala Lys Val Gly Asp Trp Phe Arg Ser Trp Gly Tyr Val Leu Leu Ile
                485                 490                 495

Val Leu Phe Cys Leu Phe Ile Phe Val Leu Ile Tyr Val Arg Val Phe
            500                 505                 510

Arg Lys Ser Arg Arg Ser Leu Asn Ser Gln Pro Leu Asn Leu Ala Leu
        515                 520                 525

Ser Pro Gln Gln Ser Ala Gln Leu Leu Val Ser Glu Thr Ser Cys Gln
    530                 535                 540

Val Ser Asn Arg Ala Met Lys Gly Leu Thr Thr His Gln Tyr Asp Thr
545                 550                 555                 560

Ser Leu Leu
```

<210> SEQ ID NO 3
<211> LENGTH: 342
<212> TYPE: DNA
<213> ORGANISM: homo sapiens

<400> SEQUENCE: 3

```
gatcagcttt atggtgtgtg tcttaaggct tcagaatgaa actacaaaaa gttctgataa    60
ggcttattta caataccttg ggaggtccta gtgctaagtg cccttataag aggaacactc   120
agaggagggt tttggcagct gaattctcgg taagacctgc tttactcatc aaagtttagc   180
taaggctttt tgtctgcagc tgctgtttgt tcagatattc tcaaagtaga cttgtgtcat   240
attgatgggt tgttagtccc ttcattgccc tatttgaaac ttgacatgaa gtttcactga   300
caaggagctg tgctgattgc tgtggagata aggctaggtt ca                     342
```

<210> SEQ ID NO 4
<211> LENGTH: 576
<212> TYPE: PRT
<213> ORGANISM: homo sapiens

<400> SEQUENCE: 4

```
Ser Asn Thr Ser Thr Leu Met Lys Phe Tyr Ser Leu Leu Tyr Ser
  1               5                  10                  15

Leu Leu Phe Ser Phe Pro Phe Leu Cys His Pro Leu Pro Leu Pro Ser
                20                  25                  30

Tyr Leu His His Thr Ile Asn Leu Thr His Ser Leu Leu Ala Ala Ser
            35                  40                  45

Asn Pro Ser Leu Val Asn Cys Trp Leu Cys Ile Ser Leu Ser Ser
    50                  55                  60
```

```
Ser Ala Tyr Thr Ala Val Pro Ala Val Gln Thr Asp Trp Ala Thr Ser
 65                  70                  75                  80

Pro Ile Ser Leu His Leu Arg Thr Ser Phe Asn Ser Pro His Leu Tyr
                 85                  90                  95

Pro Pro Glu Glu Leu Ile Tyr Phe Leu Asp Arg Ser Ser Lys Thr Ser
            100                 105                 110

Pro Asp Ile Ser His Gln Gln Ala Ala Leu Leu Arg Thr Tyr Leu
        115                 120                 125

Lys Asn Leu Ser Pro Tyr Ile Asn Ser Thr Pro Ile Phe Gly Pro
    130                 135                 140

Leu Thr Thr Gln Thr Thr Ile Pro Val Ala Ala Pro Leu Cys Ile Ser
145                 150                 155                 160

Trp Gln Arg Pro Thr Gly Ile Pro Leu Gly Asn Leu Ser Pro Ser Arg
                165                 170                 175

Cys Ser Phe Thr Leu His Leu Arg Ser Pro Thr Thr Asn Ile Asn Glu
                180                 185                 190

Thr Ile Gly Ala Phe Gln Leu His Ile Thr Asp Lys Pro Ser Ile Asn
                195                 200                 205

Thr Asp Lys Leu Lys Asn Ile Ser Ser Asn Tyr Cys Leu Gly Arg His
    210                 215                 220

Leu Pro Cys Ile Ser Leu His Pro Trp Leu Ser Ser Pro Cys Ser Ser
225                 230                 235                 240

Asp Ser Pro Pro Arg Pro Ser Ser Cys Leu Leu Ile Pro Ser Pro Glu
                245                 250                 255

Asn Asn Ser Glu Arg Leu Leu Val Asp Thr Arg Arg Phe Leu Ile His
            260                 265                 270

His Glu Asn Arg Thr Phe Pro Ser Thr Gln Leu Pro His Gln Ser Pro
                275                 280                 285

Leu Gln Pro Leu Thr Ala Ala Leu Ala Gly Ser Leu Gly Val Trp
    290                 295                 300

Val Gln Asp Thr Pro Phe Ser Thr Pro Ser His Leu Phe Thr Leu His
305                 310                 315                 320

Leu Gln Phe Cys Leu Ala Gln Gly Leu Phe Phe Leu Cys Gly Ser Ser
                325                 330                 335

Thr Tyr Met Cys Leu Pro Ala Asn Trp Thr Gly Thr Cys Thr Leu Val
            340                 345                 350

Phe Leu Thr Pro Lys Ile Gln Phe Ala Asn Gly Thr Glu Glu Leu Pro
            355                 360                 365

Val Pro Leu Met Thr Pro Thr Gln Gln Lys Arg Val Ile Pro Leu Ile
    370                 375                 380

Pro Leu Met Val Gly Leu Gly Leu Ser Ala Ser Thr Val Ala Leu Gly
385                 390                 395                 400

Thr Gly Ile Ala Gly Ile Ser Thr Ser Val Met Thr Phe Arg Ser Leu
                405                 410                 415

Ser Asn Asp Phe Ser Ala Ser Ile Thr Asp Ile Ser Gln Thr Leu Ser
            420                 425                 430

Val Leu Gln Ala Gln Val Asp Ser Leu Ala Ala Val Val Leu Gln Asn
    435                 440                 445

Arg Arg Gly Leu Asp Leu Leu Thr Ala Glu Lys Gly Gly Leu Cys Ile
    450                 455                 460

Phe Leu Asn Glu Glu Cys Cys Phe Tyr Leu Asn Gln Ser Gly Leu Val
465                 470                 475                 480
```

```
Tyr Asp Asn Ile Lys Lys Leu Lys Asp Arg Ala Gln Lys Leu Ala Asn
                485                 490                 495

Gln Ala Ser Asn Tyr Ala Glu Pro Pro Trp Ala Leu Ser Asn Trp Met
            500                 505                 510

Ser Trp Val Leu Pro Ile Val Ser Pro Leu Ile Pro Ile Phe Leu Leu
        515                 520                 525

Leu Leu Phe Gly Pro Cys Ile Phe Arg Leu Val Ser Gln Phe Ile Gln
        530                 535                 540

Asn Arg Ile Gln Ala Ile Thr Asn His Ser Ile Arg Gln Met Phe Leu
545                 550                 555                 560

Leu Thr Ser Pro Gln Tyr His Pro Leu Pro Gln Asp Leu Pro Ser Ala
                565                 570                 575

<210> SEQ ID NO 5
<211> LENGTH: 14
<212> TYPE: PRT
<213> ORGANISM: homo sapiens

<400> SEQUENCE: 5

Asp Val Thr Asn Glu Ser Arg Asn Asp Asp Asp Thr Ser
 1               5                  10

<210> SEQ ID NO 6
<211> LENGTH: 24
<212> TYPE: DNA
<213> ORGANISM: Artificial Sequence
<220> FEATURE:
<223> OTHER INFORMATION: FLAG sequence

<400> SEQUENCE: 6
gattacaagg atgacgacga taag                                           24

<210> SEQ ID NO 7
<211> LENGTH: 14
<212> TYPE: DNA
<213> ORGANISM: Artificial Sequence
<220> FEATURE:
<223> OTHER INFORMATION: primer

<400> SEQUENCE: 7
ttttgatcaa gctt                                                      14

<210> SEQ ID NO 8
<211> LENGTH: 42
<212> TYPE: DNA
<213> ORGANISM: Artificial Sequence
<220> FEATURE:
<223> OTHER INFORMATION: adaptor

<400> SEQUENCE: 8
ctaatacgac tcactatagg gctcgagcgg ccgcccgggc ag                       42

<210> SEQ ID NO 9
<211> LENGTH: 12
<212> TYPE: DNA
<213> ORGANISM: Artificial Sequence
<220> FEATURE:
<223> OTHER INFORMATION: adaptor

<400> SEQUENCE: 9
ggcccgtcct ag                                                        12

<210> SEQ ID NO 10
```

```
<211> LENGTH: 40
<212> TYPE: DNA
<213> ORGANISM: Artificial Sequence
<220> FEATURE:
<223> OTHER INFORMATION: adaptor

<400> SEQUENCE: 10
gtaatacgac tcactatagg gcagcgtggt cgcggccgag                              40

<210> SEQ ID NO 11
<211> LENGTH: 10
<212> TYPE: DNA
<213> ORGANISM: Artificial Sequence
<220> FEATURE:
<223> OTHER INFORMATION: adaptor

<400> SEQUENCE: 11
cggctcctag                                                              10

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
ctaatacgac tcactatagg gc                                                22

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
tcgagcggcc gcccgggcag ga                                                22

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
agcgtggtcg cggccgagga                                                   20

<210> SEQ ID NO 15
<211> LENGTH: 9
<212> TYPE: PRT
<213> ORGANISM: homo sapiens

<400> SEQUENCE: 15

Asn Ala Glu Gln Pro Glu Leu Val Phe
 1               5

<210> SEQ ID NO 16
<211> LENGTH: 9
<212> TYPE: PRT
<213> ORGANISM: homo sapiens

<400> SEQUENCE: 16

Leu Thr Glu Ala His Gly Lys Trp Arg
 1               5
```

```
<210> SEQ ID NO 17
<211> LENGTH: 9
<212> TYPE: PRT
<213> ORGANISM: homo sapiens

<400> SEQUENCE: 17

Ser Met Glu Ala Gln Gly Leu Ser Phe
1               5

<210> SEQ ID NO 18
<211> LENGTH: 9
<212> TYPE: PRT
<213> ORGANISM: homo sapiens

<400> SEQUENCE: 18

Asp Thr Asp Asn Pro Pro Leu Tyr Cys
1               5

<210> SEQ ID NO 19
<211> LENGTH: 9
<212> TYPE: PRT
<213> ORGANISM: homo sapiens

<400> SEQUENCE: 19

Ser Thr Asp Gly Thr Phe Met Pro Ser
1               5

<210> SEQ ID NO 20
<211> LENGTH: 9
<212> TYPE: PRT
<213> ORGANISM: homo sapiens

<400> SEQUENCE: 20

Ser Ile Asp Val Thr Asn Glu Ser Arg
1               5

<210> SEQ ID NO 21
<211> LENGTH: 9
<212> TYPE: PRT
<213> ORGANISM: homo sapiens

<400> SEQUENCE: 21

Tyr Leu Val Pro Ser Leu Thr Arg Tyr
1               5

<210> SEQ ID NO 22
<211> LENGTH: 9
<212> TYPE: PRT
<213> ORGANISM: homo sapiens

<400> SEQUENCE: 22

Ala Leu Phe Pro Ser Leu Gly Thr Tyr
1               5

<210> SEQ ID NO 23
<211> LENGTH: 9
<212> TYPE: PRT
<213> ORGANISM: homo sapiens

<400> SEQUENCE: 23

Val Leu Asp Ile Pro Thr Thr Gln Arg
1               5
```

```
<210> SEQ ID NO 24
<211> LENGTH: 9
<212> TYPE: PRT
<213> ORGANISM: homo sapiens

<400> SEQUENCE: 24

Leu Leu Asp Trp Gln Gly Ile Phe Ala
1               5

<210> SEQ ID NO 25
<211> LENGTH: 9
<212> TYPE: PRT
<213> ORGANISM: homo sapiens

<400> SEQUENCE: 25

Cys Leu Phe Ile Phe Val Leu Ile Tyr
1               5

<210> SEQ ID NO 26
<211> LENGTH: 9
<212> TYPE: PRT
<213> ORGANISM: homo sapiens

<400> SEQUENCE: 26

Thr Gln Asp Tyr Lys Trp Val Asp Arg
1               5

<210> SEQ ID NO 27
<211> LENGTH: 9
<212> TYPE: PRT
<213> ORGANISM: homo sapiens

<400> SEQUENCE: 27

Val Ser Glu Thr Ser Cys Gln Val Ser
1               5

<210> SEQ ID NO 28
<211> LENGTH: 9
<212> TYPE: PRT
<213> ORGANISM: homo sapiens

<400> SEQUENCE: 28

Tyr Ser Glu Glu Ile Lys Ser Asn Ile
1               5

<210> SEQ ID NO 29
<211> LENGTH: 9
<212> TYPE: PRT
<213> ORGANISM: homo sapiens

<400> SEQUENCE: 29

Ile Gly Leu Pro Asn Thr Gln Asp Tyr
1               5

<210> SEQ ID NO 30
<211> LENGTH: 9
<212> TYPE: PRT
<213> ORGANISM: homo sapiens

<400> SEQUENCE: 30

Trp Thr Tyr Ser Gly Gln Trp Met Tyr
1               5

<210> SEQ ID NO 31
<211> LENGTH: 9
```

```
<212> TYPE: PRT
<213> ORGANISM: homo sapiens

<400> SEQUENCE: 31

Leu Ile Tyr Val Arg Val Phe Arg Lys
 1               5

<210> SEQ ID NO 32
<211> LENGTH: 9
<212> TYPE: PRT
<213> ORGANISM: homo sapiens

<400> SEQUENCE: 32

Gln Thr Ala Cys Gly Thr Val Gly Lys
 1               5

<210> SEQ ID NO 33
<211> LENGTH: 9
<212> TYPE: PRT
<213> ORGANISM: homo sapiens

<400> SEQUENCE: 33

Ser Leu Gly Thr Tyr Asp Leu Glu Lys
 1               5

<210> SEQ ID NO 34
<211> LENGTH: 9
<212> TYPE: PRT
<213> ORGANISM: homo sapiens

<400> SEQUENCE: 34

Thr Leu Glu Ala His Gln Ser Lys Val
 1               5

<210> SEQ ID NO 35
<211> LENGTH: 9
<212> TYPE: PRT
<213> ORGANISM: homo sapiens

<400> SEQUENCE: 35

Leu His Glu Ala Ser Glu Asn Leu Lys
 1               5

<210> SEQ ID NO 36
<211> LENGTH: 9
<212> TYPE: PRT
<213> ORGANISM: homo sapiens

<400> SEQUENCE: 36

Leu Leu Glu Gly Asn Phe Ser Leu Cys
 1               5

<210> SEQ ID NO 37
<211> LENGTH: 9
<212> TYPE: PRT
<213> ORGANISM: homo sapiens

<400> SEQUENCE: 37

Cys Val Glu Asn Lys Asn Gly Ser Gly
 1               5

<210> SEQ ID NO 38
<211> LENGTH: 9
<212> TYPE: PRT
<213> ORGANISM: homo sapiens
```

```
<400> SEQUENCE: 38

Gln Ala Glu Val Gln Asn His Ser Thr
1               5

<210> SEQ ID NO 39
<211> LENGTH: 9
<212> TYPE: PRT
<213> ORGANISM: homo sapiens

<400> SEQUENCE: 39

Asn Ser Gln Pro Leu Asn Leu Ala Leu
1               5

<210> SEQ ID NO 40
<211> LENGTH: 9
<212> TYPE: PRT
<213> ORGANISM: homo sapiens

<400> SEQUENCE: 40

Ala Ser Ala Ser Thr Trp Trp Thr Tyr
1               5

<210> SEQ ID NO 41
<211> LENGTH: 9
<212> TYPE: PRT
<213> ORGANISM: homo sapiens

<400> SEQUENCE: 41

Trp Ser Gly Asn Asp Thr Cys Leu Tyr
1               5

<210> SEQ ID NO 42
<211> LENGTH: 9
<212> TYPE: PRT
<213> ORGANISM: homo sapiens

<400> SEQUENCE: 42

Gln Asn Gln Thr Lys Gly Leu Leu Tyr
1               5

<210> SEQ ID NO 43
<211> LENGTH: 9
<212> TYPE: PRT
<213> ORGANISM: homo sapiens

<400> SEQUENCE: 43

Leu Val Gln Pro Gln His Leu Leu Ala
1               5

<210> SEQ ID NO 44
<211> LENGTH: 9
<212> TYPE: PRT
<213> ORGANISM: homo sapiens

<400> SEQUENCE: 44

Gln Thr Leu Glu Ala His Gln Ser Lys
1               5

<210> SEQ ID NO 45
<211> LENGTH: 9
<212> TYPE: PRT
<213> ORGANISM: homo sapiens

<400> SEQUENCE: 45
```

```
Phe Leu Gly Asn Ile Pro Lys Gln Tyr
 1               5
```

```
<210> SEQ ID NO 46
<211> LENGTH: 9
<212> TYPE: PRT
<213> ORGANISM: homo sapiens

<400> SEQUENCE: 46

Ile Val Leu Phe Cys Leu Phe Ile Phe
 1               5
```

```
<210> SEQ ID NO 47
<211> LENGTH: 9
<212> TYPE: PRT
<213> ORGANISM: homo sapiens

<400> SEQUENCE: 47

Ser Val Asn Asn Ser Gly Leu Phe Phe
 1               5
```

```
<210> SEQ ID NO 48
<211> LENGTH: 9
<212> TYPE: PRT
<213> ORGANISM: homo sapiens

<400> SEQUENCE: 48

Asp Leu Glu Lys Ala Ile Leu Asn Ile
 1               5
```

```
<210> SEQ ID NO 49
<211> LENGTH: 9
<212> TYPE: PRT
<213> ORGANISM: homo sapiens

<400> SEQUENCE: 49

Ala Met Glu Gln Glu Phe Ser Ala Thr
 1               5
```

```
<210> SEQ ID NO 50
<211> LENGTH: 9
<212> TYPE: PRT
<213> ORGANISM: homo sapiens

<400> SEQUENCE: 50

Gln Pro Glu Leu Val Phe Val Pro Ala
 1               5
```

```
<210> SEQ ID NO 51
<211> LENGTH: 9
<212> TYPE: PRT
<213> ORGANISM: homo sapiens

<400> SEQUENCE: 51

Phe Leu Cys Gly Asn Gly Val Tyr Lys
 1               5
```

```
<210> SEQ ID NO 52
<211> LENGTH: 9
<212> TYPE: PRT
<213> ORGANISM: homo sapiens

<400> SEQUENCE: 52

Trp Ser Gly Arg Cys Gly Leu Gly Tyr
```

```
1               5
```

<210> SEQ ID NO 53
<211> LENGTH: 9
<212> TYPE: PRT
<213> ORGANISM: homo sapiens

<400> SEQUENCE: 53

```
Lys Gln Cys Cys Leu Tyr Ile Asn Tyr
1               5
```

<210> SEQ ID NO 54
<211> LENGTH: 9
<212> TYPE: PRT
<213> ORGANISM: homo sapiens

<400> SEQUENCE: 54

```
Ser Ser Leu Ala Ser Ala Ser Arg Lys
1               5
```

<210> SEQ ID NO 55
<211> LENGTH: 9
<212> TYPE: PRT
<213> ORGANISM: homo sapiens

<400> SEQUENCE: 55

```
Val Ser Ser Leu Ala Ser Ala Ser Arg
1               5
```

<210> SEQ ID NO 56
<211> LENGTH: 9
<212> TYPE: PRT
<213> ORGANISM: homo sapiens

<400> SEQUENCE: 56

```
Tyr Ser Gly Gln Trp Met Tyr Glu Arg
1               5
```

<210> SEQ ID NO 57
<211> LENGTH: 9
<212> TYPE: PRT
<213> ORGANISM: homo sapiens

<400> SEQUENCE: 57

```
Gly Pro Phe Leu Gly Asn Ile Pro Lys
1               5
```

<210> SEQ ID NO 58
<211> LENGTH: 9
<212> TYPE: PRT
<213> ORGANISM: homo sapiens

<400> SEQUENCE: 58

```
Gln Gly Asp Thr Asp Asn Pro Pro Leu
1               5
```

<210> SEQ ID NO 59
<211> LENGTH: 9
<212> TYPE: PRT
<213> ORGANISM: homo sapiens

<400> SEQUENCE: 59

```
Asp Thr Ser Val Cys Leu Gly Thr Arg
1               5
```

```
<210> SEQ ID NO 60
<211> LENGTH: 9
<212> TYPE: PRT
<213> ORGANISM: homo sapiens

<400> SEQUENCE: 60

Gly Asn Asp Thr Cys Leu Tyr Ser Cys
 1               5

<210> SEQ ID NO 61
<211> LENGTH: 9
<212> TYPE: PRT
<213> ORGANISM: homo sapiens

<400> SEQUENCE: 61

Glu Thr Ser Cys Gln Val Ser Asn Arg
 1               5

<210> SEQ ID NO 62
<211> LENGTH: 9
<212> TYPE: PRT
<213> ORGANISM: homo sapiens

<400> SEQUENCE: 62

Trp Phe Asp Ser Thr Asp Gly Thr Phe
 1               5

<210> SEQ ID NO 63
<211> LENGTH: 9
<212> TYPE: PRT
<213> ORGANISM: homo sapiens

<400> SEQUENCE: 63

Phe Ile Phe Val Leu Ile Tyr Val Arg
 1               5

<210> SEQ ID NO 64
<211> LENGTH: 9
<212> TYPE: PRT
<213> ORGANISM: homo sapiens

<400> SEQUENCE: 64

Val Leu Ile Tyr Val Arg Val Phe Arg
 1               5

<210> SEQ ID NO 65
<211> LENGTH: 10
<212> TYPE: PRT
<213> ORGANISM: homo sapiens

<400> SEQUENCE: 65

Leu Leu Asp Trp Gln Gly Ile Phe Ala Lys
 1               5                  10

<210> SEQ ID NO 66
<211> LENGTH: 10
<212> TYPE: PRT
<213> ORGANISM: homo sapiens

<400> SEQUENCE: 66

Ala Met Glu Gln Glu Phe Ser Ala Thr Lys
 1               5                  10

<210> SEQ ID NO 67
```

```
<211> LENGTH: 10
<212> TYPE: PRT
<213> ORGANISM: homo sapiens

<400> SEQUENCE: 67

Gln Gly Asp Thr Asp Asn Pro Pro Leu Tyr
1               5                   10

<210> SEQ ID NO 68
<211> LENGTH: 10
<212> TYPE: PRT
<213> ORGANISM: homo sapiens

<400> SEQUENCE: 68

Cys Ala Asp Ala Ser Ile Thr Asn Asp Lys
1               5                   10

<210> SEQ ID NO 69
<211> LENGTH: 10
<212> TYPE: PRT
<213> ORGANISM: homo sapiens

<400> SEQUENCE: 69

Val Gly Asp Trp Phe Arg Ser Trp Gly Tyr
1               5                   10

<210> SEQ ID NO 70
<211> LENGTH: 10
<212> TYPE: PRT
<213> ORGANISM: homo sapiens

<400> SEQUENCE: 70

Leu Leu Glu Gly Asn Phe Ser Leu Cys Val
1               5                   10

<210> SEQ ID NO 71
<211> LENGTH: 10
<212> TYPE: PRT
<213> ORGANISM: homo sapiens

<400> SEQUENCE: 71

Ala Ser Glu Asn Leu Lys Asn Val Pro Leu
1               5                   10

<210> SEQ ID NO 72
<211> LENGTH: 10
<212> TYPE: PRT
<213> ORGANISM: homo sapiens

<400> SEQUENCE: 72

Val Ser Glu Thr Ser Cys Gln Val Ser Asn
1               5                   10

<210> SEQ ID NO 73
<211> LENGTH: 10
<212> TYPE: PRT
<213> ORGANISM: homo sapiens

<400> SEQUENCE: 73

Ser Thr Asp Gly Thr Phe Met Pro Ser Ile
1               5                   10

<210> SEQ ID NO 74
<211> LENGTH: 10
<212> TYPE: PRT
```

```
<213> ORGANISM: homo sapiens

<400> SEQUENCE: 74

Asp Thr Asp Asn Pro Pro Leu Tyr Cys Asn
 1               5                  10

<210> SEQ ID NO 75
<211> LENGTH: 10
<212> TYPE: PRT
<213> ORGANISM: homo sapiens

<400> SEQUENCE: 75

Ile Thr Asn Leu Arg Ser Phe Ile His Lys
 1               5                  10

<210> SEQ ID NO 76
<211> LENGTH: 10
<212> TYPE: PRT
<213> ORGANISM: homo sapiens

<400> SEQUENCE: 76

Phe Cys Leu Phe Ile Phe Val Leu Ile Tyr
 1               5                  10

<210> SEQ ID NO 77
<211> LENGTH: 10
<212> TYPE: PRT
<213> ORGANISM: homo sapiens

<400> SEQUENCE: 77

Ser Glu Glu Ile Lys Ser Asn Ile Gln Arg
 1               5                  10

<210> SEQ ID NO 78
<211> LENGTH: 10
<212> TYPE: PRT
<213> ORGANISM: homo sapiens

<400> SEQUENCE: 78

Leu Thr Glu Ala His Gly Lys Trp Arg Cys
 1               5                  10

<210> SEQ ID NO 79
<211> LENGTH: 10
<212> TYPE: PRT
<213> ORGANISM: homo sapiens

<400> SEQUENCE: 79

Leu Cys Glu His Leu Asp Asn Ala Glu Gln
 1               5                  10

<210> SEQ ID NO 80
<211> LENGTH: 10
<212> TYPE: PRT
<213> ORGANISM: homo sapiens

<400> SEQUENCE: 80

Asn Ala Glu Gln Pro Glu Leu Val Phe Val
 1               5                  10

<210> SEQ ID NO 81
<211> LENGTH: 10
<212> TYPE: PRT
<213> ORGANISM: homo sapiens
```

<400> SEQUENCE: 81

Tyr Ser Glu Glu Ile Lys Ser Asn Ile Gln
1               5                   10

<210> SEQ ID NO 82
<211> LENGTH: 10
<212> TYPE: PRT
<213> ORGANISM: homo sapiens

<400> SEQUENCE: 82

Gly Thr Val Gly Lys Gln Cys Cys Leu Tyr
1               5                   10

<210> SEQ ID NO 83
<211> LENGTH: 10
<212> TYPE: PRT
<213> ORGANISM: homo sapiens

<400> SEQUENCE: 83

Val Leu Ile Tyr Val Arg Val Phe Arg Lys
1               5                   10

<210> SEQ ID NO 84
<211> LENGTH: 10
<212> TYPE: PRT
<213> ORGANISM: homo sapiens

<400> SEQUENCE: 84

His Leu Asp Asn Ala Glu Gln Pro Glu Leu
1               5                   10

<210> SEQ ID NO 85
<211> LENGTH: 10
<212> TYPE: PRT
<213> ORGANISM: homo sapiens

<400> SEQUENCE: 85

Gln Ala Glu Val Gln Asn His Ser Thr Ser
1               5                   10

<210> SEQ ID NO 86
<211> LENGTH: 10
<212> TYPE: PRT
<213> ORGANISM: homo sapiens

<400> SEQUENCE: 86

Thr Leu Glu Ala His Gln Ser Lys Val Ser
1               5                   10

<210> SEQ ID NO 87
<211> LENGTH: 10
<212> TYPE: PRT
<213> ORGANISM: homo sapiens

<400> SEQUENCE: 87

Ala Ser Met Glu Ala Gln Gly Leu Ser Phe
1               5                   10

<210> SEQ ID NO 88
<211> LENGTH: 10
<212> TYPE: PRT
<213> ORGANISM: homo sapiens

<400> SEQUENCE: 88

Leu Ser Val Asn Asn Ser Gly Leu Phe Phe
1               5                   10

<210> SEQ ID NO 89
<211> LENGTH: 10
<212> TYPE: PRT
<213> ORGANISM: homo sapiens

<400> SEQUENCE: 89

Ile Gly Leu Pro Asn Thr Gln Asp Tyr Lys
1               5                   10

<210> SEQ ID NO 90
<211> LENGTH: 10
<212> TYPE: PRT
<213> ORGANISM: homo sapiens

<400> SEQUENCE: 90

Ser Ile Asp Val Thr Asn Glu Ser Arg Asn
1               5                   10

<210> SEQ ID NO 91
<211> LENGTH: 10
<212> TYPE: PRT
<213> ORGANISM: homo sapiens

<400> SEQUENCE: 91

Leu Ile Gly Leu Pro Asn Thr Gln Asp Tyr
1               5                   10

<210> SEQ ID NO 92
<211> LENGTH: 10
<212> TYPE: PRT
<213> ORGANISM: homo sapiens

<400> SEQUENCE: 92

Val Leu Asp Ile Pro Thr Thr Gln Arg Gln
1               5                   10

<210> SEQ ID NO 93
<211> LENGTH: 10
<212> TYPE: PRT
<213> ORGANISM: homo sapiens

<400> SEQUENCE: 93

Asp Asn Pro Pro Leu Tyr Cys Asn Pro Lys
1               5                   10

<210> SEQ ID NO 94
<211> LENGTH: 10
<212> TYPE: PRT
<213> ORGANISM: homo sapiens

<400> SEQUENCE: 94

Arg Ala Leu Phe Pro Ser Leu Gly Thr Tyr
1               5                   10

<210> SEQ ID NO 95
<211> LENGTH: 10
<212> TYPE: PRT
<213> ORGANISM: homo sapiens

<400> SEQUENCE: 95

Asn Thr Gln Asp Tyr Lys Trp Val Asp Arg
1               5                   10

<210> SEQ ID NO 96
<211> LENGTH: 10
<212> TYPE: PRT
<213> ORGANISM: homo sapiens

<400> SEQUENCE: 96

Leu Ile Val Leu Phe Cys Leu Phe Ile Phe
1               5                   10

<210> SEQ ID NO 97
<211> LENGTH: 10
<212> TYPE: PRT
<213> ORGANISM: homo sapiens

<400> SEQUENCE: 97

Glu Val Gln Asn His Ser Thr Ser Ser Tyr
1               5                   10

<210> SEQ ID NO 98
<211> LENGTH: 10
<212> TYPE: PRT
<213> ORGANISM: homo sapiens

<400> SEQUENCE: 98

Ser Ala Val Pro Leu Ile Gly Leu Pro Asn
1               5                   10

<210> SEQ ID NO 99
<211> LENGTH: 10
<212> TYPE: PRT
<213> ORGANISM: homo sapiens

<400> SEQUENCE: 99

Gln Pro Glu Leu Val Phe Val Pro Ala Ser
1               5                   10

<210> SEQ ID NO 100
<211> LENGTH: 10
<212> TYPE: PRT
<213> ORGANISM: homo sapiens

<400> SEQUENCE: 100

Ser Met Glu Ala Gln Gly Leu Ser Phe Ala
1               5                   10

<210> SEQ ID NO 101
<211> LENGTH: 10
<212> TYPE: PRT
<213> ORGANISM: homo sapiens

<400> SEQUENCE: 101

Ser Cys Gln Val Ser Asn Arg Ala Met Lys
1               5                   10

<210> SEQ ID NO 102
<211> LENGTH: 10
<212> TYPE: PRT
<213> ORGANISM: homo sapiens

<400> SEQUENCE: 102

Cys Gln Asn Gln Thr Lys Gly Leu Leu Tyr
1               5                   10

```
<210> SEQ ID NO 103
<211> LENGTH: 10
<212> TYPE: PRT
<213> ORGANISM: homo sapiens

<400> SEQUENCE: 103

Val Ser Ser Leu Ala Ser Ala Ser Arg Lys
 1               5                  10

<210> SEQ ID NO 104
<211> LENGTH: 10
<212> TYPE: PRT
<213> ORGANISM: homo sapiens

<400> SEQUENCE: 104

Asn Ser Gln Pro Leu Asn Leu Ala Leu Ser
 1               5                  10

<210> SEQ ID NO 105
<211> LENGTH: 10
<212> TYPE: PRT
<213> ORGANISM: homo sapiens

<400> SEQUENCE: 105

Trp Val Asp Arg Asn Ser Gly Leu Thr Trp
 1               5                  10

<210> SEQ ID NO 106
<211> LENGTH: 10
<212> TYPE: PRT
<213> ORGANISM: homo sapiens

<400> SEQUENCE: 106

Lys Gly Phe Pro Pro Lys Trp Ser Gly Arg
 1               5                  10

<210> SEQ ID NO 107
<211> LENGTH: 10
<212> TYPE: PRT
<213> ORGANISM: homo sapiens

<400> SEQUENCE: 107

Ser Gly Pro Phe Leu Gly Asn Ile Pro Lys
 1               5                  10

<210> SEQ ID NO 108
<211> LENGTH: 10
<212> TYPE: PRT
<213> ORGANISM: homo sapiens

<400> SEQUENCE: 108

Leu His Glu Ala Ser Glu Asn Leu Lys Asn
 1               5                  10

<210> SEQ ID NO 109
<211> LENGTH: 10
<212> TYPE: PRT
<213> ORGANISM: homo sapiens

<400> SEQUENCE: 109

Lys Val Ser Ser Leu Ala Ser Ala Ser Arg
 1               5                  10

<210> SEQ ID NO 110
<211> LENGTH: 10
```

```
<212> TYPE: PRT
<213> ORGANISM: homo sapiens

<400> SEQUENCE: 110

Phe Val Leu Ile Tyr Val Arg Val Phe Arg
1               5                   10

<210> SEQ ID NO 111
<211> LENGTH: 10
<212> TYPE: PRT
<213> ORGANISM: homo sapiens

<400> SEQUENCE: 111

Arg Leu His Glu Ala Ser Glu Asn Leu Lys
1               5                   10

<210> SEQ ID NO 112
<211> LENGTH: 10
<212> TYPE: PRT
<213> ORGANISM: homo sapiens

<400> SEQUENCE: 112

Cys Leu Tyr Ser Cys Gln Asn Gln Thr Lys
1               5                   10

<210> SEQ ID NO 113
<211> LENGTH: 10
<212> TYPE: PRT
<213> ORGANISM: homo sapiens

<400> SEQUENCE: 113

Ala Leu Ser Pro Gln Gln Ser Ala Gln Leu
1               5                   10

<210> SEQ ID NO 114
<211> LENGTH: 10
<212> TYPE: PRT
<213> ORGANISM: homo sapiens

<400> SEQUENCE: 114

Pro Ser Leu Gly Thr Tyr Asp Leu Glu Lys
1               5                   10

<210> SEQ ID NO 115
<211> LENGTH: 9
<212> TYPE: PRT
<213> ORGANISM: homo sapiens

<400> SEQUENCE: 115

Val Leu Phe Cys Leu Phe Ile Phe Val
1               5

<210> SEQ ID NO 116
<211> LENGTH: 9
<212> TYPE: PRT
<213> ORGANISM: homo sapiens

<400> SEQUENCE: 116

Arg Leu Leu Glu Gly Asn Phe Ser Leu
1               5

<210> SEQ ID NO 117
<211> LENGTH: 9
<212> TYPE: PRT
<213> ORGANISM: homo sapiens
```

```
<400> SEQUENCE: 117

Val Leu Leu Ile Val Leu Phe Cys Leu
1               5

<210> SEQ ID NO 118
<211> LENGTH: 9
<212> TYPE: PRT
<213> ORGANISM: homo sapiens

<400> SEQUENCE: 118

Trp Leu Cys Glu His Leu Asp Asn Ala
1               5

<210> SEQ ID NO 119
<211> LENGTH: 9
<212> TYPE: PRT
<213> ORGANISM: homo sapiens

<400> SEQUENCE: 119

Trp Leu Thr Gly Ser Asn Leu Thr Leu
1               5

<210> SEQ ID NO 120
<211> LENGTH: 9
<212> TYPE: PRT
<213> ORGANISM: homo sapiens

<400> SEQUENCE: 120

Tyr Val Leu Leu Ile Val Leu Phe Cys
1               5

<210> SEQ ID NO 121
<211> LENGTH: 9
<212> TYPE: PRT
<213> ORGANISM: homo sapiens

<400> SEQUENCE: 121

Thr Leu Thr Ala Phe Leu Thr Ile Leu
1               5

<210> SEQ ID NO 122
<211> LENGTH: 9
<212> TYPE: PRT
<213> ORGANISM: homo sapiens

<400> SEQUENCE: 122

Leu Gln Leu Thr Leu Thr Ala Phe Leu
1               5

<210> SEQ ID NO 123
<211> LENGTH: 9
<212> TYPE: PRT
<213> ORGANISM: homo sapiens

<400> SEQUENCE: 123

Trp Met Tyr Glu Arg Val Trp Tyr Pro
1               5

<210> SEQ ID NO 124
<211> LENGTH: 9
<212> TYPE: PRT
<213> ORGANISM: homo sapiens

<400> SEQUENCE: 124
```

```
Leu Ile Val Leu Phe Cys Leu Phe Ile
  1               5

<210> SEQ ID NO 125
<211> LENGTH: 9
<212> TYPE: PRT
<213> ORGANISM: homo sapiens

<400> SEQUENCE: 125

Arg Val Trp Tyr Pro Gln Ala Glu Val
  1               5

<210> SEQ ID NO 126
<211> LENGTH: 9
<212> TYPE: PRT
<213> ORGANISM: homo sapiens

<400> SEQUENCE: 126

Gly Leu Gly Tyr Leu Val Pro Ser Leu
  1               5

<210> SEQ ID NO 127
<211> LENGTH: 9
<212> TYPE: PRT
<213> ORGANISM: homo sapiens

<400> SEQUENCE: 127

Tyr Leu Thr Leu Asn Ala Ser Gln Ile
  1               5

<210> SEQ ID NO 128
<211> LENGTH: 9
<212> TYPE: PRT
<213> ORGANISM: homo sapiens

<400> SEQUENCE: 128

Tyr Gln Leu Phe Arg Asn Leu Phe Cys
  1               5

<210> SEQ ID NO 129
<211> LENGTH: 9
<212> TYPE: PRT
<213> ORGANISM: homo sapiens

<400> SEQUENCE: 129

Asn Leu Arg Ser Phe Ile His Lys Val
  1               5

<210> SEQ ID NO 130
<211> LENGTH: 9
<212> TYPE: PRT
<213> ORGANISM: homo sapiens

<400> SEQUENCE: 130

Leu Leu Tyr Gln Leu Phe Arg Asn Leu
  1               5

<210> SEQ ID NO 131
<211> LENGTH: 9
<212> TYPE: PRT
<213> ORGANISM: homo sapiens

<400> SEQUENCE: 131

Gln Leu Thr Leu Thr Ala Phe Leu Thr
```

```
1               5
```

<210> SEQ ID NO 132
<211> LENGTH: 9
<212> TYPE: PRT
<213> ORGANISM: homo sapiens

<400> SEQUENCE: 132

```
Arg Leu His Glu Ala Ser Glu Asn Leu
 1               5
```

<210> SEQ ID NO 133
<211> LENGTH: 9
<212> TYPE: PRT
<213> ORGANISM: homo sapiens

<400> SEQUENCE: 133

```
Leu Val Ser Glu Thr Ser Cys Gln Val
 1               5
```

<210> SEQ ID NO 134
<211> LENGTH: 9
<212> TYPE: PRT
<213> ORGANISM: homo sapiens

<400> SEQUENCE: 134

```
Ile Leu Val Gln Pro Gln His Leu Leu
 1               5
```

<210> SEQ ID NO 135
<211> LENGTH: 9
<212> TYPE: PRT
<213> ORGANISM: homo sapiens

<400> SEQUENCE: 135

```
Cys Leu Tyr Ser Cys Gln Asn Gln Thr
 1               5
```

<210> SEQ ID NO 136
<211> LENGTH: 9
<212> TYPE: PRT
<213> ORGANISM: homo sapiens

<400> SEQUENCE: 136

```
Gly Leu Ser Phe Ala Gln Val Arg Leu
 1               5
```

<210> SEQ ID NO 137
<211> LENGTH: 9
<212> TYPE: PRT
<213> ORGANISM: homo sapiens

<400> SEQUENCE: 137

```
Ser Leu Asn Ser Gln Pro Leu Asn Leu
 1               5
```

<210> SEQ ID NO 138
<211> LENGTH: 9
<212> TYPE: PRT
<213> ORGANISM: homo sapiens

<400> SEQUENCE: 138

```
Thr Leu Ser Val Asn Asn Ser Gly Leu
 1               5
```

```
<210> SEQ ID NO 139
<211> LENGTH: 9
<212> TYPE: PRT
<213> ORGANISM: homo sapiens

<400> SEQUENCE: 139

Lys Ala Met Glu Gln Glu Phe Ser Ala
 1               5

<210> SEQ ID NO 140
<211> LENGTH: 9
<212> TYPE: PRT
<213> ORGANISM: homo sapiens

<400> SEQUENCE: 140

Leu Leu Asp Trp Gln Gly Ile Phe Ala
 1               5

<210> SEQ ID NO 141
<211> LENGTH: 9
<212> TYPE: PRT
<213> ORGANISM: homo sapiens

<400> SEQUENCE: 141

Gln Leu Leu Val Ser Glu Thr Ser Cys
 1               5

<210> SEQ ID NO 142
<211> LENGTH: 9
<212> TYPE: PRT
<213> ORGANISM: homo sapiens

<400> SEQUENCE: 142

Ala Leu Leu Gln Leu Thr Leu Thr Ala
 1               5

<210> SEQ ID NO 143
<211> LENGTH: 9
<212> TYPE: PRT
<213> ORGANISM: homo sapiens

<400> SEQUENCE: 143

Val Asn Asn Ser Gly Leu Phe Phe Leu
 1               5

<210> SEQ ID NO 144
<211> LENGTH: 9
<212> TYPE: PRT
<213> ORGANISM: homo sapiens

<400> SEQUENCE: 144

Ala Glu Gln Pro Glu Leu Val Phe Val
 1               5

<210> SEQ ID NO 145
<211> LENGTH: 9
<212> TYPE: PRT
<213> ORGANISM: homo sapiens

<400> SEQUENCE: 145

Leu Leu Ala Pro Val Phe Arg Thr Leu
 1               5

<210> SEQ ID NO 146
```

```
<211> LENGTH: 9
<212> TYPE: PRT
<213> ORGANISM: homo sapiens

<400> SEQUENCE: 146

Ala Gln Gly Leu Ser Phe Ala Gln Val
1               5

<210> SEQ ID NO 147
<211> LENGTH: 9
<212> TYPE: PRT
<213> ORGANISM: homo sapiens

<400> SEQUENCE: 147

His Leu Leu Ala Pro Val Phe Arg Thr
1               5

<210> SEQ ID NO 148
<211> LENGTH: 9
<212> TYPE: PRT
<213> ORGANISM: homo sapiens

<400> SEQUENCE: 148

Thr Ile Leu Val Gln Pro Gln His Leu
1               5

<210> SEQ ID NO 149
<211> LENGTH: 9
<212> TYPE: PRT
<213> ORGANISM: homo sapiens

<400> SEQUENCE: 149

Leu Glu Gly Asn Phe Ser Leu Cys Val
1               5

<210> SEQ ID NO 150
<211> LENGTH: 9
<212> TYPE: PRT
<213> ORGANISM: homo sapiens

<400> SEQUENCE: 150

Gln Ile Thr Asn Leu Arg Ser Phe Ile
1               5

<210> SEQ ID NO 151
<211> LENGTH: 9
<212> TYPE: PRT
<213> ORGANISM: homo sapiens

<400> SEQUENCE: 151

Gly Leu Thr Trp Ser Gly Asn Asp Thr
1               5

<210> SEQ ID NO 152
<211> LENGTH: 9
<212> TYPE: PRT
<213> ORGANISM: homo sapiens

<400> SEQUENCE: 152

Gly Leu Thr Thr His Gln Tyr Asp Thr
1               5

<210> SEQ ID NO 153
<211> LENGTH: 9
<212> TYPE: PRT
```

<213> ORGANISM: homo sapiens

<400> SEQUENCE: 153

Asn Leu Phe Cys Ser Tyr Gly Leu Thr
1               5

<210> SEQ ID NO 154
<211> LENGTH: 9
<212> TYPE: PRT
<213> ORGANISM: homo sapiens

<400> SEQUENCE: 154

Thr Leu Glu Ala His Gln Ser Lys Val
1               5

<210> SEQ ID NO 155
<211> LENGTH: 9
<212> TYPE: PRT
<213> ORGANISM: homo sapiens

<400> SEQUENCE: 155

Gln Leu Phe Arg Asn Leu Phe Cys Ser
1               5

<210> SEQ ID NO 156
<211> LENGTH: 9
<212> TYPE: PRT
<213> ORGANISM: homo sapiens

<400> SEQUENCE: 156

Gly Leu Leu Tyr Gln Leu Phe Arg Asn
1               5

<210> SEQ ID NO 157
<211> LENGTH: 9
<212> TYPE: PRT
<213> ORGANISM: homo sapiens

<400> SEQUENCE: 157

Gly Thr Phe Met Pro Ser Ile Asp Val
1               5

<210> SEQ ID NO 158
<211> LENGTH: 9
<212> TYPE: PRT
<213> ORGANISM: homo sapiens

<400> SEQUENCE: 158

Leu Val Pro Ser Leu Thr Arg Tyr Leu
1               5

<210> SEQ ID NO 159
<211> LENGTH: 9
<212> TYPE: PRT
<213> ORGANISM: homo sapiens

<400> SEQUENCE: 159

Leu Thr Asn Gln Ser Asn Cys Trp Leu
1               5

<210> SEQ ID NO 160
<211> LENGTH: 9
<212> TYPE: PRT
<213> ORGANISM: homo sapiens

```
<400> SEQUENCE: 160

Ser Ile Leu Thr Asn Gln Ser Asn Cys
1               5

<210> SEQ ID NO 161
<211> LENGTH: 9
<212> TYPE: PRT
<213> ORGANISM: homo sapiens

<400> SEQUENCE: 161

Ala Ile Leu Asn Ile Ser Lys Ala Met
1               5

<210> SEQ ID NO 162
<211> LENGTH: 9
<212> TYPE: PRT
<213> ORGANISM: homo sapiens

<400> SEQUENCE: 162

Phe Cys Leu Phe Ile Phe Val Leu Ile
1               5

<210> SEQ ID NO 163
<211> LENGTH: 9
<212> TYPE: PRT
<213> ORGANISM: homo sapiens

<400> SEQUENCE: 163

Met Glu Ala Gln Gly Leu Ser Phe Ala
1               5

<210> SEQ ID NO 164
<211> LENGTH: 9
<212> TYPE: PRT
<213> ORGANISM: homo sapiens

<400> SEQUENCE: 164

Trp Gly Tyr Val Leu Leu Ile Val Leu
1               5

<210> SEQ ID NO 165
<211> LENGTH: 10
<212> TYPE: PRT
<213> ORGANISM: homo sapiens

<400> SEQUENCE: 165

Cys Leu Phe Ile Phe Val Leu Ile Tyr Val
1               5                   10

<210> SEQ ID NO 166
<211> LENGTH: 10
<212> TYPE: PRT
<213> ORGANISM: homo sapiens

<400> SEQUENCE: 166

Val Leu Phe Cys Leu Phe Ile Phe Val Leu
1               5                   10

<210> SEQ ID NO 167
<211> LENGTH: 10
<212> TYPE: PRT
<213> ORGANISM: homo sapiens

<400> SEQUENCE: 167
```

Tyr Val Leu Leu Ile Val Leu Phe Cys Leu
1               5                  10

<210> SEQ ID NO 168
<211> LENGTH: 10
<212> TYPE: PRT
<213> ORGANISM: homo sapiens

<400> SEQUENCE: 168

Ile Val Leu Phe Cys Leu Phe Ile Phe Val
1               5                  10

<210> SEQ ID NO 169
<211> LENGTH: 10
<212> TYPE: PRT
<213> ORGANISM: homo sapiens

<400> SEQUENCE: 169

Leu Leu Ile Val Leu Phe Cys Leu Phe Ile
1               5                  10

<210> SEQ ID NO 170
<211> LENGTH: 10
<212> TYPE: PRT
<213> ORGANISM: homo sapiens

<400> SEQUENCE: 170

Gly Leu Phe Phe Leu Cys Gly Asn Gly Val
1               5                  10

<210> SEQ ID NO 171
<211> LENGTH: 10
<212> TYPE: PRT
<213> ORGANISM: homo sapiens

<400> SEQUENCE: 171

Phe Ile Phe Val Leu Ile Tyr Val Arg Val
1               5                  10

<210> SEQ ID NO 172
<211> LENGTH: 10
<212> TYPE: PRT
<213> ORGANISM: homo sapiens

<400> SEQUENCE: 172

Ile Leu Thr Asn Gln Ser Asn Cys Trp Leu
1               5                  10

<210> SEQ ID NO 173
<211> LENGTH: 10
<212> TYPE: PRT
<213> ORGANISM: homo sapiens

<400> SEQUENCE: 173

Leu Leu Gln Leu Thr Leu Thr Ala Phe Leu
1               5                  10

<210> SEQ ID NO 174
<211> LENGTH: 10
<212> TYPE: PRT
<213> ORGANISM: homo sapiens

<400> SEQUENCE: 174

Arg Leu Leu Glu Gly Asn Phe Ser Leu Cys
1               5                  10

```
<210> SEQ ID NO 175
<211> LENGTH: 10
<212> TYPE: PRT
<213> ORGANISM: homo sapiens

<400> SEQUENCE: 175

Ser Val Asn Asn Ser Gly Leu Phe Phe Leu
 1               5                  10

<210> SEQ ID NO 176
<211> LENGTH: 10
<212> TYPE: PRT
<213> ORGANISM: homo sapiens

<400> SEQUENCE: 176

Phe Leu Gly Asn Ile Pro Lys Gln Tyr Cys
 1               5                  10

<210> SEQ ID NO 177
<211> LENGTH: 10
<212> TYPE: PRT
<213> ORGANISM: homo sapiens

<400> SEQUENCE: 177

Leu Leu Val Ser Glu Thr Ser Cys Gln Val
 1               5                  10

<210> SEQ ID NO 178
<211> LENGTH: 10
<212> TYPE: PRT
<213> ORGANISM: homo sapiens

<400> SEQUENCE: 178

Tyr Leu Val Pro Ser Leu Thr Arg Tyr Leu
 1               5                  10

<210> SEQ ID NO 179
<211> LENGTH: 10
<212> TYPE: PRT
<213> ORGANISM: homo sapiens

<400> SEQUENCE: 179

Thr Leu Thr Ala Phe Leu Thr Ile Leu Val
 1               5                  10

<210> SEQ ID NO 180
<211> LENGTH: 10
<212> TYPE: PRT
<213> ORGANISM: homo sapiens

<400> SEQUENCE: 180

Ile Leu Trp Phe Asp Ser Thr Asp Gly Thr
 1               5                  10

<210> SEQ ID NO 181
<211> LENGTH: 10
<212> TYPE: PRT
<213> ORGANISM: homo sapiens

<400> SEQUENCE: 181

Thr Leu Asn Ala Ser Gln Ile Thr Asn Leu
 1               5                  10
```

-continued

```
<210> SEQ ID NO 182
<211> LENGTH: 10
<212> TYPE: PRT
<213> ORGANISM: homo sapiens

<400> SEQUENCE: 182

Ser Leu Ser Asn Cys Ala Leu Leu Gln Leu
1               5                   10

<210> SEQ ID NO 183
<211> LENGTH: 10
<212> TYPE: PRT
<213> ORGANISM: homo sapiens

<400> SEQUENCE: 183

Gly Leu Leu Tyr Gln Leu Phe Arg Asn Leu
1               5                   10

<210> SEQ ID NO 184
<211> LENGTH: 10
<212> TYPE: PRT
<213> ORGANISM: homo sapiens

<400> SEQUENCE: 184

Leu Leu Glu Gly Asn Phe Ser Leu Cys Val
1               5                   10

<210> SEQ ID NO 185
<211> LENGTH: 10
<212> TYPE: PRT
<213> ORGANISM: homo sapiens

<400> SEQUENCE: 185

Val Gln Pro Gln His Leu Leu Ala Pro Val
1               5                   10

<210> SEQ ID NO 186
<211> LENGTH: 10
<212> TYPE: PRT
<213> ORGANISM: homo sapiens

<400> SEQUENCE: 186

Leu Gln Leu Thr Leu Thr Ala Phe Leu Thr
1               5                   10

<210> SEQ ID NO 187
<211> LENGTH: 10
<212> TYPE: PRT
<213> ORGANISM: homo sapiens

<400> SEQUENCE: 187

Ala Leu Ser Pro Gln Gln Ser Ala Gln Leu
1               5                   10

<210> SEQ ID NO 188
<211> LENGTH: 10
<212> TYPE: PRT
<213> ORGANISM: homo sapiens

<400> SEQUENCE: 188

Gln Leu Thr Leu Thr Ala Phe Leu Thr Ile
1               5                   10

<210> SEQ ID NO 189
<211> LENGTH: 10
```

```
<212> TYPE: PRT
<213> ORGANISM: homo sapiens

<400> SEQUENCE: 189

Cys Leu Tyr Ile Asn Tyr Ser Glu Glu Ile
 1               5                  10

<210> SEQ ID NO 190
<211> LENGTH: 10
<212> TYPE: PRT
<213> ORGANISM: homo sapiens

<400> SEQUENCE: 190

Thr Asn Leu Arg Ser Phe Ile His Lys Val
 1               5                  10

<210> SEQ ID NO 191
<211> LENGTH: 10
<212> TYPE: PRT
<213> ORGANISM: homo sapiens

<400> SEQUENCE: 191

Gln Thr Leu Glu Ala His Gln Ser Lys Val
 1               5                  10

<210> SEQ ID NO 192
<211> LENGTH: 10
<212> TYPE: PRT
<213> ORGANISM: homo sapiens

<400> SEQUENCE: 192

Tyr Leu Thr Leu Asn Ala Ser Gln Ile Thr
 1               5                  10

<210> SEQ ID NO 193
<211> LENGTH: 10
<212> TYPE: PRT
<213> ORGANISM: homo sapiens

<400> SEQUENCE: 193

Ser Leu Asn Ser Gln Pro Leu Asn Leu Ala
 1               5                  10

<210> SEQ ID NO 194
<211> LENGTH: 10
<212> TYPE: PRT
<213> ORGANISM: homo sapiens

<400> SEQUENCE: 194

Thr Ile Leu Val Gln Pro Gln His Leu Leu
 1               5                  10

<210> SEQ ID NO 195
<211> LENGTH: 10
<212> TYPE: PRT
<213> ORGANISM: homo sapiens

<400> SEQUENCE: 195

Lys Ala Met Glu Gln Glu Phe Ser Ala Thr
 1               5                  10

<210> SEQ ID NO 196
<211> LENGTH: 10
<212> TYPE: PRT
<213> ORGANISM: homo sapiens
```

```
<400> SEQUENCE: 196

Gly Leu Ser Phe Ala Gln Val Arg Leu Leu
 1               5                  10

<210> SEQ ID NO 197
<211> LENGTH: 10
<212> TYPE: PRT
<213> ORGANISM: homo sapiens

<400> SEQUENCE: 197

Pro Leu Leu Asp Trp Gln Gly Ile Phe Ala
 1               5                  10

<210> SEQ ID NO 198
<211> LENGTH: 10
<212> TYPE: PRT
<213> ORGANISM: homo sapiens

<400> SEQUENCE: 198

Thr Gln Gly Asp Thr Asp Asn Pro Pro Leu
 1               5                  10

<210> SEQ ID NO 199
<211> LENGTH: 10
<212> TYPE: PRT
<213> ORGANISM: homo sapiens

<400> SEQUENCE: 199

Ile Leu Val Gln Pro Gln His Leu Leu Ala
 1               5                  10

<210> SEQ ID NO 200
<211> LENGTH: 10
<212> TYPE: PRT
<213> ORGANISM: homo sapiens

<400> SEQUENCE: 200

Gly Leu Gly Tyr Leu Val Pro Ser Leu Thr
 1               5                  10

<210> SEQ ID NO 201
<211> LENGTH: 10
<212> TYPE: PRT
<213> ORGANISM: homo sapiens

<400> SEQUENCE: 201

Leu Thr Leu Thr Ala Phe Leu Thr Ile Leu
 1               5                  10

<210> SEQ ID NO 202
<211> LENGTH: 10
<212> TYPE: PRT
<213> ORGANISM: homo sapiens

<400> SEQUENCE: 202

Leu Pro Asn Thr Gln Asp Tyr Lys Trp Val
 1               5                  10

<210> SEQ ID NO 203
<211> LENGTH: 10
<212> TYPE: PRT
<213> ORGANISM: homo sapiens

<400> SEQUENCE: 203
```

```
Ser Gln Ile Thr Asn Leu Arg Ser Phe Ile
1               5                   10

<210> SEQ ID NO 204
<211> LENGTH: 10
<212> TYPE: PRT
<213> ORGANISM: homo sapiens

<400> SEQUENCE: 204

Ser Leu Gly Thr Tyr Asp Leu Glu Lys Ala
1               5                   10

<210> SEQ ID NO 205
<211> LENGTH: 10
<212> TYPE: PRT
<213> ORGANISM: homo sapiens

<400> SEQUENCE: 205

Thr Val Gly Lys Gln Cys Cys Leu Tyr Ile
1               5                   10

<210> SEQ ID NO 206
<211> LENGTH: 10
<212> TYPE: PRT
<213> ORGANISM: homo sapiens

<400> SEQUENCE: 206

Asn Gln Thr Lys Gly Leu Leu Tyr Gln Leu
1               5                   10

<210> SEQ ID NO 207
<211> LENGTH: 10
<212> TYPE: PRT
<213> ORGANISM: homo sapiens

<400> SEQUENCE: 207

Ser Leu Thr Arg Tyr Leu Thr Leu Asn Ala
1               5                   10

<210> SEQ ID NO 208
<211> LENGTH: 10
<212> TYPE: PRT
<213> ORGANISM: homo sapiens

<400> SEQUENCE: 208

Asn Leu Ala Leu Ser Pro Gln Gln Ser Ala
1               5                   10

<210> SEQ ID NO 209
<211> LENGTH: 10
<212> TYPE: PRT
<213> ORGANISM: homo sapiens

<400> SEQUENCE: 209

Gln Val Ser Asn Arg Ala Met Lys Gly Leu
1               5                   10

<210> SEQ ID NO 210
<211> LENGTH: 10
<212> TYPE: PRT
<213> ORGANISM: homo sapiens

<400> SEQUENCE: 210

Leu Thr Trp Ser Gly Asn Asp Thr Cys Leu
```

```
                1               5                   10
```

\<210\> SEQ ID NO 211
\<211\> LENGTH: 10
\<212\> TYPE: PRT
\<213\> ORGANISM: homo sapiens

\<400\> SEQUENCE: 211

```
Leu Val Phe Val Pro Ala Ser Ala Ser Thr
1               5                   10
```

\<210\> SEQ ID NO 212
\<211\> LENGTH: 10
\<212\> TYPE: PRT
\<213\> ORGANISM: homo sapiens

\<400\> SEQUENCE: 212

```
Arg Ser Trp Gly Tyr Val Leu Leu Ile Val
1               5                   10
```

\<210\> SEQ ID NO 213
\<211\> LENGTH: 10
\<212\> TYPE: PRT
\<213\> ORGANISM: homo sapiens

\<400\> SEQUENCE: 213

```
Val Pro Ala Ser Ala Ser Thr Trp Trp Thr
1               5                   10
```

\<210\> SEQ ID NO 214
\<211\> LENGTH: 10
\<212\> TYPE: PRT
\<213\> ORGANISM: homo sapiens

\<400\> SEQUENCE: 214

```
Phe Ile His Lys Val Thr Pro His Arg Cys
1               5                   10
```

\<210\> SEQ ID NO 215
\<211\> LENGTH: 9
\<212\> TYPE: PRT
\<213\> ORGANISM: homo sapiens

\<400\> SEQUENCE: 215

```
Cys Leu Phe Ile Phe Val Leu Ile Tyr
1               5
```

\<210\> SEQ ID NO 216
\<211\> LENGTH: 9
\<212\> TYPE: PRT
\<213\> ORGANISM: homo sapiens

\<400\> SEQUENCE: 216

```
Ser Leu Gly Thr Tyr Asp Leu Glu Lys
1               5
```

\<210\> SEQ ID NO 217
\<211\> LENGTH: 9
\<212\> TYPE: PRT
\<213\> ORGANISM: homo sapiens

\<400\> SEQUENCE: 217

```
Gly Val Tyr Lys Gly Phe Pro Pro Lys
1               5
```

-continued

```
<210> SEQ ID NO 218
<211> LENGTH: 9
<212> TYPE: PRT
<213> ORGANISM: homo sapiens

<400> SEQUENCE: 218

Leu Ile Tyr Val Arg Val Phe Arg Lys
 1               5

<210> SEQ ID NO 219
<211> LENGTH: 9
<212> TYPE: PRT
<213> ORGANISM: homo sapiens

<400> SEQUENCE: 219

Gly Leu Pro Asn Thr Gln Asp Tyr Lys
 1               5

<210> SEQ ID NO 220
<211> LENGTH: 9
<212> TYPE: PRT
<213> ORGANISM: homo sapiens

<400> SEQUENCE: 220

Phe Leu Cys Gly Asn Gly Val Tyr Lys
 1               5

<210> SEQ ID NO 221
<211> LENGTH: 9
<212> TYPE: PRT
<213> ORGANISM: homo sapiens

<400> SEQUENCE: 221

Tyr Leu Val Pro Ser Leu Thr Arg Tyr
 1               5

<210> SEQ ID NO 222
<211> LENGTH: 9
<212> TYPE: PRT
<213> ORGANISM: homo sapiens

<400> SEQUENCE: 222

Ala Leu Phe Pro Ser Leu Gly Thr Tyr
 1               5

<210> SEQ ID NO 223
<211> LENGTH: 9
<212> TYPE: PRT
<213> ORGANISM: homo sapiens

<400> SEQUENCE: 223

Val Leu Ile Tyr Val Arg Val Phe Arg
 1               5

<210> SEQ ID NO 224
<211> LENGTH: 9
<212> TYPE: PRT
<213> ORGANISM: homo sapiens

<400> SEQUENCE: 224

Leu Leu Ile Val Leu Phe Cys Leu Phe
 1               5

<210> SEQ ID NO 225
```

```
<211> LENGTH: 9
<212> TYPE: PRT
<213> ORGANISM: homo sapiens

<400> SEQUENCE: 225

Phe Ile Phe Val Leu Ile Tyr Val Arg
1               5

<210> SEQ ID NO 226
<211> LENGTH: 9
<212> TYPE: PRT
<213> ORGANISM: homo sapiens

<400> SEQUENCE: 226

Val Leu Leu Ile Val Leu Phe Cys Leu
1               5

<210> SEQ ID NO 227
<211> LENGTH: 9
<212> TYPE: PRT
<213> ORGANISM: homo sapiens

<400> SEQUENCE: 227

Val Leu Asp Ile Pro Thr Thr Gln Arg
1               5

<210> SEQ ID NO 228
<211> LENGTH: 9
<212> TYPE: PRT
<213> ORGANISM: homo sapiens

<400> SEQUENCE: 228

Gly Pro Phe Leu Gly Asn Ile Pro Lys
1               5

<210> SEQ ID NO 229
<211> LENGTH: 9
<212> TYPE: PRT
<213> ORGANISM: homo sapiens

<400> SEQUENCE: 229

Val Leu Phe Cys Leu Phe Ile Phe Val
1               5

<210> SEQ ID NO 230
<211> LENGTH: 9
<212> TYPE: PRT
<213> ORGANISM: homo sapiens

<400> SEQUENCE: 230

Gly Leu Gly Tyr Leu Val Pro Ser Leu
1               5

<210> SEQ ID NO 231
<211> LENGTH: 9
<212> TYPE: PRT
<213> ORGANISM: homo sapiens

<400> SEQUENCE: 231

Arg Leu Leu Glu Gly Asn Phe Ser Leu
1               5

<210> SEQ ID NO 232
<211> LENGTH: 9
<212> TYPE: PRT
```

```
<213> ORGANISM: homo sapiens

<400> SEQUENCE: 232

Cys Leu Gly Thr Arg Gln Cys Ser Arg
1               5

<210> SEQ ID NO 233
<211> LENGTH: 9
<212> TYPE: PRT
<213> ORGANISM: homo sapiens

<400> SEQUENCE: 233

Ser Met Glu Ala Gln Gly Leu Ser Phe
1               5

<210> SEQ ID NO 234
<211> LENGTH: 9
<212> TYPE: PRT
<213> ORGANISM: homo sapiens

<400> SEQUENCE: 234

Phe Leu Gly Asn Ile Pro Lys Gln Tyr
1               5

<210> SEQ ID NO 235
<211> LENGTH: 9
<212> TYPE: PRT
<213> ORGANISM: homo sapiens

<400> SEQUENCE: 235

Trp Thr Tyr Ser Gly Gln Trp Met Tyr
1               5

<210> SEQ ID NO 236
<211> LENGTH: 9
<212> TYPE: PRT
<213> ORGANISM: homo sapiens

<400> SEQUENCE: 236

Leu Leu Gln Leu Thr Leu Thr Ala Phe
1               5

<210> SEQ ID NO 237
<211> LENGTH: 9
<212> TYPE: PRT
<213> ORGANISM: homo sapiens

<400> SEQUENCE: 237

Thr Leu Thr Ala Phe Leu Thr Ile Leu
1               5

<210> SEQ ID NO 238
<211> LENGTH: 9
<212> TYPE: PRT
<213> ORGANISM: homo sapiens

<400> SEQUENCE: 238

Gln Thr Leu Glu Ala His Gln Ser Lys
1               5

<210> SEQ ID NO 239
<211> LENGTH: 9
<212> TYPE: PRT
<213> ORGANISM: homo sapiens
```

```
<400> SEQUENCE: 239

His Leu Leu Ala Pro Val Phe Arg Thr
1               5

<210> SEQ ID NO 240
<211> LENGTH: 9
<212> TYPE: PRT
<213> ORGANISM: homo sapiens

<400> SEQUENCE: 240

Tyr Ile Asn Tyr Ser Glu Glu Ile Lys
1               5

<210> SEQ ID NO 241
<211> LENGTH: 9
<212> TYPE: PRT
<213> ORGANISM: homo sapiens

<400> SEQUENCE: 241

Gly Leu Ser Phe Ala Gln Val Arg Leu
1               5

<210> SEQ ID NO 242
<211> LENGTH: 9
<212> TYPE: PRT
<213> ORGANISM: homo sapiens

<400> SEQUENCE: 242

Trp Leu Thr Gly Ser Asn Leu Thr Leu
1               5

<210> SEQ ID NO 243
<211> LENGTH: 9
<212> TYPE: PRT
<213> ORGANISM: homo sapiens

<400> SEQUENCE: 243

Ile Leu Val Gln Pro Gln His Leu Leu
1               5

<210> SEQ ID NO 244
<211> LENGTH: 9
<212> TYPE: PRT
<213> ORGANISM: homo sapiens

<400> SEQUENCE: 244

Trp Met Tyr Glu Arg Val Trp Tyr Pro
1               5

<210> SEQ ID NO 245
<211> LENGTH: 9
<212> TYPE: PRT
<213> ORGANISM: homo sapiens

<400> SEQUENCE: 245

Ile Val Leu Phe Cys Leu Phe Ile Phe
1               5

<210> SEQ ID NO 246
<211> LENGTH: 9
<212> TYPE: PRT
<213> ORGANISM: homo sapiens

<400> SEQUENCE: 246
```

```
Ser Leu Asn Ser Gln Pro Leu Asn Leu
 1               5
```

<210> SEQ ID NO 247
<211> LENGTH: 9
<212> TYPE: PRT
<213> ORGANISM: homo sapiens

<400> SEQUENCE: 247

```
Gln Thr Ala Cys Gly Thr Val Gly Lys
 1               5
```

<210> SEQ ID NO 248
<211> LENGTH: 9
<212> TYPE: PRT
<213> ORGANISM: homo sapiens

<400> SEQUENCE: 248

```
Gly Leu Thr Thr His Gln Tyr Asp Thr
 1               5
```

<210> SEQ ID NO 249
<211> LENGTH: 9
<212> TYPE: PRT
<213> ORGANISM: homo sapiens

<400> SEQUENCE: 249

```
Leu Leu Glu Gly Asn Phe Ser Leu Cys
 1               5
```

<210> SEQ ID NO 250
<211> LENGTH: 9
<212> TYPE: PRT
<213> ORGANISM: homo sapiens

<400> SEQUENCE: 250

```
Asn Leu Arg Ser Phe Ile His Lys Val
 1               5
```

<210> SEQ ID NO 251
<211> LENGTH: 9
<212> TYPE: PRT
<213> ORGANISM: homo sapiens

<400> SEQUENCE: 251

```
Leu Leu Tyr Gln Leu Phe Arg Asn Leu
 1               5
```

<210> SEQ ID NO 252
<211> LENGTH: 9
<212> TYPE: PRT
<213> ORGANISM: homo sapiens

<400> SEQUENCE: 252

```
Arg Leu His Glu Ala Ser Glu Asn Leu
 1               5
```

<210> SEQ ID NO 253
<211> LENGTH: 9
<212> TYPE: PRT
<213> ORGANISM: homo sapiens

<400> SEQUENCE: 253

```
Cys Gln Val Ser Asn Arg Ala Met Lys
 1               5
```

<210> SEQ ID NO 254
<211> LENGTH: 9
<212> TYPE: PRT
<213> ORGANISM: homo sapiens

<400> SEQUENCE: 254

Gln Leu Phe Arg Asn Leu Phe Cys Ser
1               5

<210> SEQ ID NO 255
<211> LENGTH: 9
<212> TYPE: PRT
<213> ORGANISM: homo sapiens

<400> SEQUENCE: 255

Lys Gln Cys Cys Leu Tyr Ile Asn Tyr
1               5

<210> SEQ ID NO 256
<211> LENGTH: 9
<212> TYPE: PRT
<213> ORGANISM: homo sapiens

<400> SEQUENCE: 256

Thr Leu Ser Val Asn Asn Ser Gly Leu
1               5

<210> SEQ ID NO 257
<211> LENGTH: 9
<212> TYPE: PRT
<213> ORGANISM: homo sapiens

<400> SEQUENCE: 257

Asn Pro Pro Leu Tyr Cys Asn Pro Lys
1               5

<210> SEQ ID NO 258
<211> LENGTH: 9
<212> TYPE: PRT
<213> ORGANISM: homo sapiens

<400> SEQUENCE: 258

Phe Ile His Lys Val Thr Pro His Arg
1               5

<210> SEQ ID NO 259
<211> LENGTH: 9
<212> TYPE: PRT
<213> ORGANISM: homo sapiens

<400> SEQUENCE: 259

Tyr Leu Thr Leu Asn Ala Ser Gln Ile
1               5

<210> SEQ ID NO 260
<211> LENGTH: 9
<212> TYPE: PRT
<213> ORGANISM: homo sapiens

<400> SEQUENCE: 260

Tyr Val Arg Val Phe Arg Lys Ser Arg
1               5

```
<210> SEQ ID NO 261
<211> LENGTH: 9
<212> TYPE: PRT
<213> ORGANISM: homo sapiens

<400> SEQUENCE: 261

Ala Leu Leu Gln Leu Thr Leu Thr Ala
1               5

<210> SEQ ID NO 262
<211> LENGTH: 9
<212> TYPE: PRT
<213> ORGANISM: homo sapiens

<400> SEQUENCE: 262

Leu Ile Val Leu Phe Cys Leu Phe Ile
1               5

<210> SEQ ID NO 263
<211> LENGTH: 9
<212> TYPE: PRT
<213> ORGANISM: homo sapiens

<400> SEQUENCE: 263

Asp Leu Glu Lys Ala Ile Leu Asn Ile
1               5

<210> SEQ ID NO 264
<211> LENGTH: 9
<212> TYPE: PRT
<213> ORGANISM: homo sapiens

<400> SEQUENCE: 264

Cys Leu Tyr Ser Cys Gln Asn Gln Thr
1               5

<210> SEQ ID NO 265
<211> LENGTH: 10
<212> TYPE: PRT
<213> ORGANISM: homo sapiens

<400> SEQUENCE: 265

Val Leu Ile Tyr Val Arg Val Phe Arg Lys
1               5                   10

<210> SEQ ID NO 266
<211> LENGTH: 10
<212> TYPE: PRT
<213> ORGANISM: homo sapiens

<400> SEQUENCE: 266

Cys Leu Tyr Ser Cys Gln Asn Gln Thr Lys
1               5                   10

<210> SEQ ID NO 267
<211> LENGTH: 10
<212> TYPE: PRT
<213> ORGANISM: homo sapiens

<400> SEQUENCE: 267

Leu Leu Asp Trp Gln Gly Ile Phe Ala Lys
1               5                   10

<210> SEQ ID NO 268
<211> LENGTH: 10
```

-continued

```
<212> TYPE: PRT
<213> ORGANISM: homo sapiens

<400> SEQUENCE: 268

Ala Met Glu Gln Glu Phe Ser Ala Thr Lys
 1               5                  10

<210> SEQ ID NO 269
<211> LENGTH: 10
<212> TYPE: PRT
<213> ORGANISM: homo sapiens

<400> SEQUENCE: 269

Gln Leu Phe Arg Asn Leu Phe Cys Ser Tyr
 1               5                  10

<210> SEQ ID NO 270
<211> LENGTH: 10
<212> TYPE: PRT
<213> ORGANISM: homo sapiens

<400> SEQUENCE: 270

Val Leu Phe Cys Leu Phe Ile Phe Val Leu
 1               5                  10

<210> SEQ ID NO 271
<211> LENGTH: 10
<212> TYPE: PRT
<213> ORGANISM: homo sapiens

<400> SEQUENCE: 271

Arg Leu His Glu Ala Ser Glu Asn Leu Lys
 1               5                  10

<210> SEQ ID NO 272
<211> LENGTH: 10
<212> TYPE: PRT
<213> ORGANISM: homo sapiens

<400> SEQUENCE: 272

Leu Leu Tyr Gln Leu Phe Arg Asn Leu Phe
 1               5                  10

<210> SEQ ID NO 273
<211> LENGTH: 10
<212> TYPE: PRT
<213> ORGANISM: homo sapiens

<400> SEQUENCE: 273

Gly Leu Thr Glu Ala His Gly Lys Trp Arg
 1               5                  10

<210> SEQ ID NO 274
<211> LENGTH: 10
<212> TYPE: PRT
<213> ORGANISM: homo sapiens

<400> SEQUENCE: 274

Val Leu Leu Ile Val Leu Phe Cys Leu Phe
 1               5                  10

<210> SEQ ID NO 275
<211> LENGTH: 10
<212> TYPE: PRT
<213> ORGANISM: homo sapiens
```

```
<400> SEQUENCE: 275

Cys Leu Tyr Ile Asn Tyr Ser Glu Glu Ile
1               5                   10

<210> SEQ ID NO 276
<211> LENGTH: 10
<212> TYPE: PRT
<213> ORGANISM: homo sapiens

<400> SEQUENCE: 276

Ile Thr Asn Leu Arg Ser Phe Ile His Lys
1               5                   10

<210> SEQ ID NO 277
<211> LENGTH: 10
<212> TYPE: PRT
<213> ORGANISM: homo sapiens

<400> SEQUENCE: 277

Ala Met Lys Gly Leu Thr Thr His Gln Tyr
1               5                   10

<210> SEQ ID NO 278
<211> LENGTH: 10
<212> TYPE: PRT
<213> ORGANISM: homo sapiens

<400> SEQUENCE: 278

Leu Leu Ile Val Leu Phe Cys Leu Phe Ile
1               5                   10

<210> SEQ ID NO 279
<211> LENGTH: 10
<212> TYPE: PRT
<213> ORGANISM: homo sapiens

<400> SEQUENCE: 279

Cys Leu Phe Ile Phe Val Leu Ile Tyr Val
1               5                   10

<210> SEQ ID NO 280
<211> LENGTH: 10
<212> TYPE: PRT
<213> ORGANISM: homo sapiens

<400> SEQUENCE: 280

Ala Leu Leu Gln Leu Thr Leu Thr Ala Phe
1               5                   10

<210> SEQ ID NO 281
<211> LENGTH: 10
<212> TYPE: PRT
<213> ORGANISM: homo sapiens

<400> SEQUENCE: 281

Gly Ile Phe Ala Lys Val Gly Asp Trp Phe
1               5                   10

<210> SEQ ID NO 282
<211> LENGTH: 10
<212> TYPE: PRT
<213> ORGANISM: homo sapiens

<400> SEQUENCE: 282
```

Gln Leu Thr Leu Thr Ala Phe Leu Thr Ile
1               5                   10

<210> SEQ ID NO 283
<211> LENGTH: 10
<212> TYPE: PRT
<213> ORGANISM: homo sapiens

<400> SEQUENCE: 283

Gly Leu Phe Phe Leu Cys Gly Asn Gly Val
1               5                   10

<210> SEQ ID NO 284
<211> LENGTH: 10
<212> TYPE: PRT
<213> ORGANISM: homo sapiens

<400> SEQUENCE: 284

Lys Gln Tyr Cys Asn Gln Ile Leu Trp Phe
1               5                   10

<210> SEQ ID NO 285
<211> LENGTH: 10
<212> TYPE: PRT
<213> ORGANISM: homo sapiens

<400> SEQUENCE: 285

Cys Leu Gly Thr Arg Gln Cys Ser Arg Phe
1               5                   10

<210> SEQ ID NO 286
<211> LENGTH: 10
<212> TYPE: PRT
<213> ORGANISM: homo sapiens

<400> SEQUENCE: 286

Gly Asn Phe Ser Leu Cys Val Glu Asn Lys
1               5                   10

<210> SEQ ID NO 287
<211> LENGTH: 10
<212> TYPE: PRT
<213> ORGANISM: homo sapiens

<400> SEQUENCE: 287

Gly Gln Trp Met Tyr Glu Arg Val Trp Tyr
1               5                   10

<210> SEQ ID NO 288
<211> LENGTH: 10
<212> TYPE: PRT
<213> ORGANISM: homo sapiens

<400> SEQUENCE: 288

Leu Leu Glu Gly Asn Phe Ser Leu Cys Val
1               5                   10

<210> SEQ ID NO 289
<211> LENGTH: 10
<212> TYPE: PRT
<213> ORGANISM: homo sapiens

<400> SEQUENCE: 289

Ser Leu Ser Asn Cys Ala Leu Leu Gln Leu

```
                1               5                  10
```

\<210\> SEQ ID NO 290
\<211\> LENGTH: 10
\<212\> TYPE: PRT
\<213\> ORGANISM: homo sapiens

\<400\> SEQUENCE: 290

```
Lys Gln Thr Leu Glu Ala His Gln Ser Lys
 1               5                  10
```

\<210\> SEQ ID NO 291
\<211\> LENGTH: 10
\<212\> TYPE: PRT
\<213\> ORGANISM: homo sapiens

\<400\> SEQUENCE: 291

```
Gly Leu Pro Asn Thr Gln Asp Tyr Lys Trp
 1               5                  10
```

\<210\> SEQ ID NO 292
\<211\> LENGTH: 10
\<212\> TYPE: PRT
\<213\> ORGANISM: homo sapiens

\<400\> SEQUENCE: 292

```
Leu Ile Val Leu Phe Cys Leu Phe Ile Phe
 1               5                  10
```

\<210\> SEQ ID NO 293
\<211\> LENGTH: 10
\<212\> TYPE: PRT
\<213\> ORGANISM: homo sapiens

\<400\> SEQUENCE: 293

```
Arg Leu Leu Glu Gly Asn Phe Ser Leu Cys
 1               5                  10
```

\<210\> SEQ ID NO 294
\<211\> LENGTH: 10
\<212\> TYPE: PRT
\<213\> ORGANISM: homo sapiens

\<400\> SEQUENCE: 294

```
Gly Thr Val Gly Lys Gln Cys Cys Leu Tyr
 1               5                  10
```

\<210\> SEQ ID NO 295
\<211\> LENGTH: 10
\<212\> TYPE: PRT
\<213\> ORGANISM: homo sapiens

\<400\> SEQUENCE: 295

```
Lys Val Ser Ser Leu Ala Ser Ala Ser Arg
 1               5                  10
```

\<210\> SEQ ID NO 296
\<211\> LENGTH: 10
\<212\> TYPE: PRT
\<213\> ORGANISM: homo sapiens

\<400\> SEQUENCE: 296

```
Phe Cys Leu Phe Ile Phe Val Leu Ile Tyr
 1               5                  10
```

```
<210> SEQ ID NO 297
<211> LENGTH: 10
<212> TYPE: PRT
<213> ORGANISM: homo sapiens

<400> SEQUENCE: 297

Thr Leu Asn Ala Ser Gln Ile Thr Asn Leu
1               5                   10

<210> SEQ ID NO 298
<211> LENGTH: 10
<212> TYPE: PRT
<213> ORGANISM: homo sapiens

<400> SEQUENCE: 298

Gly Val Tyr Lys Gly Phe Pro Pro Lys Trp
1               5                   10

<210> SEQ ID NO 299
<211> LENGTH: 10
<212> TYPE: PRT
<213> ORGANISM: homo sapiens

<400> SEQUENCE: 299

Ala Leu Ser Pro Gln Gln Ser Ala Gln Leu
1               5                   10

<210> SEQ ID NO 300
<211> LENGTH: 10
<212> TYPE: PRT
<213> ORGANISM: homo sapiens

<400> SEQUENCE: 300

Phe Val Leu Ile Tyr Val Arg Val Phe Arg
1               5                   10

<210> SEQ ID NO 301
<211> LENGTH: 10
<212> TYPE: PRT
<213> ORGANISM: homo sapiens

<400> SEQUENCE: 301

Asn Leu Lys Asn Val Pro Leu Leu Asp Trp
1               5                   10

<210> SEQ ID NO 302
<211> LENGTH: 10
<212> TYPE: PRT
<213> ORGANISM: homo sapiens

<400> SEQUENCE: 302

His Val Leu Asp Ile Pro Thr Thr Gln Arg
1               5                   10

<210> SEQ ID NO 303
<211> LENGTH: 10
<212> TYPE: PRT
<213> ORGANISM: homo sapiens

<400> SEQUENCE: 303

Gly Leu Leu Tyr Gln Leu Phe Arg Asn Leu
1               5                   10

<210> SEQ ID NO 304
```

```
<211> LENGTH: 10
<212> TYPE: PRT
<213> ORGANISM: homo sapiens

<400> SEQUENCE: 304

Trp Met Tyr Glu Arg Val Trp Tyr Pro Gln
1               5                   10

<210> SEQ ID NO 305
<211> LENGTH: 10
<212> TYPE: PRT
<213> ORGANISM: homo sapiens

<400> SEQUENCE: 305

Tyr Val Leu Leu Ile Val Leu Phe Cys Leu
1               5                   10

<210> SEQ ID NO 306
<211> LENGTH: 10
<212> TYPE: PRT
<213> ORGANISM: homo sapiens

<400> SEQUENCE: 306

His Leu Asp Asn Ala Glu Gln Pro Glu Leu
1               5                   10

<210> SEQ ID NO 307
<211> LENGTH: 10
<212> TYPE: PRT
<213> ORGANISM: homo sapiens

<400> SEQUENCE: 307

Gly Leu Thr Trp Ser Gly Asn Asp Thr Cys
1               5                   10

<210> SEQ ID NO 308
<211> LENGTH: 10
<212> TYPE: PRT
<213> ORGANISM: homo sapiens

<400> SEQUENCE: 308

Asn Leu Phe Cys Ser Tyr Gly Leu Thr Glu
1               5                   10

<210> SEQ ID NO 309
<211> LENGTH: 10
<212> TYPE: PRT
<213> ORGANISM: homo sapiens

<400> SEQUENCE: 309

Ile Leu Val Gln Pro Gln His Leu Leu Ala
1               5                   10

<210> SEQ ID NO 310
<211> LENGTH: 10
<212> TYPE: PRT
<213> ORGANISM: homo sapiens

<400> SEQUENCE: 310

Leu Leu Gln Leu Thr Leu Thr Ala Phe Leu
1               5                   10

<210> SEQ ID NO 311
<211> LENGTH: 10
<212> TYPE: PRT
```

```
<213> ORGANISM: homo sapiens

<400> SEQUENCE: 311

Thr Leu Ser Val Asn Asn Ser Gly Leu Phe
 1               5                  10

<210> SEQ ID NO 312
<211> LENGTH: 10
<212> TYPE: PRT
<213> ORGANISM: homo sapiens

<400> SEQUENCE: 312

Ile Leu Thr Asn Gln Ser Asn Cys Trp Leu
 1               5                  10

<210> SEQ ID NO 313
<211> LENGTH: 10
<212> TYPE: PRT
<213> ORGANISM: homo sapiens

<400> SEQUENCE: 313

Arg Gln Thr Ala Cys Gly Thr Val Gly Lys
 1               5                  10

<210> SEQ ID NO 314
<211> LENGTH: 10
<212> TYPE: PRT
<213> ORGANISM: homo sapiens

<400> SEQUENCE: 314

Gly Leu Ser Phe Ala Gln Val Arg Leu Leu
 1               5                  10

<210> SEQ ID NO 315
<211> LENGTH: 9
<212> TYPE: PRT
<213> ORGANISM: homo sapiens

<400> SEQUENCE: 315

Gly Val Tyr Lys Gly Phe Pro Pro Lys
 1               5

<210> SEQ ID NO 316
<211> LENGTH: 9
<212> TYPE: PRT
<213> ORGANISM: homo sapiens

<400> SEQUENCE: 316

Gly Pro Phe Leu Gly Asn Ile Pro Lys
 1               5

<210> SEQ ID NO 317
<211> LENGTH: 9
<212> TYPE: PRT
<213> ORGANISM: homo sapiens

<400> SEQUENCE: 317

Leu Ile Tyr Val Arg Val Phe Arg Lys
 1               5

<210> SEQ ID NO 318
<211> LENGTH: 9
<212> TYPE: PRT
<213> ORGANISM: homo sapiens
```

```
<400> SEQUENCE: 318

Gln Thr Leu Glu Ala His Gln Ser Lys
 1               5

<210> SEQ ID NO 319
<211> LENGTH: 9
<212> TYPE: PRT
<213> ORGANISM: homo sapiens

<400> SEQUENCE: 319

Gly Leu Pro Asn Thr Gln Asp Tyr Lys
 1               5

<210> SEQ ID NO 320
<211> LENGTH: 9
<212> TYPE: PRT
<213> ORGANISM: homo sapiens

<400> SEQUENCE: 320

Gln Thr Ala Cys Gly Thr Val Gly Lys
 1               5

<210> SEQ ID NO 321
<211> LENGTH: 9
<212> TYPE: PRT
<213> ORGANISM: homo sapiens

<400> SEQUENCE: 321

Cys Gln Val Ser Asn Arg Ala Met Lys
 1               5

<210> SEQ ID NO 322
<211> LENGTH: 9
<212> TYPE: PRT
<213> ORGANISM: homo sapiens

<400> SEQUENCE: 322

Ser Leu Gly Thr Tyr Asp Leu Glu Lys
 1               5

<210> SEQ ID NO 323
<211> LENGTH: 9
<212> TYPE: PRT
<213> ORGANISM: homo sapiens

<400> SEQUENCE: 323

Gly Tyr Leu Val Pro Ser Leu Thr Arg
 1               5

<210> SEQ ID NO 324
<211> LENGTH: 9
<212> TYPE: PRT
<213> ORGANISM: homo sapiens

<400> SEQUENCE: 324

Leu Tyr Ser Cys Gln Asn Gln Thr Lys
 1               5

<210> SEQ ID NO 325
<211> LENGTH: 9
<212> TYPE: PRT
<213> ORGANISM: homo sapiens

<400> SEQUENCE: 325
```

Tyr Ile Asn Tyr Ser Glu Glu Ile Lys
1               5

<210> SEQ ID NO 326
<211> LENGTH: 9
<212> TYPE: PRT
<213> ORGANISM: homo sapiens

<400> SEQUENCE: 326

Phe Leu Cys Gly Asn Gly Val Tyr Lys
1               5

<210> SEQ ID NO 327
<211> LENGTH: 9
<212> TYPE: PRT
<213> ORGANISM: homo sapiens

<400> SEQUENCE: 327

Phe Ile Phe Val Leu Ile Tyr Val Arg
1               5

<210> SEQ ID NO 328
<211> LENGTH: 9
<212> TYPE: PRT
<213> ORGANISM: homo sapiens

<400> SEQUENCE: 328

Asn Phe Ser Leu Cys Val Glu Asn Lys
1               5

<210> SEQ ID NO 329
<211> LENGTH: 9
<212> TYPE: PRT
<213> ORGANISM: homo sapiens

<400> SEQUENCE: 329

Tyr Val Arg Val Phe Arg Lys Ser Arg
1               5

<210> SEQ ID NO 330
<211> LENGTH: 9
<212> TYPE: PRT
<213> ORGANISM: homo sapiens

<400> SEQUENCE: 330

Asn Pro Pro Leu Tyr Cys Asn Pro Lys
1               5

<210> SEQ ID NO 331
<211> LENGTH: 9
<212> TYPE: PRT
<213> ORGANISM: homo sapiens

<400> SEQUENCE: 331

Thr Asn Leu Arg Ser Phe Ile His Lys
1               5

<210> SEQ ID NO 332
<211> LENGTH: 9
<212> TYPE: PRT
<213> ORGANISM: homo sapiens

<400> SEQUENCE: 332

Leu Asp Trp Gln Gly Ile Phe Ala Lys
1               5

```
<210> SEQ ID NO 333
<211> LENGTH: 9
<212> TYPE: PRT
<213> ORGANISM: homo sapiens

<400> SEQUENCE: 333

Gly Thr Phe Met Pro Ser Ile Asp Val
 1               5

<210> SEQ ID NO 334
<211> LENGTH: 9
<212> TYPE: PRT
<213> ORGANISM: homo sapiens

<400> SEQUENCE: 334

Val Leu Ile Tyr Val Arg Val Phe Arg
 1               5

<210> SEQ ID NO 335
<211> LENGTH: 9
<212> TYPE: PRT
<213> ORGANISM: homo sapiens

<400> SEQUENCE: 335

Thr Gln Asp Tyr Lys Trp Val Asp Arg
 1               5

<210> SEQ ID NO 336
<211> LENGTH: 9
<212> TYPE: PRT
<213> ORGANISM: homo sapiens

<400> SEQUENCE: 336

Gly Phe Pro Pro Lys Trp Ser Gly Arg
 1               5

<210> SEQ ID NO 337
<211> LENGTH: 9
<212> TYPE: PRT
<213> ORGANISM: homo sapiens

<400> SEQUENCE: 337

Arg Val Trp Tyr Pro Gln Ala Glu Val
 1               5

<210> SEQ ID NO 338
<211> LENGTH: 9
<212> TYPE: PRT
<213> ORGANISM: homo sapiens

<400> SEQUENCE: 338

Leu Thr Glu Ala His Gly Lys Trp Arg
 1               5

<210> SEQ ID NO 339
<211> LENGTH: 9
<212> TYPE: PRT
<213> ORGANISM: homo sapiens

<400> SEQUENCE: 339

Ile Val Leu Phe Cys Leu Phe Ile Phe
 1               5
```

```
<210> SEQ ID NO 340
<211> LENGTH: 9
<212> TYPE: PRT
<213> ORGANISM: homo sapiens

<400> SEQUENCE: 340

Cys Leu Gly Thr Arg Gln Cys Ser Arg
 1               5

<210> SEQ ID NO 341
<211> LENGTH: 9
<212> TYPE: PRT
<213> ORGANISM: homo sapiens

<400> SEQUENCE: 341

Val Leu Asp Ile Pro Thr Thr Gln Arg
 1               5

<210> SEQ ID NO 342
<211> LENGTH: 9
<212> TYPE: PRT
<213> ORGANISM: homo sapiens

<400> SEQUENCE: 342

Phe Ile His Lys Val Thr Pro His Arg
 1               5

<210> SEQ ID NO 343
<211> LENGTH: 9
<212> TYPE: PRT
<213> ORGANISM: homo sapiens

<400> SEQUENCE: 343

Ser Ile Asp Val Thr Asn Glu Ser Arg
 1               5

<210> SEQ ID NO 344
<211> LENGTH: 9
<212> TYPE: PRT
<213> ORGANISM: homo sapiens

<400> SEQUENCE: 344

Phe Ala Lys Val Gly Asp Trp Phe Arg
 1               5

<210> SEQ ID NO 345
<211> LENGTH: 9
<212> TYPE: PRT
<213> ORGANISM: homo sapiens

<400> SEQUENCE: 345

Lys Gln Tyr Cys Asn Gln Ile Leu Trp
 1               5

<210> SEQ ID NO 346
<211> LENGTH: 9
<212> TYPE: PRT
<213> ORGANISM: homo sapiens

<400> SEQUENCE: 346

Glu Thr Ser Cys Gln Val Ser Asn Arg
 1               5

<210> SEQ ID NO 347
<211> LENGTH: 9
```

```
<212> TYPE: PRT
<213> ORGANISM: homo sapiens

<400> SEQUENCE: 347

Met Glu Gln Glu Phe Ser Ala Thr Lys
 1               5

<210> SEQ ID NO 348
<211> LENGTH: 9
<212> TYPE: PRT
<213> ORGANISM: homo sapiens

<400> SEQUENCE: 348

Asp Thr Ser Val Cys Leu Gly Thr Arg
 1               5

<210> SEQ ID NO 349
<211> LENGTH: 9
<212> TYPE: PRT
<213> ORGANISM: homo sapiens

<400> SEQUENCE: 349

Arg Leu Leu Glu Gly Asn Phe Ser Leu
 1               5

<210> SEQ ID NO 350
<211> LENGTH: 9
<212> TYPE: PRT
<213> ORGANISM: homo sapiens

<400> SEQUENCE: 350

Gly Thr Val Gly Lys Gln Cys Cys Leu
 1               5

<210> SEQ ID NO 351
<211> LENGTH: 9
<212> TYPE: PRT
<213> ORGANISM: homo sapiens

<400> SEQUENCE: 351

Asn Pro Lys Asp Asn Ser Thr Ile Arg
 1               5

<210> SEQ ID NO 352
<211> LENGTH: 9
<212> TYPE: PRT
<213> ORGANISM: homo sapiens

<400> SEQUENCE: 352

Leu Val Gln Pro Gln His Leu Leu Ala
 1               5

<210> SEQ ID NO 353
<211> LENGTH: 9
<212> TYPE: PRT
<213> ORGANISM: homo sapiens

<400> SEQUENCE: 353

Trp Thr Tyr Ser Gly Gln Trp Met Tyr
 1               5

<210> SEQ ID NO 354
<211> LENGTH: 9
<212> TYPE: PRT
<213> ORGANISM: homo sapiens
```

<400> SEQUENCE: 354

Ser Val Asn Asn Ser Gly Leu Phe Phe
1               5

<210> SEQ ID NO 355
<211> LENGTH: 9
<212> TYPE: PRT
<213> ORGANISM: homo sapiens

<400> SEQUENCE: 355

Asn His Ser Thr Ser Ser Tyr Arg Lys
1               5

<210> SEQ ID NO 356
<211> LENGTH: 9
<212> TYPE: PRT
<213> ORGANISM: homo sapiens

<400> SEQUENCE: 356

Asn Ala Ser Gln Ile Thr Asn Leu Arg
1               5

<210> SEQ ID NO 357
<211> LENGTH: 9
<212> TYPE: PRT
<213> ORGANISM: homo sapiens

<400> SEQUENCE: 357

Lys Gly Leu Leu Tyr Gln Leu Phe Arg
1               5

<210> SEQ ID NO 358
<211> LENGTH: 9
<212> TYPE: PRT
<213> ORGANISM: homo sapiens

<400> SEQUENCE: 358

Lys Ala Met Glu Gln Glu Phe Ser Ala
1               5

<210> SEQ ID NO 359
<211> LENGTH: 9
<212> TYPE: PRT
<213> ORGANISM: homo sapiens

<400> SEQUENCE: 359

Lys Gln Cys Cys Leu Tyr Ile Asn Tyr
1               5

<210> SEQ ID NO 360
<211> LENGTH: 9
<212> TYPE: PRT
<213> ORGANISM: homo sapiens

<400> SEQUENCE: 360

Tyr Gly Leu Thr Glu Ala His Gly Lys
1               5

<210> SEQ ID NO 361
<211> LENGTH: 9
<212> TYPE: PRT
<213> ORGANISM: homo sapiens

<400> SEQUENCE: 361

```
Ser Ser Leu Ala Ser Ala Ser Arg Lys
1               5
```

<210> SEQ ID NO 362
<211> LENGTH: 9
<212> TYPE: PRT
<213> ORGANISM: homo sapiens

<400> SEQUENCE: 362

```
Leu Thr Leu Thr Ala Phe Leu Thr Ile
1               5
```

<210> SEQ ID NO 363
<211> LENGTH: 9
<212> TYPE: PRT
<213> ORGANISM: homo sapiens

<400> SEQUENCE: 363

```
Ile Thr Asn Leu Arg Ser Phe Ile His
1               5
```

<210> SEQ ID NO 364
<211> LENGTH: 9
<212> TYPE: PRT
<213> ORGANISM: homo sapiens

<400> SEQUENCE: 364

```
Gly Thr Tyr Asp Leu Glu Lys Ala Ile
1               5
```

<210> SEQ ID NO 365
<211> LENGTH: 10
<212> TYPE: PRT
<213> ORGANISM: homo sapiens

<400> SEQUENCE: 365

```
Ile Thr Asn Leu Arg Ser Phe Ile His Lys
1               5                   10
```

<210> SEQ ID NO 366
<211> LENGTH: 10
<212> TYPE: PRT
<213> ORGANISM: homo sapiens

<400> SEQUENCE: 366

```
Val Leu Ile Tyr Val Arg Val Phe Arg Lys
1               5                   10
```

<210> SEQ ID NO 367
<211> LENGTH: 10
<212> TYPE: PRT
<213> ORGANISM: homo sapiens

<400> SEQUENCE: 367

```
Arg Gln Thr Ala Cys Gly Thr Val Gly Lys
1               5                   10
```

<210> SEQ ID NO 368
<211> LENGTH: 10
<212> TYPE: PRT
<213> ORGANISM: homo sapiens

<400> SEQUENCE: 368

```
Lys Gln Thr Leu Glu Ala His Gln Ser Lys
```

```
1               5                  10
```

<210> SEQ ID NO 369
<211> LENGTH: 10
<212> TYPE: PRT
<213> ORGANISM: homo sapiens

<400> SEQUENCE: 369

```
Leu Leu Asp Trp Gln Gly Ile Phe Ala Lys
 1               5                  10
```

<210> SEQ ID NO 370
<211> LENGTH: 10
<212> TYPE: PRT
<213> ORGANISM: homo sapiens

<400> SEQUENCE: 370

```
Lys Val Ser Ser Leu Ala Ser Ala Ser Arg
 1               5                  10
```

<210> SEQ ID NO 371
<211> LENGTH: 10
<212> TYPE: PRT
<213> ORGANISM: homo sapiens

<400> SEQUENCE: 371

```
Arg Leu His Glu Ala Ser Glu Asn Leu Lys
 1               5                  10
```

<210> SEQ ID NO 372
<211> LENGTH: 10
<212> TYPE: PRT
<213> ORGANISM: homo sapiens

<400> SEQUENCE: 372

```
Cys Leu Tyr Ser Cys Gln Asn Gln Thr Lys
 1               5                  10
```

<210> SEQ ID NO 373
<211> LENGTH: 10
<212> TYPE: PRT
<213> ORGANISM: homo sapiens

<400> SEQUENCE: 373

```
Phe Val Leu Ile Tyr Val Arg Val Phe Arg
 1               5                  10
```

<210> SEQ ID NO 374
<211> LENGTH: 10
<212> TYPE: PRT
<213> ORGANISM: homo sapiens

<400> SEQUENCE: 374

```
Leu Tyr Ile Asn Tyr Ser Glu Glu Ile Lys
 1               5                  10
```

<210> SEQ ID NO 375
<211> LENGTH: 10
<212> TYPE: PRT
<213> ORGANISM: homo sapiens

<400> SEQUENCE: 375

```
His Val Leu Asp Ile Pro Thr Thr Gln Arg
 1               5                  10
```

<210> SEQ ID NO 376
<211> LENGTH: 10
<212> TYPE: PRT
<213> ORGANISM: homo sapiens

<400> SEQUENCE: 376

Tyr Val Arg Val Phe Arg Lys Ser Arg Arg
1               5                   10

<210> SEQ ID NO 377
<211> LENGTH: 10
<212> TYPE: PRT
<213> ORGANISM: homo sapiens

<400> SEQUENCE: 377

Ser Tyr Gly Leu Thr Glu Ala His Gly Lys
1               5                   10

<210> SEQ ID NO 378
<211> LENGTH: 10
<212> TYPE: PRT
<213> ORGANISM: homo sapiens

<400> SEQUENCE: 378

Ala Met Glu Gln Glu Phe Ser Ala Thr Lys
1               5                   10

<210> SEQ ID NO 379
<211> LENGTH: 10
<212> TYPE: PRT
<213> ORGANISM: homo sapiens

<400> SEQUENCE: 379

Phe Phe Leu Cys Gly Asn Gly Val Tyr Lys
1               5                   10

<210> SEQ ID NO 380
<211> LENGTH: 10
<212> TYPE: PRT
<213> ORGANISM: homo sapiens

<400> SEQUENCE: 380

Gly Asn Phe Ser Leu Cys Val Glu Asn Lys
1               5                   10

<210> SEQ ID NO 381
<211> LENGTH: 10
<212> TYPE: PRT
<213> ORGANISM: homo sapiens

<400> SEQUENCE: 381

Ser Cys Gln Val Ser Asn Arg Ala Met Lys
1               5                   10

<210> SEQ ID NO 382
<211> LENGTH: 10
<212> TYPE: PRT
<213> ORGANISM: homo sapiens

<400> SEQUENCE: 382

Cys Ala Asp Ala Ser Ile Thr Asn Asp Lys
1               5                   10

<210> SEQ ID NO 383

```
<211> LENGTH: 10
<212> TYPE: PRT
<213> ORGANISM: homo sapiens

<400> SEQUENCE: 383

Asn Thr Gln Asp Tyr Lys Trp Val Asp Arg
1               5                   10

<210> SEQ ID NO 384
<211> LENGTH: 10
<212> TYPE: PRT
<213> ORGANISM: homo sapiens

<400> SEQUENCE: 384

Thr Tyr Ser Gly Gln Trp Met Tyr Glu Arg
1               5                   10

<210> SEQ ID NO 385
<211> LENGTH: 10
<212> TYPE: PRT
<213> ORGANISM: homo sapiens

<400> SEQUENCE: 385

Val Gln Asn His Ser Thr Ser Ser Tyr Arg
1               5                   10

<210> SEQ ID NO 386
<211> LENGTH: 10
<212> TYPE: PRT
<213> ORGANISM: homo sapiens

<400> SEQUENCE: 386

Gly Val Tyr Lys Gly Phe Pro Pro Lys Trp
1               5                   10

<210> SEQ ID NO 387
<211> LENGTH: 10
<212> TYPE: PRT
<213> ORGANISM: homo sapiens

<400> SEQUENCE: 387

Ala Gln Gly Leu Ser Phe Ala Gln Val Arg
1               5                   10

<210> SEQ ID NO 388
<211> LENGTH: 10
<212> TYPE: PRT
<213> ORGANISM: homo sapiens

<400> SEQUENCE: 388

Leu Glu Lys Ala Ile Leu Asn Ile Ser Lys
1               5                   10

<210> SEQ ID NO 389
<211> LENGTH: 10
<212> TYPE: PRT
<213> ORGANISM: homo sapiens

<400> SEQUENCE: 389

Gly Leu Thr Glu Ala His Gly Lys Trp Arg
1               5                   10

<210> SEQ ID NO 390
<211> LENGTH: 10
<212> TYPE: PRT
```

-continued

<213> ORGANISM: homo sapiens

<400> SEQUENCE: 390

Leu Phe Ile Phe Val Leu Ile Tyr Val Arg
 1               5                   10

<210> SEQ ID NO 391
<211> LENGTH: 10
<212> TYPE: PRT
<213> ORGANISM: homo sapiens

<400> SEQUENCE: 391

Tyr Val Leu Leu Ile Val Leu Phe Cys Leu
 1               5                   10

<210> SEQ ID NO 392
<211> LENGTH: 10
<212> TYPE: PRT
<213> ORGANISM: homo sapiens

<400> SEQUENCE: 392

Ile Phe Ala Lys Val Gly Asp Trp Phe Arg
 1               5                   10

<210> SEQ ID NO 393
<211> LENGTH: 10
<212> TYPE: PRT
<213> ORGANISM: homo sapiens

<400> SEQUENCE: 393

Gln Asn His Ser Thr Ser Ser Tyr Arg Lys
 1               5                   10

<210> SEQ ID NO 394
<211> LENGTH: 10
<212> TYPE: PRT
<213> ORGANISM: homo sapiens

<400> SEQUENCE: 394

Lys Gln Tyr Cys Asn Gln Ile Leu Trp Phe
 1               5                   10

<210> SEQ ID NO 395
<211> LENGTH: 10
<212> TYPE: PRT
<213> ORGANISM: homo sapiens

<400> SEQUENCE: 395

Arg Thr Trp Asn Ser Ser Ala Val Pro Leu
 1               5                   10

<210> SEQ ID NO 396
<211> LENGTH: 10
<212> TYPE: PRT
<213> ORGANISM: homo sapiens

<400> SEQUENCE: 396

Ser Val Asn Asn Ser Gly Leu Phe Phe Leu
 1               5                   10

<210> SEQ ID NO 397
<211> LENGTH: 10
<212> TYPE: PRT
<213> ORGANISM: homo sapiens

```
<400> SEQUENCE: 397

Lys Val Thr Trp His Trp Glu Ala Ser Met
  1               5                  10

<210> SEQ ID NO 398
<211> LENGTH: 10
<212> TYPE: PRT
<213> ORGANISM: homo sapiens

<400> SEQUENCE: 398

Gly Thr Tyr Asp Leu Glu Lys Ala Ile Leu
  1               5                  10

<210> SEQ ID NO 399
<211> LENGTH: 10
<212> TYPE: PRT
<213> ORGANISM: homo sapiens

<400> SEQUENCE: 399

Val Cys Leu Gly Thr Arg Gln Cys Ser Arg
  1               5                  10

<210> SEQ ID NO 400
<211> LENGTH: 10
<212> TYPE: PRT
<213> ORGANISM: homo sapiens

<400> SEQUENCE: 400

Ile Val Leu Phe Cys Leu Phe Ile Phe Val
  1               5                  10

<210> SEQ ID NO 401
<211> LENGTH: 10
<212> TYPE: PRT
<213> ORGANISM: homo sapiens

<400> SEQUENCE: 401

Ile Tyr Val Arg Val Phe Arg Lys Ser Arg
  1               5                  10

<210> SEQ ID NO 402
<211> LENGTH: 10
<212> TYPE: PRT
<213> ORGANISM: homo sapiens

<400> SEQUENCE: 402

Ser Phe Ile His Lys Val Thr Pro His Arg
  1               5                  10

<210> SEQ ID NO 403
<211> LENGTH: 10
<212> TYPE: PRT
<213> ORGANISM: homo sapiens

<400> SEQUENCE: 403

Gly Thr Val Gly Lys Gln Cys Cys Leu Tyr
  1               5                  10

<210> SEQ ID NO 404
<211> LENGTH: 10
<212> TYPE: PRT
<213> ORGANISM: homo sapiens

<400> SEQUENCE: 404
```

```
Thr Val Gly Lys Gln Cys Cys Leu Tyr Ile
1               5                   10
```

<210> SEQ ID NO 405
<211> LENGTH: 10
<212> TYPE: PRT
<213> ORGANISM: homo sapiens

<400> SEQUENCE: 405

```
Trp Val Asp Arg Asn Ser Gly Leu Thr Trp
1               5                   10
```

<210> SEQ ID NO 406
<211> LENGTH: 10
<212> TYPE: PRT
<213> ORGANISM: homo sapiens

<400> SEQUENCE: 406

```
Ser Gly Pro Phe Leu Gly Asn Ile Pro Lys
1               5                   10
```

<210> SEQ ID NO 407
<211> LENGTH: 10
<212> TYPE: PRT
<213> ORGANISM: homo sapiens

<400> SEQUENCE: 407

```
Gly Gln Trp Met Tyr Glu Arg Val Trp Tyr
1               5                   10
```

<210> SEQ ID NO 408
<211> LENGTH: 10
<212> TYPE: PRT
<213> ORGANISM: homo sapiens

<400> SEQUENCE: 408

```
Asn Gly Val Tyr Lys Gly Phe Pro Pro Lys
1               5                   10
```

<210> SEQ ID NO 409
<211> LENGTH: 10
<212> TYPE: PRT
<213> ORGANISM: homo sapiens

<400> SEQUENCE: 409

```
Ile Gly Leu Pro Asn Thr Gln Asp Tyr Lys
1               5                   10
```

<210> SEQ ID NO 410
<211> LENGTH: 10
<212> TYPE: PRT
<213> ORGANISM: homo sapiens

<400> SEQUENCE: 410

```
Lys Gly Phe Pro Pro Lys Trp Ser Gly Arg
1               5                   10
```

<210> SEQ ID NO 411
<211> LENGTH: 10
<212> TYPE: PRT
<213> ORGANISM: homo sapiens

<400> SEQUENCE: 411

```
Gly Ile Phe Ala Lys Val Gly Asp Trp Phe
1               5                   10
```

```
<210> SEQ ID NO 412
<211> LENGTH: 10
<212> TYPE: PRT
<213> ORGANISM: homo sapiens

<400> SEQUENCE: 412

Ser Glu Glu Ile Lys Ser Asn Ile Gln Arg
 1               5                  10

<210> SEQ ID NO 413
<211> LENGTH: 10
<212> TYPE: PRT
<213> ORGANISM: homo sapiens

<400> SEQUENCE: 413

Gly Leu Pro Asn Thr Gln Asp Tyr Lys Trp
 1               5                  10

<210> SEQ ID NO 414
<211> LENGTH: 10
<212> TYPE: PRT
<213> ORGANISM: homo sapiens

<400> SEQUENCE: 414

Gly Leu Phe Phe Leu Cys Gly Asn Gly Val
 1               5                  10

<210> SEQ ID NO 415
<211> LENGTH: 9
<212> TYPE: PRT
<213> ORGANISM: homo sapiens

<400> SEQUENCE: 415

Thr Tyr Asp Leu Glu Lys Ala Ile Leu
 1               5

<210> SEQ ID NO 416
<211> LENGTH: 9
<212> TYPE: PRT
<213> ORGANISM: homo sapiens

<400> SEQUENCE: 416

Gly Tyr Val Leu Leu Ile Val Leu Phe
 1               5

<210> SEQ ID NO 417
<211> LENGTH: 9
<212> TYPE: PRT
<213> ORGANISM: homo sapiens

<400> SEQUENCE: 417

Leu Tyr Gln Leu Phe Arg Asn Leu Phe
 1               5

<210> SEQ ID NO 418
<211> LENGTH: 9
<212> TYPE: PRT
<213> ORGANISM: homo sapiens

<400> SEQUENCE: 418

Gln Tyr Cys Asn Gln Ile Leu Trp Phe
 1               5
```

```
<210> SEQ ID NO 419
<211> LENGTH: 9
<212> TYPE: PRT
<213> ORGANISM: homo sapiens

<400> SEQUENCE: 419

Leu Tyr Ile Asn Tyr Ser Glu Glu Ile
 1               5

<210> SEQ ID NO 420
<211> LENGTH: 9
<212> TYPE: PRT
<213> ORGANISM: homo sapiens

<400> SEQUENCE: 420

Glu Phe Ser Ala Thr Lys Gln Thr Leu
 1               5

<210> SEQ ID NO 421
<211> LENGTH: 9
<212> TYPE: PRT
<213> ORGANISM: homo sapiens

<400> SEQUENCE: 421

Trp Phe Arg Ser Trp Gly Tyr Val Leu
 1               5

<210> SEQ ID NO 422
<211> LENGTH: 9
<212> TYPE: PRT
<213> ORGANISM: homo sapiens

<400> SEQUENCE: 422

Leu Phe Cys Leu Phe Ile Phe Val Leu
 1               5

<210> SEQ ID NO 423
<211> LENGTH: 9
<212> TYPE: PRT
<213> ORGANISM: homo sapiens

<400> SEQUENCE: 423

Val Phe Arg Lys Ser Arg Arg Ser Leu
 1               5

<210> SEQ ID NO 424
<211> LENGTH: 9
<212> TYPE: PRT
<213> ORGANISM: homo sapiens

<400> SEQUENCE: 424

Lys Trp Val Asp Arg Asn Ser Gly Leu
 1               5

<210> SEQ ID NO 425
<211> LENGTH: 9
<212> TYPE: PRT
<213> ORGANISM: homo sapiens

<400> SEQUENCE: 425

Arg Leu Leu Glu Gly Asn Phe Ser Leu
 1               5

<210> SEQ ID NO 426
<211> LENGTH: 9
```

<212> TYPE: PRT
<213> ORGANISM: homo sapiens

<400> SEQUENCE: 426

Ile Phe Ala Lys Val Gly Asp Trp Phe
1               5

<210> SEQ ID NO 427
<211> LENGTH: 9
<212> TYPE: PRT
<213> ORGANISM: homo sapiens

<400> SEQUENCE: 427

Ile Tyr Val Arg Val Phe Arg Lys Ser
1               5

<210> SEQ ID NO 428
<211> LENGTH: 9
<212> TYPE: PRT
<213> ORGANISM: homo sapiens

<400> SEQUENCE: 428

Arg Asn Leu Phe Cys Ser Tyr Gly Leu
1               5

<210> SEQ ID NO 429
<211> LENGTH: 9
<212> TYPE: PRT
<213> ORGANISM: homo sapiens

<400> SEQUENCE: 429

Trp Phe Asp Ser Thr Asp Gly Thr Phe
1               5

<210> SEQ ID NO 430
<211> LENGTH: 9
<212> TYPE: PRT
<213> ORGANISM: homo sapiens

<400> SEQUENCE: 430

Arg Leu His Glu Ala Ser Glu Asn Leu
1               5

<210> SEQ ID NO 431
<211> LENGTH: 9
<212> TYPE: PRT
<213> ORGANISM: homo sapiens

<400> SEQUENCE: 431

Asn Ser Gln Pro Leu Asn Leu Ala Leu
1               5

<210> SEQ ID NO 432
<211> LENGTH: 9
<212> TYPE: PRT
<213> ORGANISM: homo sapiens

<400> SEQUENCE: 432

Val Leu Leu Ile Val Leu Phe Cys Leu
1               5

<210> SEQ ID NO 433
<211> LENGTH: 9
<212> TYPE: PRT
<213> ORGANISM: homo sapiens

```
<400> SEQUENCE: 433

Leu Leu Ala Pro Val Phe Arg Thr Leu
1               5

<210> SEQ ID NO 434
<211> LENGTH: 9
<212> TYPE: PRT
<213> ORGANISM: homo sapiens

<400> SEQUENCE: 434

Trp Tyr Pro Gln Ala Glu Val Gln Asn
1               5

<210> SEQ ID NO 435
<211> LENGTH: 9
<212> TYPE: PRT
<213> ORGANISM: homo sapiens

<400> SEQUENCE: 435

Ser Pro Gln Gln Ser Ala Gln Leu Leu
1               5

<210> SEQ ID NO 436
<211> LENGTH: 9
<212> TYPE: PRT
<213> ORGANISM: homo sapiens

<400> SEQUENCE: 436

Leu Gln Leu Thr Leu Thr Ala Phe Leu
1               5

<210> SEQ ID NO 437
<211> LENGTH: 9
<212> TYPE: PRT
<213> ORGANISM: homo sapiens

<400> SEQUENCE: 437

Leu Val Pro Ser Leu Thr Arg Tyr Leu
1               5

<210> SEQ ID NO 438
<211> LENGTH: 9
<212> TYPE: PRT
<213> ORGANISM: homo sapiens

<400> SEQUENCE: 438

Thr Ile Leu Val Gln Pro Gln His Leu
1               5

<210> SEQ ID NO 439
<211> LENGTH: 9
<212> TYPE: PRT
<213> ORGANISM: homo sapiens

<400> SEQUENCE: 439

Ser Tyr Arg Lys Val Thr Trp His Trp
1               5

<210> SEQ ID NO 440
<211> LENGTH: 9
<212> TYPE: PRT
<213> ORGANISM: homo sapiens

<400> SEQUENCE: 440
```

Asp Tyr Lys Trp Val Asp Arg Asn Ser
1               5

<210> SEQ ID NO 441
<211> LENGTH: 9
<212> TYPE: PRT
<213> ORGANISM: homo sapiens

<400> SEQUENCE: 441

Leu Thr Asn Gln Ser Asn Cys Trp Leu
1               5

<210> SEQ ID NO 442
<211> LENGTH: 9
<212> TYPE: PRT
<213> ORGANISM: homo sapiens

<400> SEQUENCE: 442

Asn Tyr Ser Glu Glu Ile Lys Ser Asn
1               5

<210> SEQ ID NO 443
<211> LENGTH: 9
<212> TYPE: PRT
<213> ORGANISM: homo sapiens

<400> SEQUENCE: 443

Ile Leu Val Gln Pro Gln His Leu Leu
1               5

<210> SEQ ID NO 444
<211> LENGTH: 9
<212> TYPE: PRT
<213> ORGANISM: homo sapiens

<400> SEQUENCE: 444

Val Ser Asn Arg Ala Met Lys Gly Leu
1               5

<210> SEQ ID NO 445
<211> LENGTH: 9
<212> TYPE: PRT
<213> ORGANISM: homo sapiens

<400> SEQUENCE: 445

Leu Ser Asn Cys Ala Leu Leu Gln Leu
1               5

<210> SEQ ID NO 446
<211> LENGTH: 9
<212> TYPE: PRT
<213> ORGANISM: homo sapiens

<400> SEQUENCE: 446

Val Asn Asn Ser Gly Leu Phe Phe Leu
1               5

<210> SEQ ID NO 447
<211> LENGTH: 9
<212> TYPE: PRT
<213> ORGANISM: homo sapiens

<400> SEQUENCE: 447

Ser Cys Gln Asn Gln Thr Lys Gly Leu

```
                    1               5

<210> SEQ ID NO 448
<211> LENGTH: 9
<212> TYPE: PRT
<213> ORGANISM: homo sapiens

<400> SEQUENCE: 448

Leu Ser Pro Gln Gln Ser Ala Gln Leu
 1               5

<210> SEQ ID NO 449
<211> LENGTH: 9
<212> TYPE: PRT
<213> ORGANISM: homo sapiens

<400> SEQUENCE: 449

Gly Ser Leu Ser Asn Cys Ala Leu Leu
 1               5

<210> SEQ ID NO 450
<211> LENGTH: 9
<212> TYPE: PRT
<213> ORGANISM: homo sapiens

<400> SEQUENCE: 450

Ser Leu Asn Ser Gln Pro Leu Asn Leu
 1               5

<210> SEQ ID NO 451
<211> LENGTH: 9
<212> TYPE: PRT
<213> ORGANISM: homo sapiens

<400> SEQUENCE: 451

Gly Thr Val Gly Lys Gln Cys Cys Leu
 1               5

<210> SEQ ID NO 452
<211> LENGTH: 9
<212> TYPE: PRT
<213> ORGANISM: homo sapiens

<400> SEQUENCE: 452

Cys Gln Asn Gln Thr Lys Gly Leu Leu
 1               5

<210> SEQ ID NO 453
<211> LENGTH: 9
<212> TYPE: PRT
<213> ORGANISM: homo sapiens

<400> SEQUENCE: 453

Glu Asn Leu Lys Asn Val Pro Leu Leu
 1               5

<210> SEQ ID NO 454
<211> LENGTH: 9
<212> TYPE: PRT
<213> ORGANISM: homo sapiens

<400> SEQUENCE: 454

Thr Trp Asn Ser Ser Ala Val Pro Leu
 1               5
```

```
<210> SEQ ID NO 455
<211> LENGTH: 9
<212> TYPE: PRT
<213> ORGANISM: homo sapiens

<400> SEQUENCE: 455

Thr Ile Arg Ala Leu Phe Pro Ser Leu
1               5

<210> SEQ ID NO 456
<211> LENGTH: 9
<212> TYPE: PRT
<213> ORGANISM: homo sapiens

<400> SEQUENCE: 456

Leu Leu Tyr Gln Leu Phe Arg Asn Leu
1               5

<210> SEQ ID NO 457
<211> LENGTH: 9
<212> TYPE: PRT
<213> ORGANISM: homo sapiens

<400> SEQUENCE: 457

Val Tyr Lys Gly Phe Pro Pro Lys Trp
1               5

<210> SEQ ID NO 458
<211> LENGTH: 9
<212> TYPE: PRT
<213> ORGANISM: homo sapiens

<400> SEQUENCE: 458

Leu Tyr Cys Asn Pro Lys Asp Asn Ser
1               5

<210> SEQ ID NO 459
<211> LENGTH: 9
<212> TYPE: PRT
<213> ORGANISM: homo sapiens

<400> SEQUENCE: 459

Asn Cys Ala Leu Leu Gln Leu Thr Leu
1               5

<210> SEQ ID NO 460
<211> LENGTH: 9
<212> TYPE: PRT
<213> ORGANISM: homo sapiens

<400> SEQUENCE: 460

Gln Thr Lys Gly Leu Leu Tyr Gln Leu
1               5

<210> SEQ ID NO 461
<211> LENGTH: 9
<212> TYPE: PRT
<213> ORGANISM: homo sapiens

<400> SEQUENCE: 461

Ser Asn Cys Trp Leu Cys Glu His Leu
1               5

<210> SEQ ID NO 462
```

```
<211> LENGTH: 9
<212> TYPE: PRT
<213> ORGANISM: homo sapiens

<400> SEQUENCE: 462

Glu Ala Ser Met Glu Ala Gln Gly Leu
1               5

<210> SEQ ID NO 463
<211> LENGTH: 9
<212> TYPE: PRT
<213> ORGANISM: homo sapiens

<400> SEQUENCE: 463

Trp Gly Tyr Val Leu Leu Ile Val Leu
1               5

<210> SEQ ID NO 464
<211> LENGTH: 9
<212> TYPE: PRT
<213> ORGANISM: homo sapiens

<400> SEQUENCE: 464

Gly Leu Gly Tyr Leu Val Pro Ser Leu
1               5

<210> SEQ ID NO 465
<211> LENGTH: 10
<212> TYPE: PRT
<213> ORGANISM: homo sapiens

<400> SEQUENCE: 465

Arg Tyr Leu Thr Leu Asn Ala Ser Gln Ile
1               5                   10

<210> SEQ ID NO 466
<211> LENGTH: 10
<212> TYPE: PRT
<213> ORGANISM: homo sapiens

<400> SEQUENCE: 466

Asn Tyr Ser Glu Glu Ile Lys Ser Asn Ile
1               5                   10

<210> SEQ ID NO 467
<211> LENGTH: 10
<212> TYPE: PRT
<213> ORGANISM: homo sapiens

<400> SEQUENCE: 467

Leu Phe Pro Ser Leu Gly Thr Tyr Asp Leu
1               5                   10

<210> SEQ ID NO 468
<211> LENGTH: 10
<212> TYPE: PRT
<213> ORGANISM: homo sapiens

<400> SEQUENCE: 468

Trp Phe Arg Ser Trp Gly Tyr Val Leu Leu
1               5                   10

<210> SEQ ID NO 469
<211> LENGTH: 10
<212> TYPE: PRT
```

<213> ORGANISM: homo sapiens

<400> SEQUENCE: 469

Ile Phe Val Leu Ile Tyr Val Arg Val Phe
1               5                   10

<210> SEQ ID NO 470
<211> LENGTH: 10
<212> TYPE: PRT
<213> ORGANISM: homo sapiens

<400> SEQUENCE: 470

Arg Ser Leu Asn Ser Gln Pro Leu Asn Leu
1               5                   10

<210> SEQ ID NO 471
<211> LENGTH: 10
<212> TYPE: PRT
<213> ORGANISM: homo sapiens

<400> SEQUENCE: 471

Gly Tyr Val Leu Leu Ile Val Leu Phe Cys
1               5                   10

<210> SEQ ID NO 472
<211> LENGTH: 10
<212> TYPE: PRT
<213> ORGANISM: homo sapiens

<400> SEQUENCE: 472

His Leu Leu Ala Pro Val Phe Arg Thr Leu
1               5                   10

<210> SEQ ID NO 473
<211> LENGTH: 10
<212> TYPE: PRT
<213> ORGANISM: homo sapiens

<400> SEQUENCE: 473

Ser Thr Ile Arg Ala Leu Phe Pro Ser Leu
1               5                   10

<210> SEQ ID NO 474
<211> LENGTH: 10
<212> TYPE: PRT
<213> ORGANISM: homo sapiens

<400> SEQUENCE: 474

Gly Leu Leu Tyr Gln Leu Phe Arg Asn Leu
1               5                   10

<210> SEQ ID NO 475
<211> LENGTH: 10
<212> TYPE: PRT
<213> ORGANISM: homo sapiens

<400> SEQUENCE: 475

Tyr Leu Val Pro Ser Leu Thr Arg Tyr Leu
1               5                   10

<210> SEQ ID NO 476
<211> LENGTH: 10
<212> TYPE: PRT
<213> ORGANISM: homo sapiens

```
<400> SEQUENCE: 476

Leu Phe Cys Leu Phe Ile Phe Val Leu Ile
 1               5                  10

<210> SEQ ID NO 477
<211> LENGTH: 10
<212> TYPE: PRT
<213> ORGANISM: homo sapiens

<400> SEQUENCE: 477

Tyr Val Leu Leu Ile Val Leu Phe Cys Leu
 1               5                  10

<210> SEQ ID NO 478
<211> LENGTH: 10
<212> TYPE: PRT
<213> ORGANISM: homo sapiens

<400> SEQUENCE: 478

Arg Val Phe Arg Lys Ser Arg Arg Ser Leu
 1               5                  10

<210> SEQ ID NO 479
<211> LENGTH: 10
<212> TYPE: PRT
<213> ORGANISM: homo sapiens

<400> SEQUENCE: 479

Arg Thr Trp Asn Ser Ser Ala Val Pro Leu
 1               5                  10

<210> SEQ ID NO 480
<211> LENGTH: 10
<212> TYPE: PRT
<213> ORGANISM: homo sapiens

<400> SEQUENCE: 480

Leu Tyr Gln Leu Phe Arg Asn Leu Phe Cys
 1               5                  10

<210> SEQ ID NO 481
<211> LENGTH: 10
<212> TYPE: PRT
<213> ORGANISM: homo sapiens

<400> SEQUENCE: 481

Gly Tyr Leu Val Pro Ser Leu Thr Arg Tyr
 1               5                  10

<210> SEQ ID NO 482
<211> LENGTH: 10
<212> TYPE: PRT
<213> ORGANISM: homo sapiens

<400> SEQUENCE: 482

Met Tyr Glu Arg Val Trp Tyr Pro Gln Ala
 1               5                  10

<210> SEQ ID NO 483
<211> LENGTH: 10
<212> TYPE: PRT
<213> ORGANISM: homo sapiens

<400> SEQUENCE: 483
```

Gln Ser Asn Cys Trp Leu Cys Glu His Leu
1               5                   10

<210> SEQ ID NO 484
<211> LENGTH: 10
<212> TYPE: PRT
<213> ORGANISM: homo sapiens

<400> SEQUENCE: 484

Leu Thr Ile Leu Val Gln Pro Gln His Leu
1               5                   10

<210> SEQ ID NO 485
<211> LENGTH: 10
<212> TYPE: PRT
<213> ORGANISM: homo sapiens

<400> SEQUENCE: 485

Leu Ser Pro Gln Gln Ser Ala Gln Leu Leu
1               5                   10

<210> SEQ ID NO 486
<211> LENGTH: 10
<212> TYPE: PRT
<213> ORGANISM: homo sapiens

<400> SEQUENCE: 486

Leu Leu Gln Leu Thr Leu Thr Ala Phe Leu
1               5                   10

<210> SEQ ID NO 487
<211> LENGTH: 10
<212> TYPE: PRT
<213> ORGANISM: homo sapiens

<400> SEQUENCE: 487

Cys Gly Leu Gly Tyr Leu Val Pro Ser Leu
1               5                   10

<210> SEQ ID NO 488
<211> LENGTH: 10
<212> TYPE: PRT
<213> ORGANISM: homo sapiens

<400> SEQUENCE: 488

Gln Gly Leu Ser Phe Ala Gln Val Arg Leu
1               5                   10

<210> SEQ ID NO 489
<211> LENGTH: 10
<212> TYPE: PRT
<213> ORGANISM: homo sapiens

<400> SEQUENCE: 489

Ala Pro Val Phe Arg Thr Leu Ser Ile Leu
1               5                   10

<210> SEQ ID NO 490
<211> LENGTH: 10
<212> TYPE: PRT
<213> ORGANISM: homo sapiens

<400> SEQUENCE: 490

Thr Leu Asn Ala Ser Gln Ile Thr Asn Leu
1               5                   10

```
<210> SEQ ID NO 491
<211> LENGTH: 10
<212> TYPE: PRT
<213> ORGANISM: homo sapiens

<400> SEQUENCE: 491

Ala Ser Glu Asn Leu Lys Asn Val Pro Leu
 1               5                  10

<210> SEQ ID NO 492
<211> LENGTH: 10
<212> TYPE: PRT
<213> ORGANISM: homo sapiens

<400> SEQUENCE: 492

Leu Thr Leu Ser Val Asn Asn Ser Gly Leu
 1               5                  10

<210> SEQ ID NO 493
<211> LENGTH: 10
<212> TYPE: PRT
<213> ORGANISM: homo sapiens

<400> SEQUENCE: 493

Ser Cys Gln Asn Gln Thr Lys Gly Leu Leu
 1               5                  10

<210> SEQ ID NO 494
<211> LENGTH: 10
<212> TYPE: PRT
<213> ORGANISM: homo sapiens

<400> SEQUENCE: 494

Trp Trp Leu Thr Gly Ser Asn Leu Thr Leu
 1               5                  10

<210> SEQ ID NO 495
<211> LENGTH: 10
<212> TYPE: PRT
<213> ORGANISM: homo sapiens

<400> SEQUENCE: 495

Leu Tyr Cys Asn Pro Lys Asp Asn Ser Thr
 1               5                  10

<210> SEQ ID NO 496
<211> LENGTH: 10
<212> TYPE: PRT
<213> ORGANISM: homo sapiens

<400> SEQUENCE: 496

Ser Val Asn Asn Ser Gly Leu Phe Phe Leu
 1               5                  10

<210> SEQ ID NO 497
<211> LENGTH: 10
<212> TYPE: PRT
<213> ORGANISM: homo sapiens

<400> SEQUENCE: 497

Leu Thr Leu Thr Ala Phe Leu Thr Ile Leu
 1               5                  10
```

```
<210> SEQ ID NO 498
<211> LENGTH: 10
<212> TYPE: PRT
<213> ORGANISM: homo sapiens

<400> SEQUENCE: 498

Thr Ile Leu Val Gln Pro Gln His Leu Leu
 1               5                  10

<210> SEQ ID NO 499
<211> LENGTH: 10
<212> TYPE: PRT
<213> ORGANISM: homo sapiens

<400> SEQUENCE: 499

Thr Tyr Asp Leu Glu Lys Ala Ile Leu Asn
 1               5                  10

<210> SEQ ID NO 500
<211> LENGTH: 10
<212> TYPE: PRT
<213> ORGANISM: homo sapiens

<400> SEQUENCE: 500

Val Tyr Lys Gly Phe Pro Pro Lys Trp Ser
 1               5                  10

<210> SEQ ID NO 501
<211> LENGTH: 10
<212> TYPE: PRT
<213> ORGANISM: homo sapiens

<400> SEQUENCE: 501

Ser Trp Gly Tyr Val Leu Leu Ile Val Leu
 1               5                  10

<210> SEQ ID NO 502
<211> LENGTH: 10
<212> TYPE: PRT
<213> ORGANISM: homo sapiens

<400> SEQUENCE: 502

Asn Gln Thr Lys Gly Leu Leu Tyr Gln Leu
 1               5                  10

<210> SEQ ID NO 503
<211> LENGTH: 10
<212> TYPE: PRT
<213> ORGANISM: homo sapiens

<400> SEQUENCE: 503

Gly Thr Tyr Asp Leu Glu Lys Ala Ile Leu
 1               5                  10

<210> SEQ ID NO 504
<211> LENGTH: 10
<212> TYPE: PRT
<213> ORGANISM: homo sapiens

<400> SEQUENCE: 504

Leu Asn Ser Gln Pro Leu Asn Leu Ala Leu
 1               5                  10

<210> SEQ ID NO 505
<211> LENGTH: 10
```

```
<212> TYPE: PRT
<213> ORGANISM: homo sapiens

<400> SEQUENCE: 505

Ile Pro Lys Gln Tyr Cys Asn Gln Ile Leu
 1               5                  10

<210> SEQ ID NO 506
<211> LENGTH: 10
<212> TYPE: PRT
<213> ORGANISM: homo sapiens

<400> SEQUENCE: 506

Ser Asn Cys Ala Leu Leu Gln Leu Thr Leu
 1               5                  10

<210> SEQ ID NO 507
<211> LENGTH: 10
<212> TYPE: PRT
<213> ORGANISM: homo sapiens

<400> SEQUENCE: 507

Thr Gln Gly Asp Thr Asp Asn Pro Pro Leu
 1               5                  10

<210> SEQ ID NO 508
<211> LENGTH: 10
<212> TYPE: PRT
<213> ORGANISM: homo sapiens

<400> SEQUENCE: 508

Ala Leu Ser Pro Gln Gln Ser Ala Gln Leu
 1               5                  10

<210> SEQ ID NO 509
<211> LENGTH: 10
<212> TYPE: PRT
<213> ORGANISM: homo sapiens

<400> SEQUENCE: 509

His Leu Asp Asn Ala Glu Gln Pro Glu Leu
 1               5                  10

<210> SEQ ID NO 510
<211> LENGTH: 10
<212> TYPE: PRT
<213> ORGANISM: homo sapiens

<400> SEQUENCE: 510

Val Leu Leu Ile Val Leu Phe Cys Leu Phe
 1               5                  10

<210> SEQ ID NO 511
<211> LENGTH: 10
<212> TYPE: PRT
<213> ORGANISM: homo sapiens

<400> SEQUENCE: 511

Gln Val Ser Asn Arg Ala Met Lys Gly Leu
 1               5                  10

<210> SEQ ID NO 512
<211> LENGTH: 10
<212> TYPE: PRT
<213> ORGANISM: homo sapiens
```

```
<400> SEQUENCE: 512

Val Pro Ser Leu Thr Arg Tyr Leu Thr Leu
1               5                   10

<210> SEQ ID NO 513
<211> LENGTH: 10
<212> TYPE: PRT
<213> ORGANISM: homo sapiens

<400> SEQUENCE: 513

Met Gly Ser Leu Ser Asn Cys Ala Leu Leu
1               5                   10

<210> SEQ ID NO 514
<211> LENGTH: 10
<212> TYPE: PRT
<213> ORGANISM: homo sapiens

<400> SEQUENCE: 514

Asp Trp Phe Arg Ser Trp Gly Tyr Val Leu
1               5                   10

<210> SEQ ID NO 515
<211> LENGTH: 9
<212> TYPE: PRT
<213> ORGANISM: homo sapiens

<400> SEQUENCE: 515

Phe Pro Ser Leu Gly Thr Tyr Asp Leu
1               5

<210> SEQ ID NO 516
<211> LENGTH: 9
<212> TYPE: PRT
<213> ORGANISM: homo sapiens

<400> SEQUENCE: 516

Ser Pro Gln Gln Ser Ala Gln Leu Leu
1               5

<210> SEQ ID NO 517
<211> LENGTH: 9
<212> TYPE: PRT
<213> ORGANISM: homo sapiens

<400> SEQUENCE: 517

Thr Ile Arg Ala Leu Phe Pro Ser Leu
1               5

<210> SEQ ID NO 518
<211> LENGTH: 9
<212> TYPE: PRT
<213> ORGANISM: homo sapiens

<400> SEQUENCE: 518

Ser Gly Arg Cys Gly Leu Gly Tyr Leu
1               5

<210> SEQ ID NO 519
<211> LENGTH: 9
<212> TYPE: PRT
<213> ORGANISM: homo sapiens

<400> SEQUENCE: 519
```

Ala Pro Val Phe Arg Thr Leu Ser Ile
1               5

<210> SEQ ID NO 520
<211> LENGTH: 9
<212> TYPE: PRT
<213> ORGANISM: homo sapiens

<400> SEQUENCE: 520

Leu Val Pro Ser Leu Thr Arg Tyr Leu
1               5

<210> SEQ ID NO 521
<211> LENGTH: 9
<212> TYPE: PRT
<213> ORGANISM: homo sapiens

<400> SEQUENCE: 521

Glu Ala Ser Met Glu Ala Gln Gly Leu
1               5

<210> SEQ ID NO 522
<211> LENGTH: 9
<212> TYPE: PRT
<213> ORGANISM: homo sapiens

<400> SEQUENCE: 522

Ser Ala Ser Arg Lys Asp His Val Leu
1               5

<210> SEQ ID NO 523
<211> LENGTH: 9
<212> TYPE: PRT
<213> ORGANISM: homo sapiens

<400> SEQUENCE: 523

Val Pro Leu Leu Asp Trp Gln Gly Ile
1               5

<210> SEQ ID NO 524
<211> LENGTH: 9
<212> TYPE: PRT
<213> ORGANISM: homo sapiens

<400> SEQUENCE: 524

Ile Pro Lys Gln Tyr Cys Asn Gln Ile
1               5

<210> SEQ ID NO 525
<211> LENGTH: 9
<212> TYPE: PRT
<213> ORGANISM: homo sapiens

<400> SEQUENCE: 525

Ile Leu Val Gln Pro Gln His Leu Leu
1               5

<210> SEQ ID NO 526
<211> LENGTH: 9
<212> TYPE: PRT
<213> ORGANISM: homo sapiens

<400> SEQUENCE: 526

Ser Ser Ala Val Pro Leu Ile Gly Leu

```
<210> SEQ ID NO 527
<211> LENGTH: 9
<212> TYPE: PRT
<213> ORGANISM: homo sapiens

<400> SEQUENCE: 527

Gly His Arg Thr Pro Thr Trp Trp Leu
1               5

<210> SEQ ID NO 528
<211> LENGTH: 9
<212> TYPE: PRT
<213> ORGANISM: homo sapiens

<400> SEQUENCE: 528

Val Phe Arg Lys Ser Arg Arg Ser Leu
1               5

<210> SEQ ID NO 529
<211> LENGTH: 9
<212> TYPE: PRT
<213> ORGANISM: homo sapiens

<400> SEQUENCE: 529

Gln Thr Lys Gly Leu Leu Tyr Gln Leu
1               5

<210> SEQ ID NO 530
<211> LENGTH: 9
<212> TYPE: PRT
<213> ORGANISM: homo sapiens

<400> SEQUENCE: 530

Glu Ile Lys Ser Asn Ile Gln Arg Leu
1               5

<210> SEQ ID NO 531
<211> LENGTH: 9
<212> TYPE: PRT
<213> ORGANISM: homo sapiens

<400> SEQUENCE: 531

Gly Leu Ser Phe Ala Gln Val Arg Leu
1               5

<210> SEQ ID NO 532
<211> LENGTH: 9
<212> TYPE: PRT
<213> ORGANISM: homo sapiens

<400> SEQUENCE: 532

Val Leu Leu Ile Val Leu Phe Cys Leu
1               5

<210> SEQ ID NO 533
<211> LENGTH: 9
<212> TYPE: PRT
<213> ORGANISM: homo sapiens

<400> SEQUENCE: 533

Trp Phe Arg Ser Trp Gly Tyr Val Leu
1               5
```

<210> SEQ ID NO 534
<211> LENGTH: 9
<212> TYPE: PRT
<213> ORGANISM: homo sapiens

<400> SEQUENCE: 534

Trp Leu Thr Gly Ser Asn Leu Thr Leu
1               5

<210> SEQ ID NO 535
<211> LENGTH: 9
<212> TYPE: PRT
<213> ORGANISM: homo sapiens

<400> SEQUENCE: 535

Leu Ser Asn Cys Ala Leu Leu Gln Leu
1               5

<210> SEQ ID NO 536
<211> LENGTH: 9
<212> TYPE: PRT
<213> ORGANISM: homo sapiens

<400> SEQUENCE: 536

Val Ser Asn Arg Ala Met Lys Gly Leu
1               5

<210> SEQ ID NO 537
<211> LENGTH: 9
<212> TYPE: PRT
<213> ORGANISM: homo sapiens

<400> SEQUENCE: 537

Asn Ser Gln Pro Leu Asn Leu Ala Leu
1               5

<210> SEQ ID NO 538
<211> LENGTH: 9
<212> TYPE: PRT
<213> ORGANISM: homo sapiens

<400> SEQUENCE: 538

Ser Asn Cys Trp Leu Cys Glu His Leu
1               5

<210> SEQ ID NO 539
<211> LENGTH: 9
<212> TYPE: PRT
<213> ORGANISM: homo sapiens

<400> SEQUENCE: 539

Ser Cys Gln Asn Gln Thr Lys Gly Leu
1               5

<210> SEQ ID NO 540
<211> LENGTH: 9
<212> TYPE: PRT
<213> ORGANISM: homo sapiens

<400> SEQUENCE: 540

Leu Leu Tyr Gln Leu Phe Arg Asn Leu
1               5

<210> SEQ ID NO 541

```
<211> LENGTH: 9
<212> TYPE: PRT
<213> ORGANISM: homo sapiens

<400> SEQUENCE: 541

Leu Ser Pro Gln Gln Ser Ala Gln Leu
 1               5

<210> SEQ ID NO 542
<211> LENGTH: 9
<212> TYPE: PRT
<213> ORGANISM: homo sapiens

<400> SEQUENCE: 542

Thr Leu Thr Ala Phe Leu Thr Ile Leu
 1               5

<210> SEQ ID NO 543
<211> LENGTH: 9
<212> TYPE: PRT
<213> ORGANISM: homo sapiens

<400> SEQUENCE: 543

Leu Gln Leu Thr Leu Thr Ala Phe Leu
 1               5

<210> SEQ ID NO 544
<211> LENGTH: 9
<212> TYPE: PRT
<213> ORGANISM: homo sapiens

<400> SEQUENCE: 544

Trp Gly Tyr Val Leu Leu Ile Val Leu
 1               5

<210> SEQ ID NO 545
<211> LENGTH: 9
<212> TYPE: PRT
<213> ORGANISM: homo sapiens

<400> SEQUENCE: 545

Leu Leu Ala Pro Val Phe Arg Thr Leu
 1               5

<210> SEQ ID NO 546
<211> LENGTH: 9
<212> TYPE: PRT
<213> ORGANISM: homo sapiens

<400> SEQUENCE: 546

Leu Ser Phe Ala Gln Val Arg Leu Leu
 1               5

<210> SEQ ID NO 547
<211> LENGTH: 9
<212> TYPE: PRT
<213> ORGANISM: homo sapiens

<400> SEQUENCE: 547

Glu Asn Leu Lys Asn Val Pro Leu Leu
 1               5

<210> SEQ ID NO 548
<211> LENGTH: 9
<212> TYPE: PRT
```

<213> ORGANISM: homo sapiens

<400> SEQUENCE: 548

Ser Leu Asn Ser Gln Pro Leu Asn Leu
1               5

<210> SEQ ID NO 549
<211> LENGTH: 9
<212> TYPE: PRT
<213> ORGANISM: homo sapiens

<400> SEQUENCE: 549

Gly Ser Leu Ser Asn Cys Ala Leu Leu
1               5

<210> SEQ ID NO 550
<211> LENGTH: 9
<212> TYPE: PRT
<213> ORGANISM: homo sapiens

<400> SEQUENCE: 550

Thr Ile Leu Val Gln Pro Gln His Leu
1               5

<210> SEQ ID NO 551
<211> LENGTH: 9
<212> TYPE: PRT
<213> ORGANISM: homo sapiens

<400> SEQUENCE: 551

Asn Cys Ala Leu Leu Gln Leu Thr Leu
1               5

<210> SEQ ID NO 552
<211> LENGTH: 9
<212> TYPE: PRT
<213> ORGANISM: homo sapiens

<400> SEQUENCE: 552

Gly Leu Gly Tyr Leu Val Pro Ser Leu
1               5

<210> SEQ ID NO 553
<211> LENGTH: 9
<212> TYPE: PRT
<213> ORGANISM: homo sapiens

<400> SEQUENCE: 553

Leu Asn Ala Ser Gln Ile Thr Asn Leu
1               5

<210> SEQ ID NO 554
<211> LENGTH: 9
<212> TYPE: PRT
<213> ORGANISM: homo sapiens

<400> SEQUENCE: 554

Arg Leu His Glu Ala Ser Glu Asn Leu
1               5

<210> SEQ ID NO 555
<211> LENGTH: 9
<212> TYPE: PRT
<213> ORGANISM: homo sapiens

<400> SEQUENCE: 555

Met Gly Ser Leu Ser Asn Cys Ala Leu
1               5

<210> SEQ ID NO 556
<211> LENGTH: 9
<212> TYPE: PRT
<213> ORGANISM: homo sapiens

<400> SEQUENCE: 556

Thr Leu Ser Val Asn Asn Ser Gly Leu
1               5

<210> SEQ ID NO 557
<211> LENGTH: 9
<212> TYPE: PRT
<213> ORGANISM: homo sapiens

<400> SEQUENCE: 557

Gln Pro Gln His Leu Leu Ala Pro Val
1               5

<210> SEQ ID NO 558
<211> LENGTH: 9
<212> TYPE: PRT
<213> ORGANISM: homo sapiens

<400> SEQUENCE: 558

Gly Thr Val Gly Lys Gln Cys Cys Leu
1               5

<210> SEQ ID NO 559
<211> LENGTH: 9
<212> TYPE: PRT
<213> ORGANISM: homo sapiens

<400> SEQUENCE: 559

Cys Gln Asn Gln Thr Lys Gly Leu Leu
1               5

<210> SEQ ID NO 560
<211> LENGTH: 9
<212> TYPE: PRT
<213> ORGANISM: homo sapiens

<400> SEQUENCE: 560

Arg Asn Leu Phe Cys Ser Tyr Gly Leu
1               5

<210> SEQ ID NO 561
<211> LENGTH: 9
<212> TYPE: PRT
<213> ORGANISM: homo sapiens

<400> SEQUENCE: 561

Leu Thr Asn Gln Ser Asn Cys Trp Leu
1               5

<210> SEQ ID NO 562
<211> LENGTH: 9
<212> TYPE: PRT
<213> ORGANISM: homo sapiens

<400> SEQUENCE: 562

```
Arg Leu Leu Glu Gly Asn Phe Ser Leu
 1               5
```

```
<210> SEQ ID NO 563
<211> LENGTH: 9
<212> TYPE: PRT
<213> ORGANISM: homo sapiens

<400> SEQUENCE: 563

Val Asn Asn Ser Gly Leu Phe Phe Leu
 1               5
```

```
<210> SEQ ID NO 564
<211> LENGTH: 9
<212> TYPE: PRT
<213> ORGANISM: homo sapiens

<400> SEQUENCE: 564

Thr Thr His Gln Tyr Asp Thr Ser Leu
 1               5
```

```
<210> SEQ ID NO 565
<211> LENGTH: 10
<212> TYPE: PRT
<213> ORGANISM: homo sapiens

<400> SEQUENCE: 565

Ala Pro Val Phe Arg Thr Leu Ser Ile Leu
 1               5                  10
```

```
<210> SEQ ID NO 566
<211> LENGTH: 10
<212> TYPE: PRT
<213> ORGANISM: homo sapiens

<400> SEQUENCE: 566

Ile Pro Lys Gln Tyr Cys Asn Gln Ile Leu
 1               5                  10
```

```
<210> SEQ ID NO 567
<211> LENGTH: 10
<212> TYPE: PRT
<213> ORGANISM: homo sapiens

<400> SEQUENCE: 567

Val Pro Ser Leu Thr Arg Tyr Leu Thr Leu
 1               5                  10
```

```
<210> SEQ ID NO 568
<211> LENGTH: 10
<212> TYPE: PRT
<213> ORGANISM: homo sapiens

<400> SEQUENCE: 568

Arg Val Phe Arg Lys Ser Arg Arg Ser Leu
 1               5                  10
```

```
<210> SEQ ID NO 569
<211> LENGTH: 10
<212> TYPE: PRT
<213> ORGANISM: homo sapiens

<400> SEQUENCE: 569

Tyr Val Leu Leu Ile Val Leu Phe Cys Leu
 1               5                  10
```

```
<210> SEQ ID NO 570
<211> LENGTH: 10
<212> TYPE: PRT
<213> ORGANISM: homo sapiens

<400> SEQUENCE: 570

Ser Val Asn Asn Ser Gly Leu Phe Phe Leu
 1               5                  10

<210> SEQ ID NO 571
<211> LENGTH: 10
<212> TYPE: PRT
<213> ORGANISM: homo sapiens

<400> SEQUENCE: 571

Gln Val Ser Asn Arg Ala Met Lys Gly Leu
 1               5                  10

<210> SEQ ID NO 572
<211> LENGTH: 10
<212> TYPE: PRT
<213> ORGANISM: homo sapiens

<400> SEQUENCE: 572

Pro Pro Lys Trp Ser Gly Arg Cys Gly Leu
 1               5                  10

<210> SEQ ID NO 573
<211> LENGTH: 10
<212> TYPE: PRT
<213> ORGANISM: homo sapiens

<400> SEQUENCE: 573

Ala Ser Ala Ser Arg Lys Asp His Val Leu
 1               5                  10

<210> SEQ ID NO 574
<211> LENGTH: 10
<212> TYPE: PRT
<213> ORGANISM: homo sapiens

<400> SEQUENCE: 574

Ala Leu Ser Pro Gln Gln Ser Ala Gln Leu
 1               5                  10

<210> SEQ ID NO 575
<211> LENGTH: 10
<212> TYPE: PRT
<213> ORGANISM: homo sapiens

<400> SEQUENCE: 575

Glu Ala His Gln Ser Lys Val Ser Ser Leu
 1               5                  10

<210> SEQ ID NO 576
<211> LENGTH: 10
<212> TYPE: PRT
<213> ORGANISM: homo sapiens

<400> SEQUENCE: 576

Ala Ser Arg Lys Asp His Val Leu Asp Ile
 1               5                  10
```

```
<210> SEQ ID NO 577
<211> LENGTH: 10
<212> TYPE: PRT
<213> ORGANISM: homo sapiens

<400> SEQUENCE: 577

Asn Ser Ser Ala Val Pro Leu Ile Gly Leu
 1               5                  10

<210> SEQ ID NO 578
<211> LENGTH: 10
<212> TYPE: PRT
<213> ORGANISM: homo sapiens

<400> SEQUENCE: 578

Asp Gly His Arg Thr Pro Thr Trp Trp Leu
 1               5                  10

<210> SEQ ID NO 579
<211> LENGTH: 10
<212> TYPE: PRT
<213> ORGANISM: homo sapiens

<400> SEQUENCE: 579

Thr Ile Leu Val Gln Pro Gln His Leu Leu
 1               5                  10

<210> SEQ ID NO 580
<211> LENGTH: 10
<212> TYPE: PRT
<213> ORGANISM: homo sapiens

<400> SEQUENCE: 580

Lys Val Thr Trp His Trp Glu Ala Ser Met
 1               5                  10

<210> SEQ ID NO 581
<211> LENGTH: 10
<212> TYPE: PRT
<213> ORGANISM: homo sapiens

<400> SEQUENCE: 581

Gln Gly Leu Ser Phe Ala Gln Val Arg Leu
 1               5                  10

<210> SEQ ID NO 582
<211> LENGTH: 10
<212> TYPE: PRT
<213> ORGANISM: homo sapiens

<400> SEQUENCE: 582

Leu Thr Trp Ser Gly Asn Asp Thr Cys Leu
 1               5                  10

<210> SEQ ID NO 583
<211> LENGTH: 10
<212> TYPE: PRT
<213> ORGANISM: homo sapiens

<400> SEQUENCE: 583

Leu Ser Pro Gln Gln Ser Ala Gln Leu Leu
 1               5                  10

<210> SEQ ID NO 584
<211> LENGTH: 10
```

```
<212> TYPE: PRT
<213> ORGANISM: homo sapiens

<400> SEQUENCE: 584

Thr Leu Asn Ala Ser Gln Ile Thr Asn Leu
 1               5                  10

<210> SEQ ID NO 585
<211> LENGTH: 10
<212> TYPE: PRT
<213> ORGANISM: homo sapiens

<400> SEQUENCE: 585

Ser Thr Ile Arg Ala Leu Phe Pro Ser Leu
 1               5                  10

<210> SEQ ID NO 586
<211> LENGTH: 10
<212> TYPE: PRT
<213> ORGANISM: homo sapiens

<400> SEQUENCE: 586

Cys Gly Thr Val Gly Lys Gln Cys Cys Leu
 1               5                  10

<210> SEQ ID NO 587
<211> LENGTH: 10
<212> TYPE: PRT
<213> ORGANISM: homo sapiens

<400> SEQUENCE: 587

Gly Leu Ser Phe Ala Gln Val Arg Leu Leu
 1               5                  10

<210> SEQ ID NO 588
<211> LENGTH: 10
<212> TYPE: PRT
<213> ORGANISM: homo sapiens

<400> SEQUENCE: 588

Ser Cys Gln Asn Gln Thr Lys Gly Leu Leu
 1               5                  10

<210> SEQ ID NO 589
<211> LENGTH: 10
<212> TYPE: PRT
<213> ORGANISM: homo sapiens

<400> SEQUENCE: 589

Thr Gln Gly Asp Thr Asp Asn Pro Pro Leu
 1               5                  10

<210> SEQ ID NO 590
<211> LENGTH: 10
<212> TYPE: PRT
<213> ORGANISM: homo sapiens

<400> SEQUENCE: 590

Arg Thr Trp Asn Ser Ser Ala Val Pro Leu
 1               5                  10

<210> SEQ ID NO 591
<211> LENGTH: 10
<212> TYPE: PRT
<213> ORGANISM: homo sapiens
```

```
<400> SEQUENCE: 591

Arg Ser Leu Asn Ser Gln Pro Leu Asn Leu
1               5                   10

<210> SEQ ID NO 592
<211> LENGTH: 10
<212> TYPE: PRT
<213> ORGANISM: homo sapiens

<400> SEQUENCE: 592

Gln Ser Asn Cys Trp Leu Cys Glu His Leu
1               5                   10

<210> SEQ ID NO 593
<211> LENGTH: 10
<212> TYPE: PRT
<213> ORGANISM: homo sapiens

<400> SEQUENCE: 593

Leu Asn Ser Gln Pro Leu Asn Leu Ala Leu
1               5                   10

<210> SEQ ID NO 594
<211> LENGTH: 10
<212> TYPE: PRT
<213> ORGANISM: homo sapiens

<400> SEQUENCE: 594

Gly Leu Leu Tyr Gln Leu Phe Arg Asn Leu
1               5                   10

<210> SEQ ID NO 595
<211> LENGTH: 10
<212> TYPE: PRT
<213> ORGANISM: homo sapiens

<400> SEQUENCE: 595

His Leu Leu Ala Pro Val Phe Arg Thr Leu
1               5                   10

<210> SEQ ID NO 596
<211> LENGTH: 10
<212> TYPE: PRT
<213> ORGANISM: homo sapiens

<400> SEQUENCE: 596

Asn Gln Thr Lys Gly Leu Leu Tyr Gln Leu
1               5                   10

<210> SEQ ID NO 597
<211> LENGTH: 10
<212> TYPE: PRT
<213> ORGANISM: homo sapiens

<400> SEQUENCE: 597

Leu Pro Asn Thr Gln Asp Tyr Lys Trp Val
1               5                   10

<210> SEQ ID NO 598
<211> LENGTH: 10
<212> TYPE: PRT
<213> ORGANISM: homo sapiens

<400> SEQUENCE: 598
```

Glu Asn Lys Asn Gly Ser Gly Pro Phe Leu
1               5                   10

<210> SEQ ID NO 599
<211> LENGTH: 10
<212> TYPE: PRT
<213> ORGANISM: homo sapiens

<400> SEQUENCE: 599

Trp Phe Arg Ser Trp Gly Tyr Val Leu Leu
1               5                   10

<210> SEQ ID NO 600
<211> LENGTH: 10
<212> TYPE: PRT
<213> ORGANISM: homo sapiens

<400> SEQUENCE: 600

Leu Thr Leu Thr Ala Phe Leu Thr Ile Leu
1               5                   10

<210> SEQ ID NO 601
<211> LENGTH: 10
<212> TYPE: PRT
<213> ORGANISM: homo sapiens

<400> SEQUENCE: 601

Ser Pro Gln Gln Ser Ala Gln Leu Leu Val
1               5                   10

<210> SEQ ID NO 602
<211> LENGTH: 10
<212> TYPE: PRT
<213> ORGANISM: homo sapiens

<400> SEQUENCE: 602

Leu Thr Thr His Gln Tyr Asp Thr Ser Leu
1               5                   10

<210> SEQ ID NO 603
<211> LENGTH: 10
<212> TYPE: PRT
<213> ORGANISM: homo sapiens

<400> SEQUENCE: 603

Cys Gly Leu Gly Tyr Leu Val Pro Ser Leu
1               5                   10

<210> SEQ ID NO 604
<211> LENGTH: 10
<212> TYPE: PRT
<213> ORGANISM: homo sapiens

<400> SEQUENCE: 604

Leu Thr Leu Ser Val Asn Asn Ser Gly Leu
1               5                   10

<210> SEQ ID NO 605
<211> LENGTH: 10
<212> TYPE: PRT
<213> ORGANISM: homo sapiens

<400> SEQUENCE: 605

Gly Thr Tyr Asp Leu Glu Lys Ala Ile Leu

```
                1               5                    10
```

<210> SEQ ID NO 606
<211> LENGTH: 10
<212> TYPE: PRT
<213> ORGANISM: homo sapiens

<400> SEQUENCE: 606

```
Leu Thr Ile Leu Val Gln Pro Gln His Leu
 1               5                   10
```

<210> SEQ ID NO 607
<211> LENGTH: 10
<212> TYPE: PRT
<213> ORGANISM: homo sapiens

<400> SEQUENCE: 607

```
Thr Thr His Gln Tyr Asp Thr Ser Leu Leu
 1               5                   10
```

<210> SEQ ID NO 608
<211> LENGTH: 10
<212> TYPE: PRT
<213> ORGANISM: homo sapiens

<400> SEQUENCE: 608

```
Ile Leu Thr Asn Gln Ser Asn Cys Trp Leu
 1               5                   10
```

<210> SEQ ID NO 609
<211> LENGTH: 10
<212> TYPE: PRT
<213> ORGANISM: homo sapiens

<400> SEQUENCE: 609

```
Ser Arg Arg Ser Leu Asn Ser Gln Pro Leu
 1               5                   10
```

<210> SEQ ID NO 610
<211> LENGTH: 10
<212> TYPE: PRT
<213> ORGANISM: homo sapiens

<400> SEQUENCE: 610

```
Leu Leu Gln Leu Thr Leu Thr Ala Phe Leu
 1               5                   10
```

<210> SEQ ID NO 611
<211> LENGTH: 10
<212> TYPE: PRT
<213> ORGANISM: homo sapiens

<400> SEQUENCE: 611

```
Tyr Leu Val Pro Ser Leu Thr Arg Tyr Leu
 1               5                   10
```

<210> SEQ ID NO 612
<211> LENGTH: 10
<212> TYPE: PRT
<213> ORGANISM: homo sapiens

<400> SEQUENCE: 612

```
Val Leu Phe Cys Leu Phe Ile Phe Val Leu
 1               5                   10
```

<210> SEQ ID NO 613
<211> LENGTH: 10
<212> TYPE: PRT
<213> ORGANISM: homo sapiens

<400> SEQUENCE: 613

Ser Asn Cys Ala Leu Leu Gln Leu Thr Leu
1               5                   10

<210> SEQ ID NO 614
<211> LENGTH: 10
<212> TYPE: PRT
<213> ORGANISM: homo sapiens

<400> SEQUENCE: 614

Ser Leu Ser Asn Cys Ala Leu Leu Gln Leu
1               5                   10

<210> SEQ ID NO 615
<211> LENGTH: 9
<212> TYPE: PRT
<213> ORGANISM: homo sapiens

<400> SEQUENCE: 615

Ile Pro Lys Gln Tyr Cys Asn Gln Ile
1               5

<210> SEQ ID NO 616
<211> LENGTH: 9
<212> TYPE: PRT
<213> ORGANISM: homo sapiens

<400> SEQUENCE: 616

Phe Pro Ser Leu Gly Thr Tyr Asp Leu
1               5

<210> SEQ ID NO 617
<211> LENGTH: 9
<212> TYPE: PRT
<213> ORGANISM: homo sapiens

<400> SEQUENCE: 617

Ser Pro Gln Gln Ser Ala Gln Leu Leu
1               5

<210> SEQ ID NO 618
<211> LENGTH: 9
<212> TYPE: PRT
<213> ORGANISM: homo sapiens

<400> SEQUENCE: 618

Trp Ser Gly Asn Asp Thr Cys Leu Tyr
1               5

<210> SEQ ID NO 619
<211> LENGTH: 9
<212> TYPE: PRT
<213> ORGANISM: homo sapiens

<400> SEQUENCE: 619

Ile Ser Lys Ala Met Glu Gln Glu Phe
1               5

<210> SEQ ID NO 620

```
<211> LENGTH: 9
<212> TYPE: PRT
<213> ORGANISM: homo sapiens

<400> SEQUENCE: 620

Val Pro Leu Leu Asp Trp Gln Gly Ile
 1               5

<210> SEQ ID NO 621
<211> LENGTH: 9
<212> TYPE: PRT
<213> ORGANISM: homo sapiens

<400> SEQUENCE: 621

Ala Ser Ala Ser Thr Trp Trp Thr Tyr
 1               5

<210> SEQ ID NO 622
<211> LENGTH: 9
<212> TYPE: PRT
<213> ORGANISM: homo sapiens

<400> SEQUENCE: 622

Trp Ser Gly Arg Cys Gly Leu Gly Tyr
 1               5

<210> SEQ ID NO 623
<211> LENGTH: 9
<212> TYPE: PRT
<213> ORGANISM: homo sapiens

<400> SEQUENCE: 623

Val Pro Ala Ser Ala Ser Thr Trp Trp
 1               5

<210> SEQ ID NO 624
<211> LENGTH: 9
<212> TYPE: PRT
<213> ORGANISM: homo sapiens

<400> SEQUENCE: 624

Leu Pro Asn Thr Gln Asp Tyr Lys Trp
 1               5

<210> SEQ ID NO 625
<211> LENGTH: 9
<212> TYPE: PRT
<213> ORGANISM: homo sapiens

<400> SEQUENCE: 625

Ala Pro Val Phe Arg Thr Leu Ser Ile
 1               5

<210> SEQ ID NO 626
<211> LENGTH: 9
<212> TYPE: PRT
<213> ORGANISM: homo sapiens

<400> SEQUENCE: 626

Leu Ser Pro Gln Gln Ser Ala Gln Leu
 1               5

<210> SEQ ID NO 627
<211> LENGTH: 9
<212> TYPE: PRT
```

<213> ORGANISM: homo sapiens

<400> SEQUENCE: 627

Asn Ser Gln Pro Leu Asn Leu Ala Leu
1               5

<210> SEQ ID NO 628
<211> LENGTH: 9
<212> TYPE: PRT
<213> ORGANISM: homo sapiens

<400> SEQUENCE: 628

Val Ser Asn Arg Ala Met Lys Gly Leu
1               5

<210> SEQ ID NO 629
<211> LENGTH: 9
<212> TYPE: PRT
<213> ORGANISM: homo sapiens

<400> SEQUENCE: 629

Ser Ser Ala Val Pro Leu Ile Gly Leu
1               5

<210> SEQ ID NO 630
<211> LENGTH: 9
<212> TYPE: PRT
<213> ORGANISM: homo sapiens

<400> SEQUENCE: 630

Leu Ser Phe Ala Gln Val Arg Leu Leu
1               5

<210> SEQ ID NO 631
<211> LENGTH: 9
<212> TYPE: PRT
<213> ORGANISM: homo sapiens

<400> SEQUENCE: 631

Gly Ser Leu Ser Asn Cys Ala Leu Leu
1               5

<210> SEQ ID NO 632
<211> LENGTH: 9
<212> TYPE: PRT
<213> ORGANISM: homo sapiens

<400> SEQUENCE: 632

Leu Ser Val Asn Asn Ser Gly Leu Phe
1               5

<210> SEQ ID NO 633
<211> LENGTH: 9
<212> TYPE: PRT
<213> ORGANISM: homo sapiens

<400> SEQUENCE: 633

Leu Ser Asn Cys Ala Leu Leu Gln Leu
1               5

<210> SEQ ID NO 634
<211> LENGTH: 9
<212> TYPE: PRT
<213> ORGANISM: homo sapiens

<400> SEQUENCE: 634

Glu Ala Ser Met Glu Ala Gln Gly Leu
1               5

<210> SEQ ID NO 635
<211> LENGTH: 9
<212> TYPE: PRT
<213> ORGANISM: homo sapiens

<400> SEQUENCE: 635

Gln Pro Gln His Leu Leu Ala Pro Val
1               5

<210> SEQ ID NO 636
<211> LENGTH: 9
<212> TYPE: PRT
<213> ORGANISM: homo sapiens

<400> SEQUENCE: 636

Arg Leu Leu Glu Gly Asn Phe Ser Leu
1               5

<210> SEQ ID NO 637
<211> LENGTH: 9
<212> TYPE: PRT
<213> ORGANISM: homo sapiens

<400> SEQUENCE: 637

Arg Leu His Glu Ala Ser Glu Asn Leu
1               5

<210> SEQ ID NO 638
<211> LENGTH: 9
<212> TYPE: PRT
<213> ORGANISM: homo sapiens

<400> SEQUENCE: 638

Lys Gln Cys Cys Leu Tyr Ile Asn Tyr
1               5

<210> SEQ ID NO 639
<211> LENGTH: 9
<212> TYPE: PRT
<213> ORGANISM: homo sapiens

<400> SEQUENCE: 639

Arg Ser Trp Gly Tyr Val Leu Leu Ile
1               5

<210> SEQ ID NO 640
<211> LENGTH: 9
<212> TYPE: PRT
<213> ORGANISM: homo sapiens

<400> SEQUENCE: 640

Ser Gly Arg Cys Gly Leu Gly Tyr Leu
1               5

<210> SEQ ID NO 641
<211> LENGTH: 9
<212> TYPE: PRT
<213> ORGANISM: homo sapiens

<400> SEQUENCE: 641

```
Gln Thr Lys Gly Leu Leu Tyr Gln Leu
  1               5

<210> SEQ ID NO 642
<211> LENGTH: 9
<212> TYPE: PRT
<213> ORGANISM: homo sapiens

<400> SEQUENCE: 642

Glu Ile Lys Ser Asn Ile Gln Arg Leu
  1               5

<210> SEQ ID NO 643
<211> LENGTH: 9
<212> TYPE: PRT
<213> ORGANISM: homo sapiens

<400> SEQUENCE: 643

Ser Ala Ser Arg Lys Asp His Val Leu
  1               5

<210> SEQ ID NO 644
<211> LENGTH: 9
<212> TYPE: PRT
<213> ORGANISM: homo sapiens

<400> SEQUENCE: 644

Glu Asn Lys Asn Gly Ser Gly Pro Phe
  1               5

<210> SEQ ID NO 645
<211> LENGTH: 9
<212> TYPE: PRT
<213> ORGANISM: homo sapiens

<400> SEQUENCE: 645

Thr Ile Arg Ala Leu Phe Pro Ser Leu
  1               5

<210> SEQ ID NO 646
<211> LENGTH: 9
<212> TYPE: PRT
<213> ORGANISM: homo sapiens

<400> SEQUENCE: 646

Gln Val Arg Leu Leu Glu Gly Asn Phe
  1               5

<210> SEQ ID NO 647
<211> LENGTH: 9
<212> TYPE: PRT
<213> ORGANISM: homo sapiens

<400> SEQUENCE: 647

Thr Ser Ser Tyr Arg Lys Val Thr Trp
  1               5

<210> SEQ ID NO 648
<211> LENGTH: 9
<212> TYPE: PRT
<213> ORGANISM: homo sapiens

<400> SEQUENCE: 648

Glu Ser Arg Asn Asp Asp Asp Asp Thr
  1               5
```

<210> SEQ ID NO 649
<211> LENGTH: 9
<212> TYPE: PRT
<213> ORGANISM: homo sapiens

<400> SEQUENCE: 649

Trp Thr Tyr Ser Gly Gln Trp Met Tyr
1               5

<210> SEQ ID NO 650
<211> LENGTH: 9
<212> TYPE: PRT
<213> ORGANISM: homo sapiens

<400> SEQUENCE: 650

Lys Val Gly Asp Trp Phe Arg Ser Trp
1               5

<210> SEQ ID NO 651
<211> LENGTH: 9
<212> TYPE: PRT
<213> ORGANISM: homo sapiens

<400> SEQUENCE: 651

Val Pro Leu Ile Gly Leu Pro Asn Thr
1               5

<210> SEQ ID NO 652
<211> LENGTH: 9
<212> TYPE: PRT
<213> ORGANISM: homo sapiens

<400> SEQUENCE: 652

Phe Pro Pro Lys Trp Ser Gly Arg Cys
1               5

<210> SEQ ID NO 653
<211> LENGTH: 9
<212> TYPE: PRT
<213> ORGANISM: homo sapiens

<400> SEQUENCE: 653

Val Pro Ser Leu Thr Arg Tyr Leu Thr
1               5

<210> SEQ ID NO 654
<211> LENGTH: 9
<212> TYPE: PRT
<213> ORGANISM: homo sapiens

<400> SEQUENCE: 654

Ile Gly Leu Pro Asn Thr Gln Asp Tyr
1               5

<210> SEQ ID NO 655
<211> LENGTH: 9
<212> TYPE: PRT
<213> ORGANISM: homo sapiens

<400> SEQUENCE: 655

Phe Leu Gly Asn Ile Pro Lys Gln Tyr
1               5

```
<210> SEQ ID NO 656
<211> LENGTH: 9
<212> TYPE: PRT
<213> ORGANISM: homo sapiens

<400> SEQUENCE: 656

Cys Leu Phe Ile Phe Val Leu Ile Tyr
1               5

<210> SEQ ID NO 657
<211> LENGTH: 9
<212> TYPE: PRT
<213> ORGANISM: homo sapiens

<400> SEQUENCE: 657

Ala Ile Leu Asn Ile Ser Lys Ala Met
1               5

<210> SEQ ID NO 658
<211> LENGTH: 9
<212> TYPE: PRT
<213> ORGANISM: homo sapiens

<400> SEQUENCE: 658

Arg Asn Leu Phe Cys Ser Tyr Gly Leu
1               5

<210> SEQ ID NO 659
<211> LENGTH: 9
<212> TYPE: PRT
<213> ORGANISM: homo sapiens

<400> SEQUENCE: 659

Thr Val Gly Lys Gln Cys Cys Leu Tyr
1               5

<210> SEQ ID NO 660
<211> LENGTH: 9
<212> TYPE: PRT
<213> ORGANISM: homo sapiens

<400> SEQUENCE: 660

Tyr Leu Val Pro Ser Leu Thr Arg Tyr
1               5

<210> SEQ ID NO 661
<211> LENGTH: 9
<212> TYPE: PRT
<213> ORGANISM: homo sapiens

<400> SEQUENCE: 661

Ile Pro Thr Thr Gln Arg Gln Thr Ala
1               5

<210> SEQ ID NO 662
<211> LENGTH: 9
<212> TYPE: PRT
<213> ORGANISM: homo sapiens

<400> SEQUENCE: 662

Gly Ser Gly Pro Phe Leu Gly Asn Ile
1               5

<210> SEQ ID NO 663
<211> LENGTH: 9
```

-continued

```
<212> TYPE: PRT
<213> ORGANISM: homo sapiens

<400> SEQUENCE: 663

Val Thr Trp His Trp Glu Ala Ser Met
1               5

<210> SEQ ID NO 664
<211> LENGTH: 9
<212> TYPE: PRT
<213> ORGANISM: homo sapiens

<400> SEQUENCE: 664

Thr Pro Thr Trp Trp Leu Thr Gly Ser
1               5

<210> SEQ ID NO 665
<211> LENGTH: 10
<212> TYPE: PRT
<213> ORGANISM: homo sapiens

<400> SEQUENCE: 665

Ile Pro Lys Gln Tyr Cys Asn Gln Ile Leu
1               5                   10

<210> SEQ ID NO 666
<211> LENGTH: 10
<212> TYPE: PRT
<213> ORGANISM: homo sapiens

<400> SEQUENCE: 666

Val Pro Ser Leu Thr Arg Tyr Leu Thr Leu
1               5                   10

<210> SEQ ID NO 667
<211> LENGTH: 10
<212> TYPE: PRT
<213> ORGANISM: homo sapiens

<400> SEQUENCE: 667

Gln Pro Gln His Leu Leu Ala Pro Val Phe
1               5                   10

<210> SEQ ID NO 668
<211> LENGTH: 10
<212> TYPE: PRT
<213> ORGANISM: homo sapiens

<400> SEQUENCE: 668

Val Pro Leu Leu Asp Trp Gln Gly Ile Phe
1               5                   10

<210> SEQ ID NO 669
<211> LENGTH: 10
<212> TYPE: PRT
<213> ORGANISM: homo sapiens

<400> SEQUENCE: 669

Ala Pro Val Phe Arg Thr Leu Ser Ile Leu
1               5                   10

<210> SEQ ID NO 670
<211> LENGTH: 10
<212> TYPE: PRT
<213> ORGANISM: homo sapiens
```

```
<400> SEQUENCE: 670

Asn Pro Lys Asp Asn Ser Thr Ile Arg Ala
 1               5                  10

<210> SEQ ID NO 671
<211> LENGTH: 10
<212> TYPE: PRT
<213> ORGANISM: homo sapiens

<400> SEQUENCE: 671

Lys Ala Ile Leu Asn Ile Ser Lys Ala Met
 1               5                  10

<210> SEQ ID NO 672
<211> LENGTH: 10
<212> TYPE: PRT
<213> ORGANISM: homo sapiens

<400> SEQUENCE: 672

Arg Ala Leu Phe Pro Ser Leu Gly Thr Tyr
 1               5                  10

<210> SEQ ID NO 673
<211> LENGTH: 10
<212> TYPE: PRT
<213> ORGANISM: homo sapiens

<400> SEQUENCE: 673

Arg Ser Leu Asn Ser Gln Pro Leu Asn Leu
 1               5                  10

<210> SEQ ID NO 674
<211> LENGTH: 10
<212> TYPE: PRT
<213> ORGANISM: homo sapiens

<400> SEQUENCE: 674

Ala Ser Met Glu Ala Gln Gly Leu Ser Phe
 1               5                  10

<210> SEQ ID NO 675
<211> LENGTH: 10
<212> TYPE: PRT
<213> ORGANISM: homo sapiens

<400> SEQUENCE: 675

Thr Ser Cys Gln Val Ser Asn Arg Ala Met
 1               5                  10

<210> SEQ ID NO 676
<211> LENGTH: 10
<212> TYPE: PRT
<213> ORGANISM: homo sapiens

<400> SEQUENCE: 676

Ala Met Lys Gly Leu Thr Thr His Gln Tyr
 1               5                  10

<210> SEQ ID NO 677
<211> LENGTH: 10
<212> TYPE: PRT
<213> ORGANISM: homo sapiens

<400> SEQUENCE: 677
```

```
Pro Pro Lys Trp Ser Gly Arg Cys Gly Leu
1               5                   10

<210> SEQ ID NO 678
<211> LENGTH: 10
<212> TYPE: PRT
<213> ORGANISM: homo sapiens

<400> SEQUENCE: 678

Leu Pro Asn Thr Gln Asp Tyr Lys Trp Val
1               5                   10

<210> SEQ ID NO 679
<211> LENGTH: 10
<212> TYPE: PRT
<213> ORGANISM: homo sapiens

<400> SEQUENCE: 679

Ala Ser Arg Lys Asp His Val Leu Asp Ile
1               5                   10

<210> SEQ ID NO 680
<211> LENGTH: 10
<212> TYPE: PRT
<213> ORGANISM: homo sapiens

<400> SEQUENCE: 680

Leu Ser Pro Gln Gln Ser Ala Gln Leu Leu
1               5                   10

<210> SEQ ID NO 681
<211> LENGTH: 10
<212> TYPE: PRT
<213> ORGANISM: homo sapiens

<400> SEQUENCE: 681

Tyr Ser Cys Gln Asn Gln Thr Lys Gly Leu
1               5                   10

<210> SEQ ID NO 682
<211> LENGTH: 10
<212> TYPE: PRT
<213> ORGANISM: homo sapiens

<400> SEQUENCE: 682

Ala Ser Gln Ile Thr Asn Leu Arg Ser Phe
1               5                   10

<210> SEQ ID NO 683
<211> LENGTH: 10
<212> TYPE: PRT
<213> ORGANISM: homo sapiens

<400> SEQUENCE: 683

Trp Ser Gly Arg Cys Gly Leu Gly Tyr Leu
1               5                   10

<210> SEQ ID NO 684
<211> LENGTH: 10
<212> TYPE: PRT
<213> ORGANISM: homo sapiens

<400> SEQUENCE: 684

Gln Ser Asn Cys Trp Leu Cys Glu His Leu
```

```
1               5                  10
```

<210> SEQ ID NO 685
<211> LENGTH: 10
<212> TYPE: PRT
<213> ORGANISM: homo sapiens

<400> SEQUENCE: 685

```
Ala Ser Ala Ser Arg Lys Asp His Val Leu
 1               5                  10
```

<210> SEQ ID NO 686
<211> LENGTH: 10
<212> TYPE: PRT
<213> ORGANISM: homo sapiens

<400> SEQUENCE: 686

```
Asn Ser Ser Ala Val Pro Leu Ile Gly Leu
 1               5                  10
```

<210> SEQ ID NO 687
<211> LENGTH: 10
<212> TYPE: PRT
<213> ORGANISM: homo sapiens

<400> SEQUENCE: 687

```
Leu Ser Val Asn Asn Ser Gly Leu Phe Phe
 1               5                  10
```

<210> SEQ ID NO 688
<211> LENGTH: 10
<212> TYPE: PRT
<213> ORGANISM: homo sapiens

<400> SEQUENCE: 688

```
Ser Pro Gln Gln Ser Ala Gln Leu Leu Val
 1               5                  10
```

<210> SEQ ID NO 689
<211> LENGTH: 10
<212> TYPE: PRT
<213> ORGANISM: homo sapiens

<400> SEQUENCE: 689

```
Lys Val Thr Trp His Trp Glu Ala Ser Met
 1               5                  10
```

<210> SEQ ID NO 690
<211> LENGTH: 10
<212> TYPE: PRT
<213> ORGANISM: homo sapiens

<400> SEQUENCE: 690

```
Thr Gln Gly Asp Thr Asp Asn Pro Pro Leu
 1               5                  10
```

<210> SEQ ID NO 691
<211> LENGTH: 10
<212> TYPE: PRT
<213> ORGANISM: homo sapiens

<400> SEQUENCE: 691

```
Gln Thr Lys Gly Leu Leu Tyr Gln Leu Phe
 1               5                  10
```

```
<210> SEQ ID NO 692
<211> LENGTH: 10
<212> TYPE: PRT
<213> ORGANISM: homo sapiens

<400> SEQUENCE: 692

Glu Asn Lys Asn Gly Ser Gly Pro Phe Leu
1               5                   10

<210> SEQ ID NO 693
<211> LENGTH: 10
<212> TYPE: PRT
<213> ORGANISM: homo sapiens

<400> SEQUENCE: 693

Gly Thr Tyr Asp Leu Glu Lys Ala Ile Leu
1               5                   10

<210> SEQ ID NO 694
<211> LENGTH: 10
<212> TYPE: PRT
<213> ORGANISM: homo sapiens

<400> SEQUENCE: 694

Glu Ala His Gln Ser Lys Val Ser Ser Leu
1               5                   10

<210> SEQ ID NO 695
<211> LENGTH: 10
<212> TYPE: PRT
<213> ORGANISM: homo sapiens

<400> SEQUENCE: 695

Gly Gln Trp Met Tyr Glu Arg Val Trp Tyr
1               5                   10

<210> SEQ ID NO 696
<211> LENGTH: 10
<212> TYPE: PRT
<213> ORGANISM: homo sapiens

<400> SEQUENCE: 696

Ser Ser Tyr Arg Lys Val Thr Trp His Trp
1               5                   10

<210> SEQ ID NO 697
<211> LENGTH: 10
<212> TYPE: PRT
<213> ORGANISM: homo sapiens

<400> SEQUENCE: 697

Ile Ser Lys Ala Met Glu Gln Glu Phe Ser
1               5                   10

<210> SEQ ID NO 698
<211> LENGTH: 10
<212> TYPE: PRT
<213> ORGANISM: homo sapiens

<400> SEQUENCE: 698

Glu Ser Arg Asn Asp Asp Asp Thr Ser
1               5                   10

<210> SEQ ID NO 699
```

```
<211> LENGTH: 10
<212> TYPE: PRT
<213> ORGANISM: homo sapiens

<400> SEQUENCE: 699

Gly Thr Val Gly Lys Gln Cys Cys Leu Tyr
 1               5                  10

<210> SEQ ID NO 700
<211> LENGTH: 10
<212> TYPE: PRT
<213> ORGANISM: homo sapiens

<400> SEQUENCE: 700

Tyr Pro Gln Ala Glu Val Gln Asn His Ser
 1               5                  10

<210> SEQ ID NO 701
<211> LENGTH: 10
<212> TYPE: PRT
<213> ORGANISM: homo sapiens

<400> SEQUENCE: 701

Cys Gln Asn Gln Thr Lys Gly Leu Leu Tyr
 1               5                  10

<210> SEQ ID NO 702
<211> LENGTH: 10
<212> TYPE: PRT
<213> ORGANISM: homo sapiens

<400> SEQUENCE: 702

Gln Leu Phe Arg Asn Leu Phe Cys Ser Tyr
 1               5                  10

<210> SEQ ID NO 703
<211> LENGTH: 10
<212> TYPE: PRT
<213> ORGANISM: homo sapiens

<400> SEQUENCE: 703

Val Pro Ala Ser Ala Ser Thr Trp Trp Thr
 1               5                  10

<210> SEQ ID NO 704
<211> LENGTH: 10
<212> TYPE: PRT
<213> ORGANISM: homo sapiens

<400> SEQUENCE: 704

Arg Val Phe Arg Lys Ser Arg Arg Ser Leu
 1               5                  10

<210> SEQ ID NO 705
<211> LENGTH: 10
<212> TYPE: PRT
<213> ORGANISM: homo sapiens

<400> SEQUENCE: 705

Asp Asn Ala Glu Gln Pro Glu Leu Val Phe
 1               5                  10

<210> SEQ ID NO 706
<211> LENGTH: 10
<212> TYPE: PRT
```

<213> ORGANISM: homo sapiens

<400> SEQUENCE: 706

Met Pro Ser Ile Asp Val Thr Asn Glu Ser
1               5                   10

<210> SEQ ID NO 707
<211> LENGTH: 10
<212> TYPE: PRT
<213> ORGANISM: homo sapiens

<400> SEQUENCE: 707

Thr Pro His Arg Cys Thr Gln Gly Asp Thr
1               5                   10

<210> SEQ ID NO 708
<211> LENGTH: 10
<212> TYPE: PRT
<213> ORGANISM: homo sapiens

<400> SEQUENCE: 708

Arg Ser Trp Gly Tyr Val Leu Leu Ile Val
1               5                   10

<210> SEQ ID NO 709
<211> LENGTH: 10
<212> TYPE: PRT
<213> ORGANISM: homo sapiens

<400> SEQUENCE: 709

Thr Pro Thr Trp Trp Leu Thr Gly Ser Asn
1               5                   10

<210> SEQ ID NO 710
<211> LENGTH: 10
<212> TYPE: PRT
<213> ORGANISM: homo sapiens

<400> SEQUENCE: 710

Lys Gln Tyr Cys Asn Gln Ile Leu Trp Phe
1               5                   10

<210> SEQ ID NO 711
<211> LENGTH: 10
<212> TYPE: PRT
<213> ORGANISM: homo sapiens

<400> SEQUENCE: 711

Arg Thr Trp Asn Ser Ser Ala Val Pro Leu
1               5                   10

<210> SEQ ID NO 712
<211> LENGTH: 10
<212> TYPE: PRT
<213> ORGANISM: homo sapiens

<400> SEQUENCE: 712

Glu Val Gln Asn His Ser Thr Ser Ser Tyr
1               5                   10

<210> SEQ ID NO 713
<211> LENGTH: 10
<212> TYPE: PRT
<213> ORGANISM: homo sapiens

```
<400> SEQUENCE: 713

Leu Ile Gly Leu Pro Asn Thr Gln Asp Tyr
 1               5                  10

<210> SEQ ID NO 714
<211> LENGTH: 10
<212> TYPE: PRT
<213> ORGANISM: homo sapiens

<400> SEQUENCE: 714

Phe Cys Leu Phe Ile Phe Val Leu Ile Tyr
 1               5                  10

<210> SEQ ID NO 715
<211> LENGTH: 4
<212> TYPE: PRT
<213> ORGANISM: homo sapiens

<400> SEQUENCE: 715

Asn Gln Ser Asn
 1

<210> SEQ ID NO 716
<211> LENGTH: 4
<212> TYPE: PRT
<213> ORGANISM: homo sapiens

<400> SEQUENCE: 716

Asn His Ser Thr
 1

<210> SEQ ID NO 717
<211> LENGTH: 4
<212> TYPE: PRT
<213> ORGANISM: homo sapiens

<400> SEQUENCE: 717

Asn Phe Ser Leu
 1

<210> SEQ ID NO 718
<211> LENGTH: 4
<212> TYPE: PRT
<213> ORGANISM: homo sapiens

<400> SEQUENCE: 718

Asn Gly Ser Gly
 1

<210> SEQ ID NO 719
<211> LENGTH: 4
<212> TYPE: PRT
<213> ORGANISM: homo sapiens

<400> SEQUENCE: 719

Asn Glu Ser Arg
 1

<210> SEQ ID NO 720
<211> LENGTH: 4
<212> TYPE: PRT
<213> ORGANISM: homo sapiens

<400> SEQUENCE: 720
```

-continued

Asn Arg Thr Trp
1

<210> SEQ ID NO 721
<211> LENGTH: 4
<212> TYPE: PRT
<213> ORGANISM: homo sapiens

<400> SEQUENCE: 721

Asn Ser Ser Ala
1

<210> SEQ ID NO 722
<211> LENGTH: 4
<212> TYPE: PRT
<213> ORGANISM: homo sapiens

<400> SEQUENCE: 722

Asn Asp Thr Cys
1

<210> SEQ ID NO 723
<211> LENGTH: 4
<212> TYPE: PRT
<213> ORGANISM: homo sapiens

<400> SEQUENCE: 723

Asn Gln Thr Lys
1

<210> SEQ ID NO 724
<211> LENGTH: 4
<212> TYPE: PRT
<213> ORGANISM: homo sapiens

<400> SEQUENCE: 724

Asn Leu Thr Leu
1

<210> SEQ ID NO 725
<211> LENGTH: 4
<212> TYPE: PRT
<213> ORGANISM: homo sapiens

<400> SEQUENCE: 725

Asn Asn Ser Gly
1

<210> SEQ ID NO 726
<211> LENGTH: 4
<212> TYPE: PRT
<213> ORGANISM: homo sapiens

<400> SEQUENCE: 726

Asn Ala Ser Gln
1

<210> SEQ ID NO 727
<211> LENGTH: 4
<212> TYPE: PRT
<213> ORGANISM: homo sapiens

<400> SEQUENCE: 727

Asn Ser Thr Ile
1

```
<210> SEQ ID NO 728
<211> LENGTH: 4
<212> TYPE: PRT
<213> ORGANISM: homo sapiens

<400> SEQUENCE: 728

Asn Ile Ser Lys
  1

<210> SEQ ID NO 729
<211> LENGTH: 4
<212> TYPE: PRT
<213> ORGANISM: homo sapiens

<400> SEQUENCE: 729

Asn Tyr Ser Glu
  1

<210> SEQ ID NO 730
<211> LENGTH: 4
<212> TYPE: PRT
<213> ORGANISM: homo sapiens

<400> SEQUENCE: 730

Arg Lys Val Thr
  1

<210> SEQ ID NO 731
<211> LENGTH: 4
<212> TYPE: PRT
<213> ORGANISM: homo sapiens

<400> SEQUENCE: 731

Ser Arg Asn Asp
  1

<210> SEQ ID NO 732
<211> LENGTH: 4
<212> TYPE: PRT
<213> ORGANISM: homo sapiens

<400> SEQUENCE: 732

Ser Gly Asn Asp
  1

<210> SEQ ID NO 733
<211> LENGTH: 4
<212> TYPE: PRT
<213> ORGANISM: homo sapiens

<400> SEQUENCE: 733

Thr Gln Gly Asp
  1

<210> SEQ ID NO 734
<211> LENGTH: 4
<212> TYPE: PRT
<213> ORGANISM: homo sapiens

<400> SEQUENCE: 734

Ser Arg Lys Asp
  1
```

```
<210> SEQ ID NO 735
<211> LENGTH: 6
<212> TYPE: PRT
<213> ORGANISM: homo sapiens

<400> SEQUENCE: 735

Gly Ser Leu Ser Asn Cys
1               5

<210> SEQ ID NO 736
<211> LENGTH: 6
<212> TYPE: PRT
<213> ORGANISM: homo sapiens

<400> SEQUENCE: 736

Gly Leu Ser Phe Ala Gln
1               5

<210> SEQ ID NO 737
<211> LENGTH: 6
<212> TYPE: PRT
<213> ORGANISM: homo sapiens

<400> SEQUENCE: 737

Gly Thr Arg Gln Cys Ser
1               5

<210> SEQ ID NO 738
<211> LENGTH: 6
<212> TYPE: PRT
<213> ORGANISM: homo sapiens

<400> SEQUENCE: 738

Gly Leu Pro Asn Thr Gln
1               5

<210> SEQ ID NO 739
<211> LENGTH: 6
<212> TYPE: PRT
<213> ORGANISM: homo sapiens

<400> SEQUENCE: 739

Gly Leu Thr Trp Ser Gly
1               5

<210> SEQ ID NO 740
<211> LENGTH: 6
<212> TYPE: PRT
<213> ORGANISM: homo sapiens

<400> SEQUENCE: 740

Gly Asn Asp Thr Cys Leu
1               5

<210> SEQ ID NO 741
<211> LENGTH: 6
<212> TYPE: PRT
<213> ORGANISM: homo sapiens

<400> SEQUENCE: 741

Gly Leu Thr Glu Ala His
1               5

<210> SEQ ID NO 742
<211> LENGTH: 6
```

```
<212> TYPE: PRT
<213> ORGANISM: homo sapiens

<400> SEQUENCE: 742

Gly Ser Asn Leu Thr Leu
1               5

<210> SEQ ID NO 743
<211> LENGTH: 6
<212> TYPE: PRT
<213> ORGANISM: homo sapiens

<400> SEQUENCE: 743

Gly Val Tyr Lys Gly Phe
1               5

<210> SEQ ID NO 744
<211> LENGTH: 22
<212> TYPE: PRT
<213> ORGANISM: homo sapiens

<400> SEQUENCE: 744

Leu Thr Ala Phe Leu Thr Ile Leu Val Gln Pro Gln His Leu Leu Ala
1               5                   10                  15

Pro Val Phe Arg Thr Leu
            20

<210> SEQ ID NO 745
<211> LENGTH: 34
<212> TYPE: PRT
<213> ORGANISM: homo sapiens

<400> SEQUENCE: 745

Gly Asp Trp Phe Arg Ser Trp Gly Tyr Val Leu Leu Ile Val Leu Phe
1               5                   10                  15

Cys Leu Phe Ile Phe Val Leu Ile Tyr Val Arg Val Phe Arg Lys Ser
            20                  25                  30

Arg Arg

<210> SEQ ID NO 746
<211> LENGTH: 21
<212> TYPE: PRT
<213> ORGANISM: homo sapiens

<400> SEQUENCE: 746

Phe Arg Ser Trp Gly Tyr Val Leu Leu Ile Val Leu Phe Cys Leu Phe
1               5                   10                  15

Ile Phe Val Leu Ile
            20

<210> SEQ ID NO 747
<211> LENGTH: 17
<212> TYPE: PRT
<213> ORGANISM: homo sapiens

<400> SEQUENCE: 747

Val Leu Leu Ile Val Leu Phe Cys Leu Phe Ile Phe Val Leu Ile Tyr
1               5                   10                  15

Val

<210> SEQ ID NO 748
<211> LENGTH: 24
```

```
<212> TYPE: PRT
<213> ORGANISM: homo sapiens

<400> SEQUENCE: 748

Met Gly Ser Leu Ser Asn Cys Ala Leu Leu Gln Leu Thr Leu Thr Ala
 1               5                  10                  15

Phe Leu Thr Ile Leu Val Gln Pro
            20

<210> SEQ ID NO 749
<211> LENGTH: 25
<212> TYPE: DNA
<213> ORGANISM: homo sapiens

<400> SEQUENCE: 749
atatcgccgc gctcgtcgtc gacaa                                      25

<210> SEQ ID NO 750
<211> LENGTH: 26
<212> TYPE: DNA
<213> ORGANISM: homo sapiens

<400> SEQUENCE: 750
agccacacgc agctcattgt agaagg                                     26

<210> SEQ ID NO 751
<211> LENGTH: 24
<212> TYPE: DNA
<213> ORGANISM: homo sapiens

<400> SEQUENCE: 751
cttgggaggt cctagtgcta agtg                                       24

<210> SEQ ID NO 752
<211> LENGTH: 24
<212> TYPE: DNA
<213> ORGANISM: homo sapiens

<400> SEQUENCE: 752
caatgaaggg actaacaacc catc                                       24
```